(12) United States Patent
Zhou et al.

(10) Patent No.: US 10,967,054 B2
(45) Date of Patent: Apr. 6, 2021

(54) METHODS OF CANCER TREATMENT USING ACTIVATED T CELLS

(71) Applicant: SYZ CELL THERAPY CO., Guangdong (CN)

(72) Inventors: Xiangjun Zhou, Guangdong (CN); Jin Li, Guangdong (CN); Yanyan Han, Guangdong (CN); Dongyun Wu, Guangdong (CN); Junyun Liu, Guangdong (CN); Longqing Tang, Guangdong (CN)

(73) Assignee: SYZ CELL THERAPY CO., Guangdong (CN)

( * ) Notice: Subject to any disclaimer, the term of this patent is extended or adjusted under 35 U.S.C. 154(b) by 83 days.

(21) Appl. No.: 15/557,794

(22) PCT Filed: Mar. 11, 2016

(86) PCT No.: PCT/CN2016/076165
§ 371 (c)(1),
(2) Date: Sep. 12, 2017

(87) PCT Pub. No.: WO2016/146035
PCT Pub. Date: Sep. 22, 2016

(65) Prior Publication Data
US 2018/0078624 A1 Mar. 22, 2018

(30) Foreign Application Priority Data
Mar. 13, 2015 (WO) ................ PCT/CN2015/074227

(51) Int. Cl.
| | |
|---|---|
| *A61K 35/14* | (2015.01) |
| *A61K 35/15* | (2015.01) |
| *A61K 35/17* | (2015.01) |
| *A61K 39/00* | (2006.01) |
| *C12N 5/0783* | (2010.01) |
| *C12N 5/0784* | (2010.01) |
| *A61K 45/06* | (2006.01) |

(52) U.S. Cl.
CPC .......... *A61K 39/0011* (2013.01); *A61K 35/14* (2013.01); *A61K 35/17* (2013.01); *A61K 45/06* (2013.01); *C12N 5/0636* (2013.01); *C12N 5/0639* (2013.01); *A61K 2039/5154* (2013.01); *A61K 2039/5158* (2013.01); *C12N 2501/998* (2013.01); *C12N 2502/1114* (2013.01); *C12N 2502/1121* (2013.01)

(58) Field of Classification Search
CPC .... A61K 39/0011; A61K 35/14; A61K 35/15; A61K 35/17; C12N 5/0636; C12N 5/0639
See application file for complete search history.

(56) References Cited

U.S. PATENT DOCUMENTS

| | | | |
|---|---|---|---|
| 5,976,546 | A | 11/1999 | Laus et al. |
| 6,080,409 | A | 6/2000 | Laus et al. |
| 6,210,662 | B1 | 4/2001 | Laus et al. |
| 7,999,092 | B2 | 8/2011 | Han |
| 2003/0082806 | A1 | 5/2003 | Berenson et al. |
| 2005/0170503 | A1* | 8/2005 | Falo, Jr. ............. A61K 39/0011 435/372 |
| 2006/0153821 | A1 | 7/2006 | Falo, Jr. et al. |
| 2012/0244620 | A1 | 9/2012 | Boynton et al. |
| 2012/0269860 | A1 | 10/2012 | Karlsson-Parra et al. |
| 2015/0202291 | A1 | 7/2015 | Bosch |
| 2016/0362658 | A1 | 12/2016 | Leen et al. |

FOREIGN PATENT DOCUMENTS

| | | |
|---|---|---|
| CN | 1353575 A | 6/2002 |
| CN | 1541113 A | 10/2004 |
| CN | 101336291 A | 12/2008 |
| CN | 102597222 A | 7/2012 |
| CN | 102625832 A | 8/2012 |
| JP | 2002539805 A | 11/2002 |
| JP | 2013502235 A | 1/2013 |
| WO | WO200057705 A1 | 10/2000 |
| WO | WO0129192 A2 | 4/2001 |

(Continued)

OTHER PUBLICATIONS

Altadill, A. et al. (Oct. 2009; e-published on Apr. 16, 2009). "Liver Expression of Matrix Metalloproteases and Their Inhibitors in Hepatocellular Carcinoma," *Dig. Liver. Dis.* 41(10):740-748.

Boß, C.N. et al. (Jun. 1, 2007). "Identification and Characterization of T-Cell Epitopes Deduced from RGS5, a Novel Broadly Expressed Tumor Antigen," *Clinical Cancer Research* 13(11):3347-3355.

Boix, L. et al. (Jan. 1994). "c-met mRNA Overexpression in Human Hepatocellular Carcinoma," *Hepatology* 19(1):88-91.

Boussiotis, V.A. (2014). "Somatic Mutations and Immunotherapy Outcome With CTLA-4 Blockade in Melanoma" *N. Engl. J. Med.* 371(23):2230-2232.

(Continued)

*Primary Examiner* — Yan Xiao
(74) *Attorney, Agent, or Firm* — Morrison & Foerster LLP

(57) ABSTRACT

Provided is a method of treating a cancer in an individual using activated T cells or PBMCs induced by antigen presenting cells (such as dendritic cells) loaded with a plurality of tumor antigen peptides. The method may further comprise administration of the antigen presenting cells loaded with the plurality of tumor antigen peptides to the individual. The methods may be used singly or in combination with an immune checkpoint inhibitor. Also provided are precision therapy methods customized for the individual using neoantigen peptides or based on the mutation load in the tumor of the individual, methods of preparing the activated T cells, methods of monitoring the treatment, methods of cloning tumor-specific T cell receptors, an isolated population of cells comprising the activated T cells, and compositions and kits useful for cancer immunotherapy.

17 Claims, 36 Drawing Sheets

Specification includes a Sequence Listing.

(56) References Cited

FOREIGN PATENT DOCUMENTS

| WO | 2002000730 A2 | 1/2002 |
|---|---|---|
| WO | 2007067782 A2 | 6/2007 |
| WO | WO2011028531 A1 | 3/2011 |
| WO | 2011053223 A1 | 5/2011 |
| WO | 2015069770 A1 | 5/2015 |
| WO | WO-2016/145578 A1 | 9/2016 |
| WO | WO-2016/146035 A1 | 9/2016 |
| WO | 2019183924 A1 | 10/2019 |
| WO | 2019185041 A1 | 10/2019 |

OTHER PUBLICATIONS

Bressac, B. et al. (Mar. 1, 1990). "Abnormal Structure and Expression of p53 Gene in Human Hepatocellular Carcinoma," *Proc. Natl. Acad. Sci. U.S.A.* 87(5):1973-1977.

Butterfield, L.H. et al. (May 1, 2006). "A Phase I/II Trial Testing Immunization of Hepatocellular Carcinoma Patients with Dendritic Cells Pulsed with Four α-Fetoprotein Peptides," *Clinical Cancer Research* 12(9):2817-2825.

Cha, E. et al. (May 28, 2014). "Improved Survival with T Cell Clonotype Stability after Anti-CTLA-4 Treatment in Cancer Patients," *Sci. Transl. Med.* 6(238):238r-270r.

Challa-Malladi, M. et al. (Dec. 13, 2011; e-published on Dec. 1, 2011). "Combined Genetic Inactivation of β2-Microglobulin and CD58 Reveals Frequent Escape from Immune Recognition in Diffuse Large B Cell Lymphoma," *Cancer Cell* 20(6):728-740.

Chapuis, A.G. et al. (Mar. 20, 2012; e-published on Mar. 5, 2012). "Transferred Melanoma-Specific CD8+ T Cells Persist, Mediate Tumor Regression, and Acquire Central Memory Phenotype," *Proc Natl Acad Sci USA* 109(12):4592-4597.

Cheever M.A. et al. (Jun. 1, 2011; e-published on Apr. 6, 2011). "Provenge (Sipuleucel-T) in Prostate Cancer: The First FDA-Approved Therapeutic Cancer Vaccine," *Clinical Cancer Research* 17(11):3520-3526.

Chen, J.L. et al. (Jul. 15, 2000). "Identification of NY-ESO-1 Peptide Analogues Capable of Improved Stimulation of Tumor-Reactive CTL," *The Journal of Immunology* 165(2):948-955.

Chen, W. et al. (Mar./Apr. 2016). "Cancer Statistics in China, 2015" *CA. Cancer. J. Clin.* 66(2):115-132.

Chen, W. et al. (May 31, 2004). "Immune Responses of Dendritic Cells Pulsed With Myeloma Antigen," *J Clin Intern Med* 21(5):331-333, (English Abstract only).

Cicinnati, V.R. et al. (Dec. 15, 2006; e-published Sep. 22, 2006). "Increased Frequencies of CD8+ T Lymphocytes Recognizing Wild-Type P53-Derived Epitopes in Peripheral Blood Correlate with Presence of Epitope Loss Tumor Variants in Patients with Hepatocellular Carcinoma," *International Journal of Cancer* 119(12):2851-2860.

Deng J. et al. (Jan. 31, 2007). "Anti-Tumor Immunity Induced by Activated Dendritic Cells with Tumor Antigen from HIFU-Treated Tumors," *Chin J Cancer Prev.Treat,* 14(3):181-184.

Garrido, F. et al. (Jul. 15, 2010). "'Hard' and 'Soft' Lesions Underlying the HLA Class I Alterations in Cancer Cells: Implications for Immunotherapy," *International Journal of Cancer* 127(2):249-256.

Gehring, A.J. et al. (2009; e-published on Apr. 23, 2009). "Profile of Tumor Antigen-Specific CD8 T Cells in Patients with Hepatitis B Virus-Related Hepatocellular Carcinoma," *Gastroenterology* 137(2):682-690.

Gehring, A.J. et al. (2011). Engineering Virus-Specific T cells that Target HBV Infected Hepatocytes and Hepatocellular Carcinoma Cell Lines. *Journal of Hepatology* 55:103-110.

Golub, T.R. et al. (Oct. 15, 1999). "Molecular Classification of Cancer: Class Discovery and Class Prediction by Gene Expression Monitoring," *Science* 286(5439):531-537.

Grupp, S.A. et al. (Apr. 18, 2013). "Chimeric Antigen Receptor-Modified T Cells for Acute Lymphoid Leukemia," *The New England Journal of Medicine* 368:1509-1518.

Holmes, I. et al. (Feb. 3, 2012). "Dirichlet Multinomial Mixtures: Generative Models for Microbial Metagenomics," *PLoS One* 7(2):e30126, pp. 1-15.

Hu, M. et al. (Sep. 2013; e-published on Jul. 19, 2013). "Over-Expression of Regulator of G Protein Signaling 5 Promotes Tumor Metastasis by Inducing Epithelial-Mesenchymal Transition in Hepatocellular Carcinoma Cells," *Journal of Surgical Oncology* 108(3):192-196.

Idenoue, S. et al. (Feb. 15, 2005). "A Potent Immunogenic General Cancer Vaccine That Targets Survivin, an Inhibitor of Apoptosis Proteins," *Clinical Cancer Research* 11(4):1474-1482.

Ito, T. et al. (May 2000). "Survivin Promotes Cell Proliferation in Human Hepatocellular Carcinoma," *Hepatology* 31(5):1080-1085.

Jiao, B. et al. (2007). "Effect of Anti2carcinoma of T Lymphocyte Activated by Dendritic Cells Modified by Large Intestine Tumor Antigen," *Journal of Zhengzhou University* (medical Sciences), 42(6):1094-1096, (English Translation of the introduction only).

Kalos, M. et al. (Jul. 25, 2013). "Adoptive T Cell Transfer for Cancer Immunotherapy in the Era of Synthetic Biology," *Immunity* 39(1):49-60.

Kantoff, P.W. et al. (Jul. 29, 2010). "Sipuleucel-T immunotherapy for Castration-Resistant Prostate Cancer." *The New England Journal of Medicine* 363(5):411-422.

Komori, H. et al. (May 1, 2006). "Identification of HLA-A2- or HLA-A24-Restricted CTL Epitopes Possibly Useful for Glypican-3-Specific Immunotherapy of Hepatocellular Carcinoma," *Clinical Cancer Research* 12(9):2689-2697.

Koopman, L.A. et al. (Mar. 20, 2000). "Multiple Genetic Alterations Cause Frequent and Heterogeneous Human Histocompatibility Leukocyte Antigen Class I Loss in Cervical Cancer," *The Journal of Experimental Medicine* 191(6):961-975.

Le, DT et al. (Jun. 25, 2015). "PD-1 Blockade in Tumors With Mismatch-Repair Deficiency," *The New England Journal of Medicine* 372(26):2509-2520.

Li, X. et al. (Aug. 2009). "Anti-tumor Effect of Cytotoxicity T Lymphocytes Activated by Dendritic Cells Loaded with Salivary Adenoid Cystic Carcinoma Antigen," *Modern Oncology* 17(8):1434-1436, (English Translation of the Abstract only).

Marshall, J.L. et al. (Feb. 1, 2005; e-published on Dec. 21, 2004). "Phase I Study of Sequential Vaccinations with Fowlpox-CEA(6D)-TRICOM Alone and Sequentially with Vaccinia-CEA(6D)-TRICOM, with and Without Granulocyte-Macrophage Colony-Stimulating Factor, in Patients with Carcinoembryonic Antigen-Expressing Carcinomas," *Journal of Clinical Oncology* 23(4):720-731.

Martin, B. et al. (2014, e-pub. Jun. 4, 2014). "Restoration of HCV-Specific CD8+ T Cell Function by Interferon-Free Therapy," *Journal of Hepatology* 61:538-543.

Melia, W. M. et al. (Aug. 15, 1981). "Plasma Carcinoembryonic Antigen in the Diagnosis and Management of Patients with Hepatocellular Carcinoma," *Cancer* 48(4):1004-1008.

Mizukoshi, E. et al. (Jun. 2006). "Cytotoxic T Cell Responses to Human Telomerase Reverse Transcriptase in Patients with Hepatocellular Carcinoma," *Hepatology* 43(6):1284-1294.

Nakamura, S. et al. (Aug. 2006). "Expression and Immunogenicity of NY-ESO-1 in Hepatocellular Carcinoma," *Journal of Gastroenterology Hepatology* 21(8):1281-1285.

Nishida, N. et al. (Jun. 15, 1994). "Amplification and Overexpression of the Cyclin D1 Gene in Aggressive Human Hepatocellular Carcinoma," *Cancer Research* 54(12):3107-3110.

Niu, H. et al. (Sep. 30, 2004). "Experimental and Clinical Research of Dendritic Cell and Syngeneic 1-12 Immunotherapy of Brain Glioma" *The Chinese-German Journal of Clinical Oncology* 3(3):147-150.

Okuyama, R. (Nov. 2013). "Immunological Responses to a Multi-Peptide Vaccine Targeting Cancer-Testis Antigens and VEGFR5 in Advanced Pancreatic Cancer Patients," *OncoImmunology* 2(11):e27010-1-e27010-7.

Palucka, K. et al. (Jul. 25, 2013). "Dendritic-Cell-Based Therapeutic Cancer Vaccines," *Immunity* 39(1):38-48.

Porter, D.L. et al. (Aug. 25, 2011). "Chimeric Antigen Receptor-Modified T Cells in Chronic Lymphoid Leukemia," *The New England Journal of Medicine* 365:725-733.

(56) References Cited

OTHER PUBLICATIONS

Powell, Jr., D.J., et al. (Jan. 1, 2005; e-published on Dec. 20, 2004). "Transition of Late-Stage Effector T Cells to CD27+ CD28+ Tumor-Reactive Effector Memory T Cells in Humans After Adoptive Cell Transfer Therapy," *Blood* 105(1):241-250.

Qijun, Q. et al. (2015). "Precision cancer immunotherapy: From theory to practice," *Chin J Cancer Biother* 22(2):151-158, (English Translation of the Abstract only).

Rapoport, A.P. et al. (Jan. 20, 2011; e-published on Oct. 28, 2010). "Combination Immunotherapy Using Adoptive T-Cell Transfer and Tumor Antigen Vaccination on the Basis of hTERT and Survivin After ASCT for Myeloma," *Blood* 117(3):788-797.

Restifo, N.P. et al. (Apr. 2012). "Adoptive Immunotherapy for Cancer: Harnessing the T Cell Response," *Nat. Rev. Immunol.* 12:269-281.

Robbins, P.F. et al. (Jun. 2013; e-published on May 5, 2013). "Mining Exomic Sequencing Data to Identify Mutated Antigens Recognized by Adoptively Transferred Tumor-Reactive T Cells." *Nature Medicine* 19(6):747-752.

Sawada, Y. et al. (2016; e-published on Jan. 19, 2016). "Phase II Study of the GPC3-Derived Peptide Vaccine as an Adjuvant Therapy for Hepatocellular Carcinoma Patients," *OncoImmunology* 5(5):e1129483-1-e1129483-8.

Sayem, M.A. et al. (Jan. 2016; e-published Aug. 31, 2015). "Identification of Glypican-3-Derived Long Peptides Activating Both CD8+ and CD4+ T Cells; Prolonged Overall Survival in Cancer Patients with Th Cell Response," *OncoImmunology* 5(1):e1062209-1-e1062209-14.

Schag, K. et al. (Jun. 1, 2004). "Identification of C-Met Oncogene as a Broadly Expressed Tumor-Associated Antigen Recognized by Cytotoxic T-Lymphocytes," *Clinical Cancer Research* 10(11):3658-3666.

Schuler, P. J. et al. (May 1, 2014; e-published on Feb. 28, 2014). "Phase I Dendritic Cell p53 Peptide Vaccine for Head and Neck Cancer," *Clin. Cancer. Res.* 20(9):2433-2444.

Schurich, A. et al. (May 2011). "Role of the Coinhibitory Receptor Cytotoxic T Lymphocyte Antigen-4 on Apoptosis-Prone CD8 T Cells in Persistent Hepatitis B Virus Infection," *Hepatology* 53(5):1494-1503.

Shukla, S.A. et al. (Nov. 2015; e-published on Sep. 15, 2015). "Comprehensive Analysis of Cancer-Associated Somatic Mutations in Class I HLA Genes," *Nature Biotechnology* 33(11):1152-1158.

Snyder, A. et al. (Dec. 4, 2014). "Genetic Basis for Clinical Response to CTLA-4 Blockade in Melanoma," *The New England Journal of Medicine* 371(23):2189-2199.

Suzuki, H. et al. (2013). "Multiple Therapeutic Peptide Vaccines Consisting of Combined Novel Cancer Testis Antigens and Anti-Angiogenic Peptides for Patients with Non-Small Cell Lung Cancer," *Journal of Translational Medicine* 11:97, pp. 1-10.

Topalian, S.L. et al. (Apr. 1, 2014; e-published Mar. 3, 2014). "Survival, Durable Tumor Remission, and Long-Term Safety in Patients With Advanced Melanoma Receiving Nivolumab," *J Clin Oncol* 32(10):1020-1030.

Tran, E. et al. (May 9, 2014). "Cancer Immunotherapy Based on Mutation Specific CD4+ T Cells in a Patient with Epithelial Cancer," *Science* 344(6184):641-645.

Trimble, C. L. et al. (Nov. 21, 2015; e-published on Sep. 17, 2015). "Safety, Efficacy, and Immunogenicity of VGX-3100, a Therapeutic Synthetic DNA Vaccine Targeting Human Papillomavirus 16 and 18 E6 and E7 Proteins for Cervical Intraepithelial Neoplasia 2/3: A Randomised, Double-Blind, Placebo-Controlled Phase 2b Trial," *The Lancet* 386(10008):2078-2088.

Umemoto, Y. et al. (Jan. 2015; e-published Feb. 8, 2014). "Prognostic Impact of Programmed Cell Death 1 Ligand 1 Expression in Human Leukocyte Antigen Class I—Positive Hepatocellular Carcinoma After Curative Hepatectomy," *J Gastroenterol* 50(1):65-75.

Van Allen, E.M. et al. (Oct. 9, 2015; e-published on Sep. 10, 2015). "Genomic Correlates of Response to CTLA-4 Blockade in Metastatic Melanoma," *Science* 350(6257):207-211.

Vigneron, N. et al. (Jul. 15, 2013). "Database of T Cell-Defined Human Tumor Antigens: the 2013 Update," *Cancer Immunity* 13:15, pp. 1-6.

Walter, S. et al. (Aug. 2012; e-published on Jul. 29, 2012). "Multipeptide Immune Response to Cancer Vaccine IMA901 After Single-Dose Cyclophosphamide Associates with Longer Patient Survival," *Nature Medicine* 18(8):1254-1261.

Wolchok, J.D. et al. (Nov. 27, 2014). "Cancer: Antitumor Immunity Gets a Boost," *Nature* 515(7528):496-498.

Yang, X. et al. (2009; e-published on Dec. 19, 2008). "An Introduction to Epitope Prediction Methods and Software" *Rev. Med. Virol.* 19(2):77-96.

Ye, Y. et al. (Sep. 30, 2007). "T Lymphocytes Activation by Dendritic Cells Loaded with the Tumor Antigen From 1-12 Breast Cancer Cells MCF-7," *Chin J Cancer Prevtreat* 14(17):1288-1289, (English Translation of the Abstract only).

Yuan, J. et al. (Dec. 23, 2008). "CTLA-4 Blockade Enhances Polyfunctional NY-ESO-1 Specific T Cell Responses in Metastatic Melanoma Patients with Clinical Benefit," *Proceedings of the National Academy of Sciences USA* 105(51):20410-20415.

Zhang, Hong-Mei, et al. (2009). "Experimental Study of Hepatoma Specific T-cell Response Induced by Dendritic Cells Loaded with Whole Cell Antigen in Different Strategies," *China Cancer* 18(3):226-229., (English Translation of the Abstract only).

International Search Report and Written Opinion dated Jun. 16, 2016 for PCT Application No. PCT/CN2016/076165 filed on Mar. 11, 2016, seventeen pages.

International Search Report dated Dec. 22, 2015 for PCT Application No. PCT/CN2015/074227 filed on Mar. 13, 2015, eight pages. Written mailed on Dec. 22, 2015 for PCT Application No. PCT/CN2015/074227 filed on Mar. 13, 2015, six pages.

European Supplementary Search Report dated Jul. 6, 2018 for EP Application No. 16764215.6 filed on Aug. 22, 2017, seven pages.

Han, Y. (May 27, 2015). "Abstract 19: A Novel Cancer Immunotherapy with Multiple Tumor Antigen Activated Autologous T Cells for Hepatocellular Carcinoma," *Cytotherapy* 17(Suppl. S):512, one page.

Ciygan, V.N. (2004). "Anticancer Immune System," Reviews of Human Pharmacology and Drug Therapy 3(3):68-74. English Abstract.

Yoshida, T. et al. (Nov. 2015). "The History of the Research and Development of Human Anti-Human PD-1 Antibody Nivolumab as a new Immune Checkpoint Inhibitor," Medchem News 25(4):193-197. English Abstract.

Andreatta, M. (Feb. 15, 2016, e-pub, Oct. 29, 2015). "Gapped Sequence Alignment Using Artificial Neural Networks: Application to the MHC Class I System," Nielsen M. Bioinformatics 32(4):511-517.

Bernal, M. et al. (Sep. 2012, e-pub. Jul. 26, 2012). "Implication of the β2-microglobulin Gene in the. Generation of Tumor Escape Phenotypes" Cancer Immunol. Immunother 61(9):1359-1371.

Ito, T. et al. (May 2000). "Surviving Promotes Cell Proliferation in Human Hepatocellular Carcinoma," Hepatology 31 (5):1080-1085.

Jiao, B. et al. (2007). "Effect of Anti-Carcinoma of T Lymphocyte Activated by Dendritic Cells Modified by Large Intestine Tumor Antigen," Journal of Zhengzhou University, Medical Sciences (Department of General Surgery the Affiliated Hospital, Zunyi Medical College) 42(6):1094-1096, 4 pages.

Kobayashi, E. et al. (Nov. 2013, e-pub. Oct. 13, 2013). "A New Cloning and Expression System Yields and Validates TCRs From Blood Lymphocytes of Patients With Cancer Within 10 Days," Nature Medicine 19 (11):1542-1546.

U.S. Appl. No. 17/043,613, filed Mar. 29, 2019, by Xiangjuri Zhou et al.

* cited by examiner

| No. | Tumor Antigen Peptides | Overexpression in HCC | Clinical trials | References |
|---|---|---|---|---|
| 1 | hTERT | + | OC, BC, PC, Melanoma | 1, 2 |
| 2 | p53 | + (loss of function) | LC, BC, OC, Melanoma | 3 |
| 3 | Survivin | + | OC, PC, RCC, Melanoma | 4, 5 |
| 4 | NY-ESO-1 | + | HCC | 1, 6 |
| 5 | CEA | + | HCC | 7 |
| 6 | CCND1 | + | RCC | 8, 9 |
| 7 | MET | + | RCC | 8, 10 |
| 8 | RGS5 | + | RCC | 8, 11 |
| 9 | MMP7 | + | RCC | 8 |
| 10 | VEGFR | + | HCC | 12 |
| 11 | AFP | + | HCC | 1, 13 |
| 12 | GPC3 | + | - | 14 |
| 13 | HBV core antigen | + (when HBV+) | - | 13, 15 |
| 14 | HBV DNA polymerase | + (when HBV+) | - | 1, 13 |

FIG 2C.

| No. | Tumor antigen peptides | Description | Containing epitopes |
|---|---|---|---|
| 1 | hTERT | human Telomerase Reverse Transcriptase | VYAETKHFL (SEQ ID NO: 1), VYGFVRACL (SEQ ID NO: 2), ILAKFLHWL (SEQ ID NO: 3), LTDLQPYMR (SEQ ID NO: 4), DLQVNSLQTV (SEQ ID NO: 5) |
| 2 | p53 | Tumor suppressing antigen | STPPPGTRV (SEQ ID NO: 6), AIYKQSQHM (SEQ ID NO: 7), EYLDDRNTF (SEQ ID NO: 8), LLGRNSFEVRV (SEQ ID NO: 9) |
| 3 | Survivin | Apoptosis inhibitor | RISTFKNWPFL (SEQ ID NO: 10), DLAQCFFCFK (SEQ ID NO: 11), ELTLGEFLKL (SEQ ID NO: 12) |
| 4 | NY-ESO-1 | Tumor-testis antigen | YLAMPFATPM (SEQ ID NO: 13), SLLMWITQC (SEQ ID NO: 14) |
| 5 | CEA | Carcinoembryonic Antigen | YLSGANLNL (SEQ ID NO: 15), TYACFVSNL (SEQ ID NO: 16) |
| 6 | CCND1 | Cyclin D1 | LLGATCMFV (SEQ ID NO: 17) |
| 7 | MET | HGF-hepatocyte growth factor receptor | YVDPVITSI (SEQ ID NO: 18) |
| 8 | RGS5 | Regulators of G protein Signaling 5 | LAALPHSCL (SEQ ID NO: 19) |
| 9 | MMP7 | Matrix Metalloproteinase 7 | SQDDIKGIQK (SEQ ID NO: 20) |
| 10 | VEGFR | Vascular Endothelial Growth Factor Receptor | TLFWLLLTL (SEQ ID NO: 21), SYGVLLWEI (SEQ ID NO: 22), RFVPDGNRI (SEQ ID NO: 23), SYMISYAGM (SEQ ID NO: 24) |
| 11 | AFP | Alpha Fetoprotein | PLFQVPEPV (SEQ ID NO: 25), FMNKFIYEI (SEQ ID NO: 26), GLSPNLNRF (SEQ ID NO: 27), GVALQTMKQ (SEQ ID NO: 28) |
| 12 | GPC3 | Glypican-3 | FVGEFFTD (SEQ ID NO: 29), EYILSLEEL (SEQ ID NO: 30) |
| 13 | HBVc | HBV core antigen | FLPSDFFPS (SEQ ID NO: 31), YVNVNMGLK (SEQ ID NO: 32) |
| 14 | HBVp | HBV DNA polymerase | GLSRYVARL (SEQ ID NO: 33), FLLSLGIHL (SEQ ID NO: 34), RKYTSFPWLL (SEQ ID NO: 35) |

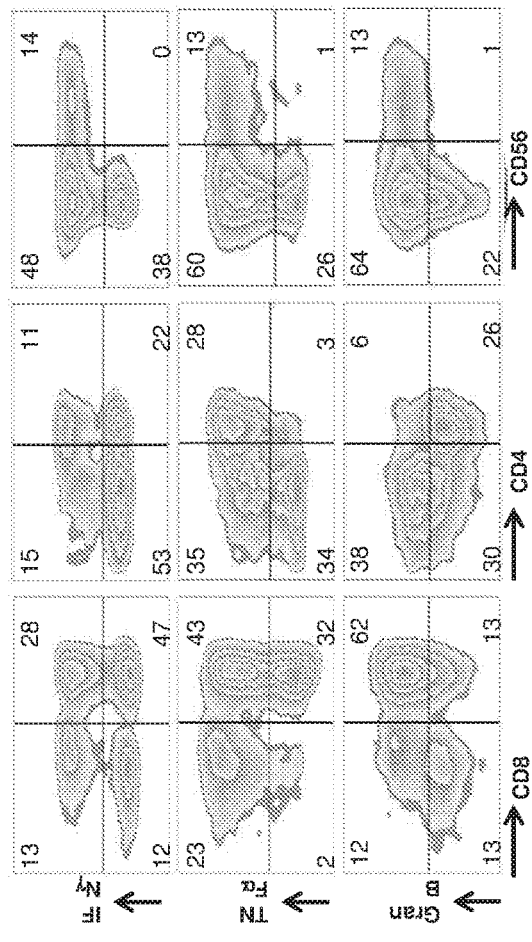
FIG. 5D
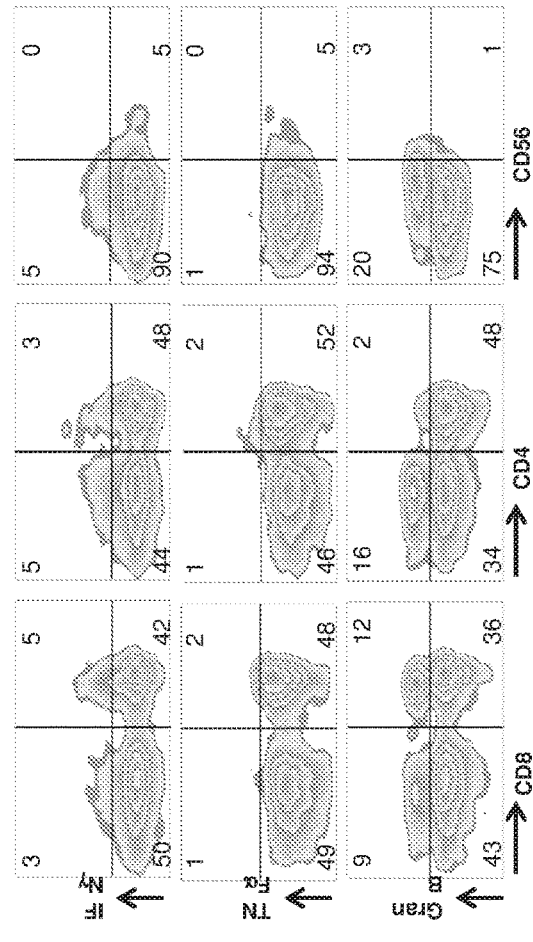
FIG. 5E
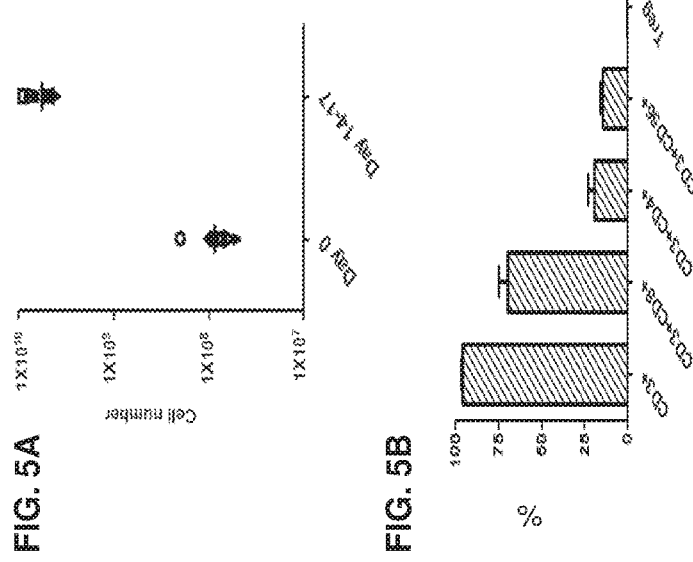
FIG. 5A
FIG. 5B
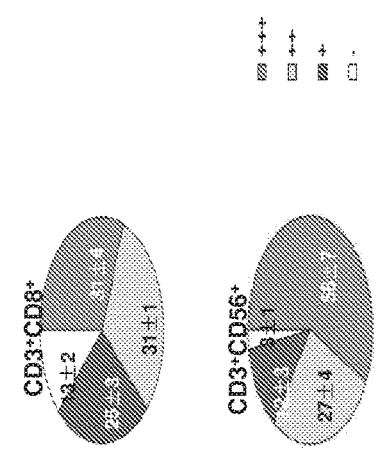
FIG. 5C

FIG. 8A

Characteristics, treatments and RECIST evaluation of patients with hepatocellular carcinoma (B stage) who did not receive MASCT cell therapy during 1 year after diagnosis (n=15).

| Patients No. | Age | Sex | Diagnosis | HBV | Anti-HBV therapy | Treatments until PD/1 year | RECIST evaluation* | Time to PD |
|---|---|---|---|---|---|---|---|---|
| 1-1 | 59 | M | 2012.1 | + | + | Resection (1), TACE (3) | PD | 8 months |
| 1-2 | 60 | M | 2012.2 | + | - | TACE (2), RFA (1) | CR | - |
| 1-3 | 42 | M | 2012.6 | + | + | TACE (3), Radiotherapy (2) | PD | 10 months |
| 1-4 | 53 | M | 2012.6 | + | - | TACE (3) | PD | 6 months |
| 1-5 | 54 | M | 2012.6 | + | - | TACE (3) | PD | 4 months |
| 1-6 | 65 | M | 2012.7 | + | + | TACE (1) | PD | 9 months |
| 1-7 | 58 | F | 2012.7 | + | - | TACE (4) | PD | 8 months |
| 1-8 | 54 | M | 2012.9 | + | - | TACE (4) | SD | - |
| 1-9 | 57 | M | 2012.11 | + | - | TACE (3), Sorafenib | PD | 9 months |
| 1-10 | 44 | M | 2012.12 | + | - | TACE (2), RFA (2) | PD | 6 months |
| 1-11 | 49 | M | 2012.12 | + | + | TACE (4), Cryoablation | PD | 7 months |
| 1-12 | 76 | M | 2013.1 | + | + | TACE (2) | PD | 10 months |
| 1-13 | 59 | M | 2013.3 | + | + | TACE (3) | PD | 8 months |
| 1-14 | 65 | M | 2013.6 | + | + | Resection (1), TACE (1) | PD | 3 months |
| 1-15 | 66 | M | 2013.8 | + | + | TACE (3) | PD | 5 months |

M: male, F: female, HBV: hepatitis B virus, TACE: Transcatheter arterial chemoembolization, RFA: Radiofrequency ablation, PD: progressive disease, SD: Stable disease, CR: Complete response
The times of treatment were shown in ( ).
*: RECIST evaluation on the time point of 1 year after diagnosis is shown if the patient has not been evaluated as PD before.

FIG. 8B

| Patients No. | Age | Sex | Diagnosis Time | HBsAg | Anti-HBV therapy | Treatments until PD/1 year | RECIST evaluation* | Time to PD |
|---|---|---|---|---|---|---|---|---|
| 1-1 | 57 | M | 2012.1 | + | LAM | Resection, TACE (1) | PD | 8 m |
| 1-2 | 58 | M | 2012.2 | + | - | TACE (2), RFA (1) | CR | - |
| 1-3 | 60 | M | 2012.3 | + | LAM,ETV | TACE (3), Raltitrexed (2) | PD | 12 m |
| 1-4 | 41 | M | 2012.6 | + | LAM | TACE (3) | PD | 6 m |
| 1-5 | 53 | M | 2012.6 | + | - | TACE (3) | PD | 4 m |
| 1-6 | 63 | M | 2012.7 | + | NA | TACE (1) | PD | 9 m |
| 1-7 | 52 | F | 2012.7 | + | - | TACE (4) | PD | 8 m |
| 1-8 | 52 | M | 2012.9 | + | - | TACE (4) | SD | - |
| 1-9 | 58 | M | 2012.11 | + | - | TACE (3), Sorafenib | PD | 9 m |
| 1-10 | 42 | M | 2012.12 | + | - | TACE (2), RFA (2) | PD | 6 m |
| 1-11 | 58 | M | 2012.12 | + | - | TACE (3), Cryoablation (1) | PD | 7 m |
| 1-12 | 75 | M | 2013.1 | + | ETV,LAM | TACE (2) | PD | 10 m |
| 1-13 | 59 | M | 2013.3 | + | LAM | TACE (3) | PD | 8 m |
| 1-14 | 64 | M | 2013.6 | + | ETV | Resection (1), TACE (1) | PD | 3 m |
| 1-15 | 58 | M | 2013.6 | + | ETV | TACE (3) | PD | 5 m |
| 1-16 | 52 | F | 2013.12 | + | ETV | TACE (2), Cryoablation (1), PEI | SD | - |
| 1-17 | 46 | M | 2014.1 | + | NA | TACE (2), RFA (1) | PD | 10 m |

M: male; F: female; HBV: hepatitis B virus; TACE: Transcatheter arterial chemoembolization; RFA: Radiofrequency ablation;

PEI: percutaneous ethanol injection; PD: progressive disease; SD: Stable disease; CR: Complete response; NA: not available; LAM:

Lamivudine; ETV: Entecavir Tablets; m: month;

The times of treatment were shown in ( ).

*: RECIST evaluation on the time point of 1 year after diagnosis is shown if the patient has not been evaluated as PD before.

FIG. 9A

Characteristics, treatments and RECIST evaluation of patients with hepatocellular carcinoma (B stage) who received multiple treatments of MASCT cell therapy during 1 year after diagnosis (n=13).

| Patients No. | Age | Sex | Diagnosis time | HBV | Anti-HBV therapy | Treatments during the first 3 months | Following Treatments until PD/1 year | RECIST evaluation* |
|---|---|---|---|---|---|---|---|---|
| 2-1 | 57 | M | 2012.2 | + | – | TACE (1), Cryoablation (1), MASCT (1) | MASCT (3) | SD |
| 2-2 | 63 | F | 2012.2 | + | + | TACE (1), Cryoablation (1) | MASCT (3) | SD |
| 2-3 | 68 | M | 2012.3 | + | – | TACE (1), Cryoablation (1), MASCT (1) | MASCT (3) | SD |
| 2-4 | 34 | M | 2012.4 | + | – | RFA (1) | MASCT (5) | SD |
| 2-5 | 55 | F | 2012.5 | + | + | TACE (3) | MASCT (3) | PD/11 months |
| 2-6 | 56 | M | 2012.7 | + | + | TACE (3), MASCT (3) | TACE (2), Cryoablation (1), MASCT (5) | SD |
| 2-7 | 63 | M | 2012.8 | + | + | TACE (3), Cryoablation 2, MASCT (3) | MASCT (4) | SD |
| 2-8 | 46 | M | 2012.10 | + | + | TACE (1), Cryoablation (1), MASCT (1) | MASCT (5), RFA (1) | SD |
| 2-9 | 37 | M | 2013.1 | + | + | TACE (2), RFA (1) | MASCT (6) | PR |
| 2-10 | 75 | M | 2013.1 | + | + | TACE (1), Cryoablation (1), MASCT (1) | MASCT (3) | SD |
| 2-11 | 51 | M | 2013.4 | + | – | TACE (1), Cryoablation (1), MASCT (1) | MASCT (3) | CR |
| 2-12 | 57 | F | 2013.4 | + | + | TACE (1) | MASCT (7) | SD |
| 2-13 | 40 | M | 2013.4 | + | + | TACE (2) | TACE (1), MASCT (6) | SD |

M: male, F: female, HBV: hepatitis B virus, TACE: Transcatheter arterial chemoembolization, RFA: Radiofrequency ablation, PD: Progressive disease, SD: Stable disease, PR: Partial response, CR: Complete response
The times of treatment were shown in ( ).
*: RECIST evaluation on the time point of 1 year after diagnosis is shown if the patient has not been evaluated as PD before.

FIG. 9B

| Patient No. | Age | Sex | Diagnosis time | HBsAg | Anti-HBV therapy | Treatments during the first 3 months | Following Treatments until PD/1 year | RECIST evaluation* | Time to PD |
|---|---|---|---|---|---|---|---|---|---|
| 2-1 | 67 | M | 2012.1 | + | - | TACE (1), Cryoablation (1), MASCT (1) | MASCT (6) | SD | - |
| 2-2 | 63 | F | 2012.2 | + | ETV | TACE (1), Cryoablation (1) | MASCT (3) | SD | - |
| 2-3 | 56 | M | 2012.2 | + | - | TACE (1), Cryoablation (1), MASCT (1) | MASCT (6) | PR | - |
| 2-4 | 34 | M | 2012.4 | + | - | RFA (1) | MASCT (5) | SD | - |
| 2-5 | 55 | F | 2012.6 | + | - | TACE (1) | MASCT (1), TACE (2) | PD | 11 m |
| 2-6 | 56 | M | 2012.7 | + | LAM | TACE (3), MASCT (3) | Cryoablation (1), MASCT (5) | PR | - |
| 2-7 | 62 | M | 2012.8 | + | ETV | TACE (1), Cryoablation (1), MASCT (1) | MASCT (4) | SD | - |
| 2-8 | 44 | M | 2012.10 | + | LAM | TACE (1), Cryoablation (1), MASCT (1) | MASCT (5), RFA (1) | SD | - |
| 2-9 | 57 | M | 2012.11 | + | - | TACE+RFA (1) | MASCT (8) | PR | - |
| 2-10 | 76 | M | 2013.1 | + | ETV | TACE (1), Cryoablation (1), MASCT (1) | MASCT (3) | SD | - |
| 2-11 | 64 | M | 2013.4 | + | ADV | TACE (1), Cryoablation (1), MASCT (1) | MASCT (5) | CR | - |
| 2-12 | 46 | M | 2013.4 | + | ADV | TACE (1) | MASCT (7) | SD | - |
| 2-13 | 58 | M | 2013.4 | + | NA | TACE (2) | TACE (1), MASCT (5) | SD | - |
| 2-14 | 49 | F | 2013.7 | + | ADV | TACE (1), MASCT (1), Resection (1) | MASCT (3) | PD | 12 m |
| 2-15 | 61 | M | 2013.9 | + | - | TACE (1), Chemotherapy (1), MASCT (2) | TACE (2), MASCT (2) | PD | 4 m |

M: male; F: female; HBV: hepatitis B virus; TACE: Transcatheter arterial chemoembolization; RFA: Radiofrequency ablation; PEI: percutaneous ethanol injection; PD: Progressive disease; SD: Stable disease; PR: Partial response; CR: Complete response; NA: not available; LAM: Lamivudine; ETV: Entecavir Tablets; ADV: Adefovir Dipivoxil Tablets. The times of treatment were shown in ().  *: RECIST evaluation on the time point of 1 year after diagnosis is shown if the patient has not been evaluated as PD before.

FIG. 10A

The characteristics of patients with hepatocellular carcinoma (B stage) enrolled in the retrospective analysis.

| | Multiple "MASCT" n=13 | No "MASCT" n=15 |
|---|---|---|
| Median age (range), year | 56 (34-73) | 54 (38-70) |
| Sex (male), No. (%) | 11 (84.6) | 14 (93.3) |
| Chronic HBV infection, No. (%) | 13 (100) | 15 (100) |
| Anti-HBV therapies, No. (%) | 7 (53.8) | 8 (53.3) |
| Completed therapies, No. | | |
| Resection | 4 | 4 |
| TACE | 0 | 2 |
| RFA | 22 | 40 |
| Cryoablation | 3 | 3 |
| Radiotherapy | 5 | 1 |
| Sorafenib | 0 | 2 |
| | 0 | 1 |
| Therapies per patient, No. | 2.62 | 3.27 |

HBV: hepatitis B virus; TACE: Transcatheter arterial chemoembolization; RFA: Radiofrequency ablation

FIG. 10B

| | Con+MASCT (n=15) | Con (n=17) |
|---|---|---|
| Median age (range), year | 56 (24-78) | 52 (37-78) |
| Sex (male), No. (%) | 12 (80%) | 15 (88.24%) |
| Chronic HBV infection, No. (%) | 15 (100%) | 17 (100%) |
| Anti-HBV therapies, No. (%) | 7 (47.06%) | 8 (46.67%) |
| Combined therapies, No. | 39 | 63 |
| Resection | 1 | 4 |
| TACE | 25 | 47 |
| RFA | 3 | 4 |
| Cryoablation | 0 | 1 |
| Radiotherapy | 0 | 1 |
| Sorafenib | 1 | 3 |
| PEI | 0 | 3 |
| Chemotherapy | 0 | 0 |
| Therapies per patient, No. | 2.6 | 3.71 |

HBV: hepatitis B virus; TACE: Transcatheter arterial chemoembolization; RFA: Radiofrequency ablation; PEI: percutaneous ethanol injection

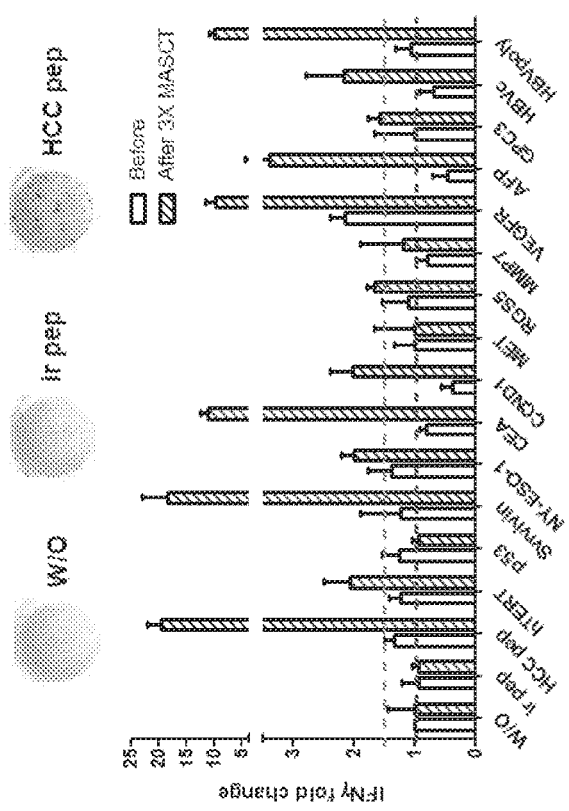
FIG. 12A
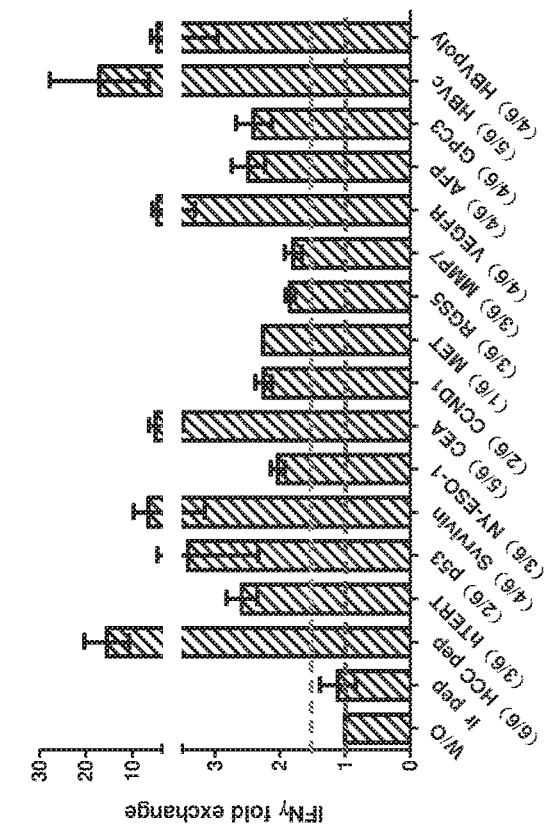
FIG. 12C
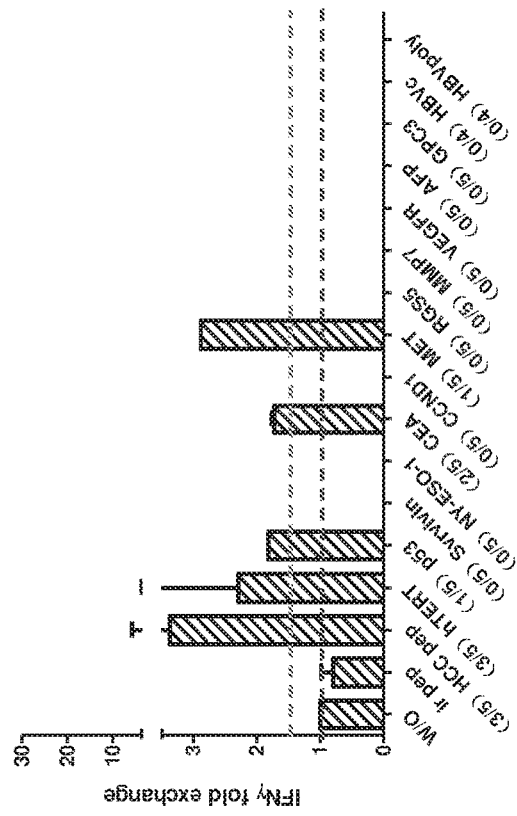
FIG. 12B
FIG. 12D

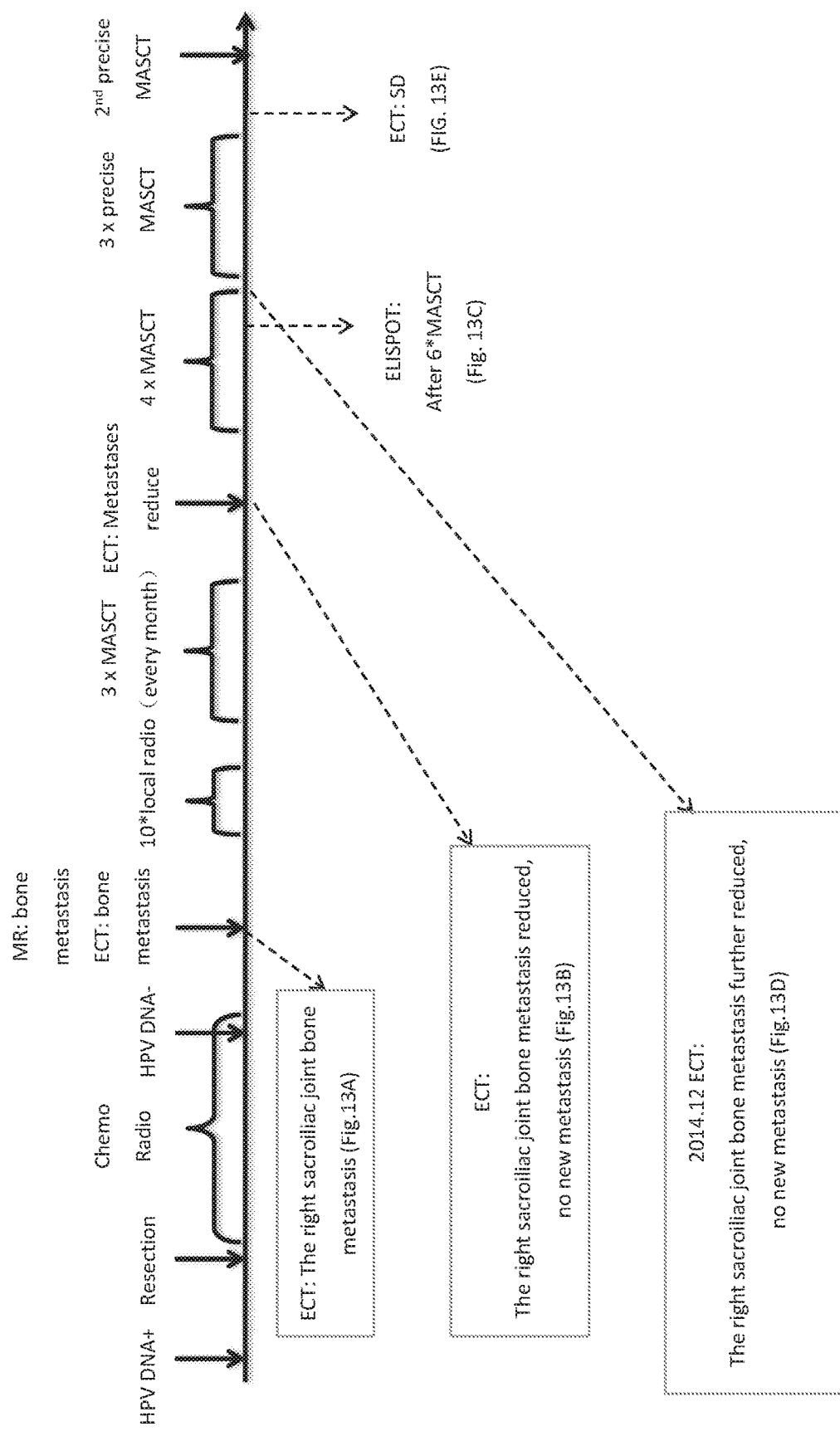

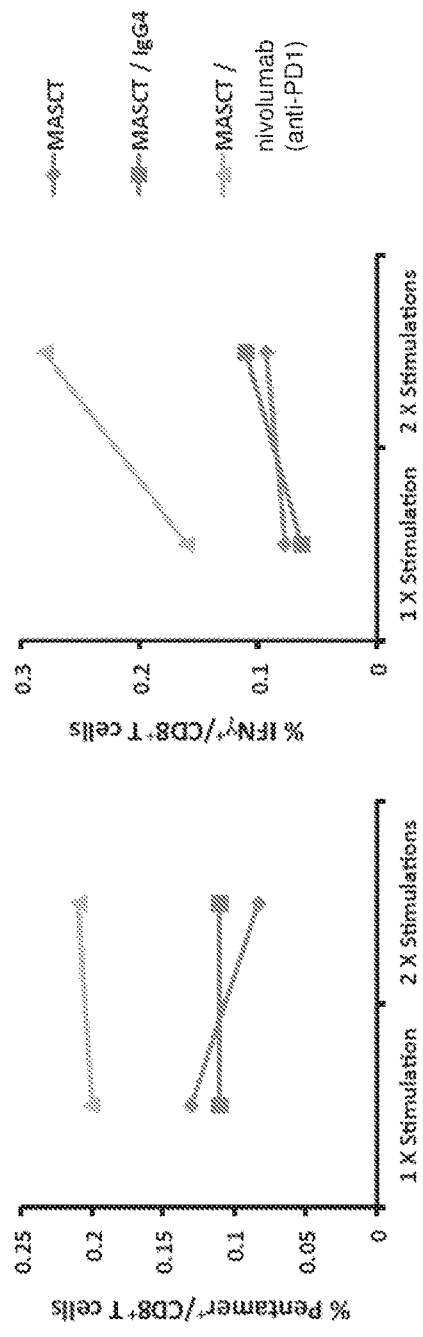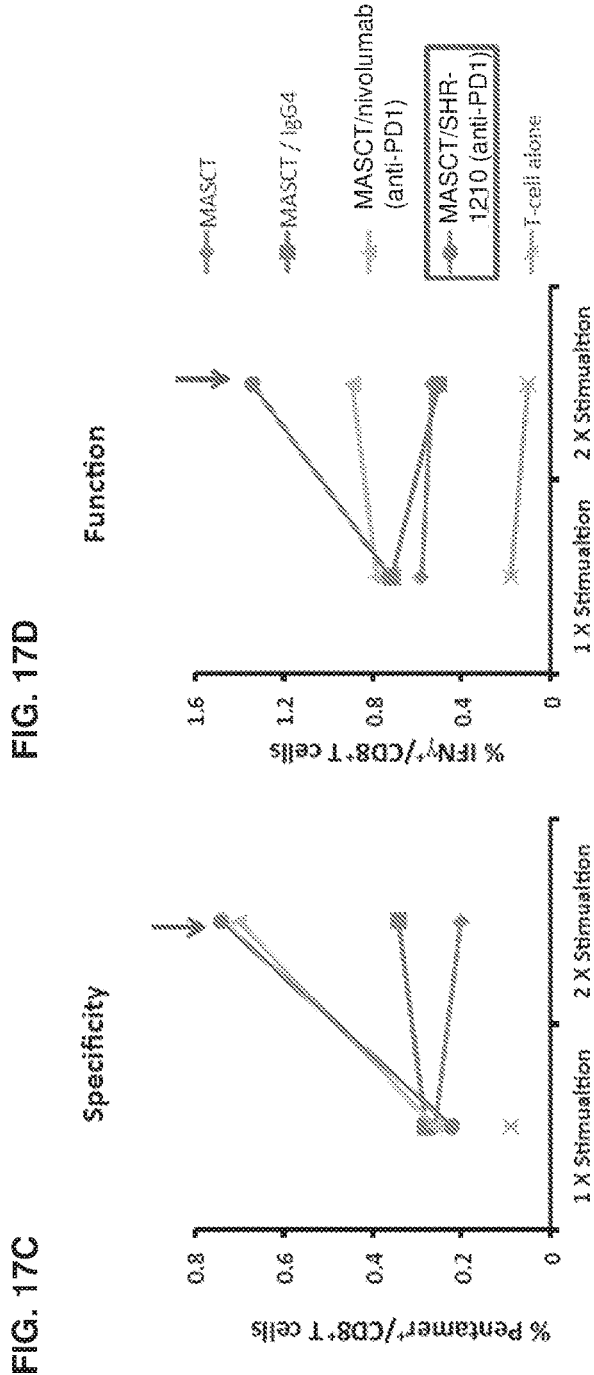

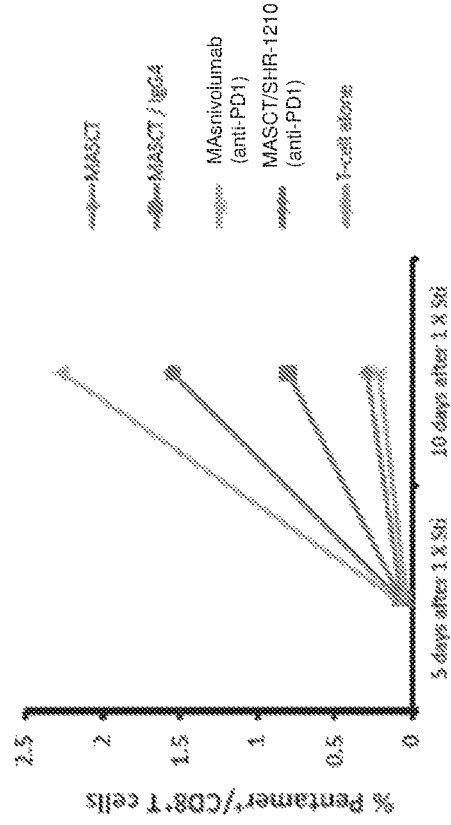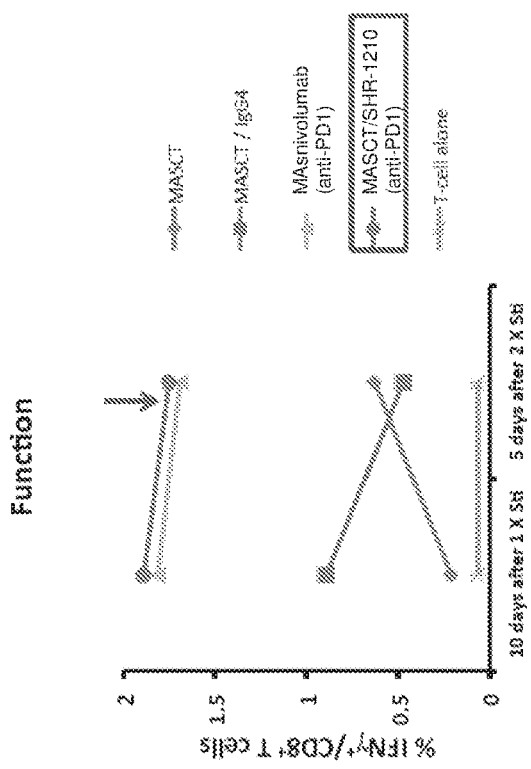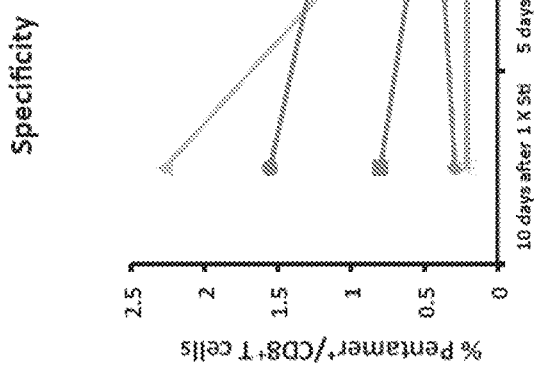
FIG. 19A
FIG. 19B
FIG. 19C

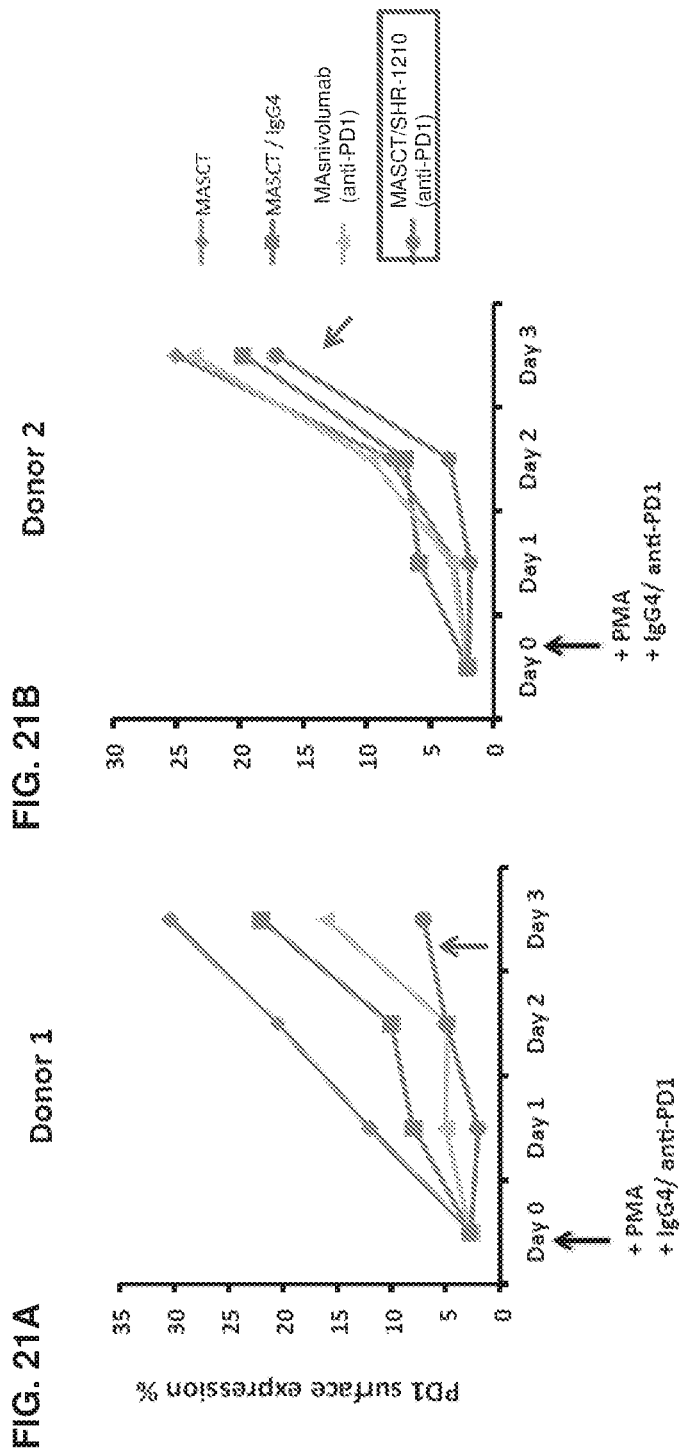

FIG. 22

| ID | Cancer type | MMR | | | | | Mutation load | Neoantigen prediction | | HLA | | | | Clinical data | |
|---|---|---|---|---|---|---|---|---|---|---|---|---|---|---|---|
| | | ML H1 | MS H2 | MS H6 | PMS 2 | MMR result* | | Point Mutation with improved MHC I affinity | Point Mutation with improved TCR I affinity | HLA A | HLA B | HLA C | B2 M | DM M | Anti-PD-1 (X/times) | MASCT (X/times) | Response |
| LQL | Lung adenocarcinoma | 5 | 4 | 14 | 7 | 1 | 3243 | NA | NA | 20 | 14 | 21 | 2 | 1 | 3X | 4X | PD |
| SJS | Esophageal cancer | 0 | 0 | 0 | 0 | 0 | 86 | 17 | 3 | 4 | 1 | 3 | 0 | 1 | - | 3X | PD* |
| HJL | Renal pelvis cancer | 0 | 0 | 0 | 0 | 0 | 130 | 19 | 6 | 1 | 0 | 1 | 0 | 0 | 5X | 5X | PR |
| LKS | Left lower lob lung adenocarcinoma | 0 | 0 | 0 | 0 | 0 | 141 | 24 | 6 | 1 | 0 | 1 | 0 | 0 | 5X | - | PR |
| WHQ | Moderately differentiated colon cancer | 0 | 0 | 3 | 0 | 1 | 121 | 14 | 7 | 1 | 1 | 3 | 0 | 0 | - | 4X | SD |

*MMR result: 0=MMR proficient, 1=MMR deficient

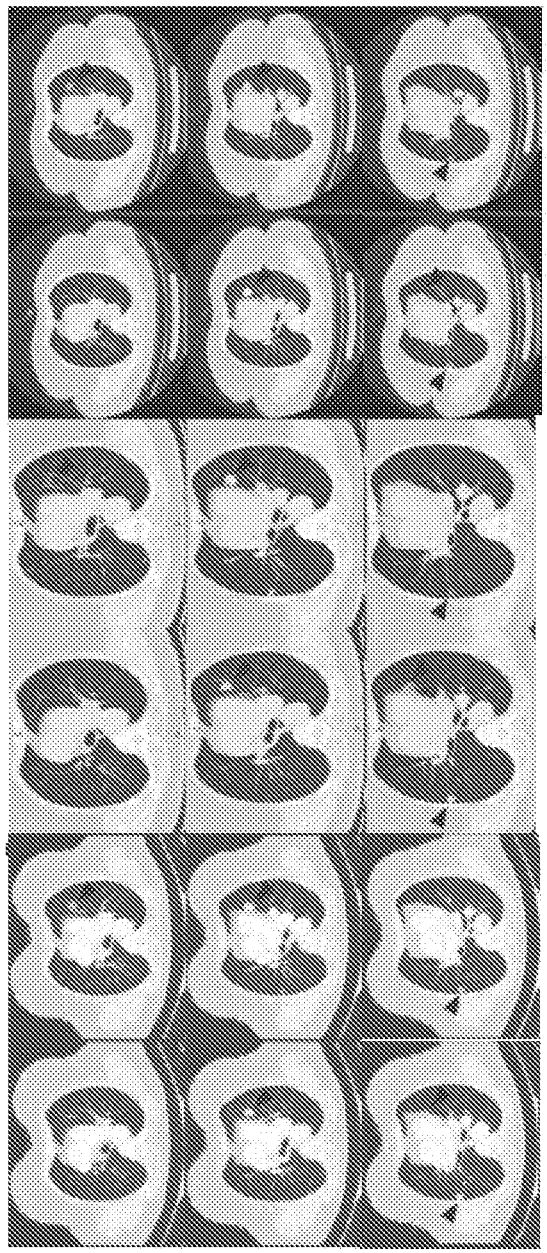
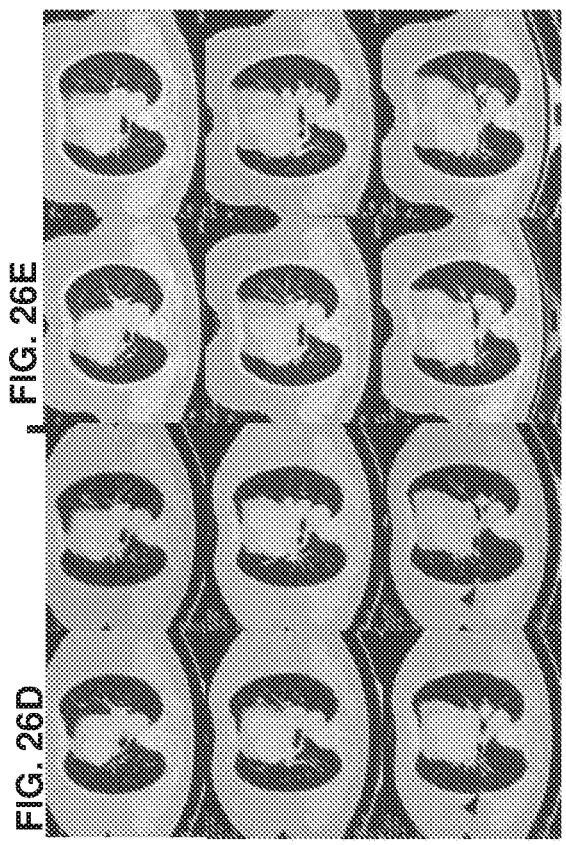
FIG. 26A  FIG. 26B  FIG. 26C  FIG. 26D  FIG. 26E

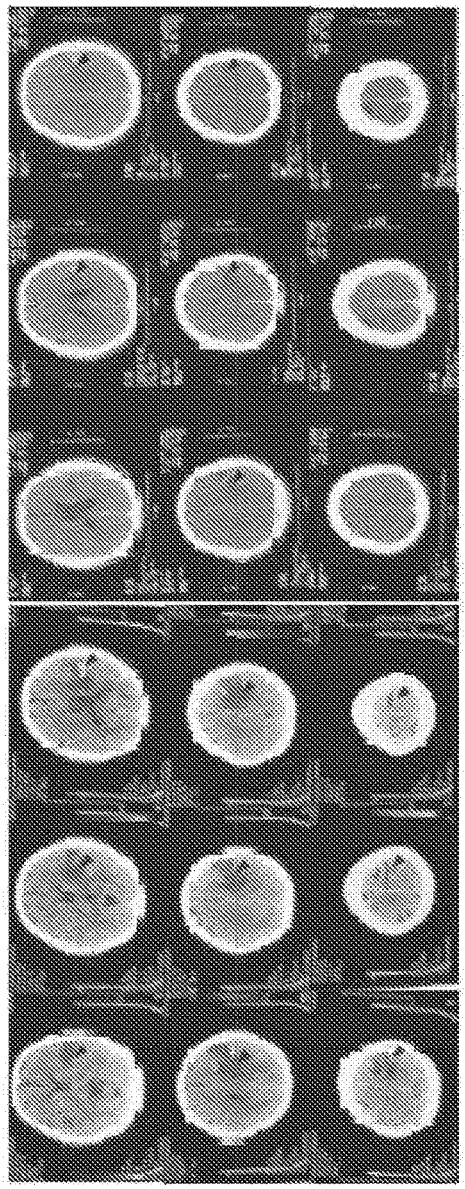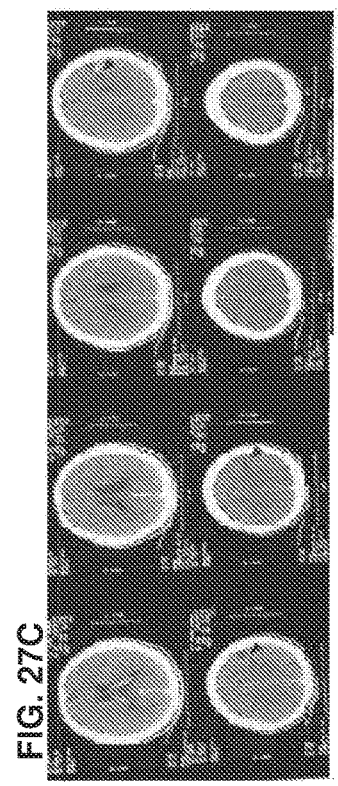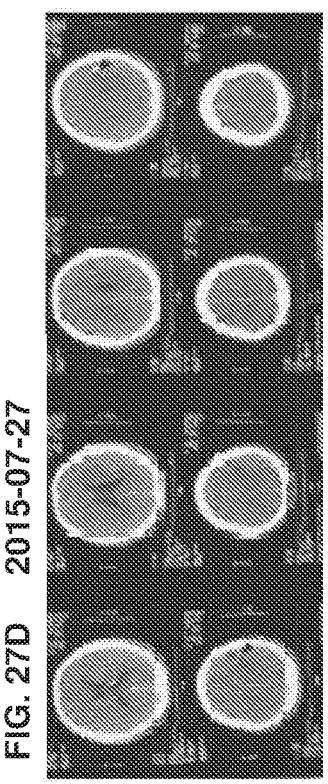
FIG. 27A  FIG. 27B  FIG. 27C  FIG. 27D

FIG. 29A

| Neoantigen names | epitope | Mutation (patient sample) | | | | | Predicted HLA affinity | epitope | Wild type | | | | | Predicted HLA affinity | Prediction |
| --- | --- | --- | --- | --- | --- | --- | --- | --- | --- | --- | --- | --- | --- | --- | --- |
| | | HLA-A02:06 | HLA-A24:02 | HLA-B15:02 | HLA-B51:01 | | | | HLA-A02:06 | HLA-A24:02 | HLA-B15:02 | HLA-B51:01 | | | |
| >MTHFR_A222V | KVSAGVDFI (SEQ ID NO: 36) | 35 | 12533 | 24786 | 19241 | 39 | KVSAGADFI (SEQ ID NO: 41) | | 68 | 13721 | 34250 | 19288 | 68 | best |
| >MLL3_C988F | GQCYHPYFV (SEQ ID NO: 37) | 46 | 20210 | 23199 | 22786 | 46 | GQCYHPYCV (SEQ ID NO: 42) | | 349 | 24235 | 24311 | 23167 | 349 | best |
| >MLL3_C988F | CYHPYFVSI (SEQ ID NO: 38) | 2376 | 35 | 27516 | 12976 | 26 | CYHPYCVSI (SEQ ID NO: 43) | | 10257 | 50 | 29503 | 13920 | 50 | best |
| >PARP4_T1130H | LHQFTSFV (SEQ ID NO: 39) | 9 | 21517 | 9810 | 16691 | 9 | LHQFTSFV (SEQ ID NO: 44) | | 27 | 25616 | 12369 | 18860 | 27 | best |
| >KRAS_G12A | LVVVGAAGV (SEQ ID NO: 40) | 46 | 35843 | 11477 | 13957 | 46 | LVVVGAGGV (SEQ ID NO: 45) | | 57 | 38853 | 10338 | 14891 | 57 | best |

FIG. 29B

| Sampling time | Individual CTC | CTC cluster |
| --- | --- | --- |
| Before progression | 0/10 mL | 0/10mL |
| 3 years after cystectomy | 194/10 mL | 0/10mL |
| After 3x Precision MASCT | 6/10 mL | 0/10 mL |

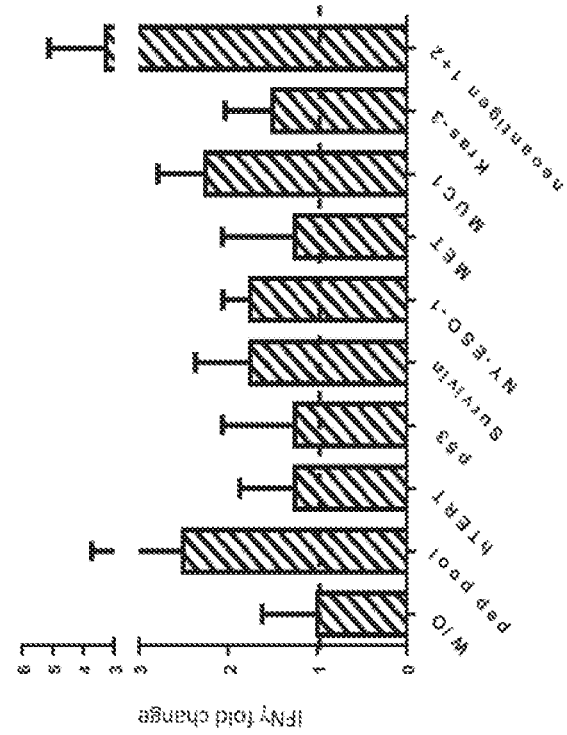

FIG. 29C

FIG. 30A Clinical characteristics of the 45 patients with HCC [n (%)]

| Variable | HCC patients |
|---|---|
| Age (y/a) | 53.78 ± 10.9 |
| Male sex | 43(95.6) |
| HBsAg-positive | 40(88.9) |
| Anti-HCV-positive | 1(2.2) |
| Child-Pugh class( A/B ) | 26/19( 57.8/42.2 ) |
| BCLC stage ( B/C ) | 13/19( 28.9/42.2 ) |
| Treatment | |
| Surgery | 14( 31.1 ) |
| RFA | 10( 22.2 ) |
| TACE | 33( 73.3 ) |
| MASCT treatment times | |
| 1 | 16( 35.5 ) |
| 2 | 7( 15.6 ) |
| ≥3 | 22( 48.9 ) |

FIG. 30B Variation of blood routine examination after MASCT™ therapy ( n =45 )

| Index | Before treatment | After treatment | P |
|---|---|---|---|
| WBC ( ×10⁹/L ) | 5.41 ± 2.11 | 6.78 ± 3.82 | 0.0411 |
| Neu ( ×10⁹/L ) | 62.34 ± 12.28 | 70.92 ± 13.32 | 0.0015 |
| HB ( g/L ) | 125.71 ± 21.70 | 114.20 ± 31.74 | 0.0508 |
| PLT ( ×10⁹/L ) | 143.76 ± 70.76 | 120.84 ± 75.02 | 0.1361 |

FIG. 30C ALT, AST, TBIL, CR and BUN after MASCT™ therapy

| Index | Before treatment (n=45) | After treatment (n=43) | P |
|---|---|---|---|
| ALT( IU/L ) | 52.79 ± 74.76 | 99.64 ± 168.50 | 0.1018 |
| AST( IU/L ) | 70.40 ± 64.20 | 148.71 ± 202.63 | 0.0193 |
| TBIL ( umol/L ) | 23.64 ± 14.141 | 66.14 ± 112.01 | 0.0177 |
| CR ( umol/L ) | 86.23 ± 97.35 | 92.61 ± 87.87 | 0.7610 |
| BUN ( mmol/L ) | 5.52 ± 3.64 | 6.14 ± 3.85 | 0.4822 |

FIG. 30D Dynamic number of ALT, AST after MASCT™ therapy( n =8 )

| Index | Baseline | 1 | 2 | 3 | 4 | 5 | P |
|---|---|---|---|---|---|---|---|
| ALT( IU/L ) | 39.91 ± 23.62 | 35.15 ± 18.89 | 35.46 ± 18.3 | 37.53 ± 20.25 | 40.69 ± 23.07 | 49.53 ± 35.39 | 0.4679 |
| AST( IU/L ) | 37.34 ± 17.04 | 44.26 ± 26.23 | 43.71 ± 25.41 | 46.56 ± 21.32 | 47.25 ± 32.38 | 54.69 ± 39.91 | 0.1661 |

SEQUENCE LISTING

<160> NUMBER OF SEQ ID NOS: 45

<210> SEQ ID NO 1
<211> LENGTH: 9
<212> TYPE: PRT
<213> ORGANISM: Homo sapiens

<400> SEQUENCE: 1

Val Tyr Ala Glu Thr Lys His Phe Leu

```
1               5

<210> SEQ ID NO 2
<211> LENGTH: 9
<212> TYPE: PRT
<213> ORGANISM: Homo sapiens

<400> SEQUENCE: 2

Val Tyr Gly Phe Val Arg Ala Cys Leu
1               5

<210> SEQ ID NO 3
<211> LENGTH: 9
<212> TYPE: PRT
<213> ORGANISM: Homo sapiens

<400> SEQUENCE: 3

Ile Leu Ala Lys Phe Leu His Trp Leu
1               5

<210> SEQ ID NO 4
<211> LENGTH: 9
<212> TYPE: PRT
<213> ORGANISM: Homo sapiens

<400> SEQUENCE: 4

Leu Thr Asp Leu Gln Pro Tyr Met Arg
1               5

<210> SEQ ID NO 5
<211> LENGTH: 10
<212> TYPE: PRT
<213> ORGANISM: Homo sapiens

<400> SEQUENCE: 5

Asp Leu Gln Val Asn Ser Leu Gln Thr Val
1               5                   10

<210> SEQ ID NO 6
<211> LENGTH: 9
<212> TYPE: PRT
<213> ORGANISM: Homo sapiens

<400> SEQUENCE: 6

Ser Thr Pro Pro Pro Gly Thr Arg Val
1               5

<210> SEQ ID NO 7
<211> LENGTH: 9
<212> TYPE: PRT
<213> ORGANISM: Homo sapiens

<400> SEQUENCE: 7

Ala Ile Tyr Lys Gln Ser Gln His Met
1               5

<210> SEQ ID NO 8
<211> LENGTH: 9
<212> TYPE: PRT
<213> ORGANISM: Homo sapiens

<400> SEQUENCE: 8

Glu Tyr Leu Asp Asp Arg Asn Thr Phe
1               5
```

<210> SEQ ID NO 9
<211> LENGTH: 11
<212> TYPE: PRT
<213> ORGANISM: Homo sapiens

<400> SEQUENCE: 9

Leu Leu Gly Arg Asn Ser Phe Glu Val Arg Val
1               5                   10

<210> SEQ ID NO 10
<211> LENGTH: 11
<212> TYPE: PRT
<213> ORGANISM: Homo sapiens

<400> SEQUENCE: 10

Arg Ile Ser Thr Phe Lys Asn Trp Pro Phe Leu
1               5                   10

<210> SEQ ID NO 11
<211> LENGTH: 10
<212> TYPE: PRT
<213> ORGANISM: Homo sapiens

<400> SEQUENCE: 11

Asp Leu Ala Gln Cys Phe Phe Cys Phe Lys
1               5                   10

<210> SEQ ID NO 12
<211> LENGTH: 10
<212> TYPE: PRT
<213> ORGANISM: Homo sapiens

<400> SEQUENCE: 12

Glu Leu Thr Leu Gly Glu Phe Leu Lys Leu
1               5                   10

<210> SEQ ID NO 13
<211> LENGTH: 10
<212> TYPE: PRT
<213> ORGANISM: Homo sapiens

<400> SEQUENCE: 13

Tyr Leu Ala Met Pro Phe Ala Thr Pro Met
1               5                   10

<210> SEQ ID NO 14
<211> LENGTH: 9
<212> TYPE: PRT
<213> ORGANISM: Homo sapiens

<400> SEQUENCE: 14

Ser Leu Leu Met Trp Ile Thr Gln Cys
1               5

<210> SEQ ID NO 15
<211> LENGTH: 9
<212> TYPE: PRT
<213> ORGANISM: Homo sapiens

<400> SEQUENCE: 15

Tyr Leu Ser Gly Ala Asn Leu Asn Leu
1               5

<210> SEQ ID NO 16

```
<211> LENGTH: 9
<212> TYPE: PRT
<213> ORGANISM: Homo sapiens

<400> SEQUENCE: 16

Thr Tyr Ala Cys Phe Val Ser Asn Leu
1               5

<210> SEQ ID NO 17
<211> LENGTH: 9
<212> TYPE: PRT
<213> ORGANISM: Homo sapiens

<400> SEQUENCE: 17

Leu Leu Gly Ala Thr Cys Met Phe Val
1               5

<210> SEQ ID NO 18
<211> LENGTH: 9
<212> TYPE: PRT
<213> ORGANISM: Homo sapiens

<400> SEQUENCE: 18

Tyr Val Asp Pro Val Ile Thr Ser Ile
1               5

<210> SEQ ID NO 19
<211> LENGTH: 9
<212> TYPE: PRT
<213> ORGANISM: Homo sapiens

<400> SEQUENCE: 19

Leu Ala Ala Leu Pro His Ser Cys Leu
1               5

<210> SEQ ID NO 20
<211> LENGTH: 10
<212> TYPE: PRT
<213> ORGANISM: Homo sapiens

<400> SEQUENCE: 20

Ser Gln Asp Asp Ile Lys Gly Ile Gln Lys
1               5                   10

<210> SEQ ID NO 21
<211> LENGTH: 9
<212> TYPE: PRT
<213> ORGANISM: Homo sapiens

<400> SEQUENCE: 21

Thr Leu Phe Trp Leu Leu Leu Thr Leu
1               5

<210> SEQ ID NO 22
<211> LENGTH: 9
<212> TYPE: PRT
<213> ORGANISM: Homo sapiens

<400> SEQUENCE: 22

Ser Tyr Gly Val Leu Leu Trp Glu Ile
1               5

<210> SEQ ID NO 23
<211> LENGTH: 9
<212> TYPE: PRT
```

```
<213> ORGANISM: Homo sapiens

<400> SEQUENCE: 23

Arg Phe Val Pro Asp Gly Asn Arg Ile
1               5

<210> SEQ ID NO 24
<211> LENGTH: 9
<212> TYPE: PRT
<213> ORGANISM: Homo sapiens

<400> SEQUENCE: 24

Ser Tyr Met Ile Ser Tyr Ala Gly Met
1               5

<210> SEQ ID NO 25
<211> LENGTH: 9
<212> TYPE: PRT
<213> ORGANISM: Homo sapiens

<400> SEQUENCE: 25

Pro Leu Phe Gln Val Pro Glu Pro Val
1               5

<210> SEQ ID NO 26
<211> LENGTH: 9
<212> TYPE: PRT
<213> ORGANISM: Homo sapiens

<400> SEQUENCE: 26

Phe Met Asn Lys Phe Ile Tyr Glu Ile
1               5

<210> SEQ ID NO 27
<211> LENGTH: 9
<212> TYPE: PRT
<213> ORGANISM: Homo sapiens

<400> SEQUENCE: 27

Gly Leu Ser Pro Asn Leu Asn Arg Phe
1               5

<210> SEQ ID NO 28
<211> LENGTH: 9
<212> TYPE: PRT
<213> ORGANISM: Homo sapiens

<400> SEQUENCE: 28

Gly Val Ala Leu Gln Thr Met Lys Gln
1               5

<210> SEQ ID NO 29
<211> LENGTH: 8
<212> TYPE: PRT
<213> ORGANISM: Homo sapiens

<400> SEQUENCE: 29

Phe Val Gly Glu Phe Phe Thr Asp
1               5

<210> SEQ ID NO 30
<211> LENGTH: 9
<212> TYPE: PRT
<213> ORGANISM: Homo sapiens
```

```
<400> SEQUENCE: 30

Glu Tyr Ile Leu Ser Leu Glu Glu Leu
1               5

<210> SEQ ID NO 31
<211> LENGTH: 9
<212> TYPE: PRT
<213> ORGANISM: Homo sapiens

<400> SEQUENCE: 31

Phe Leu Pro Ser Asp Phe Phe Pro Ser
1               5

<210> SEQ ID NO 32
<211> LENGTH: 9
<212> TYPE: PRT
<213> ORGANISM: Homo sapiens

<400> SEQUENCE: 32

Tyr Val Asn Val Asn Met Gly Leu Lys
1               5

<210> SEQ ID NO 33
<211> LENGTH: 9
<212> TYPE: PRT
<213> ORGANISM: Homo sapiens

<400> SEQUENCE: 33

Gly Leu Ser Arg Tyr Val Ala Arg Leu
1               5

<210> SEQ ID NO 34
<211> LENGTH: 9
<212> TYPE: PRT
<213> ORGANISM: Homo sapiens

<400> SEQUENCE: 34

Phe Leu Leu Ser Leu Gly Ile His Leu
1               5

<210> SEQ ID NO 35
<211> LENGTH: 10
<212> TYPE: PRT
<213> ORGANISM: Homo sapiens

<400> SEQUENCE: 35

Arg Lys Tyr Thr Ser Phe Pro Trp Leu Leu
1               5                   10

<210> SEQ ID NO 36
<211> LENGTH: 9
<212> TYPE: PRT
<213> ORGANISM: Homo sapiens

<400> SEQUENCE: 36

Lys Val Ser Ala Gly Val Asp Phe Ile
1               5

<210> SEQ ID NO 37
<211> LENGTH: 9
<212> TYPE: PRT
<213> ORGANISM: Homo sapiens

<400> SEQUENCE: 37
```

```
Gly Gln Cys Tyr His Pro Tyr Phe Val
1               5
```

<210> SEQ ID NO 38
<211> LENGTH: 9
<212> TYPE: PRT
<213> ORGANISM: Homo sapiens

<400> SEQUENCE: 38

```
Cys Tyr His Pro Tyr Phe Val Ser Ile
1               5
```

<210> SEQ ID NO 39
<211> LENGTH: 9
<212> TYPE: PRT
<213> ORGANISM: Homo sapiens

<400> SEQUENCE: 39

```
Leu Ile Ile Gln Phe Thr Ser Phe Val
1               5
```

<210> SEQ ID NO 40
<211> LENGTH: 9
<212> TYPE: PRT
<213> ORGANISM: Homo sapiens

<400> SEQUENCE: 40

```
Leu Val Val Val Gly Ala Ala Gly Val
1               5
```

<210> SEQ ID NO 41
<211> LENGTH: 9
<212> TYPE: PRT
<213> ORGANISM: Homo sapiens

<400> SEQUENCE: 41

```
Lys Val Ser Ala Gly Ala Asp Phe Ile
1               5
```

<210> SEQ ID NO 42
<211> LENGTH: 9
<212> TYPE: PRT
<213> ORGANISM: Homo sapiens

<400> SEQUENCE: 42

```
Gly Gln Cys Tyr His Pro Tyr Cys Val
1               5
```

<210> SEQ ID NO 43
<211> LENGTH: 9
<212> TYPE: PRT
<213> ORGANISM: Homo sapiens

<400> SEQUENCE: 43

```
Cys Tyr His Pro Tyr Cys Val Ser Ile
1               5
```

<210> SEQ ID NO 44
<211> LENGTH: 9
<212> TYPE: PRT
<213> ORGANISM: Homo sapiens

<400> SEQUENCE: 44

```
Leu Ile Thr Gln Phe Thr Ser Phe Val
1               5
```

```
<210> SEQ ID NO 45
<211> LENGTH: 9
<212> TYPE: PRT
<213> ORGANISM: Homo sapiens

<400> SEQUENCE: 45

Leu Val Val Val Gly Ala Gly Gly Val
1               5
```

METHODS OF CANCER TREATMENT USING ACTIVATED T CELLS

CROSS-REFERENCE TO RELATED APPLICATION

This application is a U.S. national phase application of PCT International Application No. PCT/CN2016/076165, filed Nov. 3, 2016, which claims priority benefit of International Application No. PCT/CN2015/074227, filed Mar. 13, 2015, the contents of which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 744852000100SEQLIST.TXT, date recorded: Sep. 11, 2017, size: 7 KB).

FIELD OF THE INVENTION

The present invention relates to the field of cancer immunotherapy. More specifically, this invention provides methods, compositions and kits for treating cancer in an individual using activated T cells.

BACKGROUND OF THE INVENTION

The human body has an elaborate immune system to defend itself against diseases, including internal malignancies. Unleashing the body's own immune power to treat and prevent cancer has therefore been a long-standing ideal in oncology. The natural immune response against a tumor is typically elicited by tumor antigens, including mutated proteins exclusively expressed in cancer cells, and tumor-associated antigens (TAAs) overexpressed in cancer's tissue of origin but are nonetheless not completely recognized as "self". Antigen presenting cells (APCs), notably dendritic cells (DCs), that encounter tumor antigens can process and present the tumor antigens on their cell surface. Upon maturation, DCs loaded with tumor antigens can trigger T cell response, which involves cytotoxic T cells, helper T cells, and functionally distinct effecter and memory T cells, against cancer cells hosting the tumor antigens. A particularly powerful type of T cell response involves production of cytotoxic T cells that can kill cancer cells by releasing cytokines, enzymes, and cytotoxins, or by inducing pro-apoptosis signaling cascade via cell-cell interactions.

Cancer immunotherapies aim to take advantage of the above process to treat cancer, but success has been rather limited until recently. Initial attempts have focused on developing cancer vaccines based on particular antigen peptides, full-length antigen proteins, or viral vectors encoding tumor antigens. Few cancer vaccines have made into the clinics, and even fewer generated any impressive clinical outcome. Unlike traditional cancer therapy, such as chemotherapy, radiation therapy and surgical resection, in general, the bodily response to cancer immunotherapy treatments, especially cancer vaccines, is much delayed because it takes time for APCs to process and present the antigen to T cells, and for T cells to mature and to elicit an immune response. When a tumor is present in a patient, the cancer cells in the tumor already have mechanisms to escape surveillance by the immune system. Therefore, a successful tumor vaccine must be able to bypass the defects in immune surveillance to elicit a strong immune response. Additionally, several bottleneck issues exist in cancer vaccines that prevent the approach from producing specific and durable clinical effects. First, cancer cells, even of the same histological type, are rather heterogeneous in their genetic composition and expression profile among different patients and among different lesions within the same patient—a phenomenon well documented by a plethora of genetic data from recent next-generation sequencing experiments on cancer cells available in the literature and public databases. Consequently, the limited number of tumor antigen(s) in a particular cancer vaccine treatment is unlikely to represent the spectrum of antigens characteristic of individual tumors in all patients. Secondly, many antigen moieties in cancer vaccines are not effectively loaded onto the APCs due to serum half-life and bioavailability issues. Third, even when APCs are properly primed by antigens contained in cancer vaccines, lack of suitable activation signals and microenvironments can result in production of the wrong subpopulation of T cells, especially immunosuppressive regulatory T cells ($T_{REG}$), which inhibit, instead of stimulate, immune response against tumors. The origin of the last two issues has to do with the complete lack of control by clinicians in patients' actual response to any cancer vaccine once it is administered.

Cell-based cancer immunotherapy approach alleviates some of the above challenges in cancer vaccines by administering to patients immunity-mediating cells or cell products that are prepared under relatively defined and controlled conditions. In particular, DC-based methods have garnered much interest, especially after the FDA approved PROVENGE® (sipuleucel-T) in April 2010 for advanced prostate cancer. A typical DC-based immunotherapy method involves isolating DCs from a cancer patient, loading the DCs with a tumor antigen (or antigens, including tumor cell lysates and total mRNA) ex vivo, and then administering the DCs back to the patient to elicit cancer-killing T cell response. PROVENGE®, for example, comprises exposing a patient's peripheral blood mononuclear cells (PBMCs) to a fusion protein comprising a tumor-derived antigen coupled to a cytokine (such as GM-CSF), and then infusing the PBMCs (presumably containing activated DCs that can present the tumor-derived antigen to T cells) to the patient (see U.S. Pat. Nos. 5,976,546, 6,080,409, and 6,210,662). In the pivotal Phase III trial (Kantoff P W, Higano C S et al. (2010) "Sipuleucel-T immunotherapy for castration-resistant prostate cancer." N J Med 363:411-22), the specific embodiment of PROVENGE® was prepared using a recombinant protein of prostatic acid phosphatase (PAP), a prostate cancer-associated antigen, fused to GM-CSF, a cytokine known to attract and induce DCs. Although PROVENGE® was able to prolong median survival of the patients in the experimental group (25.8 months) as compared to those in the control group (21.7 months), the clinical trial results did not show evidence of statistically significant delay in tumor progression or reduction in tumor size. More troubling is the fact that survival of individual patients does not seem to correlate with specific T cell responses to either the fusion protein or PAP in the PROVENGE® treatment (Cheever M A, Higano C S (2011) "PROVENGE (Sipuleucel-T) in prostate cancer: the first FDA-approved therapeutic cancer vaccine." Clin. Cancer Res. 17:3520-6).

A second method in the cell-based immunotherapy approach, named adoptive lymphocyte therapy, involves isolating tumor-infiltrating lymphocytes (TIL) from a patient's tumor, expanding the TILs ex vivo, and infusing the TILs back to the patient after depleting the patient's native non-myeloid lymphocytes. Dramatic clinical responses, including complete tumor recession and long disease-free survival, have been reported in clinical applications of adoptive lymphocyte therapy to patients with melanoma (Restifo N P, Dudley M E, and Rosenberg S A. (2012) "Adoptive immunotherapy for cancer: harnessing the T cell response." Nat. Rev. Immunol. 12: 269-81). It has further been shown that the clinical benefits of TIL are correlated with or resulting from tumor-specific T cells present in the TIL population (Robbins P F et al. (2013) "Mining exomic sequencing data to identify mutated antigens recognized by adoptively transferred tumor-reactive T cells." Nature Medicine 19: 747-752; and Tran E et al. (2014) "Cancer immunotherapy based on mutation-specific CD4+ T cells in a patient with epithelial cancer" Science 344: 641-645). Recently, T cells with engineered T cell receptors having modified affinity to certain tumor antigens or chimeric antigen receptors (CAR-T) further expand the capacity of the adoptive lymphocyte therapy method by modifying the microenvironment of T cell-tumor interactions. A major issue with the current adoptive lymphocytes therapy methods concerns multiple reports of severe adverse events, including CNS toxicity, in clinical trials, likely having to do with improper selection of targets (so called on-target off tumor effect) and biased expansion of T cell populations. Another issue of the approach is the lack of durable response in some patients, because of rapidly developed immune tolerance to the tumor-specific antigens presented on the infused T lymphocytes, as well as immune escape by cancer cells.

Immune tolerance and immune escape are often mediated by checkpoint molecules, or co-inhibitory signals, on cells interacting with T cells in the microenvironment of the tumor site, in addition to an elevated level of immunosuppressive cells, such as $T_{REG}$ and MDSC (myeloid-derived suppressor cells). A well-studied pair of checkpoint molecules involves the immune-inhibitory PD-1 receptor on T cells and the PD-L1 ligand on APCs (such as DCs), MDSCs and cancer cells. Binding of PD-L1 to PD-1 triggers a signal to inhibit pro-inflammatory cytokine (e.g. IL-2) production and proliferation of cytotoxic T cells. In many scenarios, PD-L1 binding to PD-1 triggers apoptosis of cytotoxic T cells. On the other hand, the PD-1/PD-L1 signaling induces $T_{REG}$ cells, which act to further inhibit T cells with tumor-attacking capacity. Antibodies against PD-1, PD-L1, and other checkpoint molecules (such as CTLA-4 on T cells) are currently developed by several pharmaceutical companies as a distinct approach in cancer immunotherapy, based on the theory that blockade of the T-cell checkpoints can help overcome immune tolerance and immune escape in the tumor site. It is worth noting that the anti-tumor effects of the checkpoint blockade approach require pre-existence of tumor-specific T cells in vivo (Boussiotis V A (2014) "Somatic mutations and immunotherapy outcome with CTLA-4 blockade in melanoma" N. Engl. J. Med. 371:2230-2232; Wolchok J D and Chan T A, (2014) "Cancer: antitumor immunity gets a boost" Nature 515: 496-498).

Given the promises and challenges of the various cancer immunotherapy approaches as described above, it is desirable to provide a new cancer immunotherapy method that combines the advantages of the previous methods while avoiding the known pitfalls.

The disclosures of all publications, patents, patent applications and published patent applications referred to herein are hereby incorporated herein by reference in their entirety.

BRIEF SUMMARY OF THE INVENTION

The present invention provides methods, compositions and kits for treating cancer in an individual using activated T cells induced by antigen presenting cells (such as dendritic cells) loaded with a plurality of tumor antigen peptides.

One aspect of the present application provides a method of treating a cancer in an individual (such as a human individual), comprising administering to the individual an effective amount of activated T cells, wherein the activated T cells are prepared by co-culturing a population of T cells with a population of dendritic cells loaded with a plurality of tumor antigen peptides. In some embodiments, the individual has previously been administered with an effective amount of dendritic cells loaded with the plurality of tumor antigen peptides. In some embodiments, the method further comprises administering to the individual an effective amount of the dendritic cells loaded with the plurality of tumor antigen peptides. In some embodiments, the dendritic cells are administered prior (for example, about 7 days to about 14 days, about 14 days to about 21 days, or about 7 days to about 21 days prior) to the administration of the activated T cells.

In some embodiments according to any one of the methods described above, the method further comprises preparing the activated T cells by co-culturing the population of T cells with the population of dendritic cells loaded with the plurality of tumor antigen peptides prior to the administration steps. In some embodiments, the population of T cells is co-cultured with the population of dendritic cells loaded with the plurality of tumor antigen peptides for about 7 days to about 21 days (such as about 7 days to about 14 days, or about 14 days to about 21 days).

In some embodiments according to any one of the methods described above, the population of T cells is contacted with an immune checkpoint inhibitor prior to the co-culturing. In some embodiments, the population of T cells is co-cultured with the population of dendritic cells loaded with the plurality of tumor antigen peptides in the presence of an immune checkpoint inhibitor. In some embodiments, the immune checkpoint inhibitor is an inhibitor of an immune checkpoint molecule selected from the group consisting of PD-1, PD-L1, and CTLA-4.

In some embodiments according to any one of the methods described above, the method further comprises preparing the population of dendritic cells loaded with the plurality of tumor antigen peptides. In some embodiments, the population of dendritic cells loaded with the plurality of tumor antigen peptides is prepared by contacting a population of dendritic cells with the plurality of tumor antigen peptides. In some embodiments, the population of dendritic cells loaded with the plurality of tumor antigen peptides is prepared by contacting the population of dendritic cells with the plurality of tumor antigen peptides in the presence of a composition that facilitates the uptake of the plurality of tumor antigen peptides by the dendritic cells.

In some embodiments according to any one of the methods described above, the population of T cells and the population of dendritic cells are derived from the same individual. In some embodiments, the population of T cells and the population of dendritic cells are derived from the individual being treated.

One aspect of the present application provides a method of preparing a population of activated T cells, the method comprising: (a) inducing differentiation of a population of monocytes into a population of dendritic cells; (b) contacting the population of dendritic cells with a plurality of tumor antigen peptides to obtain a population of dendritic cells loaded with the plurality of tumor antigen peptides; and (c) co-culturing the population of dendritic cells loaded with the plurality of tumor antigen peptides and a population of non-adherent PBMCs to obtain the population of activated T cells, wherein the population of monocytes and the population of non-adherent PBMCs are obtained from a population of PBMCs from an individual. In some embodiments, step b) comprises contacting the population of dendritic cells with the plurality of tumor antigen peptides in the presence of a composition that facilitates the uptake of the plurality of tumor antigen peptides by the dendritic cells. In some embodiments, step b) further comprises contacting the population of dendritic cells loaded with the plurality of tumor antigen peptides with a plurality of Toll-like Receptor (TLR) agonists (such as polyIC, MALP, R848, or any combination thereof) to induce maturation of the population of dendritic cells loaded with the plurality of tumor antigen peptides. In some embodiments, step c) further comprises contacting the population of activated T cells with a plurality of cytokines and optionally an anti-CD3 antibody to induce proliferation and differentiation of the population of activated T cells. In some embodiments, the plurality of cytokines comprises IL-2, IL-7, IL-15 or IL-21. In some embodiments, the population of non-adherent PBMCs is contacted with an immune checkpoint inhibitor prior to the co-culturing. In some embodiments, step c) comprises co-culturing the population of dendritic cells loaded with the plurality of tumor antigen peptides and the population of non-adherent PBMCs in the presence of an immune checkpoint inhibitor. In some embodiments, the immune checkpoint inhibitor is an inhibitor of an immune checkpoint molecule selected from the group consisting of PD-1, PD-L1, and CTLA-4.

Further provided is a method of treating a cancer in an individual (such as a human individual), comprising administering to the individual an effective amount of a population of activated T cells prepared by the method of any one of the methods described in the preceding paragraph. In some embodiments, the population of PBMCs is obtained from the individual being treated.

In some embodiments according to any one of the methods of treating a cancer as described above, the activated T cells are administered to the individual for at least three times. In some embodiments, the interval between each administration of the activated T cells is about 0.5 month to about 5 months (such as about 0.5 month to about 2 month).

In some embodiments according to any one of the methods of treating a cancer as described above, the activated T cells are administered intravenously. In some embodiments, the activated T cells are administered at a dose of at least about $3 \times 10^9$ cells/individual. In some embodiments, the activated T cells are administered at about $1 \times 10^9$ to about $1 \times 10^{10}$ cells/individual.

In some embodiments according to any one of the methods of treating a cancer as described above, the dendritic cells loaded with the plurality of tumor antigen peptides are administered for at least three times. In some embodiments, the interval between each administration of the dendritic cells is about 0.5 month to about 5 months (such as about 0.5 month to about 2 months).

In some embodiments according to any one of the methods of treating a cancer as described above, the dendritic cells loaded with the plurality of tumor antigen peptides are administered subcutaneously. In some embodiments, the dendritic cells are administered at a dose of about $1 \times 10^6$ to about $5 \times 10^6$ cells/individual.

One aspect of the present application provides a method of treating a cancer in an individual (such as a human individual), comprising: a) contacting a population of PBMCs with a plurality of tumor antigen peptides to obtain a population of activated PBMCs, and b) administering to the individual an effective amount of the activated PBMCs. In some embodiments, step (a) comprises contacting the population of PBMCs with a plurality of tumor antigen peptides in the presence of an immune checkpoint inhibitor. In some embodiments, the immune checkpoint inhibitor is an inhibitor of an immune checkpoint molecule selected from the group consisting of PD-1, PD-L1, CTLA-4, IDO, TIM-3, BTLA, VISTA, and LAG-3. In some embodiments, the activated PBMCs are administered for at least three times. In some embodiments, the interval between each administration of the activated PBMCs is about 0.5 month to about 5 months (such as about 0.5 month to about 2 months). In some embodiments, the activated PBMCs are administered intravenously. In some embodiments, the activated PBMCs are administered at a dose of about $1 \times 10^9$ to about $1 \times 10^{10}$ cells/individual.

In some embodiments according to any of the methods described above, the plurality of tumor antigen peptides is each about 20 to about 40 amino acids long. In some embodiments, the plurality of tumor antigen peptides comprises at least one peptide comprising an MHC-I epitope. In some embodiments, the at least one peptide comprising an MHC-I epitope further comprises additional amino acids flanking the epitope at the N-terminus, the C-terminus, or both.

In some embodiments according to any of the methods described above, the plurality of tumor antigen peptides comprises at least one peptide comprising an MHC-II epitope. In some embodiments, the at least one peptide comprising an MHC-II epitope further comprises additional amino acids flanking the epitope at the N-terminus, the C-terminus, or both.

In some embodiments according to any of the methods described above, the plurality of tumor antigen peptides comprises a first core group of general tumor antigen peptides. In some embodiments, the plurality of tumor antigen peptides further comprises a second group of cancer-type specific antigen peptides. In some embodiments, the first core group comprises about 10 to about 20 general tumor antigen peptides. In some embodiments, the second group comprises about 1 to about 10 cancer-type specific antigen peptides.

In some embodiments according to any of the methods described above, the plurality of tumor antigen peptides comprises a neoantigen peptide. In some embodiments, the neoantigen peptide is selected based on the genetic profile of a tumor sample from the individual.

In some embodiments according to any of the methods of treating a cancer as described above, the cancer is selected from the group consisting of hepatic cellular carcinoma, cervical cancer, lung cancer, colorectal cancer, lymphoma, renal cancer, breast cancer, pancreatic cancer, gastric cancer, esophageal cancer, ovarian cancer, prostate cancer, nasopharyngeal cancer, melanoma and brain cancer.

In some embodiments according to any of the methods of treating a cancer as described above, the method further comprises administering to the individual an effective amount of an immune checkpoint inhibitor. In some embodiments, the immune checkpoint inhibitor is an inhibitor of an immune checkpoint molecule selected from the group consisting of PD-1, PD-L1, and CTLA-4.

In some embodiments according to any of the methods of treating a cancer as described above, the individual is selected for the method of treating based on the mutation load in the cancer. In some embodiments, the individual has a low mutation load in the cancer. In some embodiments, the individual has a low mutation load in one or more MHC genes. In some embodiments, the individual has no more than about 10 mutations in the one or more MHC genes. In some embodiments, the one or more MHC genes are MHC class I genes. In some embodiments, wherein the individual is a human individual, the one or more MHC genes are selected from the group consisting of HLA-A, HLA-B, HLA-C and B2M. In some embodiments, the individual has no mutation in B2M. In some embodiments, the individual has no mutation in the functional regions (such as leader peptide sequence, a1 domain, a2 domain, or a3 domain) of the one or more MHC genes. In some embodiments, the mutation load of the cancer is determined by sequencing a tumor sample from the individual.

In some embodiments according to any of the methods of treating a cancer as described above, the individual is selected for the method of treating based on having one or more neoantigens in the cancer. In some embodiments, the individual has at least 5 neoantigens. In some embodiments, the method further comprises identifying a neoantigen of the cancer, and incorporating a neoantigen peptide in the plurality of tumor antigen peptides, wherein the neoantigen peptide comprises a neoepitope in the neoantigen. In some embodiments, the neoantigen is identified by sequencing a tumor sample from the individual. In some embodiments, said sequencing is targeted sequencing of cancer-associated genes. In some embodiments, the method further comprises determining the affinity of the neoepitope to an MHC molecule. In some embodiments, the method further comprises determining the affinity of the complex comprising the neoepitope and an MHC molecule to a T cell receptor. In some embodiments, the MHC molecule is an MHC class I molecule. In some embodiments, the MHC molecule is from the individual.

In some embodiments according to any of the methods of treating a cancer as described above, the method further comprises monitoring the individual after the administration of the activated T cells or the activated PBMCs. In some embodiments, the monitoring comprises determining the number of circulating tumor cells (CTC) in the individual. In some embodiments, the monitoring comprises detecting a specific immune response against the plurality of tumor antigen peptides in the individual. In some embodiments, the plurality of tumor antigen peptides is adjusted based on the specific immune response to provide a plurality of customized tumor antigen peptides. In some embodiments, the method of treating is repeated using the plurality of customized tumor antigen peptides.

One aspect of the present application provides a method of cloning a tumor-specific T cell receptor, comprising: (a) treating an individual with any one of the methods of treating cancer as described above; (b) isolating a T cell from the individual, wherein the T cell specifically recognizes a tumor antigen peptide in the plurality of tumor antigen peptides; and (c) cloning a T cell receptor from the T cell to provide the tumor-specific T cell receptor. In some embodiments, the individual has a strong specific immune response against the tumor antigen peptide. In some embodiments, the T cell is isolated from a PBMC sample of the individual. In some embodiments, the tumor antigen peptide is a neoantigen peptide.

Also provided are a tumor-specific T cell receptor cloned using any one of the methods of cloning a tumor-specific T cell receptor as described above, an isolated T cell comprising the tumor-specific T cell receptor, and a method of treating a cancer in an individual comprising administering to the individual an effective amount of the isolated T cell.

Further provided is an isolated population of cells (such as activated T cells, or activated PBMCs) prepared by the method of any one of the methods of preparing as described above.

One aspect of the present application provides an isolated population of cells comprising activated T cells, wherein less than about 1% of the activated T cells are regulatory T ($T_{REG}$) cells.

In some embodiments according to any one of the isolated population of cells described above, the isolated population of cells comprises about 0.3% to about 0.5% CD4$^+$CD25$^+$Foxp3$^+$ cells. In some embodiments, the isolated population of cells comprises about 65% to about 75% CD3$^+$CD8$^+$ cells. In some embodiments, the isolated population of cells comprises about 16% to about 22% of CD3$^+$CD4$^+$ cells. In some embodiments, the isolated population of cells comprises about 13% to about 15/CD3$^+$CD56$^+$ cells.

In some embodiments according to any one of the isolated population of cells described above, the activated T cells are capable of eliciting specific response to a plurality of tumor antigen peptides in vivo or ex vivo. In some embodiments, the activated T cells express a plurality of pro-inflammatory molecules. In some embodiments, the plurality of pro-inflammatory molecules comprises IFNγ, TNFα, granzyme B, or perforin.

In some embodiments according to any one of the isolated population of cells described above, the activated T cells have no or low expression of a plurality of immunosuppressive cytokines. In some embodiments, the plurality of immunosuppressive cytokines comprises IL-10 or 4.

In some embodiments according to any one of the isolated population of cells described above, less than about 5% of the activated T cells express immune-inhibitory molecule PD-1.

In some embodiments according to any one of the isolated population of cells described above, at least about 90% of the cells in the isolated population of cells are activated T cells.

One aspect of the present application provides a composition comprising at least 10 tumor antigen peptides, wherein each of the at least 10 tumor antigen peptides comprises at least one epitope selected from the group consisting of SEQ ID NOs: 1-35. In some embodiments, the at least 10 tumor antigen peptides are selected from the group consisting of the tumor antigen peptides in FIG. 2C. In some embodiments, the at least 10 tumor antigen peptides each comprises one or more epitopes encoded by a cancer-associated gene selected from the group consisting of hTERT, p53, Survivin, NY-ESO-1, CEA, CCND1, MET, RGS5, MMP7, VEGFR, AFP, GPC3, HBVc, HBVp, CDCA, KRAS, PARP4, MLL3, and MTHFR Further provided are kits, medicines, and articles of manufacture comprising any one of the compositions (such as isolated populations of cells or compositions of tumor antigen peptides) as described above.

These and other aspects and advantages of the present invention will become apparent from the subsequent detailed description and the appended claims. It is to be understood that one, some, or all of the properties of the various embodiments described herein may be combined to form other embodiments of the present invention.

BRIEF DESCRIPTION OF THE DRAWINGS

FIGS. 2A-2C depict the cell manufacturing process of an exemplary MASCT method described in Example 1. FIG. 2A is a schematic diagram illustrating the cell manufacturing process of a preferred embodiment of the MASCT method. FIG. 2B shows an exemplary composition of HCC antigen peptides pool loaded into DCs for the MASCT treatment in HCC patients. Some tumor antigen peptides have been used in clinical trials of cancer immunotherapies; references to such DC vaccines, adoptive cell transfer (ACT) and peptides vaccines are included. OC: ovarian cancer; BC: breast cancer; PC: pancreatic cancer; LC: lung cancer; RCC: renal carcinoma; HCC: hepatocellular carcinoma. FIG. 2C shows a list of epitopes contained in the peptides pool of HCC.

FIG. 4A shows flow cytometry results of DCs before (gray peaks) and after (black peaks) maturation with TLR agonists. Molecular markers targeted by the antibodies used to separate cells in the flow cytometry experiments are indicated above each chromatograph. Percentage of DCs with high expression levels (within the marked range) of each molecular marker is indicated inside each panel. The results show that most of the mature DCs exhibited a cell-surface expression signature to activate cytotoxic T cells. The DCs express MHC class II molecules and co-stimulatory signaling ligands CD86, CD80 and CD83, as well as maturation receptor CCR7, but is low in expression level of CD14 that is typically expressed in immature DCs. FIG. 4B shows secretion level of cytokines by the mature DCs prepared in Example 1. As expected of functional, mature DCs, the DCs secreted high level of pro-inflammatory cytokine IL-12, but low level of immunosuppressive cytokine IL-10.

FIGS. 5A-5E show characterization of the activated T cells prepared in Example 1. FIG. 5A shows T cell expansion after 14 to 17 days culturing based on cell counting using trypan blue exclusion. The median of samples from 10 patients is shown. FIG. 5B shows the percentages of subpopulations of T cells in the co-culture, indicating an extremely low level of $T_{REG}$ cells (CD4$^+$CD25$^+$Foxp3$^+$, 0.4%±0.1%) among the activated T cells. FIG. 5C shows pie charts displaying the percentages of T cell subsets that co-expressed the cytokines (IFNγ and TNFα) and enzyme granzyme B. Mean±Standard Error of Measurement (SEM) of five patients is shown for each group. Triple producers: dark gray; double producers: light gray; single producers: black; non-producer: white. FIG. 5D shows 3-dimensional flow cytometry chromatographs of activated T cells prepared from patients' PBMC and co-cultured with pulsed DCs, which was further stimulated with phorbol 12-myristate 13-acetate (PMA) for about 4 hours. Data are representative of five independent experiments. The activated T cells contained large subpopulation of CD3$^+$CD8$^+$ cytotoxic T cells, CD3$^+$CD4$^+$ helper T cells and CD3$^+$CD56$^+$ NK T cells, majority of which had high intracellular production of pro-inflammatory cytokines (IFNγ and TNFα), and protease granzyme B. FIG. 5E shows 3-dimensional flow cytometry chromatographs of non-activated T cells isolated from patients stimulated with PMA for about 4 hours. The non-activated T cells had only low expression levels of IFNγ, TNFα and granzyme B.

FIG. 6A shows secretion of various cytokines by the activated T cells. The resulting cells generated from HCC patients secreted significant amount of IFNγ and TNFα, but little to no IL10 and IL4. Mean±SEM is shown of 6 patients. FIGS. 6B-6C show reduced expression frequency of PD-1 on the surface of CD3$^+$CD8$^+$ (FIG. 6B) and CD3$^+$CD4$^+$ (FIG. 6C) subsets of T cells isolated from HCC patients compared to health donors. The expression percentage and statistic of 7 patients are shown. FIG. 6D shows reduction of the frequency of PD-1 expressing T cells in the CD3$^+$CD8$^+$ subsets of T cells after ex vivo activation. FIG. 6E shows reduction of the frequency of PD-1 expressing T cells in the CD3$^+$CD4$^+$ subsets of T cells after ex vivo activation. The expression percentage and statistic of 7 patients are shown. FIG. 6F shows HLA (or MHC) restricted cytotoxicity of the activated T cells. The activated T cells generated from PBMCs of HLA-A2$^+$ patients (n=7, left group) exhibited greater levels of cytotoxic activity to the HCC cell line HepG2 (white bars, HLA-A2$^+$) than to HuH-7 cells (hashed bars, HLA-A2$^-$), while activated T cells generated from PBMCs of HLA-A2$^-$ patients (n=7, right group) exhibited similar levels of cytotoxicity to these two cell lines. The relative ratio of effector T cells (activated T cells prepared) to target cells (HepG2 or HuH-7 cells; E:T ratio) in each cell lysis experiment was about 40:1.

FIG. 8A shows characteristics, treatment and RECIST evaluation of patients with hepatocellular carcinoma (B stage) in the control group analyzed in Example 1.

FIG. 8B shows characteristics, treatments, and RECIST evaluation of patients with hepatocellular carcinoma (B stage) who received only conventional therapy during 1 year after diagnosis (Group Con, n=17).

FIG. 9A shows characteristics, treatment and RECIST evaluation of patients with hepatocellular carcinoma (B stage) in the MASCT treatment group analyzed in Example 1.

FIG. 9B shows characteristics, treatments and RECIST evaluation of patients with hepatocellular carcinoma (B stage) who received multiple treatments of MASCT during 1 year after diagnosis (Group Con+MASCT, n=15).

FIG. 10A shows a summary of comparison of patients between the control group and the MASCT treatment group analyzed in Example 1.

FIG. 10B shows characteristics of patients with hepatocellular carcinoma (B stage) enrolled in the retrospective analysis.

FIG. 11A shows significant decrease in the percentage of $T_{REG}$ in PBMCs of 4 patients after they received 3 MASCT treatments. The expression percentage and statistics of 4 patients are shown. FIG. 11B shows increase in percentage of proliferating T cells in PBMC samples from 7 different HCC patients who received MASCT treatments. FIG. 11C shows increase in percentage of INFγ-producing cytotoxic T cells (CD8+ INFγ+) in PBMC samples from 7 different HCC patients who received MASCT treatments. FIG. 11D shows flow cytometry chromatographs of a PBMC sample from an HCC patient who received MASCT treatments. The results indicate that the INFγ-producing cytotoxic T cells (CD8+ INFγ+) co-expressed CD27 and CD28, suggesting a high potential to acquire an immune memory of the HCC-specific T cell response. FIG. 11E shows an increase in intracellular production of IFNγ by $CD8^+$ T cells from patients with HCC after 3 MASCT treatments. PBMCs were isolated from patient before and after 3 MASCT treatments respectively to measure T cell response. FIG. 11F shows specific proliferation of T cells in that sequentially increased in patients during multiple treatments of MASCT cell therapy. PBMCs were isolated from patients before and after 1 and 3 MASCT treatment(s) respectively. T cell proliferations of 2 patients were measured by EdU (5-ethynyl-2'-deoxyuridine) staining. In FIG. 11B-11F, the specific T cell responses were measured after stimulating the PBMCs with the HCC antigen peptides pool (HCC-pep). Control responses were measured after stimulating the PBMCs with a pool of irrelevant peptides (ir-pep, control). All fold changes are calculated by normalizing the specific response value to the control response value.

FIGS. 12A-12D show specific immune responses against HCC antigen peptides in patients in Example 1. Average specific immune responses against individual HCC antigen peptides in HCC patients after multiple MASCT treatments (FIG. 12A; n=6) and in HCC patients without any MASCT treatment (FIG. 12B; n=5). FIG. 12C shows specific immune response against each kind of HCC antigen peptides in one patient before (empty bar) and after 3 MASCT treatments (hashed bar). FIG. 12D shows sequential increase in specific immune response against each kind of HCC antigen peptides in a second HCC patient during multiple MASCT treatments (white bar: before treatment; gray: after 1 treatment; hashed: after 3 treatments). The IFNγ secretion of patient's PBMCs stimulated with individual HCC antigen peptides was calculated by ELISPOT. The results were shown in the mean±SEM fold change of IFNγ secretion compared to non-stimulated PBMCs. The numbers indicated the responding patients/total patients. The higher dashed line indicated a cut-off value of 1.5 fold increase. W/O: without stimulation.

FIG. 13A, FIG. 13B, FIG. 13C, and FIG. 13D are ECT results of the patent taken in December 2013 (prior to any MASCT treatments), in June 2014 (after 10 local radiotherapy treatments followed by 3 MASCT treatments), and in December 2014 (after a total of 7 MASCT treatments). The arrows and circles point to the metastasis site on the right sacroiliac joint bone, showing reduction of the metastatic tumor and no additional metastasis in response to MASCT treatments. FIGS. 13E and 13F show specific immune response against the cervical carcinoma antigen peptide pool (CC pep pool), and each type of antigen peptides in the pool after MASCT treatments. PBMCs were isolated from the patient before any MASCT treatment and after a total of 6 MASCT treatments, and were stimulated with the CC pep pool and each individual antigen peptides within the pool. Each column represents the level of immune response of the patient's PBMC after MASCT treatments against each antigen peptide (or CC pep pool) as measured by fold changes of IFNγ (Y-axis) with respect to the corresponding response of the patient's PBMC prior to MASCT treatments. W/O=response without stimulation with any antigen peptide. ENV refers to experiment with irrelevant peptide. The dotted line indicates a threshold of no elevated immune response as measured by IFNγ fold changes. Arrows point to specific antigen peptides that elicited elevated immune response as measured by IFNγ fold changes.

FIG. 14 shows a summary of the patient's treatment history in Example 2.

FIG. 17A shows percentage of peptide-specific $CD8^+$ T cells in co-culture samples with 1 time or 2 times of antigen peptide stimulation, with or without the presence of anti-PD-1 antibody (nivolumab). FIG. 17B shows percentage of functional peptide-specific $CD8^+$ T cells in co-culture samples with 1 time or 2 times of antigen peptide stimulation, with or without the presence of anti-PD-1 antibody. FIG. 17C shows percentage of peptide-specific $CD8^+$ T cells in co-culture samples with 1 time or 2 times of antigen peptide stimulation, with or without the presence of anti-PD-1 antibody (SHR-1210 or nivolumab). FIG. 17D shows percentage of functional peptide-specific CD8 T cells in co-culture samples with 1 time or 2 times of antigen peptide stimulation, with or without the presence of anti-PD-1 antibody (SHR-1210 or nivolumab).

FIG. 19A shows percentage of peptide-specific $CD8^+$ T cells in co-culture samples with 1 time of antigen peptide stimulation and cultured for 5 days or 10 days, with or without the presence of anti-PD-1 antibody (SHR-1210 or nivolumab). FIG. 19B shows percentage of peptide-specific $CD8^+$ T cells in co-culture samples with 1 time of antigen peptide stimulation and cultured for 10 days or 2 times of antigen peptide stimulation and cultured for 5 days after the second stimulation, with or without the presence of anti-PD-1 antibody (SHR-1210 or nivolumab). FIG. 19C shows percentage of functional peptide-specific $CD8^+$ T cells in co-culture samples with 1 time of antigen peptide stimulation and cultured for 10 days or 2 times of antigen peptide stimulation and cultured for 5 days after the second stimulation, with or without the presence of anti-PD-1 antibody (SHR-1210 or nivolumab).

FIGS. 21A-21B show the percentage of cells expressing PD-1 on the cell surface in the co-cultures from PBMCs of two different donors over time with or without the presence of anti-PD-1 antibody (SHR-1210 or nivolumab).

FIG. 22 shows statistical data of Next Generation Sequencing (NGS) of 333 cancer-associated genes in tumor samples and clinical evaluations of the 5 patients of Example 5.

FIG. 23A depicts the best fit classification group number. FIG. 23B depicts the DMM classification plot of 35 tumor samples. 14 samples were clustered into DMM 1 group (red, in box A), and 21 samples were clustered into DMM 0 group (green, in box B).

FIG. 24A shows a heatmap of 35 tumor samples clustered based on the mutation load detected in each of the 333 cancer-associated genes, with cancer clinical type, MMR deficiency type (0: MMR deficient, 1: MMR proficient) and DMM groups labeled. FIG. 24B shows a bar chart of HLA-I gene mutation load of each samples, ordered with the same order matching that in FIG. 24A. The black line marks 6 mutations in the HLA-I mutation load.

FIGS. 26A-26E depict the CT scans of patient 3-HJL at 5 time points. CT scans in FIG. 26A show sarcoidosis in both lobes of the lung, with the biggest one having diameter of 2 cm. FIG. 26B shows similar sarcoidosis after 2 cycles of chemotherapy. FIG. 26C shows no improvement on the lung sarcoidosis after 4 cycles of chemotherapy. CT scans in FIG. 26D depict the shrinkage of the lung sarcoidosis of ~50% in size after 3 cycles of combined therapy of PD-1 inhibitor (KEYTRUDA®) and MASCT. FIG. 26E shows the disappearance of sarcoidosis from both lobes of the lung after 5 cycles of combined therapy of PD-1 inhibitor (KEYTRUDA®) and MASCT.

FIGS. 27A-27D depict CT scans of patient 4-LKS at 4 time points. CT scans in FIG. 27A indicate brain metastasis, with the tumor size of ~3 cm. FIG. 27B shows tumor shrinkage after radiation therapy. Re-examination of CT scans in FIG. 27C indicate tumor shrinkage and alleviated brain edema. FIG. 27D shows further alleviation on tumor and edema status.

FIG. 29A shows candidate neoantigens of a patient based on sequencing analysis of the patient's tumor sample. FIG. 29B shows continuous monitoring results of circulating tumor cells (CTC) in the patient before and after MASCT treatments. FIG. 29C shows ELISPOT results of PBMC from the patient challenged with various antigen peptides after the patient received three cycles of precision MASCT treatments.

FIG. 30A shows clinical characteristics of 45 patients with hepatocellular carcinoma (HCC) who received MASCT treatments.

FIG. 30B shows results of routine blood examination of the 45 patients before and after MASCT treatments.

FIG. 30C shows liver and renal function parameters of the 45 patients before and after MASCT treatments.

FIG. 30D shows ALT and AST levels in 8 HCC patients before MASCT treatments and during the course of 5 MASCT treatments.

DETAILED DESCRIPTION OF THE INVENTION

Figure 1:
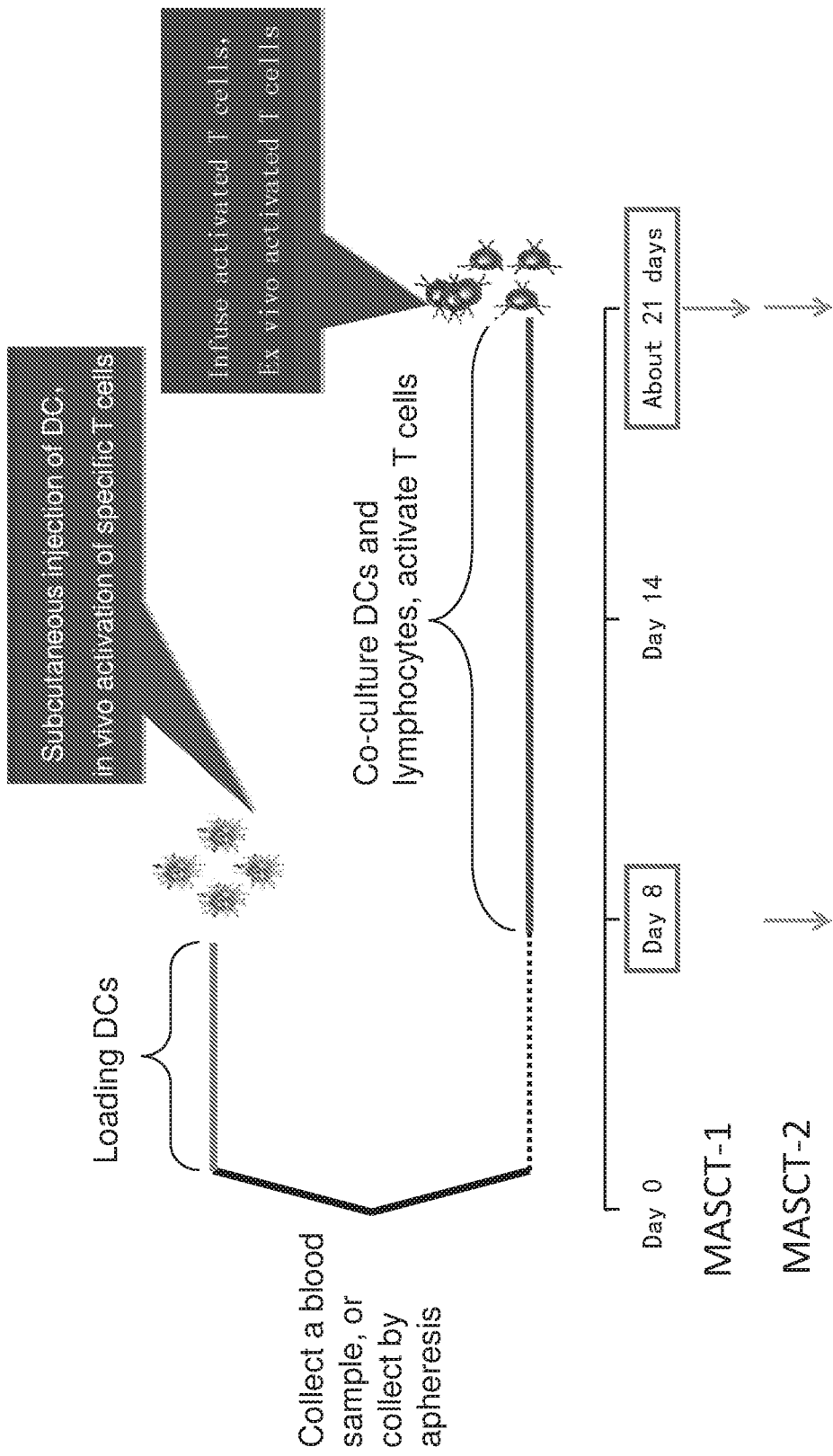
FIG. 1 depicts two preferred embodiments of the MASCT method, including timing of the DC and T cell preparation steps, and administration(s) of particular cell-based compositions. Arrows below the time line indicate administration steps.

The present invention discloses novel cell-based immunotherapy methods, collectively referred to as Multiple Antigen Specific Cell Therapy (MASCT), which are useful for treating a variety of cancers, as well as delaying the progression of, preventing relapse or metastasis of, and/or alleviating a symptom of a cancer in an individual. The methods in some embodiments utilize activated T cells induced by dendritic cells (DCs) loaded with a plurality of tumor antigen peptides. The T cells and DCs, for example, can be derived from the individual's own peripheral blood mononuclear cells (PBMCs). Multiple-antigen loaded DCs can be prepared by exposure of DCs (such as immature DCs) to a plurality of tumor antigen peptides comprising general tumor antigen peptides, and optionally cancer-type specific antigen peptides. Activated T cells can be prepared by co-culturing a population of T cells with the multiple-antigen loaded DCs. Optionally, the population of T cells is contacted with an immune checkpoint inhibitor prior to and/or during the co-culturing. The activated T cells are administered to the individual, which can elicit an adoptive immune response against the tumor antigens in vivo. Optionally, the multiple-antigen loaded DCs can be administered to the individual to trigger active immunity against the tumor antigens. Alternatively, PBMC-based MASCT methods comprising administration of activated PBMCs are provided. Any of the MASCT methods described herein may be used singly or in combination with an immune checkpoint inhibitor (such as PD-1 inhibitor) for treating cancer in the individual.

The present invention further provides precision MASCT treatment methods tailored to the individual being treated, such as the genetic profile of the tumor of the individual. For example, the individual can be selected for the MASCT treatment based on the mutation load (such as in one or more MHC genes) in the tumor of the individual. The individual may also be selected for the MASCT treatment based on the number of neoantigens found in the tumor of the individual. In some cases, one or more neoantigens can be identified by sequencing a tumor sample from the individual. Neoantigen peptides may be designed based on the neoantigens of the individual, and incorporated in the plurality of tumor antigen peptides in order to provide a precision MASCT to the individual. In some embodiments, the individual is monitored for specific immune response against each tumor antigen peptide after a MASCT treatment cycle to allow customization of the plurality of tumor antigen peptides based on the strength of the specific immune response for future MASCT treatment cycles. Additionally, tumor-specific T cell receptors (TCR), which specifically recognize an epitope in a tumor antigen peptide and elicit a strong specific immune response, can be cloned from the individual after the MASCT, and used for further precision immunotherapy on the individual.

The MASCT (including PBMC-based MASCT and precision MASCT) methods and compositions provided herein can alleviate many of the technical issues encountered by the previous cancer immunotherapy methods discussed in the background section. For example, by exposing DCs to a pool of tumor antigen peptides in vitro, a multitude of tumor antigens, as opposed to a single tumor antigen in many cancer vaccines or in PROVEGENE®, are presented by the DCs, allowing a wider spectrum of response against tumors of different antigen expression profiles within the same individual or in different individuals, as long as the tumors share one or more specific tumor antigens in the pool. The tumor antigen peptides pool can further be customized according to specific conditions of each individual, such as cancer type, viral infection status, and response to individual antigen peptides, to achieve optimal therapeutic effects in each treatment. Unlike cancer vaccines and DC-based therapies, the MASCT treatment methods comprise administering activated T cells, bypassing the in vivo T cell induction step of previous immunotherapies, which is normally associated with a weakened response in cancer patients owing to the various immune defects caused by tumor cells; thereby, the MASCT method may elicit strong, rapid and specific T cell response against cancer cells. Furthermore, the activated T cells have very low $T_{REG}$ level and PD-1 expression, leading to reduced immunosuppression on cancer-attacking T cells, thereby delaying cancer immune escape. Taken together, the present invention provides an effective, durable, and widely applicable cancer immunotherapy method to satisfy the tremendous unmet medical needs of cancer patients, especially when current standard-of-care treatments fail or are unavailable.

Definitions

Terms are used herein as generally used in the art, unless otherwise defined as follows.

As used herein, "treatment" or "treating" is an approach for obtaining beneficial or desired results including clinical results. For purposes of this invention, beneficial or desired clinical results include, but are not limited to, one or more of the following: decreasing one more symptoms resulting from the disease, diminishing the extent of the disease, stabilizing the disease (e.g., preventing or delaying the worsening of the disease), preventing or delaying the spread (e.g., metastasis) of the disease, preventing or delaying the occurrence or recurrence of the disease, delay or slowing the progression of the disease, ameliorating the disease state, providing a remission (whether partial or total) of the disease, decreasing the dose of one or more other medications required to treat the disease, delaying the progression of the disease, increasing the quality of life, and/or prolonging survival. Also encompassed by "treatment" is a reduction of pathological consequence of cancer. The methods of the invention contemplate any one or more of these aspects of treatment.

The term "individual" or "patient" is used synonymously herein to describe a mammal, including humans. An individual includes, but is not limited to, human, bovine, horse, feline, canine, rodent, or primate. In some embodiments, the individual is human. In some embodiments, an individual suffers from a disease, such as cancer. In some embodiments, the individual is in need of treatment.

As used herein, "delaying" the development of cancer means to defer, hinder, slow, retard, stabilize, and/or postpone development of the disease. This delay can be of varying lengths of time, depending on the history of the disease and/or individual being treated. As is evident to one skilled in the art, a sufficient or significant delay can, in effect, encompass prevention, in that the individual does not develop the disease. A method that "delays" development of cancer is a method that reduces probability of disease development in a given time frame and/or reduces the extent of the disease in a given time frame, when compared to not using the method. Such comparisons are typically based on clinical studies, using a statistically significant number of individuals. Cancer development can be detectable using standard methods, including, but not limited to, computerized axial tomography (CAT Scan), Magnetic Resonance Imaging (MRI), abdominal ultrasound, clotting tests, arteriography, or biopsy. Development may also refer to cancer progression that may be initially undetectable and includes occurrence, recurrence, and onset.

As is understood in the art, an "effective amount" refers to an amount of a composition (e.g. multiple-antigen loaded DCs, activated T cells, activated PMBCs, or isolated T cells), first therapy, second therapy, or a combination therapy sufficient to produce a desired therapeutic outcome (e.g., reducing the severity or duration of, stabilizing the severity of, or eliminating one or more symptoms of cancer). For therapeutic use, beneficial or desired results include, e.g., decreasing one or more symptoms resulting from the disease (biochemical, histologic and/or behavioral), including its complications and intermediate pathological phenotypes presented during development of the disease, increasing the quality of life of those suffering from the disease, decreasing the dose of other medications required to treat the disease, enhancing effect of another medication, delaying the progression of the disease, and/or prolonging survival of patients.

The methods may be practiced in an adjuvant setting. "Adjuvant setting" refers to a clinical setting in which an individual has had a history of a proliferative disease, particularly cancer, and generally (but not necessarily) been responsive to therapy, which includes, but is not limited to, surgery (such as surgical resection), radiotherapy, and chemotherapy. However, because of their history of the proliferative disease (such as cancer), these individuals are considered at risk of development of the disease. Treatment or administration in the "adjuvant setting" refers to a subsequent mode of treatment. The degree of risk (i.e., when an individual in the adjuvant setting is considered as "high risk" or "low risk") depends upon several factors, most usually the extent of disease when first treated.

The methods provided herein may also be practiced in a "neoadjuvant setting," i.e., the method may be carried out before the primary/definitive therapy. In some embodiments, the individual has previously been treated. In some embodiments, the individual has not previously been treated. In some embodiments, the treatment is a first line therapy.

As used herein, by "combination therapy" is meant that a first agent be administered in conjunction with another agent. "In conjunction with" refers to administration of one treatment modality in addition to another treatment modality, such as administration of activated T cells or PBMCs described herein in addition to administration of another agent (such as an immune checkpoint inhibitor) to the same individual. As such, "in conjunction with" refers to administration of one treatment modality before, during, or after delivery of the other treatment modality to the individual. Such combinations are considered to be part of a single treatment regimen or regime.

The term "simultaneous administration," as used herein, means that a first therapy and second therapy in a combination therapy are administered with a time separation of no more than about 15 minutes, such as no more than about any of 10, 5, or 1 minutes. When the first and second therapies are administered simultaneously, the first and second therapies may be contained in the same composition (e.g., a composition comprising both a first and second therapy) or in separate compositions (e.g., a first therapy in one composition and a second therapy is contained in another composition).

As used herein, the term "sequential administration" means that the first therapy and second therapy in a combination therapy are administered with a time separation of more than about 15 minutes, such as more than about any of 20, 30, 40, 50, 60, or more minutes. Either the first therapy or the second therapy may be administered first. The first and second therapies are contained in separate compositions, which may be contained in the same or different packages or kits.

As used herein, the term "concurrent administration" means that the administration of the first therapy and that of a second therapy in a combination therapy overlap with each other.

As used herein, by "pharmaceutically acceptable" or "pharmacologically compatible" is meant a material that is not biologically or otherwise undesirable, e.g., the material may be incorporated into a pharmaceutical composition administered to an individual without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

An "adverse event" or "AE" as used herein refers to any untoward medical occurrence in an individual receiving a marketed pharmaceutical product or in an individual who is participating on a clinical trial who is receiving an investigational or non-investigational pharmaceutical agent. The AE does not necessarily have a causal relationship with the individual's treatment. Therefore, an AE can be any unfavorable and unintended sign, symptom, or disease temporally associated with the use of a medicinal product, whether or not considered to be related to the medicinal product. An AE includes, but is not limited to: an exacerbation of a pre-existing illness; an increase in frequency or intensity of a pre-existing episodic event or condition; a condition detected or diagnosed after study drug administration even though it may have been present prior to the start of the study; and continuously persistent disease or symptoms that were present at baseline and worsen following the start of the study. An AE generally does not include: medical or surgical procedures (e.g., surgery, endoscopy, tooth extraction, or transfusion); however, the condition that leads to the procedure is an adverse event; pre-existing diseases, conditions, or laboratory abnormalities present or detected at the start of the study that do not worsen; hospitalizations or procedures that are done for elective purposes not related to an untoward medical occurrence (e.g., hospitalizations for cosmetic or elective surgery or social/convenience admissions); the disease being studied or signs/symptoms associated with the disease unless more severe than expected for the individual's condition; and overdose of study drug without any clinical signs or symptoms.

A "serious adverse event" or (SAE) as used herein refers to any untoward medical occurrence at any dose including, but not limited to, that: a) is fatal; b) is life-threatening (defined as an immediate risk of death from the event as it occurred); c) results in persistent or significant disability or incapacity, d) requires in-patient hospitalization or prolongs an existing hospitalization (exception: Hospitalization for elective treatment of a pre-existing condition that did not worsen during the study is not considered an adverse event. Complications that occur during hospitalization are AEs and if a complication prolongs hospitalization, then the event is serious); e) is a congenital anomaly/birth defect in the offspring of an individual who received medication; or f) conditions not included in the above definitions that may jeopardize the individual or may require intervention to prevent one of the outcomes listed above unless clearly related to the individual's underlying disease. "Lack of efficacy" (progressive disease) is not considered an AE or SAE. The signs and symptoms or clinical sequelae resulting from lack of efficacy should be reported if they fulfill the AE or SAE definitions.

The following definitions may be used to evaluate response based on target lesions: "complete response" or "CR" refers to disappearance of all target lesions; "partial response" or "PR" refers to at least a 30% decrease in the sum of the longest diameters (SLD) of target lesions, taking as reference the baseline SLD; "stable disease" or "SD" refers to neither sufficient shrinkage of target lesions to qualify for PR, nor sufficient increase to qualify for PD, taking as reference the nadir SLD since the treatment started; and "progressive disease" or "PD" refers to at least a 20% increase in the SLD of target lesions, taking as reference the nadir SLD recorded since the treatment started, or, the presence of one or more new lesions.

The following definitions of response assessments may be used to evaluate a non-target lesion: "complete response" or "CR" refers to disappearance of all non-target lesions; "stable disease" or "SD" refers to the persistence of one or more non-target lesions not qualifying for CR or PD; and "progressive disease" or "PD" refers to the "unequivocal progression" of existing non-target lesion(s) or appearance of one or more new lesion(s) is considered progressive disease (if PD for the individual is to be assessed for a time point based solely on the progression of non-target lesion(s), then additional criteria are required to be fulfilled.

"Progression free survival" (PFS) indicates the length of time during and after treatment that the cancer does not grow. Progression-free survival includes the amount of time individuals have experienced a complete response or a partial response, as well as the amount of time individuals have experienced stable disease.

"Predicting" or "prediction" is used herein to refer to the likelihood that an individual is likely to respond either favorably or unfavorably to a treatment regimen.

As used herein, "at the time of starting treatment" or "baseline" refers to the time period at or prior to the first exposure to the treatment.

As used herein, "sample" refers to a composition which contains a molecule which is to be characterized and/or identified, for example, based on physical, biochemical, chemical, physiological, and/or genetic characteristics.

"Cells," as used herein, is understood to refer not only to the particular individual cell, but to the progeny or potential progeny of such a cell. Because certain modifications may occur in succeeding generations due to either mutation or environmental influences, such progeny may not, in fact, be identical to the parent cell, but are still included within the scope of the term as used herein.

The term "peptide" refers to a polymer of amino acids no more than about 100 amino acids (including fragments of a protein), which may be linear or branched, comprise modified amino acids, and/or be interrupted by non-amino acids. The term also encompasses an amino acid polymer that has been modified naturally or by intervention, including, for example, disulfide bond formation, glycosylation, lipidation, acetylation, phosphorylation, or any other manipulation or modification. Also included within this term are, for example, polypeptides containing one or more analogs of an amino acid (including, for example, unnatural amino acids, etc.), as well as other modifications known in the art. The peptides described herein may be naturally-occurring, i.e., obtained or derived from a natural source (e.g., blood) or synthesized (e.g., chemically synthesized or by synthesized by recombinant DNA techniques).

As used herein, "a plurality of tumor antigen peptides," "multiple tumor antigen peptides," "a pool of tumor antigen peptides" and "a tumor antigen peptides pool" are used interchangeably to refer to a combination of more than one tumor antigen peptides.

As used herein, "dendritic cells loaded with a plurality of tumor antigen peptides" and "multiple-antigen loaded dendritic cells" are used interchangeably to refer to dendritic cells that have enhanced presentation of more than one tumor antigen peptides among the plurality of tumor antigen peptides. Likewise, "APCs loaded with a plurality of tumor antigen peptides" are used interchangeably with "multiple-antigen loaded APCs" to refer to antigen processing cells that have enhanced presentation of more than one tumor antigen peptides among the plurality of tumor antigen peptides.

As used herein, "activated T cells" refer to a population of monoclonal (e.g. encoding the same TCR) or polyclonal (e.g. with clones encoding different TCRs) T cells that have T cell receptors that recognize at least one tumor antigen peptide. Activated T cells may contain one or more subtypes of T cells, including, but not limited to, cytotoxic T cells, helper T cells, natural killer T cells, γδ T cells, regulatory T cells, and memory T cells.

As used herein, "immune checkpoint inhibitor" refers to a molecule or an agent (including an antibody) that inhibits or blocks an inhibitory immune checkpoint molecule on an immune cell (such as T cell, or PBMC) or a tumor cell. "Immune checkpoint molecules" include molecules that turn up an immune signal (i.e., "co-stimulatory molecules"), or molecules that turn down an immune signal (i.e., "inhibitory immune checkpoint molecules") against a tumor cell.

As used herein, "mutation load" refers to the total number of mutations accumulated at one or more loci (such as gene) in the genome of a cell (such as a tumor cell). The mutations include, but are not limited to, point mutation, insertion, deletion, frame shift mutation, gene fusion, and copy number variation. The mutations may or may not adversely affect the physical/chemical properties, and/or functions of the product encoded by the locus.

As used herein, "T cell receptor" or "TCR" refers to an endogenous or engineered T cell receptor comprising an extracellular antigen binding domain that binds to a specific antigen epitope bound in an MHC molecule. A TCR may comprise a TCRα polypeptide chain and a TCR β polypeptide chain. "Tumor-specific TCR" refers to a TCR that specifically recognizes tumor antigen expressed by a tumor cell.

As used herein, the term "HLA" or "Human Leukocyte Antigen" refers to the human genes that encode for the MHC (Major Histocompatibility Complex) proteins on the surface of cells that are responsible for regulation of the immune system. "HLA-I" or "HLA class I" refers to human MHC class I genes, including HLA-A, HLA-B, HLA-C, HLA-E, HLA-F, HLA-G, and β2-microglobulin loci. "HLA-II" or "HLA class II" refers to human MHC class II genes, including HLA-DPA1, HLA-DPB1, HLA-DQA1, HLA-DQB1, HLA-DRA1, HLA-DRB1, HLA-DRB3, HLA-DRB4, HLA-DRB5, HLA-DM, HLA-DOA, and HLA-DOB loci.

The term "antibody" used herein is used in the broadest sense and specifically covers monoclonal antibodies (including full length monoclonal antibodies), multispecific antibodies (e.g., bispecific antibodies), and antibody fragments so long as they exhibit the desired biological activity.

"Antibody fragments" comprise a portion of an intact antibody, preferably comprising the antigen binding region thereof. In some embodiments, the antibody fragment described herein is an antigen-binding fragment. Examples of antibody fragments include Fab, Fab', F(ab')$_2$, and Fv fragments; diabodies; linear antibodies; single-chain antibody molecules; and multispecific antibodies formed from antibody fragments.

As use herein, the term "specifically binds to," "recognizes," "specifically recognizes," "targets," or is "specific for" refers to measurable and reproducible interactions such as binding between a target and an antibody, or a receptor and a ligand, or a receptor and an epitope/MHC complex, which is determinative of the presence of the target in the presence of a heterogeneous population of molecules including biological molecules. For example, an antibody that binds to or specifically binds to a target (which can be an epitope) is an antibody that binds this target with greater affinity, avidity, more readily, and/or with greater duration than it binds to other targets. In one embodiment, the extent of binding of an antibody to an unrelated target is less than about 10% of the binding of the antibody to the target as measured, e.g., by a radioimmunoassay (RIA). In certain embodiments, an antibody that specifically binds to an antigen peptide (or an epitope) has a dissociation constant (Kd) of ≤1M, ≤100 nM, ≤10 nM, ≤1 nM, or ≤0.1 nM. In certain embodiments, an antibody specifically binds to an epitope on a protein that is conserved among the protein from different species. In another embodiment, specific binding can include, but does not require exclusive binding.

It is understood that aspect and embodiments of the invention described herein include "consisting" and/or "consisting essentially of" aspects and embodiments.

Reference to "about" a value or parameter herein includes (and describes) variations that are directed to that value or parameter per se. For example, description referring to "about X" includes description of "X".

The term "about X-Y" used herein has the same meaning as "about X to about Y."

As used herein, reference to "not" a value or parameter generally means and describes "other than" a value or parameter. For example, the method is not used to treat cancer of type X means the method is used to treat cancer of types other than X.

As used herein and in the appended claims, the singular forms "a," "or," and "the" include plural referents unless the context clearly dictates otherwise.

MASCT Method

The present invention provides cell-based immunotherapy methods of treating cancer in an individual, collectively referred to as Multiple Antigen Specific Cell Therapy (MASCT). The methods make use of antigen presenting cells (APCs, such as dendritic cells) loaded with a plurality of tumor antigen peptides, and activated T cells induced by the multiple-antigen loaded APCs. Both the multiple-antigen loaded APCs and the activated T cells are capable of eliciting tumor antigen-specific T cell response in vivo and ex vivo, including response by cytotoxic T cells and helper T cells, as well as generating an immune memory through memory T cells. Therefore, in various embodiments of the MASCT method, multiple-antigen loaded APCs (such as dendritic cells), activated T cells, co-culture of APCs and T cells (including activated PBMCs), or any combination thereof can be administered to an individual to treat a cancer or neoplastic condition, or to prevent tumor relapse, progression or metastasis.

The present invention in one aspect provides a method of treating a cancer in an individual, comprising administering to the individual an effective amount of activated T cells, wherein the activated T cells are prepared by co-culturing a population of T cells with a population of antigen presenting cells (such as dendritic cells) loaded with a plurality of tumor antigen peptides. In some embodiments, the activated T cells are administered intravenously. In some embodiments, the activated T cells are administered for at least three times. In some embodiments, the activated T cells and the population of antigen presenting cells are from the same individual. In some embodiments, the activated T cells and/or the population of antigen presenting cells are from the individual being treated. In some embodiments, the population of antigen presenting cells is a population of dendritic cells, B cells, or macrophages. In some embodiments, the antigen presenting cells are dendritic cells.

In some embodiments, there is provided a method of treating a cancer in an individual, comprising administering to the individual an effective amount of activated T cells, wherein the activated T cells are prepared by co-culturing a population of T cells with a population of antigen presenting cells (such as dendritic cells) loaded with a plurality of tumor antigen peptides, and wherein the individual has previously been administered an effective amount of antigen presenting cells loaded with the plurality of tumor antigen peptides. In some embodiments, the interval between administration of the antigen presenting cells and the administration of the activated T cells is about 7 days to about 21 days (such as about 7 days to about 14 days, or about 14 days to about 21 days). In some embodiments, the antigen presenting cells are administered subcutaneously. In some embodiments, the antigen presenting cells are administered for at least three times. In some embodiments, the activated T cells are administered intravenously. In some embodiments, the activated T cells are administered for at least three times. In some embodiments, the activated T cells and the population of antigen presenting cells are from the same individual. In some embodiments, the activated T cells and/or the population of antigen presenting cells are from the individual being treated. In some embodiments, the population of antigen presenting cells is a population of dendritic cells, B cells, or macrophages. In some embodiments, the antigen presenting cells are dendritic cells.

In some embodiments, there is provided a method of treating a cancer in an individual, comprising: (a) administering to the individual an effective amount of antigen presenting cells (such as dendritic cells) loaded with the plurality of tumor antigen peptides; and (b) administering to the individual an effective amount of activated T cells, wherein the activated T cells are prepared by co-culturing a population of T cells with a population of antigen presenting cells loaded with a plurality of tumor antigen peptides. In some embodiments, the antigen presenting cells are administered about 7 days to about 21 days (such as about 7 days to about 14 days, or about 14 days to about 21 days) prior to the administration of the activated T cells. In some embodiments, the antigen presenting cells are administered for at least three times. In some embodiments, the activated T cells are administered intravenously. In some embodiments, the activated T cells are administered for at least three times. In some embodiments, the activated T cells and the population of antigen presenting cells are from the same individual. In some embodiments, the activated T cells and/or the population of antigen presenting cells are from the individual being treated. In some embodiments, the population of antigen presenting cells is a population of dendritic cells, B cells, or macrophages. In some embodiments, the antigen presenting cells are dendritic cells.

Any suitable antigen presenting cells may be used in the MASCT methods, including, but not limited to, dendritic cells, B cells, and macrophages. In some embodiments, the antigen presenting cells are dendritic cells.

Thus, in some embodiments, there is provided a method of treating a cancer in an individual, comprising administering to the individual an effective amount of activated T cells, wherein the activated T cells are prepared by co-culturing a population of T cells with a population of dendritic cells loaded with a plurality of tumor antigen peptides. In some embodiments, the activated T cells are prepared by co-culturing a population of T cells with the population of dendritic cells loaded with the plurality of tumor antigen peptides prior to the administration. In some embodiments, the dendritic cells loaded with the plurality of tumor antigen peptides are administered subcutaneously. In some embodiments, the dendritic cells loaded with the plurality of tumor antigen peptides are administered for at least three times. In some embodiments, the activated T cells are administered intravenously. In some embodiments, the activated T cells are administered for at least three times. In some embodiments, the activated T cells and the population of dendritic cells are from the same individual. In some embodiments, the activated T cells and/or the population of dendritic cells are from the individual being treated.

In some embodiments, there is provided a method of treating a cancer in an individual, comprising administering to the individual an effective amount of activated T cells, wherein the activated T cells are prepared by co-culturing a population of T cells with a population of dendritic cells loaded with a plurality of tumor antigen peptides, and wherein the individual has previously been administered an effective amount of dendritic cells loaded with the plurality of tumor antigen peptides. In some embodiments, the dendritic cells are administered about 7 days to about 21 days (such as about 7 days to about 14 days, or about 14 days to about 21 days) prior to the administration of the activated T cells. In some embodiments, the dendritic cells loaded with the plurality of tumor antigen peptides are administered subcutaneously. In some embodiments, the dendritic cells loaded with the plurality of tumor antigen peptides are administered for at least three times. In some embodiments, the activated T cells are administered intravenously. In some embodiments, the activated T cells are administered for at least three times. In some embodiments, the activated T cells and the population of dendritic cells are from the same individual. In some embodiments, the activated T cells and/or the population of dendritic cells are from the individual being treated.

In some embodiments, there is provided a method of treating a cancer in an individual, comprising: (a) administering to the individual an effective amount of dendritic cells loaded with a plurality of tumor antigen peptides; and (b) administering to the individual an effective amount of activated T cells, wherein the activated T cells are prepared by co-culturing a population of T cells with a population of dendritic cells loaded with the plurality of tumor antigen peptides. In some embodiments, the dendritic cells are administered about 7 days to about 21 days (such as about 7 days to about 14 days, or about 14 days to about 21 days) prior to the administration of the activated T cells. In some embodiments, the dendritic cells loaded with the plurality of tumor antigen peptides are administered subcutaneously. In some embodiments, the dendritic cells loaded with the plurality of tumor antigen peptides are administered for at least three times. In some embodiments, the activated T cells are administered intravenously. In some embodiments, the activated T cells are administered for at least three times. In some embodiments, the activated T cells and the population of dendritic cells are from the same individual. In some embodiments, the activated T cells and/or the population of dendritic cells are from the individual being treated.

In addition to the administration step(s), some embodiments of the MASCT method further comprise one or two of the following cell preparation steps: 1) preparation of the population of antigen presenting cells (such as dendritic cells) loaded with the plurality of tumor antigen peptides; and 2) preparation of the activated T cells. In some embodiments, the activated T cells are prepared by co-culturing a population of T cells with the population of antigen presenting cells loaded with the plurality of tumor antigen peptides prior to the administration. In some embodiments, the population of T cells is co-cultured with the population of antigen presenting cells loaded with the plurality of tumor antigen peptides for about 7 days to about 21 days (such as about 7 days to about 14 days, about 14 days to about 21 days, about 10 days, about 14 days, or about 21 days). In some embodiments, the population of antigen presenting cells loaded with the plurality of tumor antigen peptides is prepared by contacting a population of antigen presenting cells with the plurality of tumor antigen peptides. In some embodiments, the population of antigen presenting cells is contacted with the plurality of tumor antigen peptides in the presence of a composition that facilitates the uptake of the plurality of tumor antigen peptides by the antigen presenting cells. In some embodiments, the population of T cells is contacted with an immune checkpoint inhibitor prior to the co-culturing. In some embodiments, the population of T cells is co-cultured with the population of antigen presenting cells in the presence of an immune checkpoint inhibitor. In some embodiments, the population of T cells and the population of antigen presenting cells are derived from the same individual. In some embodiments, the population of T cells and the population of antigen presenting cells are derived from the individual being treated.

Thus, in some embodiments, there is provided a method of treating a cancer in an individual, comprising: (a) co-culturing a population of dendritic cells loaded with a plurality of tumor antigen peptides and a population of T cells to obtain a population of activated T cells; and (b) administering to the individual an effective amount of the activated T cells. In some embodiments, the dendritic cells loaded with the plurality of tumor antigen peptides are administered subcutaneously. In some embodiments, the dendritic cells loaded with the plurality of tumor antigen peptides are administered for at least three times. In some embodiments, the activated T cells are administered intravenously. In some embodiments, the activated T cells are administered for at least three times. In some embodiments, the population of T cells is co-cultured with the population of dendritic cells loaded with the plurality of tumor antigen peptides for about 7 days to about 21 days (such as about 7 days to about 14 days, about 14 days to about 21 days, about 10 days, about 14 days, or about 21 days). In some embodiments, the population of T cells is derived from the non-adherent portion of a population of peripheral blood mononuclear cells (PBMCs). In some embodiments, the co-culturing further comprises contacting the activated T cells with a plurality of cytokines (such as IL-2, IL-7, IL-15, IL-21, or any combination thereof) and optionally an anti-CD3 antibody. In some embodiments, the population of T cells is contacted with an immune checkpoint inhibitor (such as an inhibitor of PD-1, PD-L1, or CTLA-4) prior to and/or during the co-culturing. In some embodiments, the population of dendritic cells loaded with the plurality of tumor antigen peptides is prepared by contacting a population of dendritic cells with the plurality of tumor antigen peptides. In some embodiments, the population of T cells and the population of dendritic cells are derived from the same individual. In some embodiments, the population of T cells, the population of dendritic cells, the population of PBMCs, or any combination thereof is derived from the individual being treated.

In some embodiments, there is provided a method of treating a cancer in an individual, comprising: (a) co-culturing a population of dendritic cells loaded with a plurality of tumor antigen peptides and a population of T cells to obtain a population of activated T cells; and (b) administering to the individual an effective amount of the activated T cells, wherein the individual has previously been administered an effective amount of dendritic cells loaded with the plurality of tumor antigen peptides. In some embodiments, the interval between the administration of the dendritic cells and the administration of the activated T cells is about 7 days to about 21 days (such as about 7 days to about 14 days, about 14 days to about 21 days, about 10 days or about 14 days). In some embodiments, the dendritic cells loaded with the plurality of tumor antigen peptides are administered subcutaneously. In some embodiments, the dendritic cells loaded with the plurality of tumor antigen peptides are administered for at least three times. In some embodiments, the activated T cells are administered intravenously. In some embodiments, the activated T cells are administered for at least three times. In some embodiments, the population of T cells is co-cultured with the population of dendritic cells loaded with the plurality of tumor antigen peptides for about 7 days to about 21 days (such as about 7 days to about 14 days, about 14 days to about 21 days, or about 10 days). In some embodiments, the population of T cells is derived from the non-adherent portion of a population of peripheral blood mononuclear cells (PBMCs). In some embodiments, the co-culturing further comprises contacting the activated T cells with a plurality of cytokines (such as IL-2, IL-7, IL-15, IL-21, or any combination thereof) and optionally an anti-CD3 antibody. In some embodiments, the population of T cells is contacted with an immune checkpoint inhibitor (such as an inhibitor of PD-1, PD-L1, or CTLA-4) prior to and/or during the co-culturing. In some embodiments, the population of dendritic cells loaded with the plurality of tumor antigen peptides is prepared by contacting a population of dendritic cells with the plurality of tumor antigen peptides. In some embodiments, the population of T cells and the population of dendritic cells are derived from the same individual. In some embodiments, the population of T cells, the population of dendritic cells, the population of PBMCs, or any combination thereof is derived from the individual being treated.

In some embodiments, there is provided a method of treating a cancer in an individual, comprising: (a) administering to the individual an effective amount of dendritic cells loaded with a plurality of tumor antigen peptides; (b) co-culturing a population of dendritic cells loaded with the plurality of tumor antigen peptides and a population of T cells to obtain a population of activated T cells; and (c) administering to the individual an effective amount of the activated T cells. In some embodiments, the interval between the administration of the dendritic cells and the administration of the activated T cells is about 7 days to about 21 days (such as about 7 days to about 14 days, about 14 days to about 21 days, about 10 days or about 14 days). In some embodiments, the dendritic cells loaded with the plurality of tumor antigen peptides are administered subcutaneously. In some embodiments, the dendritic cells loaded with the plurality of tumor antigen peptides are administered for at least three times. In some embodiments, the activated T cells are administered intravenously. In some embodiments, the activated T cells are administered for at least three times. In some embodiments, the population of T cells is co-cultured with the population of dendritic cells loaded with the plurality of tumor antigen peptides for about 7 days to about 21 days (such as about 7 days to about 10 days, about 10 days to about 15 days, about 15 days to about 21 days, about 14 days to about 21 days, or about 10 days). In some embodiments, the population of T cells is derived from the non-adherent portion of a population of peripheral blood mononuclear cells (PBMCs). In some embodiments, the co-culturing further comprises contacting the activated T cells with a plurality of cytokines (such as IL-2, IL-7, IL-15, IL-21, or any combination thereof) and optionally an anti-CD3 antibody. In some embodiments, the population of T cells is contacted with an immune checkpoint inhibitor (such as an inhibitor of PD-1, PD-L1, or CTLA-4) prior to and/or during the co-culturing. In some embodiments, the population of dendritic cells loaded with the plurality of tumor antigen peptides is prepared by contacting a population of dendritic cells with the plurality of tumor antigen peptides. In some embodiments, the population of T cells and the population of dendritic cells are derived from the same individual. In some embodiments, the population of T cells, the population of dendritic cells, the population of PBMCs, or any combination thereof is derived from the individual being treated.

In some embodiments, there is provided a method of treating a cancer in an individual, comprising: (a) preparing a population of dendritic cells loaded with a plurality of tumor antigen peptides; (b) co-culturing the population of dendritic cells loaded with the plurality of tumor antigen peptides and a population of T cells to obtain a population of activated T cells; and (c) administering to the individual an effective amount of the activated T cells. In some embodiments, the dendritic cells loaded with the plurality of tumor antigen peptides are administered subcutaneously. In some embodiments, the dendritic cells loaded with the plurality of tumor antigen peptides are administered for at least three times. In some embodiments, the activated T cells are administered intravenously. In some embodiments, the activated T cells are administered for at least three times. In some embodiments, the population of T cells is co-cultured with the population of dendritic cells loaded with the plurality of tumor antigen peptides for about 7 days to about 21 days (such as about 7 days to about 14 days, about 14 days to about 21 days, or about 10 days). In some embodiments, the population of T cells is derived from the non-adherent portion of a population of peripheral blood mononuclear cells (PBMCs). In some embodiments, the co-culturing further comprises contacting the activated T cells with a plurality of cytokines (such as IL-2, IL-7, IL-15, IL-21, or any combination thereof) and optionally an anti-CD3 antibody. In some embodiments, the population of T cells is contacted with an immune checkpoint inhibitor (such as an inhibitor of PD-1, PD-L1, or CTLA-4) prior to and/or during the co-culturing. In some embodiments, the population of dendritic cells loaded with the plurality of tumor antigen peptides is prepared by contacting a population of dendritic cells with the plurality of tumor antigen peptides. In some embodiments, the population of T cells and the population of dendritic cells are derived from the same individual. In some embodiments, the population of T cells, the population of dendritic cells, the population of PBMCs, or any combination thereof is derived from the individual being treated.

In some embodiments, there is provided a method of treating a cancer in an individual, comprising: (a) preparing a population of dendritic cells loaded with a plurality of tumor antigen peptides; (b) co-culturing the population of dendritic cells loaded with the plurality of tumor antigen peptides and a population of T cells to obtain a population of activated T cells; and (c) administering to the individual an effective amount of the activated T cells, wherein the individual has previously been administered an effective amount of dendritic cells loaded with the plurality of tumor antigen peptides. In some embodiments, the interval between the administration of the dendritic cells and the administration of the activated T cells is about 7 days to about 21 days (such as about 7 days to about 14 days, about 14 days to about 21 days, about 10 days or about 14 days). In some embodiments, the dendritic cells loaded with the plurality of tumor antigen peptides are administered subcutaneously. In some embodiments, the dendritic cells loaded with the plurality of tumor antigen peptides are administered for at least three times. In some embodiments, the activated T cells are administered intravenously. In some embodiments, the activated T cells are administered for at least three times. In some embodiments, the population of T cells is co-cultured with the population of dendritic cells loaded with the plurality of tumor antigen peptides for about 7 days to about 21 days (such as about 7 days to about 14 days, about 14 days to about 21 days, or about 10 days). In some embodiments, the population of T cells is derived from the non-adherent portion of a population of peripheral blood mononuclear cells (PBMCs). In some embodiments, the co-culturing further comprises contacting the activated T cells with a plurality of cytokines (such as IL-2, IL-7, IL-15, IL-21, or any combination thereof) and optionally an anti-CD3 antibody. In some embodiments, the population of T cells is contacted with an immune checkpoint inhibitor (such as an inhibitor of PD-1, PD-L1, or CTLA-4) prior to and/or during the co-culturing. In some embodiments, the population of dendritic cells loaded with the plurality of tumor antigen peptides is prepared by contacting a population of dendritic cells with the plurality of tumor antigen peptides. In some embodiments, the population of T cells and the population of dendritic cells are derived from the same individual. In some embodiments, the population of T cells, the population of dendritic cells, the population of PBMCs, or any combination thereof is derived from the individual being treated.

In some embodiments, there is provided a method of treating a cancer in an individual, comprising: (a) preparing a population of dendritic cells loaded with a plurality of tumor antigen peptides; (b) administering to the individual an effective amount of the dendritic cells loaded with the plurality of tumor antigen peptides; (c) co-culturing the population of dendritic cells loaded with the plurality of tumor antigen peptides and a population of T cells to obtain a population of activated T cells; and (d) administering to the individual an effective amount of the activated T cells. In some embodiments, the interval between the administration of the dendritic cells and the administration of the activated T cells is about 7 days to about 21 days (such as about 7 days to about 14 days, about 14 days to about 21 days, about 10 days or about 14 days). In some embodiments, the dendritic cells loaded with the plurality of tumor antigen peptides are administered subcutaneously. In some embodiments, the dendritic cells loaded with the plurality of tumor antigen peptides are administered for at least three times. In some embodiments, the activated T cells are administered intravenously. In some embodiments, the activated T cells are administered for at least three times. In some embodiments, the population of T cells is co-cultured with the population of dendritic cells loaded with the plurality of tumor antigen peptides for about 7 days to about 21 days (such as about 7 days to about 14 days, about 14 days to about 21 days, or about 10 days). In some embodiments, the population of T cells is derived from the non-adherent portion of a population of peripheral blood mononuclear cells (PBMCs). In some embodiments, the co-culturing further comprises contacting the activated T cells with a plurality of cytokines (such as IL-2, IL-7, IL-15, IL-21, or any combination thereof) and optionally an anti-CD3 antibody. In some embodiments, the population of T cells is contacted with an immune checkpoint inhibitor (such as an inhibitor of PD-1, PD-L1, or CTLA-4) prior to and/or during the co-culturing. In some embodiments, the population of T cells and the population of dendritic cells are derived from the same individual. In some embodiments, the population of dendritic cells loaded with the plurality of tumor antigen peptides is prepared by contacting a population of dendritic cells with the plurality of tumor antigen peptides. In some embodiments, the population of T cells and the population of dendritic cells are derived from the same individual. In some embodiments, the population of T cells, the population of dendritic cells, the population of PBMCs, or any combination thereof is derived from the individual being treated.

In some embodiments, there is provided a method of treating a cancer in an individual, comprising: (a) inducing differentiation of a population of monocytes into a population of dendritic cells; (b) contacting the population of dendritic cells with a plurality of tumor antigen peptides to obtain a population of dendritic cells loaded with the plurality of tumor antigen peptides; (c) co-culturing the population of dendritic cells loaded with the plurality of tumor antigen peptides and a population of non-adherent PBMCs to obtain the population of activated T cells, wherein the population of monocytes and the population of non-adherent PBMCs are obtained from a population of PBMCs; and (d) administering to the individual an effective amount of the activated T cells. In some embodiments, the dendritic cells loaded with the plurality of tumor antigen peptides are administered subcutaneously. In some embodiments, the dendritic cells loaded with the plurality of tumor antigen peptides are administered for at least three times. In some embodiments, the activated T cells are administered intravenously. In some embodiments, the activated T cells are administered for at least three times. In some embodiments, the population of T cells is co-cultured with the population of dendritic cells loaded with the plurality of tumor antigen peptides for about 7 days to about 21 days (such as about 7 days to about 14 days, about 14 days to about 21 days, or about 10 days). In some embodiments, the co-culturing further comprises contacting the activated T cells with a plurality of cytokines (such as IL-2, IL-7, IL-15, IL-21, or any combination thereof) and optionally an anti-CD3 antibody. In some embodiments, the population of non-adherent PBMCs is contacted with an immune checkpoint inhibitor (such as an inhibitor of PD-1, PD-L1, or CTLA-4) prior to and/or during the co-culturing. In some embodiments, the population of PBMCs is derived from the individual being treated.

In some embodiments, there is provided a method of treating a cancer in an individual, comprising: (a) inducing differentiation of a population of monocytes into a population of dendritic cells; (b) contacting the population of dendritic cells with a plurality of tumor antigen peptides to obtain a population of dendritic cells loaded with the plurality of tumor antigen peptides; (c) co-culturing the population of dendritic cells loaded with the plurality of tumor antigen peptides and a population of non-adherent PBMCs to obtain the population of activated T cells; and (d) administering to the individual an effective amount of the activated T cells, wherein the population of monocytes and the population of non-adherent PBMCs are obtained from a population of PBMCs, and wherein the individual has previously been administered an effective amount of dendritic cells loaded with the plurality of tumor antigen peptides. In some embodiments, the interval between the administration of the dendritic cells and the administration of the activated T cells is about 7 days to about 21 days (such as about 7 days to about 14 days, about 14 days to about 21 days, about 10 days or about 14 days). In some embodiments, the dendritic cells loaded with the plurality of tumor antigen peptides are administered subcutaneously. In some embodiments, the dendritic cells loaded with the plurality of tumor antigen peptides are administered for at least three times. In some embodiments, the activated T cells are administered intravenously. In some embodiments, the activated T cells are administered for at least three times. In some embodiments, the co-culturing is for about 7 days to about 21 days (such as about 7 days to about 14 days, about 14 days to about 21 days, or about 10 days). In some embodiments, the co-culturing further comprises contacting the activated T cells with a plurality of cytokines (such as IL-2, IL-7, IL-15, IL-21, or any combination thereof) and optionally an anti-CD3 antibody. In some embodiments, the population of non-adherent PBMCs is contacted with an immune checkpoint inhibitor (such as an inhibitor of PD-1, PD-L1, or CTLA-4) prior to and/or during the co-culturing. In some embodiments, the population of PBMCs and/or dendritic cells is obtained from the individual being treated.

In some embodiments, there is provided a method of treating a cancer in an individual, comprising: (a) inducing differentiation of a population of monocytes into a population of dendritic cells; (b) contacting the population of dendritic cells with a plurality of tumor antigen peptides to obtain a population of dendritic cells loaded with the plurality of tumor antigen peptides; (c) administering to the individual an effective amount of the dendritic cells loaded with the plurality of tumor antigen peptides; (d) co-culturing the population of dendritic cells loaded with the plurality of tumor antigen peptides and a population of non-adherent PBMCs to obtain the population of activated T cells; and (e) administering to the individual an effective amount of the activated T cells, wherein the population of monocytes and the population of non-adherent PBMCs are obtained from a population of PBMCs. In some embodiments, the interval between the administration of the dendritic cells and the administration of the activated T cells is about 7 days to about 21 days (such as about 7 days to about 14 days, about 14 days to about 21 days, about 10 days or about 14 days). In some embodiments, the dendritic cells loaded with the plurality of tumor antigen peptides are administered subcutaneously. In some embodiments, the dendritic cells loaded with the plurality of tumor antigen peptides are administered for at least three times. In some embodiments, the activated T cells are administered intravenously. In some embodiments, the activated T cells are administered for at least three times. In some embodiments, the co-culturing is for about 7 days to about 21 days (such as about 7 days to about 14 days, about 14 days to about 21 days, or about 10 days). In some embodiments, the co-culturing further comprises contacting the activated T cells with a plurality of cytokines (such as IL-2, IL-7, IL-15, IL-21, or any combination thereof) and optionally an anti-CD3 antibody. In some embodiments, the population of non-adherent PBMCs is contacted with an immune checkpoint inhibitor (such as an inhibitor of PD-1, PD-L1, or CTLA-4) prior to and/or during the co-culturing. In some embodiments, the population of PBMCs is obtained from the individual being treated.

The methods described herein are suitable for treating various cancers, such as cancers described herein, including a cancer selected from the group consisting of hepatocellular carcinoma, cervical cancer, lung cancer, colorectal cancer, lymphoma, renal carcinoma, breast cancer, pancreatic cancer, gastric cancer, esophageal cancer, ovarian cancer, prostate cancer, nasopharyngeal carcinoma, melanoma, and brain cancer. The methods are applicable to cancers of all stages, including early stage, advanced stage and metastatic cancer. In some embodiments, the cancer is solid tumor. In some embodiments, the cancer is liquid cancer.

In some embodiments, the method reduces the severity of one or more symptoms associated with the cancer by at least about any of 10%, 20%, 30%, 40%, 50%, 60%, 70%, 80%, 90%, 95% or 100% compared to the corresponding symptom in the same individual prior to treatment or compared to the corresponding symptom in other individuals not receiving the treatment method. In some embodiments, the method delays progression of the cancer.

Examples of cancers that may be treated by the methods described herein include, but are not limited to, adenocortical carcinoma, agnogenic myeloid metaplasia, anal cancer, appendix cancer, astrocytoma (e.g., cerebellar and cerebral), basal cell carcinoma, bile duct cancer (e.g., extrahepatic), bladder cancer, bone cancer, (osteosarcoma and malignant fibrous histiocytoma), brain tumor (e.g., glioma, brain stem glioma, cerebellar or cerebral astrocytoma (e.g., pilocytic astrocytoma, diffuse astrocytoma, anaplastic (malignant) astrocytoma), malignant glioma, ependymoma, oligodenglioma, meningioma, craniopharyngioma, haemangioblastomas, medulloblastoma, supratentorial primitive neuroectodermal tumors, visual pathway and hypothalamic glioma, and glioblastoma), breast cancer, bronchial adenomas/carcinoids, carcinoid tumor (e.g., gastrointestinal carcinoid tumor), carcinoma of unknown primary, central nervous system lymphoma, cervical cancer, colon cancer, colorectal cancer, chronic myeloproliferative disorders, endometrial cancer (e.g., uterine cancer), ependymoma, esophageal cancer, Ewing's family of tumors, eye cancer (e.g., intraocular melanoma and retinoblastoma), gallbladder cancer, gastric (stomach) cancer, gastrointestinal carcinoid tumor, gastrointestinal stromal tumor (GIST), germ cell tumor, (e.g., extracranial, extragonadal, ovarian), gestational trophoblastic tumor, head and neck cancer, hepatocellular (liver) cancer (e.g., hepatic carcinoma and heptoma), hypopharyngeal cancer, islet cell carcinoma (endocrine pancreas), laryngeal cancer, laryngeal cancer, leukemia (except for T-cell leukemia), lip and oral cavity cancer, oral cancer, liver cancer, lung cancer (e.g., small cell lung cancer, non-small cell lung cancer, adenocarcinoma of the lung, and squamous carcinoma of the lung), lymphoma (except for T-cell lymphoma), medulloblastoma, melanoma, mesothelioma, metastatic squamous neck cancer, mouth cancer, multiple endocrine neoplasia syndrome, myelodysplastic syndromes, myelodysplastic/myeloproliferative diseases, nasal cavity and paranasal sinus cancer, nasopharyngeal carcinoma, neuroblastoma, neuroendocrine cancer, oropharyngeal cancer, ovarian cancer (e.g., ovarian epithelial cancer, ovarian germ cell tumor, ovarian low malignant potential tumor), pancreatic cancer, parathyroid cancer, penile cancer, cancer of the peritoneal, pharyngeal cancer, pheochromocytoma, pineoblastoma and supratentorial primitive neuroectodermal tumors, pituitary tumor, pleuropulmonary blastoma, primary central nervous system lymphoma (microglioma), pulmonary lymphangiomyomatosis, rectal cancer, renal carcinoma, renal pelvis and ureter cancer (transitional cell cancer), rhabdomyosarcoma, salivary gland cancer, skin cancer (e.g., non-melanoma (e.g., squamous cell carcinoma), melanoma, and Merkel cell carcinoma), small intestine cancer, squamous cell cancer, testicular cancer, throat cancer, thyroid cancer, tuberous sclerosis, urethral cancer, vaginal cancer, vulvar cancer, Wilms' tumor, abnormal vascular proliferation associated with phakomatoses, edema (such as that associated with brain tumors), and Meigs' syndrome.

Thus, in some embodiments, there is provided a method of treating hepatocellular carcinoma (HCC) in an individual comprising administering to the individual an effective amount of activated T cells, wherein the activated T cells are prepared by co-culturing a population of T cells with a population of antigen presenting cells (such as dendritic cells) loaded with a plurality of tumor antigen peptides. In some embodiments, the individual has previously been administered with an effective amount of antigen presenting cells loaded with the plurality of tumor antigen peptides. In some embodiments, the method further comprises administering to the individual an effective amount of antigen presenting cells loaded with the plurality of tumor antigen peptides prior to the administration of the activated T cells. In some embodiments, the HCC is early stage HCC, non-metastatic HCC, primary HCC, advanced HCC, locally advanced HCC, metastatic HCC, HCC in remission, or recurrent HCC. In some embodiments, the HCC is localized resectable (i.e., tumors that are confined to a portion of the liver that allows for complete surgical removal), localized unresectable (i.e., the localized tumors may be unresectable because crucial blood vessel structures are involved or because the liver is impaired), or unresectable (i.e., the tumors involve all lobes of the liver and/or has spread to involve other organs (e.g., lung, lymph nodes, bone). In some embodiments, the HCC is, according to TNM classifications, a stage I tumor (single tumor without vascular invasion), a stage II tumor (single tumor with vascular invasion, or multiple tumors, none greater than 5 cm), a stage III tumor (multiple tumors, any greater than 5 cm, or tumors involving major branch of portal or hepatic veins), a stage IV tumor (tumors with direct invasion of adjacent organs other than the gallbladder, or perforation of visceral peritoneum), N1 tumor (regional lymph node metastasis), or M1 tumor (distant metastasis). In some embodiments, the HCC is, according to AJCC (American Joint Commission on Cancer) staging criteria, stage T1, T2, T3, or T4 HCC. In some embodiments, the HCC is any one of liver cell carcinomas, fibrolamellar variants of HCC, and mixed hepatocellularcholangiocarcinomas. In some embodiments, the HCC is caused by Hepatitis B Virus (HBV) infection.

In some embodiments, there is provided a method of treating lung cancer in an individual comprising administering to the individual an effective amount of activated T cells, wherein the activated T cells are prepared by co-culturing (such as in the presence of an immune checkpoint inhibitor) a population of T cells with a population of antigen presenting cells (such as dendritic cells) loaded with a plurality of tumor antigen peptides. In some embodiments, the individual has previously been administered with an effective amount of antigen presenting cells loaded with the plurality of tumor antigen peptides. In some embodiments, the method further comprises administering to the individual an effective amount of antigen presenting cells loaded with the plurality of tumor antigen peptides prior to the administration of the activated T cells. In some embodiments, the lung cancer is a non-small cell lung cancer (NSCLC). Examples of NCSLC include, but are not limited to, large-cell carcinoma (e.g., large-cell neuroendocrine carcinoma, combined large-cell neuroendocrine carcinoma, basaloid carcinoma, lymphoepithelioma-like carcinoma, clear cell carcinoma, and large-cell carcinoma with rhabdoid phenotype), adenocarcinoma (e.g., acinar, papillary (e.g., bronchioloalveolar carcinoma, nonmucinous, mucinous, mixed mucinous and nonmucinous and indeterminate cell type), solid adenocarcinoma with mucin, adenocarcinoma with mixed subtypes, well-differentiated fetal adenocarcinoma, mucinous (colloid) adenocarcinoma, mucinous cystadenocarcinoma, signet ring adenocarcinoma, and clear cell adenocarcinoma), neuroendocrine lung tumors, and squamous cell carcinoma (e.g., papillary, clear cell, small cell, and basaloid). In some embodiments, the NSCLC may be, according to TNM classifications, a stage T tumor (primary tumor), a stage N tumor (regional lymph nodes), or a stage M tumor (distant metastasis).

In some embodiments, the lung cancer is a carcinoid (typical or atypical), adenosquamous carcinoma, cylindroma, or carcinoma of the salivary gland (e.g., adenoid cystic carcinoma or mucoepidermoid carcinoma). In some embodiments, the lung cancer is a carcinoma with pleomorphic, sarcomatoid, or sarcomatous elements (e.g., carcinomas with spindle and/or giant cells, spindle cell carcinoma, giant cell carcinoma, carcinosarcoma, or pulmonary blastoma). In some embodiments, the lung cancer is small cell lung cancer (SCLC; also called oat cell carcinoma). The small cell lung cancer may be limited-stage, extensive stage or recurrent small cell lung cancer. In some embodiments, the individual may be a human who has a gene, genetic mutation, or polymorphism suspected or shown to be associated with lung cancer (e.g., SASH1, LATS1, IGF2R, PARK2, KRAS, PTEN, Kras2, Krag, Pas1, ERCC1, XPD, IL8RA, EGFR, $\alpha_1$-AD, EPHX, MMP1, MMP2, MMP3, MMPP12, IL1β, RAS, and/or AKT) or has one or more extra copies of a gene associated with lung cancer.

In some embodiments, there is provided a method of treating cervical cancer in an individual comprising administering to the individual an effective amount of activated T cells, wherein the activated T cells are prepared by co-culturing (such as in the presence of an immune checkpoint inhibitor) a population of T cells with a population of antigen presenting cells (such as dendritic cells) loaded with a plurality of tumor antigen peptides. In some embodiments, the individual has previously been administered with an effective amount of antigen presenting cells loaded with the plurality of tumor antigen peptides. In some embodiments, the method further comprises administering to the individual an effective amount of antigen presenting cells loaded with the plurality of tumor antigen peptides prior to the administration of the activated T cells. In some embodiments, the cervical cancer is early stage cervical cancer, non-metastatic cervical cancer, locally advanced cervical cancer, metastatic cervical cancer, cervical cancer in remission, unresectable cervical cancer, cervical cancer in an adjuvant setting, or cervical cancer in a neoadjuvant setting. In some embodiments, the cervical cancer is caused by human papillomavirus (HPV) infection. In some embodiments, the cervical cancer may be, according to TNM classifications, a stage T tumor (primary tumor), a stage N tumor (regional lymph nodes), or a stage M tumor (distant metastasis). In some embodiments, the cervical cancer is any of stage 0, stage I (Tis, N0, M0), stage IA (T1a, N0, M0), stage IB (T1b, N0, M0), stage IIA (T2a, N0, M0), stage IIB (T2b, N0, M0), stage IIIA (T3a, N0, M0), stage IIIB (T3b, N0, M0, or T1-3, N1, M0) stage IVA (T4, N0, M0), or stage IVB (T1-T3, N0-N1, M1) cervical cancer. In some embodiments, the cervical cancer is cervical squamous cell carcinoma, cervical adenocarcinoma, or adenosquamous carcinoma.

In some embodiments, there is provided a method of treating breast cancer in an individual comprising administering to the individual an effective amount of activated T cells, wherein the activated T cells are prepared by co-culturing (such as in the presence of an immune checkpoint inhibitor) a population of T cells with a population of antigen presenting cells (such as dendritic cells) loaded with a plurality of tumor antigen peptides. In some embodiments, the individual has previously been administered with an effective amount of antigen presenting cells loaded with the plurality of tumor antigen peptides. In some embodiments, the method further comprises administering to the individual an effective amount of antigen presenting cells loaded with the plurality of tumor antigen peptides prior to the administration of the activated T cells. In some embodiments, the breast cancer is early stage breast cancer, non-metastatic breast cancer, locally advanced breast cancer, metastatic breast cancer, hormone receptor positive metastatic breast cancer, breast cancer in remission, breast cancer in an adjuvant setting, ductal carcinoma in situ (DCIS), invasive ductal carcinoma (IDC), or breast cancer in a neoadjuvant setting. In some embodiments, the breast cancer is hormone receptor positive metastatic breast cancer. In some embodiments, the breast cancer (which may be HER2 positive or HER2 negative) is advanced breast cancer. In some embodiments, the breast cancer is ductal carcinoma in situ. In some embodiments, the individual may be a human who has a gene, genetic mutation, or polymorphism associated with breast cancer (e.g., BRCA1, BRCA2, ATM, CHEK2, RAD51, AR, DIRAS3, ERBB2, TP53, AKT, PTEN, and/or PI3K) or has one or more extra copies of a gene (e.g., one or more extra copies of the HER2 gene) associated with breast cancer.

In some embodiments, there is provided a method of treating pancreatic cancer in an individual comprising administering to the individual an effective amount of activated T cells, wherein the activated T cells are prepared by co-culturing (such as in the presence of an immune checkpoint inhibitor) a population of T cells with a population of antigen presenting cells (such as dendritic cells) loaded with a plurality of tumor antigen peptides. In some embodiments, the individual has previously been administered with an effective amount of antigen presenting cells loaded with the plurality of tumor antigen peptides. In some embodiments, the method further comprises administering to the individual an effective amount of antigen presenting cells loaded with the plurality of tumor antigen peptides prior to the administration of the activated T cells. In some embodiments, the pancreatic cancer includes, but is not limited to, serous microcystic adenoma, intraductal papillary mucinous neoplasm, mucinous cystic neoplasm, solid pseudopapillary neoplasm, pancreatic adenocarcinoma, pancreatic ductal carcinoma, or pancreatoblastoma. In some embodiments, the pancreatic cancer is any of early stage pancreatic cancer, non-metastatic pancreatic cancer, primary pancreatic cancer, resected pancreatic cancer, advanced pancreatic cancer, locally advanced pancreatic cancer, metastatic pancreatic cancer, unresectable pancreatic cancer, pancreatic cancer in remission, recurrent pancreatic cancer, pancreatic cancer in an adjuvant setting, or pancreatic cancer in a neoadjuvant setting.

In some embodiments, there is provided a method of treating ovarian cancer in an individual comprising administering to the individual an effective amount of activated T cells, wherein the activated T cells are prepared by co-culturing (such as in the presence of an immune checkpoint inhibitor) a population of T cells with a population of antigen presenting cells (such as dendritic cells) loaded with a plurality of tumor antigen peptides. In some embodiments, the individual has previously been administered with an effective amount of antigen presenting cells loaded with the plurality of tumor antigen peptides. In some embodiments, the method further comprises administering to the individual an effective amount of antigen presenting cells loaded with the plurality of tumor antigen peptides prior to the administration of the activated T cells. In some embodiments, the ovarian cancer is ovarian epithelial cancer. Exemplary ovarian epithelial cancer histological classifications include: serous cystomas (e.g., serous benign cystadenomas, serous cystadenomas with proliferating activity of the epithelial cells and nuclear abnormalities but with no infiltrative destructive growth, or serous cystadenocarcinomas), mucinous cystomas (e.g., mucinous benign cystadenomas, mucinous cystadenomas with proliferating activity of the epithelial cells and nuclear abnormalities but with no infiltrative destructive growth, or mucinous cystadenocarcinomas), endometrioid tumors (e.g., endometrioid benign cysts, endometrioid tumors with proliferating activity of the epithelial cells and nuclear abnormalities but with no infiltrative destructive growth, or endometrioid adenocarcinomas), clear cell (mesonephroid) tumors (e.g., benign clear cell tumors, clear cell tumors with proliferating activity of the epithelial cells and nuclear abnormalities but with no infiltrative destructive growth, or clear cell cystadenocarcinomas), unclassified tumors that cannot be allotted to one of the above groups, or other malignant tumors. In various embodiments, the ovarian epithelial cancer is stage I (e.g., stage IA, IB, or IC), stage II (e.g., stage IIA, IIB, or IIC), stage III (e.g., stage IIIA, IIIB, or IIIC), or stage IV. In some embodiments, the individual may be a human who has a gene, genetic mutation, or polymorphism associated with ovarian cancer (e.g., BRCA1 or BRCA2) or has one or more extra copies of a gene associated with ovarian cancer (e.g., one or more extra copies of the HER2 gene). In some embodiments, the ovarian cancer is an ovarian germ cell tumor. Exemplary histologic subtypes include dysgerminomas or other germ cell tumors (e.g., endodermal sinus tumors such as hepatoid or intestinal tumors, embryonal carcinomas, olyembryomas, choriocarcinomas, teratomas, or mixed form tumors). Exemplary teratomas are immature teratomas, mature teratomas, solid teratomas, and cystic teratomas (e.g., dermoid cysts such as mature cystic teratomas, and dermoid cysts with malignant transformation). Some teratomas are monodermal and highly specialized, such as struma ovarii, carcinoid, struma ovarii and carcinoid, or others (e.g., malignant neuroectodermal and ependymomas). In some embodiments, the ovarian germ cell tumor is stage I (e.g., stage IA, IB, or IC), stage II (e.g., stage IIA, IIB, or IIC), stage II (e.g., stage IIIA, IIIB, or IIIC), or stage IV.

The MASCT methods described herein in some embodiments are not applicable to patients with cancers of T-cell origin, such as T-cell lymphoma.

Several viruses are related to cancer in humans. For example, Hepatitis B virus (HBV) can cause chronic infection of the liver, increasing an individual's chance of liver cancer, or hepatocellular carcinoma (HCC). Human papilloma viruses (HPVs) are a group of more than 150 related viruses, which cause papilloma, or warts, when they infect and grow in skin or mucous membranes, such as the mouth, throat, or vagina. Several types of HPV (including types 16, 18, 31, 33, 35, 39, 45, 51, 52, 56, 58, 59 and 6) are known to cause cervical cancer. HPVs also play a role in inducing or causing other cancers of the genitalia, and are linked to some cancers of the mouth and throat. Epstein-Barr virus (EBV) is a type of herpes virus, which chronically infects and remains latent in B lymphocytes. EBV infection increases an individual's risk of developing nasopharyngeal carcinoma and certain types of fast-growing lymphomas such as Burkitt lymphoma. EBV is also linked to Hodgkin lymphoma and some cases of gastric cancer. In addition to causing cancer or increasing risk of developing cancer, viral infections, such as infections with HBV, HPV, and EBV, may result in damage to tissues or organs, which can increase the disease burden of an individual suffering from a cancer, and contribute to cancer progression.

It is known in the art that the human body can be induced to mount effective and specific immune response, including cytotoxic T cell response, against several cancer-related viruses, such as HBV, HPV and EBV, including their various subtypes. Therefore, in some embodiments, there is provided a method of treating a virus-related cancer in an individual, comprising administering to the individual an effective amount of activated T cells, wherein the activated T cells are prepared by co-culturing a population of T cells with a population of antigen presenting cells (such as dendritic cells) loaded with a plurality of tumor antigen peptides. In some embodiments, the individual has previously been administered with an effective amount of antigen presenting cells loaded with the plurality of tumor antigen peptides. In some embodiments, the method further comprises administering to the individual an effective amount of antigen presenting cells loaded with a plurality of tumor antigen peptides. In some embodiments, the virus is HBV, HPV, or EBV. In some embodiments, the cancer is HBV-related hepatocellular carcinoma, HPV-related cervical cancer, or EBV-related nasopharyngeal carcinoma.

The methods described herein can be used for any one or more of the following purposes: alleviating one or more symptoms of cancer, delaying progression of cancer, shrinking cancer tumor size, disrupting (such as destroying) cancer stroma, inhibiting cancer tumor growth, prolonging overall survival, prolonging disease-free survival, prolonging time to cancer disease progression, preventing or delaying cancer tumor metastasis, reducing (such as eradiating) preexisting cancer tumor metastasis, reducing incidence or burden of preexisting cancer tumor metastasis, preventing recurrence of cancer, and/or improving clinical benefit of cancer.

APC, T Cell, and Tumor Antigen Peptide

The methods described herein in some embodiments use Antigen presenting cells (APCs) and activated T cells. APCs are cells of the immune system that are capable of activating T-cells. APCs include, but are not limited to, certain macrophages, B cells, and dendritic cells (DCs). Dendritic Cells are members of a diverse population of morphologically similar cell types found in lymphoid or non-lymphoid tissues. These cells are characterized by their distinctive morphology and high expression levels of surface class I and class II MHC molecules, which are proteins that present antigen peptides to the T cells. DCs, other APCs, and T cells can be isolated or derived (such as differentiated) from a number of tissue sources, and conveniently, from peripheral blood, such as the peripheral blood mononuclear cells (PBMCs) derived from peripheral blood.

T cells, or T lymphocytes, play a central role in cell-mediated immunity. Each clone of activated T cells express a distinct T-cell receptor (TCR) on the surface, which is responsible for recognizing antigens bound to MHC molecules on APCs and on target cells (such as cancer cells). T cells are subdivided into several types, each expressing a unique combination of surface proteins and each having a distinct function.

Cytotoxic T cells (TC) participate in the immune response to and destruction of tumor cells and other infected cells, such as virus infected cells. Generally, TC cells function by recognizing a class I MHC presented antigen on an APC or any target cell. Stimulation of the TCR, along with a co-stimulator (for example CD28 on the T cell binding to B7 on the APC, or stimulation by a helper T cell), results in activation of the TC cell. The activated TC cell can then proliferate and release cytotoxins, thereby destroying the APC, or a target cell (such as a cancer cell). Mature TC cells generally express surface proteins CD3 and CD8. Cytotoxic T cells belong to $CD3^+CD8^+$ T cells.

Helper T cells (TH) are T cells that help the activity of other immune cells by releasing T cell cytokines, which can regulate or suppress immune responses, induce cytotoxic T cells, and maximize cell killing activities of macrophages. Generally, TH cells function by recognizing a class II MHC presented antigen on an APC. Mature TH cells express the surface proteins CD3 and CD4. Helper T cells belong to $CD3^+CD4^+$ T cells.

Natural killer (NK) T cells are a heterogeneous group of T cells that share properties of both T cells and natural killer cells. Activation of NK T cells results in production of pro-inflammatory cytokines, chemokines and cell factors. They express CD56, a surface molecule commonly expressed on natural killer cells. NK T cells belong to $CD3^+CD56^+$ T cells.

Regulatory T cells ($T_{REG}$ cells) generally modulate the immune system by promoting tolerance for self-antigens, thereby limiting autoimmune activity. In cancer immunotherapy, $T_{REG}$ contributes to escape of the cancer cells from the immune response. $T_{REG}$ cells generally express CD3, CD4, CD7, CD25, CTLA4, GITR, GARP, FOXP3, and/or LAP. $CD4^+CD25^+Foxp3^+$ T cells are one class of $T_{REG}$ cells.

Memory T cells (Tm) are T cells that have previously encountered and responded to their specific antigens, or T cells that differentiated from activated T cells. Although tumor specific Tms constitutes a small proportion of the total T cell amount, they serve critical functions in surveillance of tumor cells during a person's entire lifespan. If tumor specific Tms encounter tumor cells expressing their specific tumor antigens, the Tms are immediately activated and clonally expanded. The activated and expanded T cells differentiate into effector T cells to kill tumor cells with high efficiency. Memory T cells are important for establishing and maintaining long-term tumor antigen specific responses of T cells.

Typically, an antigen for T cells is a protein molecule or a linear fragment of a protein molecule that can be recognized by a T-cell receptor (TCR) to elicit specific T cell response. The antigen can be derived from a foreign source such as a virally encoded protein, or an endogenous source such as a protein expressed intracellularly or on the cell surface. The minimal fragment of an antigen that is directly involved in interaction with a particular TCR is known as an epitope. Multiple epitopes can exist in a single antigen, wherein each epitope is recognized by a distinct TCR encoded by a particular clone of T cells.

In order to be recognized by a TCR, an antigen peptide or antigen fragment can be processed into an epitope by an APC (such as a dendritic cell), and then bound in an extended conformation inside a Major Histocompatibility (MHC) molecule to form an MHC-peptide complex on the surface of an APC (such as a dendritic cell). MHC molecules in human are also known as human leukocyte antigens (HLA). The MHC provides an enlarged binding surface for strong association between TCR and epitope, while a combination of unique amino acid residues within the epitope ensures specificity of interaction between TCR and the epitope. The human MHC molecules are classified into two types—MHC class I and MHC class II—based on their structural features, especially the length of epitopes bound inside the corresponding MHC complexes. MHC-I epitopes are epitopes bound to and represented by an MHC class I molecule. MHC-II epitopes are epitopes bound to and represented by an MHC class II molecule. MHC-I epitopes are typically about 8 to about 11 amino acids long, whereas MHC-II epitopes are about 13 to about 17 amino acids long. Due to genetic polymorphism, various subtypes exist for both MHC class I and MHC class II molecules among the human population. T cell response to a specific antigen peptide presented by an MHC class I or MHC class II molecule on an APC or a target cell is known as MHC-restricted T cell response.

Tumor antigen peptides are derived from tumor antigen proteins (also referred to herein as "tumor antigens") that are overexpressed in cancer cells, but have little to no expression levels (such as less than about any of 10, 100, 1000, or 5000 copies per cell) in normal cells. Some tumor antigen peptides are derived from tumor-specific antigens (TSA), differentiation antigens, or overexpressed antigens (also known as tumor-associated antigens, or TAAs). Some tumor antigen peptides are derived from mutant protein antigens that are only present in cancer cells, but absent in normal cells.

Antigen Loading of Dendritic Cells

The present invention provides a method of preparing a population of dendritic cells loaded with a plurality of tumor antigen peptides useful for eliciting MHC-restricted T cell response in an individual, comprising contacting a population of dendritic cells with a plurality of tumor antigen peptides. Dendritic cells prepared by the method can be used in any embodiment of the MASCT methods described herein, or to prepare activated T cells or co-culture of dendritic cells and T cells as described in the next section.

In some embodiments of the methods of preparing the multiple-antigen loaded dendritic cells, the population of dendritic cells is contacted with more than about any of 1, 2, 3, 4, 5, 6, 7, 8, 9, 10, 11, 12, 13, 14, 15, 16, 17, 18, 19, 20, 22, 25, 30, 40, or 50 tumor antigen peptides. In some embodiments, the population of dendritic cells is contacted with a plurality of tumor antigen peptides comprising at least about any of 1, 5, 10, 15, 20, 25, 30, 35 or 40 of epitopes selected from the group consisting of SEQ ID NOs: 1-40. In some embodiments, the population of dendritic cells is contacted with about any of 1, 2, 3, 4, 5, 6, 7, 8, 9, 10, 11, 12, 13, 14, or more tumor antigen peptides selected from the group consisting of the tumor antigen peptides in FIG. 2C and FIG. 29A. In some embodiments, the population of dendritic cells is contacted with about any of 1, 2, 3, 4, 5, 6, 7, 8, 9, 10, 11, 12, 13, 14, or more tumor antigen peptides derived from proteins selected from the group consisting of hTERT, p53, Survivin, NY-ESO-1, CEA, CCND1, MET, RGS5, MMP7, VEGFR, AFP, GPC3, HBVc, HBVp, CDCA1, KRAS, PARP4, MLL3, and MTHFR.

In some embodiments, the dendritic cells are mature dendritic cells that present one or more tumor antigen peptides of the plurality of tumor antigen peptides. The mature dendritic cells prepared by any of the methods described herein may present about any one of 1, 2, 3, 4, 5, 6, 7, 8, 9, 10, 11, 12, 13, 14, 15, 16, 17, 18, 19, 20, 22, 25, 30, 40, or 50 tumor antigen peptides. Compared to naïve dendritic cells, or dendritic cells that have not been loaded with a plurality of tumor antigen peptides, the multiple-antigen loaded dendritic cells may have enhanced level of presentation for more than about any of 1, 2, 3, 4, 5, 6, 7, 8, 9, 10, 11, 12, 13, 14, 15, 16, 17, 18, 19, 20, 22, 25, 30, 40, or 50 tumor antigen peptides. In some embodiments, the mature dendritic cells have enhanced level of presentation of at least about any of 1, 5, 10, 15, 20, 25, 30, 35, or 40 of epitopes selected from the group consisting of SEQ ID NOs: 1-40. In some embodiments, the mature dendritic cells have enhanced level of presentation for more than ten of the tumor antigen peptides. In some embodiments, the mature dendritic cells have enhanced level of presentation of about any of 1, 2, 3, 4, 5, 6, 7, 8, 9, 10, 11, 12, 13, 14, or more tumor antigen peptides as shown in FIG. 2C and FIG. 29A. In some embodiments, the mature dendritic cells have enhanced level of presentation of about any of 1, 2, 3, 4, 5, 6, 7, 8, 9, 10, 11, 12, 13, 14, or more tumor antigen peptides derived from proteins selected from the group consisting of hTERT, p53, Survivin, NY-ESO-1, CEA, CCND1, MET, RGS5, MMP7, VEGFR, AFP, GPC3, HBVc, HBVp, CDCA1, KRAS, PARP4, MLL3, and MTHFR.

An exemplary embodiment of the contacting of a population of dendritic cells with a plurality of tumor antigen peptides comprises pulsing the plurality of tumor antigen peptides into the population of dendritic cells, such as immature dendritic cells, or dendritic cells contained in or derived (such as differentiated) from the PBMCs. As known in the art, pulsing refers to a process of mixing cells, such as dendritic cells, with a solution containing antigen peptides, and optionally subsequently removing the antigen peptides from the mixture. The population of dendritic cells may be contacted with a plurality of tumor antigen peptides for seconds, minutes, or hours, such as about any of 30 seconds, 1 minute, 5 minutes, 10 minutes, 15 minutes, 20 minutes, 30 minutes, 1 hour, 5 hours, 10 hours, 12 hours, 14 hours, 16 hours, 18 hours, 20 hours, 22 hours, 1 day, 2 days, 3 days, 4 days, 5 days, 6 days, one week, 10 days, or more. The concentration of each tumor antigen peptide used in the contacting step may be about any of 0.1, 0.5, 1, 2, 3, 5, or 10 µg/mL. In some embodiments, the concentration of the tumor antigen peptides is about 0.1-200 µg/mL, including for example about any of 0.1-0.5, 0.5-1, 1-10, 10-50, 50-100, 100-150, or 150-200 µg/mL.

In some embodiments, the population of dendritic cells is contacted with the plurality of tumor antigen peptides in the presence of a composition that facilitates the uptake of the plurality of tumor antigen peptides by the dendritic cells. In some embodiments, compounds, materials or compositions may be included in a solution of the plurality of tumor antigen peptides to facilitate peptide uptake by the dendritic cells. Compounds, materials or compositions that facilitate the uptake of the plurality of tumor antigen peptides by the dendritic cells include, but are not limited to, lipid molecules and peptides with multiple positively charged amino acids. In some embodiments, more than about any of 50%, 60%, 70%, 80%, 90%, or 95% of the tumor antigen peptides are uptaken by the population of dendritic cells. In some embodiments, more than about any of 50%, 60%, 70%, 80%, 90%, or 95% of the dendritic cells in the population uptake at least one tumor antigen peptide.

In some embodiments, there is provided a method of preparing a population of dendritic cells loaded with a plurality of tumor antigen peptides, comprising contacting a population of immature dendritic cells with a plurality of tumor antigen peptides. In some embodiments, the method further comprises inducing maturation of the population of immature dendritic cells with a plurality of Toll-like Receptor (TLR) agonists. In some embodiments, the method comprises contacting the population of immature dendritic cells with a plurality of TLR agonists and a plurality of tumor antigen peptides to obtain a population of mature dendritic cells loaded with the plurality of tumor antigen peptides. Exemplary TLR agonists include, but are not limited to, polyIC, MALP and R848. Cytokines and other appropriate molecules may be further included in the culturing media in the maturation step. The population of immature dendritic cells may be induced by TLR agonists to mature for at least about any of 1, 2, 3, 4, 5, 6, 7, 8, 9, 10, 15, or 20 days. In some embodiments, the population of immature dendritic cells is induced to mature for about 8 days.

Dendritic cells (such as immature dendritic cells) may be obtained from various sources, including autologous sources, i.e. from the individual receiving the treatment. A convenient source of dendritic cells is the PBMCs from the peripheral blood. For example, monocytes, a type of white blood cells, are abundant in PBMCs, comprising about 10-30% of total PBMCs. Monocytes can be induced to differentiate into dendritic cells, such as immature dendritic cells, using cytokines. In some embodiments, the immature dendritic cells are prepared by obtaining a population of PBMCs, obtaining a population of monocytes from the population of PBMCs, and contacting the population of monocytes with a plurality of cytokines to obtain a population of immature dendritic cells. Exemplary cytokines that may be used to induce differentiation of monocytes include, but are not limited to, GM-CSF and IL-4, with conditions (such as concentrations, temperature, $CO_2$ level etc.) known in the art. The adherent fraction of PBMCs contains the majority of monocytes in PBMCs. In some embodiments, the monocytes from the adherent fraction of PBMCs are contacted with cytokines to obtain a population of immature dendritic cells. PBMCs can be conveniently obtained by centrifugation of a sample of peripheral blood, or using apheresis methods to collect from an individual. In some embodiments, the population of PBMCs is obtained by density gradient centrifugation of a sample of human peripheral blood. In some embodiments, the sample is from the individual that receives the multiple-antigen loaded dendritic cells, activated T cells, or other immunotherapeutic compositions prepared using the multiple-antigen loaded dendritic cells.

In some embodiments, there is provided a method of preparing a population of dendritic cells loaded with a plurality of tumor antigen peptides useful for eliciting MHC-restricted T cell response in an individual, comprising the steps of obtaining a population of peripheral blood mononuclear cells (PBMCs) from an individual, obtaining a population of monocytes from the population of PBMCs, obtaining a population of dendritic cells from the population of monocytes, and contacting the population of dendritic cells with a plurality of tumor antigen peptides to obtain a population of dendritic cells loaded with the plurality of tumor antigen peptides. In some embodiments, there is provided a method of preparing a population of dendritic cells loaded with a plurality of tumor antigen peptides useful for eliciting MHC-restricted T cell response in an individual, comprising the steps of obtaining a population of PBMCs from an individual (such as the individual), obtaining a population of monocytes from the population of PBMCs, contacting the population of monocytes with a plurality of cytokines (such as GM-CSF and IL-4) to obtain a population of immature dendritic cells, and contacting the population of immature dendritic cells with a plurality of TLR agonists and a plurality of tumor antigen peptides to obtain the population of dendritic cells loaded with the plurality of tumor antigen peptides.

Further provided by the present invention is an isolated population of dendritic cells prepared by any of the embodiments of the methods described herein. In some embodiments, the isolated population of dendritic cells is capable of eliciting MHC-restricted T cell response in vivo or ex vivo. In some embodiments, the MHC-restricted T cell response is mediated by both MHC class I and MHC class II molecules. In some embodiments, the isolated population of dendritic cells is capable of inducing differentiation and proliferation of tumor antigen-specific T cells.

Preparation of Activated T Cells

Further provided in the present invention is a method of preparing a population of activated T cells useful for treating a cancer in an individual, comprising co-culturing a population of T cells with a population of antigen presenting cells (such as dendritic cells) loaded with a plurality of tumor antigen peptides. Any embodiment of the multiple-antigen loaded dendritic cells in the previous section may be used to prepare the activated T cells. In some embodiments, the population of T cells and the population of dendritic cells are derived from the same individual, such as an individual with a cancer (e.g. low to moderate grade cancer). In some embodiments, the population of T cells, the population of dendritic cells, or both is derived from autologous sources, i.e. from the individual that receives the activated T cells, the multiple-antigen loaded dendritic cells, or both.

In some embodiments, the population of T cells and the population of dendritic cells loaded with the plurality of tumor antigen peptides are co-cultured for at least about any of 2, 4, 6, 8, 10, 12, 14, 16, 18, 20, 22, 24, 26, 28, or 30 days. In some embodiments, the population of T cells is co-cultured with the population of dendritic cells loaded with the plurality of tumor antigen peptides for about 7 days to about 21 days (such as about 7 days to about 14 days, about 7 days to about 10 days, about 10 days to about 15 days, about 14 days to about 21 days, about 10 days, 14 days, 16 days, 18 days, or 21 days). In some embodiments, the population of T cells is co-cultured with the population of dendritic cells loaded with the plurality of tumor antigen peptides for about 10 days. In some embodiments, the population of T cells is co-cultured with the population of dendritic cells loaded with the plurality of tumor antigen peptides for about 14 days.

The population of T cells used in any embodiment of the methods described herein may be derived from a variety of sources. A convenient source of T cells is from the PBMCs of the human peripheral blood. The population of T cells may be isolated from the PBMCs, or alternatively, a population of PBMCs enriched with T cells (such as by addition of T cell specific antibodies and cytokines) can be used in the co-culture. In some embodiments, the population of T cells used in the co-culture is obtained from the non-adherent fraction of peripheral blood mononuclear cells (PBMCs). In some embodiments, the PBMCs are obtained by density gradient centrifugation of a sample of peripheral blood. In some embodiments, the population of T cells is obtained by culturing the non-adherent fraction of PBMCs with at least one cytokine (such as IL-2) with or without an anti-CD3 antibody (such as OKT3) (a process referred herein as "maintaining T cells"). In some embodiments, the non-adherent fraction of PBMCs is cultured in the presence of an immune checkpoint inhibitor. In some embodiments, the immune checkpoint inhibitor is an inhibitor of an immune checkpoint molecule selected from the group consisting of PD-1, PD-L1, CTLA-4, IDO, TIM-3, BTLA, VISTA, and LAG-3. The non-adherent fraction of PBMCs may be cultured for at least about any of 1, 2, 3, 4, 5, 6, 7, 8, 9, 10, 11, 12, 13, 14 days or more. In some embodiments, the population of activated T cells is prepared by obtaining a population of non-adherent PBMCs, and co-culturing the population of non-adherent PBMCs with a population of dendritic cells loaded with a plurality of tumor antigen peptides (such as in the presence of at least one cytokine (such as IL-2) and optionally an anti-CD3 antibody, and optionally an immune checkpoint inhibitor).

The co-culture may further include cytokines and other compounds to facilitate activation, maturation, and/or proliferation of the T cells, as well as to prime T cells for later differentiation into memory T cells. Exemplary cytokines that may be used in this step include, but are not limited to, IL-7, IL-15, IL-21 and the like. Certain cytokines may help suppress the percentage of TG in the population of activated T cells in the co-culture. For example, in some embodiments, a high dose (such as at least about any of 200, 300, 400, 500, 600, 700, 800, 900, 1000, 1200, or 1500 U/ml) of a cytokine (such as IL-2) is used to co-culture the population of T cells and the population of dendritic cells loaded with the plurality of tumor antigen peptides to obtain a population of activated T cells with a low percentage of $T_{REG}$ cells.

The co-culture may also include one or more (such as any of 1, 2, 3, or more) immune checkpoint inhibitors. In some embodiments, the population of T cells is contacted with an immune checkpoint inhibitor prior to the co-culturing. For example, the population of T cells may be isolated T cells, or T cells present in a mixture of cells, such as non-adherent fraction of PBMCs. In some embodiments, the population of non-adherent PBMCs are contacted with an immune checkpoint inhibitor prior to the co-culturing. In some embodiments, the population of T cells or non-adherent PBMCs are contacted with the immune checkpoint inhibitor for at least about any of 1, 2, 3, 4, 5, 6, 7, 8, 9, 10, 12, 14, or more days. In some embodiments, the population of T cells or non-adherent PBMCs are contacted with the immune checkpoint inhibitor for about 5 days to about 14 days. In some embodiments, the PBMCs are contacted with the immune checkpoint inhibitor for about 8 days.

In some embodiments, the population of T cells is co-cultured with the population of dendritic cells loaded with the plurality of tumor antigen peptides in the presence of an immune checkpoint inhibitor. In some embodiments, the immune checkpoint inhibitor is an inhibitor of an inhibitory checkpoint molecule selected from the group consisting of PD-1, PD-L1, PD-L2, CTLA-4, BLTA, TIM-3, and LAG-3. In some embodiments, the immune checkpoint inhibitor is an inhibitor of PD-1. In some embodiments, the immune checkpoint inhibitor is an anti-PD-1 antibody, such as nivolumab (for example, OPDIVO®), Pembrolizumab (for example, KEYTRUDA®) or SHR-1210. In some embodiments, the immune checkpoint inhibitor is an inhibitor of PD-L1. In some embodiments, the immune checkpoint inhibitor is an anti-PD-L1 antibody. In some embodiments, the immune checkpoint inhibitor is an inhibitor of CTLA-4. In some embodiments, the immune checkpoint inhibitor is an anti-CTLA-4 antibody, such as Ipilimumab (for example, YERVOY®).

The population of T cells may be stimulated with the population of DCs loaded with the plurality of tumor antigen peptides for any number of times, such as any of 1, 2, 3, or more times. In some embodiments, the population of T cells is stimulated once. In some embodiments, the population of T cells is stimulated for at least two times. In some embodiments, for each stimulation, a population of DCs loaded with the plurality of tumor antigen peptides is added to the co-culture. The population of DCs may be freshly prepared and pulsed with the plurality of tumor antigen peptides, or may be obtained from a stock of the population of DCs prepared for the initial stimulation.

Accordingly, there is provided a method of preparing a population of activated T cells, comprising: (a) preparing a population of dendritic cells loaded with a plurality of tumor antigen peptides; and (b) co-culturing a population of dendritic cells loaded with the plurality of tumor antigen peptides and a population of non-adherent PBMCs to obtain the population of activated T cells, wherein the population of dendritic cells and the population of non-adherent PBMCs are obtained from a population of PBMCs from an individual. In some embodiments, the co-culturing is in the presence of a plurality of cytokines (such as IL-2, IL-7, IL-15, IL-21 or any combination thereof). In some embodiments, the co-culturing is in the presence of an anti-CD3 antibody (such as OKT3) and a plurality of cytokines (such as IL-2, IL-7, IL-15, IL-21 or any combination thereof). In some embodiments, the population of non-adherent PBMCs is contacted with an immune checkpoint inhibitor (such as an inhibitor of PD-1, PD-L1, CTLA-4, IDO, TIM-3, BTLA, VISTA, or LAG-3) prior to and/or during the co-culturing. In some embodiments, the method further comprises obtaining the population of PBMCs from the individual.

In some embodiments, there is provided a method of preparing a population of activated T cells, comprising: (a) inducing differentiation of a population of monocytes into a population of dendritic cells (such as in the presence of GM-CSF and IL-4); (b) contacting the population of dendritic cells with a plurality of tumor antigen peptides to obtain a population of dendritic cells loaded with the plurality of tumor antigen peptides; and (c) co-culturing the population of dendritic cells loaded with the plurality of tumor antigen peptides and a population of non-adherent PBMCs to obtain the population of activated T cells, wherein the population of monocytes and the population of non-adherent PBMCs are obtained from a population of PBMCs from an individual. In some embodiments, the population of dendritic cells loaded with the plurality of tumor antigen peptides is contacted with a plurality of TLR agonists to induce maturation of the population of dendritic cells loaded with the plurality of tumor antigen peptides. In some embodiments, the co-culturing is in the presence of a plurality of cytokines (such as IL-2, IL-7, IL-15, IL-21 or any combination thereof). In some embodiments, the co-culturing is in the presence of an anti-CD3 antibody (such as OKT3) and a plurality of cytokines (such as IL-2, IL-7, IL-15, IL-21 or any combination thereof). In some embodiments, the population of non-adherent PBMCs is contacted with an immune checkpoint inhibitor (such as an inhibitor of PD-1, PD-L1, CTLA-4, IDO, TIM-3, BTLA, VISTA, or LAG-3) prior to and/or during the co-culturing. In some embodiments, the method further comprises any one or combination of the steps: (i) obtaining the population of PBMCs from the individual, (ii) obtaining the population of monocytes from the population of PBMCs; and (iii) obtaining the population of non-adherent PBMCs from the population of PBMCs.

In some embodiments, there is provided a method of preparing a population of activated T cells, the method comprising obtaining a population of peripheral blood mononuclear cells (PBMCs) from an individual, obtaining a population of monocytes from the population of PBMCs, inducing differentiation of the population of monocytes into a population of dendritic cells (such as in the presence of GM-CSF and IL-4), contacting the population of immature dendritic cells with a plurality of Toll-like Receptor (TLR) agonists and a plurality of tumor antigen peptides to obtain a population of mature dendritic cells loaded with the plurality of tumor antigen peptides, obtaining a population of non-adherent PBMCs from the population of PBMCs, and co-culturing the population of mature dendritic cells loaded with the plurality of tumor antigen peptides and the population of non-adherent PBMCs in the presence of a plurality of cytokines (such as IL-2, IL-7, IL-15, IL-21 or any combination thereof), optionally an anti-CD3 antibody (such as OKT3), and optionally an immune checkpoint inhibitor (such as an inhibitor of PD-1, PD-L1, CTLA-4, IDO, TIM-3, BTLA, VISTA, or LAG-3) to obtain the population of activated T cells.

Further provided by the present invention is an isolated population of activated T cells prepared by any embodiment of the methods described herein. Also provided herein is a co-culture useful for treating cancer in an individual, comprising a population of T cells and a population of dendritic cells loaded with a plurality of tumor antigen peptides. In some embodiments of the co-culture, the population of T cells and the population of dendritic cells loaded with the plurality of tumor antigen peptides are derived from the same individual, such as the individual being treated. In some embodiments of the co-culture, the population of multiple-antigen loaded dendritic cells is prepared by any embodiment of the methods of preparation as described in the previous section, such as pulsing a plurality of tumor antigen peptides into a population of dendritic cells, or contacting a population of dendritic cells with a plurality of tumor antigen peptides in the presence of a composition (such as lipid molecules, or peptides with multiple positively charged amino acids) that facilitates the uptake of the plurality of tumor antigen peptides by the dendritic cells. The isolated population of activated T cells and the co-culture described in this section may be used in any embodiment of the MASCT methods. Immunotherapeutic compositions comprising the isolated population of activated T cells or the co-culture are useful for treating cancer, preventing tumor progression or metastasis, or reducing cancer immune escape are provided herein. The isolated population of activated T cells and the co-culture may also be used in the manufacture of a medicament for treating cancer, preventing tumor progression or metastasis, or reducing cancer immune escape.

It is intended that any of the steps and parameters described herein for preparing a population of dendritic cells loaded with a plurality of tumor antigen peptides or for preparing a population of activated T cells can be combined with any of the steps and parameters described herein for the MASCT method, as if each and every combination is individually described.

For example, in some embodiments, there is provided an isolated population of activated T cells prepared by co-culturing a population of T cells with a population of dendritic cells loaded with a plurality of tumor antigen peptides. In some embodiments, the population of dendritic cells is prepared by contacting a population of dendritic cells with a plurality of tumor antigen peptides (such as in the presence of a composition that facilitates the uptake of the plurality of tumor antigen peptides by the dendritic cells). In some embodiments, the population of T cells is contacted with an immune checkpoint inhibitor (such as an inhibitor of PD-1, PD-L1, CTLA-4, IDO, TIM-3, BTLA, VISTA, or LAG-3) prior to and/or during the co-culturing. In some embodiments, the population of dendritic cells, and the population of T cells are from the same source (such as the individual receiving the activated T cells for treatment).

In some embodiments, there is provided an isolated population of activated T cells prepared by: (a) inducing differentiation of a population of monocytes into a population of dendritic cells (such as in the presence of GM-CSF and IL-4); (b) contacting the population of dendritic cells with a plurality of tumor antigen peptides to obtain a population of dendritic cells loaded with the plurality of tumor antigen peptides, and (c) co-culturing the population of dendritic cells loaded with the plurality of tumor antigen peptides and a population of non-adherent PBMCs, wherein the population of monocytes and the population of non-adherent PBMCs are obtained from a population of PBMCs from an individual. In some embodiments, the population of dendritic cells loaded with the plurality of tumor antigen peptides is contacted with a plurality of TLR agonists to induce maturation of the population of dendritic cells loaded with the plurality of tumor antigen peptides. In some embodiments, the co-culturing is in the presence of a plurality of cytokines (such as IL-2, IL-7, IL-15, IL-21 or any combination thereof) and optionally an anti-CD3 antibody (such as OKT3). In some embodiments, the population of non-adherent PBMCs is contacted with an immune checkpoint inhibitor (such as an inhibitor of PD-1, PD-L1, CTLA-4, IDO, TIM-3, BTLA, VISTA, or LAG-3) prior to and/or during the co-culturing. In some embodiments, the method further comprises any one or combination of the steps: (i) obtaining the population of PBMCs from the individual; (ii) obtaining the population of monocytes from the population of PBMCs; and (iii) obtaining the population of non-adherent PBMCs from the population of PBMCs.

PBMC-Based MASCT

A variation of the MASCT method, named PBMC-based MASCT, directly uses PBMCs, which comprise APCs and T cells, without isolating or deriving the APCs (such as dendritic cells) or T cells for use in treating a cancer in an individual.

Accordingly, in some embodiments, there is provided a method of treating a cancer in an individual, comprising contacting a population of peripheral blood mononuclear cells (PBMCs) with a plurality of tumor antigen peptides to obtain a population of activated PBMCs, and administering to the individual an effective amount of the activated PBMCs. In some embodiments, the population of PBMCs is contacted with the plurality of tumor antigen peptides in the presence of a composition that facilitates the uptake of the plurality of tumor antigen peptides by antigen presenting cells (such as dendritic cells) in the PBMCs. In some embodiments, the population of PBMCs is contacted with the plurality of tumor antigen peptides in the presence of an immune checkpoint inhibitor, such as an inhibitor of PD-1, PD-L1, CTLA-4, IDO, TIM-3, BTLA, VISTA, and LAG-3. In some embodiments, the population of activated PBMCs is contacted with IL-2. In some embodiments, the activated PBMCs are administered for at least three times. In some embodiments, the interval between each administration of the activated PBMCs is about 2 weeks to about 5 months (such as about 3 months). In some embodiments, the activated PBMCs are administered intravenously. In some embodiments, the population of PBMCs is obtained from the individual being treated.

The PBMC-based MASCT method is suitable to treat any cancer (including different type or stages) that can be treated by the other embodiments of the MASCT method as described in the previous sections. In some embodiments of the PBMC-based MASCT method, the cancer is selected from the group consisting of hepatic cellular carcinoma, cervical cancer, lung cancer, colorectal cancer, lymphoma, renal carcinoma, breast cancer, pancreatic cancer, gastric cancer, esophageal cancer, ovarian cancer, prostate cancer, nasopharyngeal carcinoma, melanoma and brain cancer.

In some embodiments, the PBMCs are autologous, i.e. obtained from the individual being treated. In some embodiments, the peripheral blood from the individual has a low number of dendritic cells or T cells. In some embodiments, the PBMCs are contacted with cytokines, such as IL-2, GM-CSF, or the like, to induce differentiation, maturation, or proliferation of certain cells (such as dendritic cells, T cells, or combination thereof) in the PBMCs concurrently or after the contacting step. In some embodiments, the plurality of tumor antigen peptides is removed after the contacting step. In some embodiments, the PBMCs are contacted with the plurality of tumor antigen peptides for at least about any of 10 minutes, 15 minutes, 20 minutes, 30 minutes, 1 hour, 5 hours, 10 hours, 12 hours, 14 hours, 16 hours, 18 hours, 20 hours, 22 hours, 1 day, 2 days, 3 days, 4 days, 5 days, 6 days, one week, 10 days, or more. In some embodiments, the PBMCs are contacted with the cytokines for at least about any of 2, 4, 6, 8, 10, 12, 14, 16, 18, 20, 22, 24, 26, 28, or 30 days. In some embodiments, the PBMCs are contacted with the cytokines for about 14-21 days. In some embodiments, the PBMCs are contacted with the cytokines for about 14 days.

In any of the PBMC-based MASCT methods above, the PBMCs are contacted with one or more immune checkpoint inhibitors. In some embodiments, the population of PBMCs is contacted with the plurality of tumor antigen peptides in the presence of an immune checkpoint inhibitor. In some embodiments, the PBMCs are contacted with the immune checkpoint inhibitor for at least about any of 2, 4, 6, 8, 10, 12, 14, 16, 18, 20, 22, 24, 26, 28, or 30 days. In some embodiments, the PBMCs are contacted with the immune checkpoint inhibitor for about 14 days to about 21 days.

Combination Therapy with Immune Checkpoint Inhibitor

The methods described herein for treating cancer can be used in monotherapy as well as in combination therapy with another agent. For example, any of the MASCT methods (including the PBMC-based MASCT methods) described herein may be combined with administration of one or more (such as any of 1, 2, 3, 4, or more) immune checkpoint inhibitors.

Thus, in some embodiments, there is provided a method of treating a cancer in an individual comprising: (a) optionally administering to the individual an effective amount of dendritic cells loaded with a plurality of tumor antigen peptides; (b) administering to the individual an effective amount of activated T cells, wherein the activated T cells are prepared by co-culturing a population of T cells with a population of dendritic cells loaded with the plurality of tumor antigen peptides; and (c) administering to the individual an effective amount of an immune checkpoint inhibitor. In some embodiments, the activated T cells and the immune checkpoint inhibitor are administered simultaneously, such as in the same composition. In some embodiments, the activated T cells and the immune checkpoint inhibitor are administered sequentially. In some embodiments, the interval between the administration of the dendritic cells and the administration of the activated T cells is about 7 days to about 21 days (such as about 7 days to about 14 days, about 14 days to about 21 days, about 10 days or about 14 days). In some embodiments, the dendritic cells loaded with the plurality of tumor antigen peptides are administered subcutaneously. In some embodiments, the dendritic cells loaded with the plurality of tumor antigen peptides are administered for at least three times. In some embodiments, the activated T cells are administered intravenously. In some embodiments, the activated T cells are administered for at least three times. In some embodiments, the population of T cells is co-cultured with the population of dendritic cells loaded with the plurality of tumor antigen peptides for about 7 days to about 21 days (such as about 7 days to about 14 days, about 14 days to about 21 days, or about 10 days). In some embodiments, the population of T cells is derived from the non-adherent portion of a population of peripheral blood mononuclear cells (PBMCs). In some embodiments, the co-culturing further comprises contacting the activated T cells with a plurality of cytokines (such as IL-2, IL-7, IL-15, IL-21, or any combination thereof) and optionally an anti-CD3 antibody. In some embodiments, the population of T cells is contacted with an immune checkpoint inhibitor (such as an inhibitor of PD-1, PD-L1, CTLA-4, IDO, TIM-3, BTLA, VISTA, or LAG-3) prior to and/or during the co-culturing. In some embodiments, the population of dendritic cells loaded with the plurality of tumor antigen peptides is prepared by contacting a population of dendritic cells with the plurality of tumor antigen peptides. In some embodiments, the population of T cells and the population of dendritic cells are derived from the same individual. In some embodiments, the population of T cells, the population of dendritic cells, the population of PBMCs, or any combination thereof is derived from the individual being treated.

In some embodiments, there is provided a method of treating a cancer in an individual, comprising: (a) inducing differentiation of a population of monocytes into a population of dendritic cells; (b) contacting the population of dendritic cells with a plurality of tumor antigen peptides to obtain a population of dendritic cells loaded with the plurality of tumor antigen peptides; (c) optionally administering to the individual an effective amount of the dendritic cells loaded with the plurality of tumor antigen peptides; (d) co-culturing the population of dendritic cells loaded with the plurality of tumor antigen peptides and a population of non-adherent PBMCs to obtain the population of activated T cells; (e) administering to the individual an effective amount of the activated T cells; and (f) administering to the individual an effective amount of an immune checkpoint inhibitor, wherein the population of monocytes and the population of non-adherent PBMCs are obtained from a population of PBMCs. In some embodiments, the activated T cells and the immune checkpoint inhibitor are administered simultaneously, such as in the same composition. In some embodiments, the activated T cells and the immune checkpoint inhibitor are administered sequentially. In some embodiments, the interval between the administration of the dendritic cells and the administration of the activated T cells is about 7 days to about 21 days (such as about 7 days to about 14 days, about 14 days to about 21 days, about 10 days or about 14 days). In some embodiments, the dendritic cells loaded with the plurality of tumor antigen peptides are administered subcutaneously. In some embodiments, the dendritic cells loaded with the plurality of tumor antigen peptides are administered for at least three times. In some embodiments, the activated T cells are administered intravenously. In some embodiments, the activated T cells are administered for at least three times. In some embodiments, the co-culturing is for about 7 days to about 21 days (such as about 7 days to about 14 days, about 14 days to about 21 days, or about 10 days). In some embodiments, the co-culturing further comprises contacting the activated T cells with a plurality of cytokines (such as IL-2, IL-7, IL-15, IL-21, or any combination thereof) and optionally an anti-CD3 antibody. In some embodiments, the population of non-adherent PBMCs is contacted with an immune checkpoint inhibitor (such as an inhibitor of PD-1, PD-L1, or CTLA-4) prior to and/or during the co-culturing. In some embodiments, the population of PBMCs is obtained from the individual being treated.

In some embodiments, there is provided a method of treating a cancer in an individual comprising: (a) contacting a population of PBMCs with a plurality of tumor antigen peptides to obtain a population of activated PBMCs; (b) administering to the individual an effective amount of the activated PBMCs; and (c) administering to the individual an effective amount of an immune checkpoint inhibitor. In some embodiments, the activated PBMCs and the immune checkpoint inhibitor are administered simultaneously, such as in the same composition. In some embodiments, the activated PBMCs and the immune checkpoint inhibitor are administered sequentially. In some embodiments, the PBMCs is contacted with the plurality of tumor antigen peptides in the presence of a composition that facilitates the uptake of the plurality of tumor antigen peptides by antigen presenting cells (such as dendritic cells) in the PBMCs. In some embodiments, the population of activated PBMCs is further contacted with IL-2. In some embodiments, the population of PBMCs is contacted with the plurality of tumor antigen peptides in the presence of an immune checkpoint inhibitor, such as an inhibitor of PD-1, PD-L1, CTLA-4, IDO, TIM-3, BTLA, VISTA, and LAG-3. In some embodiments, the activated PBMCs are administered for at least three times. In some embodiments, the interval between each administration of the activated PBMCs is about 2 weeks to about 5 months (such as about 3 months). In some embodiments, the activated PBMCs are administered intravenously. In some embodiments, the population of PBMCs is obtained from the individual being treated.

In some embodiments, the immune checkpoint inhibitor is an inhibitor of PD-1. In some embodiments, the immune checkpoint inhibitor is an anti-PD-1 antibody. Exemplary anti-PD-1 antibodies include, but are not limited to, Nivolumab, pembrolizumab, pidilizumab, BMS-936559, and atezolizumab, Pembrolizumab, MK-3475, AMP-224, AMP-514, STI-A1110, and TSR-042. In some embodiments, the immune checkpoint inhibitor is nivolumab (for example, OPDIVO®). In some embodiments, the immune checkpoint inhibitor is Pembrolizumab (for example, KEYTRUDA®). In some embodiments, the immune checkpoint inhibitor is SHR-1210.

Thus, in some embodiments, there is provided a method of treating a cancer in an individual comprising: (a) optionally administering to the individual an effective amount of dendritic cells loaded with a plurality of tumor antigen peptides; (b) administering to the individual an effective amount of activated T cells, wherein the activated T cells are prepared by co-culturing a population of T cells with a population of dendritic cells loaded with the plurality of tumor antigen peptides; and (c) administering to the individual an effective amount of an inhibitor of PD-1. In some embodiments, the inhibitor of PD-1 is an anti-PD-1 antibody. In some embodiments, the inhibitor of PD-1 is selected from the group consisting of nivolumab, pembrolizumab, and SHR-1210. In some embodiments, the activated T cells and the inhibitor of PD-1 are administered simultaneously, such as in the same composition. In some embodiments, the activated T cells and the inhibitor of PD-1 are administered sequentially. In some embodiments, the interval between the administration of the dendritic cells and the administration of the activated T cells is about 7 days to about 21 days (such as about 7 days to about 14 days, about 14 days to about 21 days, about 10 days or about 14 days). In some embodiments, the dendritic cells loaded with the plurality of tumor antigen peptides are administered subcutaneously. In some embodiments, the dendritic cells loaded with the plurality of tumor antigen peptides are administered for at least three times. In some embodiments, the activated T cells are administered intravenously. In some embodiments, the activated T cells are administered for at least three times. In some embodiments, the population of T cells is co-cultured with the population of dendritic cells loaded with the plurality of tumor antigen peptides for about 7 days to about 21 days (such as about 7 days to about 14 days, about 14 days to about 21 days, or about 10 days). In some embodiments, the population of T cells is derived from the non-adherent portion of a population of peripheral blood mononuclear cells (PBMCs). In some embodiments, the co-culturing further comprises contacting the activated T cells with a plurality of cytokines (such as IL-2, IL-7, IL-15, IL-21, or any combination thereof) and optionally an anti-CD3 antibody. In some embodiments, the population of T cells is contacted with an immune checkpoint inhibitor (such as an inhibitor of PD-1) prior to and/or during the co-culturing. In some embodiments, the population of dendritic cells loaded with the plurality of tumor antigen peptides is prepared by contacting a population of dendritic cells with the plurality of tumor antigen peptides. In some embodiments, the population of T cells and the population of dendritic cells are derived from the same individual. In some embodiments, the population of T cells, the population of dendritic cells, the population of PBMCs, or any combination thereof is derived from the individual being treated.

In some embodiments, there is provided a method of treating a cancer in an individual, comprising: (a) inducing differentiation of a population of monocytes into a population of dendritic cells; (b) contacting the population of dendritic cells with a plurality of tumor antigen peptides to obtain a population of dendritic cells loaded with the plurality of tumor antigen peptides; (c) optionally administering to the individual an effective amount of the dendritic cells loaded with the plurality of tumor antigen peptides; (d) co-culturing the population of dendritic cells loaded with the plurality of tumor antigen peptides and a population of non-adherent PBMCs to obtain the population of activated T cells; (e) administering to the individual an effective amount of the activated T cells; and (f) administering to the individual an effective amount of an inhibitor of PD-1, wherein the population of monocytes and the population of non-adherent PBMCs are obtained from a population of PBMCs. In some embodiments, the inhibitor of PD-1 is an anti-PD-1 antibody. In some embodiments, the inhibitor of PD-1 is selected from the group consisting of nivolumab, pembrolizumab, and SHR-1210. In some embodiments, the activated T cells and the inhibitor of PD-1 are administered simultaneously, such as in the same composition. In some embodiments, the activated T cells and the inhibitor of PD-1 are administered sequentially. In some embodiments, the interval between the administration of the dendritic cells and the administration of the activated T cells is about 7 days to about 21 days (such as about 7 days to about 14 days, about 14 days to about 21 days, about 10 days or about 14 days). In some embodiments, the dendritic cells loaded with the plurality of tumor antigen peptides are administered subcutaneously. In some embodiments, the dendritic cells loaded with the plurality of tumor antigen peptides are administered for at least three times. In some embodiments, the activated T cells are administered intravenously. In some embodiments, the activated T cells are administered for at least three times. In some embodiments, the co-culturing is for about 7 days to about 21 days (such as about 7 days to about 14 days, about 14 days to about 21 days, or about 10 days). In some embodiments, the co-culturing further comprises contacting the activated T cells with a plurality of cytokines (such as IL-2, IL-7, IL-15, IL-21, or any combination thereof) and optionally an anti-CD3 antibody. In some embodiments, the population of non-adherent PBMCs is contacted with an immune checkpoint inhibitor (such as an inhibitor of PD-1) prior to and/or during the co-culturing. In some embodiments, the population of PBMCs is obtained from the individual being treated.

In some embodiments, there is provided a method of treating a cancer in an individual comprising: (a) contacting a population of PBMCs with a plurality of tumor antigen peptides to obtain a population of activated PBMCs; (b) administering to the individual an effective amount of the activated PBMCs; and (c) administering to the individual an effective amount of an inhibitor of PD-1. In some embodiments, the inhibitor of PD-1 is an anti-PD-1 antibody. In some embodiments, the inhibitor of PD-1 is selected from the group consisting of nivolumab, pembrolizumab, and SHR-1210. In some embodiments, the activated PBMCs and the inhibitor of PD-1 are administered simultaneously, such as in the same composition. In some embodiments, the activated PBMCs and the inhibitor of PD-1 are administered sequentially. In some embodiments, the PBMCs is contacted with the plurality of tumor antigen peptides in the presence of a composition that facilitates the uptake of the plurality of tumor antigen peptides by antigen presenting cells (such as dendritic cells) in the PBMCs. In some embodiments, the population of activated PBMCs is further contacted with IL-2. In some embodiments, the population of PBMCs is contacted with the plurality of tumor antigen peptides in the presence of an immune checkpoint inhibitor, such as an inhibitor of PD-1. In some embodiments, the activated PBMCs are administered for at least three times. In some embodiments, the interval between each administration of the activated PBMCs is about 2 weeks to about 5 months (such as about 3 months). In some embodiments, the activated PBMCs are administered intravenously. In some embodiments, the population of PBMCs is obtained from the individual being treated.

In some embodiments, there is provided a method of treating a cancer in an individual comprising: (a) optionally administering to the individual an effective amount of dendritic cells loaded with a plurality of tumor antigen peptides; (b) administering to the individual an effective amount of activated T cells, wherein the activated T cells are prepared by co-culturing a population of T cells with a population of dendritic cells loaded with the plurality of tumor antigen peptides; and (c) administering to the individual an effective amount of pembrolizumab (such as KETRUDA®). In some embodiments, the activated T cells and the pembrolizumab are administered simultaneously, such as in the same composition. In some embodiments, the activated T cells and the pembrolizumab are administered sequentially. In some embodiments, the pembrolizumab is administered intravenously (such as by infusion for over about 30 minutes). In some embodiments, the pembrolizumab is administered at about 2 mg/kg. In some embodiments, the pembrolizumab is administered about once every 3 weeks. In some embodiments, the interval between the administration of the dendritic cells and the administration of the activated T cells is about 7 days to about 21 days (such as about 7 days to about 14 days, about 14 days to about 21 days, about 10 days or about 14 days). In some embodiments, the dendritic cells loaded with the plurality of tumor antigen peptides are administered subcutaneously. In some embodiments, the dendritic cells loaded with the plurality of tumor antigen peptides are administered for at least three times. In some embodiments, the activated T cells are administered intravenously. In some embodiments, the activated T cells are administered for at least three times. In some embodiments, the population of T cells is co-cultured with the population of dendritic cells loaded with the plurality of tumor antigen peptides for about 7 days to about 21 days (such as about 7 days to about 14 days, about 14 days to about 21 days, or about 10 days). In some embodiments, the population of T cells is derived from the non-adherent portion of a population of peripheral blood mononuclear cells (PBMCs). In some embodiments, the co-culturing further comprises contacting the activated T cells with a plurality of cytokines (such as IL-2, IL-7, IL-15, IL-21, or any combination thereof) and optionally an anti-CD3 antibody. In some embodiments, the population of T cells is contacted with an immune checkpoint inhibitor (such as an inhibitor of PD-1) prior to and/or during the co-culturing. In some embodiments, the population of dendritic cells loaded with the plurality of tumor antigen peptides is prepared by contacting a population of dendritic cells with the plurality of tumor antigen peptides. In some embodiments, the population of T cells and the population of dendritic cells are derived from the same individual. In some embodiments, the population of T cells, the population of dendritic cells, the population of PBMCs, or any combination thereof is derived from the individual being treated.

In some embodiments, there is provided a method of treating a cancer in an individual, comprising: (a) inducing differentiation of a population of monocytes into a population of dendritic cells; (b) contacting the population of dendritic cells with a plurality of tumor antigen peptides to obtain a population of dendritic cells loaded with the plurality of tumor antigen peptides; (c) optionally administering to the individual an effective amount of the dendritic cells loaded with the plurality of tumor antigen peptides; (d) co-culturing the population of dendritic cells loaded with the plurality of tumor antigen peptides and a population of non-adherent PBMCs to obtain the population of activated T cells; (e) administering to the individual an effective amount of the activated T cells; and (f) administering to the individual an effective amount of pembrolizumab (such as KETRUDA®), wherein the population of monocytes and the population of non-adherent PBMCs are obtained from a population of PBMCs. In some embodiments, the activated T cells and the pembrolizumab are administered simultaneously, such as in the same composition. In some embodiments, the activated T cells and the pembrolizumab are administered sequentially. In some embodiments, the pembrolizumab is administered intravenously (such as by infusion for over about 30 minutes). In some embodiments, the pembrolizumab is administered at about 2 mg/kg. In some embodiments, the pembrolizumab is administered about once every 3 weeks. In some embodiments, the interval between the administration of the dendritic cells and the administration of the activated T cells is about 7 days to about 21 days (such as about 7 days to about 14 days, about 14 days to about 21 days, about 10 days or about 14 days). In some embodiments, the dendritic cells loaded with the plurality of tumor antigen peptides are administered subcutaneously. In some embodiments, the dendritic cells loaded with the plurality of tumor antigen peptides are administered for at least three times. In some embodiments, the activated T cells are administered intravenously. In some embodiments, the activated T cells are administered for at least three times. In some embodiments, the co-culturing is for about 7 days to about 21 days (such as about 7 days to about 14 days, about 14 days to about 21 days, or about 10 days). In some embodiments, the co-culturing further comprises contacting the activated T cells with a plurality of cytokines (such as IL-2, IL-7, IL-15, IL-21, or any combination thereof) and optionally an anti-CD3 antibody. In some embodiments, the population of non-adherent PBMCs is contacted with an immune checkpoint inhibitor (such as an inhibitor of PD-1) prior to and/or during the co-culturing. In some embodiments, the population of PBMCs is obtained from the individual being treated.

In some embodiments, there is provided a method of treating a cancer in an individual comprising: (a) contacting a population of PBMCs with a plurality of tumor antigen peptides to obtain a population of activated PBMCs; (b) administering to the individual an effective amount of the activated PBMCs; and (c) administering to the individual an effective amount of pembrolizumab (such as KETRUDA®). In some embodiments, the activated PBMCs and the pembrolizumab are administered simultaneously, such as in the same composition. In some embodiments, the activated PBMCs and the pembrolizumab are administered sequentially. In some embodiments, the pembrolizumab is administered intravenously (such as by infusion for over about 30 minutes). In some embodiments, the pembrolizumab is administered at about 2 mg/kg. In some embodiments, the pembrolizumab is administered about once every 3 weeks. In some embodiments, the PBMCs is contacted with the plurality of tumor antigen peptides in the presence of a composition that facilitates the uptake of the plurality of tumor antigen peptides by antigen presenting cells (such as dendritic cells) in the PBMCs. In some embodiments, the population of activated PBMCs is further contacted with IL-2. In some embodiments, the population of PBMCs is contacted with the plurality of tumor antigen peptides in the presence of an immune checkpoint inhibitor, such as an inhibitor of PD-1. In some embodiments, the activated PBMCs are administered for at least three times. In some embodiments, the interval between each administration of the activated PBMCs is about 2 weeks to about 5 months (such as about 3 months). In some embodiments, the activated PBMCs are administered intravenously. In some embodiments, the population of PBMCs is obtained from the individual being treated.

In some embodiments, the immune checkpoint inhibitor is an inhibitor of PD-L1. In some embodiments, the immune checkpoint inhibitor is an anti-PD-L1 antibody. Exemplary anti-PD-L1 antibodies include, but are not limited to, KY-1003, MCLA-145, RG7446, BMS935559, MPDL3280A, MEDI4736, Avelumab, or STI-A1010.

Thus, in some embodiments, there is provided a method of treating a cancer in an individual comprising: (a) optionally administering to the individual an effective amount of dendritic cells loaded with a plurality of tumor antigen peptides; (b) administering to the individual an effective amount of activated T cells, wherein the activated T cells are prepared by co-culturing a population of T cells with a population of dendritic cells loaded with the plurality of tumor antigen peptides; and (c) administering to the individual an effective amount of an inhibitor of PD-L1. In some embodiments, the inhibitor of PD-L1 is an anti-PD-L1 antibody. In some embodiments, the activated T cells and the inhibitor of PD-L1 are administered simultaneously, such as in the same composition. In some embodiments, the activated T cells and the inhibitor of PD-L1 are administered sequentially. In some embodiments, the interval between the administration of the dendritic cells and the administration of the activated T cells is about 7 days to about 21 days (such as about 7 days to about 14 days, about 14 days to about 21 days, about 10 days or about 14 days). In some embodiments, the dendritic cells loaded with the plurality of tumor antigen peptides are administered subcutaneously. In some embodiments, the dendritic cells loaded with the plurality of tumor antigen peptides are administered for at least three times. In some embodiments, the activated T cells are administered intravenously. In some embodiments, the activated T cells are administered for at least three times. In some embodiments, the population of T cells is co-cultured with the population of dendritic cells loaded with the plurality of tumor antigen peptides for about 7 days to about 21 days (such as about 7 days to about 14 days, about 14 days to about 21 days, or about 10 days). In some embodiments, the population of T cells is derived from the non-adherent portion of a population of peripheral blood mononuclear cells (PBMCs). In some embodiments, the co-culturing further comprises contacting the activated T cells with a plurality of cytokines (such as IL-2, IL-7, IL-15, IL-21, or any combination thereof) and optionally an anti-CD3 antibody. In some embodiments, the population of T cells is contacted with an immune checkpoint inhibitor (such as an inhibitor of PD-L1) prior to and/or during the co-culturing. In some embodiments, the population of dendritic cells loaded with the plurality of tumor antigen peptides is prepared by contacting a population of dendritic cells with the plurality of tumor antigen peptides. In some embodiments, the population of T cells and the population of dendritic cells are derived from the same individual. In some embodiments, the population of T cells, the population of dendritic cells, the population of PBMCs, or any combination thereof is derived from the individual being treated.

In some embodiments, there is provided a method of treating a cancer in an individual, comprising: (a) inducing differentiation of a population of monocytes into a population of dendritic cells; (b) contacting the population of dendritic cells with a plurality of tumor antigen peptides to obtain a population of dendritic cells loaded with the plurality of tumor antigen peptides; (c) optionally administering to the individual an effective amount of the dendritic cells loaded with the plurality of tumor antigen peptides; (d) co-culturing the population of dendritic cells loaded with the plurality of tumor antigen peptides and a population of non-adherent PBMCs to obtain the population of activated T cells; (e) administering to the individual an effective amount of the activated T cells; and (f) administering to the individual an effective amount of an inhibitor of PD-L1, wherein the population of monocytes and the population of non-adherent PBMCs are obtained from a population of PBMCs.

In some embodiments, the inhibitor of PD-L1 is an anti-PD-L1 antibody. In some embodiments, the activated T cells and the inhibitor of PD-L1 are administered simultaneously, such as in the same composition. In some embodiments, the activated T cells and the inhibitor of PD-L1 are administered sequentially. In some embodiments, the interval between the administration of the dendritic cells and the administration of the activated T cells is about 7 days to about 21 days (such as about 7 days to about 14 days, about 14 days to about 21 days, about 10 days or about 14 days). In some embodiments, the dendritic cells loaded with the plurality of tumor antigen peptides are administered subcutaneously. In some embodiments, the dendritic cells loaded with the plurality of tumor antigen peptides are administered for at least three times. In some embodiments, the activated T cells are administered intravenously. In some embodiments, the activated T cells are administered for at least three times. In some embodiments, the co-culturing is for about 7 days to about 21 days (such as about 7 days to about 14 days, about 14 days to about 21 days, or about 10 days). In some embodiments, the co-culturing further comprises contacting the activated T cells with a plurality of cytokines (such as IL-2, IL-7, IL-15, IL-21, or any combination thereof) and optionally an anti-CD3 antibody. In some embodiments, the population of non-adherent PBMCs is contacted with an immune checkpoint inhibitor (such as an inhibitor of PD-L1) prior to and/or during the co-culturing. In some embodiments, the population of PBMCs is obtained from the individual being treated.

In some embodiments, there is provided a method of treating a cancer in an individual comprising: (a) contacting a population of PBMCs with a plurality of tumor antigen peptides to obtain a population of activated PBMCs; (b) administering to the individual an effective amount of the activated PBMCs; and (c) administering to the individual an effective amount of an inhibitor of PD-L1. In some embodiments, the inhibitor of PD-L1 is an anti-PD-L1 antibody. In some embodiments, the activated PBMCs and the inhibitor of PD-L1 are administered simultaneously, such as in the same composition. In some embodiments, the activated PBMCs and the inhibitor of PD-L1 are administered sequentially. In some embodiments, the PBMCs is contacted with the plurality of tumor antigen peptides in the presence of a composition that facilitates the uptake of the plurality of tumor antigen peptides by antigen presenting cells (such as dendritic cells) in the PBMCs. In some embodiments, the population of activated PBMCs is further contacted with IL-2. In some embodiments, the population of PBMCs is contacted with the plurality of tumor antigen peptides in the presence of an immune checkpoint inhibitor, such as an inhibitor of PD-L1. In some embodiments, the activated PBMCs are administered for at least three times. In some embodiments, the interval between each administration of the activated PBMCs is about 2 weeks to about 5 months (such as about 3 months). In some embodiments, the activated PBMCs are administered intravenously. In some embodiments, the population of PBMCs is obtained from the individual being treated.

In some embodiments, the immune checkpoint inhibitor is an inhibitor of CTLA-4. In some embodiments, the immune checkpoint inhibitor is an anti-CTLA-4 antibody. Exemplary anti-CTLA-4 antibodies include, but are not limited to, Ipilimumab, Tremelimumab, and KAHR-102. In some embodiments, the immune checkpoint inhibitor is Ipilimumab (for example, YERVOY®).

Thus, in some embodiments, there is provided a method of treating a cancer in an individual comprising: (a) optionally administering to the individual an effective amount of dendritic cells loaded with a plurality of tumor antigen peptides; (b) administering to the individual an effective amount of activated T cells, wherein the activated T cells are prepared by co-culturing a population of T cells with a population of dendritic cells loaded with the plurality of tumor antigen peptides; and (c) administering to the individual an effective amount of an inhibitor of CTLA-4. In some embodiments, the inhibitor of CTLA-4 is an anti-CTLA-4 antibody, such as Ipilimumab. In some embodiments, the activated T cells and the inhibitor of CTLA-4 are administered simultaneously, such as in the same composition. In some embodiments, the activated T cells and the inhibitor of CTLA-4 are administered sequentially. In some embodiments, the interval between the administration of the dendritic cells and the administration of the activated T cells is about 7 days to about 21 days (such as about 7 days to about 14 days, about 14 days to about 21 days, about 10 days or about 14 days). In some embodiments, the dendritic cells loaded with the plurality of tumor antigen peptides are administered subcutaneously. In some embodiments, the dendritic cells loaded with the plurality of tumor antigen peptides are administered for at least three times. In some embodiments, the activated T cells are administered intravenously. In some embodiments, the activated T cells are administered for at least three times. In some embodiments, the population of T cells is co-cultured with the population of dendritic cells loaded with the plurality of tumor antigen peptides for about 7 days to about 21 days (such as about 7 days to about 14 days, about 14 days to about 21 days, or about 10 days). In some embodiments, the population of T cells is derived from the non-adherent portion of a population of peripheral blood mononuclear cells (PBMCs). In some embodiments, the co-culturing further comprises contacting the activated T cells with a plurality of cytokines (such as IL-2, IL-7, IL-15, IL-21, or any combination thereof) and optionally an anti-CD3 antibody. In some embodiments, the population of T cells is contacted with an immune checkpoint inhibitor (such as an inhibitor of CTLA-4) prior to and/or during the co-culturing. In some embodiments, the population of dendritic cells loaded with the plurality of tumor antigen peptides is prepared by contacting a population of dendritic cells with the plurality of tumor antigen peptides. In some embodiments, the population of T cells and the population of dendritic cells are derived from the same individual. In some embodiments, the population of T cells, the population of dendritic cells, the population of PBMCs, or any combination thereof is derived from the individual being treated.

In some embodiments, there is provided a method of treating a cancer in an individual, comprising: (a) inducing differentiation of a population of monocytes into a population of dendritic cells; (b) contacting the population of dendritic cells with a plurality of tumor antigen peptides to obtain a population of dendritic cells loaded with the plurality of tumor antigen peptides; (c) optionally administering to the individual an effective amount of the dendritic cells loaded with the plurality of tumor antigen peptides; (d) co-culturing the population of dendritic cells loaded with the plurality of tumor antigen peptides and a population of non-adherent PBMCs to obtain the population of activated T cells; (e) administering to the individual an effective amount of the activated T cells; and (f) administering to the individual an effective amount of an inhibitor of CTLA-4, wherein the population of monocytes and the population of non-adherent PBMCs are obtained from a population of PBMCs. In some embodiments, the inhibitor of CTLA-4 is an anti-CTLA-4 antibody, such as Ipilimumab. In some embodiments, the activated T cells and the inhibitor of CTLA-4 are administered simultaneously, such as in the same composition. In some embodiments, the activated T cells and the inhibitor of CTLA-4 are administered sequentially. In some embodiments, the interval between the administration of the dendritic cells and the administration of the activated T cells is about 7 days to about 21 days (such as about 7 days to about 14 days, about 14 days to about 21 days, about 10 days or about 14 days). In some embodiments, the dendritic cells loaded with the plurality of tumor antigen peptides are administered subcutaneously. In some embodiments, the dendritic cells loaded with the plurality of tumor antigen peptides are administered for at least three times. In some embodiments, the activated T cells are administered intravenously. In some embodiments, the activated T cells are administered for at least three times. In some embodiments, the co-culturing is for about 7 days to about 21 days (such as about 7 days to about 14 days, about 14 days to about 21 days, or about 10 days). In some embodiments, the co-culturing further comprises contacting the activated T cells with a plurality of cytokines (such as IL-2, IL-7, IL-15, IL-21, or any combination thereof) and optionally an anti-CD3 antibody. In some embodiments, the population of non-adherent PBMCs is contacted with an immune checkpoint inhibitor (such as an inhibitor of CTLA-4) prior to and/or during the co-culturing. In some embodiments, the population of PBMCs is obtained from the individual being treated.

In some embodiments, there is provided a method of treating a cancer in an individual comprising: (a) contacting a population of PBMCs with a plurality of tumor antigen peptides to obtain a population of activated PBMCs; (b) administering to the individual an effective amount of the activated PBMCs; and (c) administering to the individual an effective amount of an inhibitor of CTLA-4. In some embodiments, the inhibitor of CTLA-4 is an anti-CTLA-4 antibody, such as Ipilimumab. In some embodiments, the activated PBMCs and the inhibitor of CTLA-4 are administered simultaneously, such as in the same composition. In some embodiments, the activated PBMCs and the inhibitor of CTLA-4 are administered sequentially. In some embodiments, the PBMCs is contacted with the plurality of tumor antigen peptides in the presence of a composition that facilitates the uptake of the plurality of tumor antigen peptides by antigen presenting cells (such as dendritic cells) in the PBMCs. In some embodiments, the population of activated PBMCs is further contacted with IL-2. In some embodiments, the population of PBMCs is contacted with the plurality of tumor antigen peptides in the presence of an immune checkpoint inhibitor, such as an inhibitor of CTLA-4. In some embodiments, the activated PBMCs are administered for at least three times. In some embodiments, the interval between each administration of the activated PBMCs is about 2 weeks to about 5 months (such as about 3 months). In some embodiments, the activated PBMCs are administered intravenously. In some embodiments, the population of PBMCs is obtained from the individual being treated.

In some embodiments, the activated T cells (or the activated PBMCs) and the immune checkpoint inhibitor are administered simultaneously. In some embodiments, the activated T cells (or the activated PBMCs) and the immune checkpoint inhibitor are administered in a single composition. In some embodiments, the immune checkpoint inhibitor is present in the co-culture. In some embodiments, the activated T cells (or the activated PBMCs) and the immune checkpoint inhibitor are admixed prior to (such as immediately prior to) the administration. In some embodiments, the activated T cells (or the activated PBMCs) and the immune checkpoint inhibitor are administered simultaneously via separate compositions.

In some embodiments, the activated T cells (or the activated PBMCs) and the immune checkpoint inhibitor are administered sequentially. In some embodiments, the immune checkpoint inhibitor is administered prior to the administration of the activated T cells (or the activated PBMCs). In some embodiments, the immune checkpoint inhibitor is administered after the administration of the activated T cells (or the activated PBMCs).

Plurality of Tumor Antigen Peptides

All of the MASCT methods (including PBMC-based MASCT methods) and cell preparation methods described herein use a plurality of tumor antigen peptides (including neoantigen peptides) to prepare APCs (such as dendritic cells) and activated T cells, or activated PBMCs that can trigger specific T cell response ex vivo and in vivo.

In some embodiments, each tumor antigen peptide in the MASCT method comprises about any of 1, 2, 3, 4, 5, or 10 epitopes from a single protein antigen (including a neoantigen). In some embodiments, each tumor antigen peptide in the plurality of tumor antigen peptides comprises at least one epitope recognizable by a T cell receptor. In some embodiments, the plurality of tumor antigen peptides comprises at least one tumor antigen peptide that comprises at least 2 epitopes from a single protein antigen. The tumor antigen peptide can be a naturally derived peptide fragment from a protein antigen containing one or more epitopes, or an artificially designed peptide with one or more natural epitope sequences, wherein a linker peptide can optionally be placed in between adjacent epitope sequences. In some preferred embodiments, the epitopes contained in the same tumor antigen peptide are derived from the same protein antigen.

The tumor antigen peptide (including neoantigen peptide) may contain at least one MHC-I epitope, at least one MHC-II epitope, or both MHC-I epitope(s) and MHC-II epitope(s). In some embodiments, the plurality of tumor antigen peptides comprises at least one peptide comprising an MHC-I epitope. In some embodiments, the plurality of tumor antigen peptides comprises at least one peptide comprising an MHC-II epitope. In some embodiments, at least one tumor antigen peptide in the plurality of tumor antigen peptides comprises both MHC-I and MHC-II epitopes.

Special design strategies can be applied to the sequence of the tumor antigen peptides (including neoantigen peptides) in order to optimize the immune response to dendritic cells loaded with the tumor antigen peptides. Typically, a peptide longer than the exact epitope peptide can increase uptake of the peptide into antigen presenting cells (such as dendritic cells). In some embodiments, an MHC-I or MHC-II epitope sequence is extended at the N terminus or the C terminus or both termini according to the natural sequence of the protein harboring the epitope to obtain an extended sequence, wherein the extended sequence is amenable for presentation by both class I and class II MHC molecules, and by different subtypes of MHC molecules in different individuals. In some embodiments, the epitope sequence is extended at one or both termini by about any of 1, 2, 3, 4, 5, 6, 7, 8, 9, 10, 12, 15, or 20 amino acid residues to generate the extended epitope. In some embodiments, the peptides comprising an MHC-I or MHC-II epitope further comprise additional amino acids flanking the epitope at the N-terminus, the C-terminus, or both. In some embodiments, each tumor antigen peptide in the plurality of tumor antigen peptides is about any of 10, 15, 20, 25, 30, 35, 40, 45, 50, 60, 70, 80, 90, or 100 amino acids long. Different tumor antigen peptides in the plurality of tumor antigen peptides may have the same length, or different lengths. In some embodiments, the plurality of tumor antigen peptides is each about 20-40 amino acids long.

In some embodiments, the amino acid sequences of one or more epitope peptides used to design a tumor antigen peptide in the present application are based on sequences known in the art or available in public databases, such as the Peptide Database (van der Bruggen P et al. (2013) "Peptide database: T cell-defined tumor antigens. *Cancer Immunity*. URL: www.cancerimmunity.org/peptide/). In some embodiments, the amino acid sequences of the one or more epitope peptides are selected from the group consisting of SEQ ID NOs: 1-35.

In some embodiments, the amino acid sequences of one or more epitope peptides are predicted based on the sequence of the antigen protein (including neoantigens) using a bioinformatics tool for T cell epitope prediction. Exemplary bioinformatics tools for T cell epitope prediction are known in the art, for example, see Yang X. and Yu X. (2009) "An introduction to epitope prediction methods and software" *Rev. Med. Virol.* 19(2): 77-96. In some embodiments, the sequence of the antigen protein is known in the art or available in public databases. In some embodiments, the sequence of the antigen protein (including neoantigens) is determined by sequencing a sample (such as a tumor sample) of the individual being treated.

The present invention contemplates tumor antigen peptides derived from any tumor antigens and epitopes known in the art, including neoantigens and neoepitopes, or specially developed or predicted using bioinformatics tools by the inventors.

In some embodiments, the plurality of tumor antigen peptides comprises a first core group of general tumor antigen peptides. In some embodiments, the plurality of tumor antigen peptides further comprises a second group of cancer-type specific antigen peptides. In some embodiments, the plurality of tumor antigen peptides comprises one or more neoantigen peptides. In some embodiments, neoantigen peptides are cancer-type specific antigen peptides. In some embodiments, the plurality of tumor antigen peptides consists of the first core group of general tumor antigen peptides. In some embodiments, the plurality of tumor antigen peptides consists of the first core group of general tumor antigen peptides and the second group of cancer-type specific antigen peptides. In some embodiments, the plurality of tumor antigen peptides consists of neoantigen peptides only. In some embodiments, the plurality of tumor antigen peptides comprises a first core group of general tumor antigen peptides and one or more neoantigen peptides. In some embodiments, the plurality of tumor antigen peptides comprises a first core group of general tumor antigen peptides, a second group of cancer-type specific antigen peptides, and one or more neoantigen peptides.

The first core group of general tumor antigen peptides is derived from tumor antigens commonly expressed or overexpressed on the surface of a variety of cancers of different types. Therefore, the first core group of general tumor antigen peptides is useful to prepare dendritic cells, or activated T cells used in any of the MASCT methods (including PBMC-based MASCT methods), or in other treatment methods or cell preparation methods described herein to treat individuals with different cancer types. For example, in some embodiments, the first core group of general tumor antigen peptides is useful for methods described herein for treating a variety of cancers, such as lung cancer, colon cancer, gastric cancer, prostate cancer, melanoma, lymphoma, pancreatic cancer, ovarian cancer, breast cancer, glioma, esophageal cancer, nasopharyngeal carcinoma, cervical cancer, renal carcinoma, or hepatocellular carcinoma. Exemplary tumor antigen peptides of the first core group include, but are not limited to, peptides derived from hTERT, p53, Survivin, NY-ESO-1, CEA, CCND1, MET, RGS5, MMP7, VEGFR, and CDCA1. The first core group may comprise peptides derived from more than about any of 1, 2, 3, 4, 5, 6, 7, 8, 9, 10, 11, 12, 13, 14, 15, 16, 17, 18, 19, 20, 22, 25, 30, 40, or 50 tumor antigens. The first core group may comprise about any of 1, 2, 3, 4, 5, 6, 7, 8, 9, 10, 11, 12, 13, 14, 15, 16, 17, 18, 19, 20, 22, 25, 30, 40, or 50 general tumor antigen peptides. In some embodiments, the first core group comprises more than one general tumor antigen peptides. In some embodiments, the first core group comprises about 10 to about 20 general tumor antigen peptides. In some embodiments, the first core group comprises general tumor antigen peptides having more than one epitopes selected from the group consisting of SEQ ID NOs: 1-24.

The second group of cancer-type specific antigen peptides is derived from tumor antigens that are expressed or over-expressed only in one or a limited number of cancer types. Therefore, the second group of cancer-type specific antigen peptides is useful to prepare dendritic cells, activated T cells used in any of the MASCT methods, or in other treatment methods or cell preparation methods described herein, to treat individuals with a particular type of cancer. Exemplary cancer-type specific antigen peptides for treating hepatocellular carcinoma (HCC) include, but are not limited to, peptides derived from AFP, and GPC3. In some embodiments, one or more cancer-specific antigen peptide is a virus-specific antigen peptide derived from a virus that can induce cancer, or relates to cancer development in the individual when infecting the individual. In some embodiments, the virus-specific antigen peptide is specific to the subtype of the virus infecting the individual. Exemplary virus-specific antigen peptides for treating an HCC patient with concurrent infection of HBV include, but are not limited to, peptides derived from HBV core antigen, and HBV DNA polymerase. In some embodiments, the virus-specific antigen peptides comprise at least one epitope selected from the group consisting of SEQ ID NOs: 31-35. In some embodiments, the second group comprises virus-specific antigen peptides derived from HBV antigens, wherein the method is to treat hepatocellular carcinoma in an individual. In some embodiments, the second group comprises virus-specific antigen peptides derived from HPV antigens, wherein the method is to treat cervical cancer in an individual. In some embodiments, the second group comprises virus-specific antigen peptides derived from EBV antigens, wherein the method is to treat nasopharyngeal carcinoma in an individual. The second group of cancer-type specific antigen peptides may comprise peptides derived from more than about any of 0, 1, 2, 3, 4, 5, 6, 7, 8, 9, 10, 11, 12, 13, 14, 15, 16, 17, 18, 19, 20, 22, 25, 30, 40, or 50 cancer-type specific antigens. The second group of cancer-type specific antigen peptides may comprise more than about any of 0, 1, 2, 3, 4, 5, 6, 7, 8, 9, 10, 11, 12, 13, 14, 15, 16, 17, 18, 19, 20, 22, 25, 30, 40, or 50 cancer-type specific antigen peptides. In some embodiments, the second group comprises more than one cancer-type specific antigen peptides. In some embodiments, the second group comprises about 1 to about 10 cancer-type specific antigen peptides. In some embodiments, the second group comprises cancer-type specific antigen peptides comprising at least one epitope selected from the group consisting of SEQ ID NOs: 25-35, wherein the cancer is hepatocellular carcinoma. In some embodiments, the type of cancer targeted by the cancer-type specific antigen peptides is selected from the group consisting essentially of hepatocellular carcinoma, cervical carcinoma, nasopharyngeal carcinoma, breast cancer, and lymphoma.

In some embodiments, the plurality of tumor antigen peptides comprises one or more (such as any of 1, 2, 3, 4, 5, 6, 7, 8, 9, 10 or more) neoantigen peptides. The neoantigen peptides are derived from neoantigens. Neoantigens are newly acquired and expressed antigens present in tumor cells of the individual, such as the individual being treated for cancer. In some embodiments, neoantigens are derived from mutant protein antigens that are only present in cancer cells, but absent in normal cells. Neoantigens may be uniquely present in the tumor cells (such as all tumor cells or a portion of tumor cells) of the individual being treated for cancer, or present in individuals having similar types of cancer as the individual being treated. In some embodiments, the neoantigen is a clonal neoantigen. In some embodiments, the neoantigen is a subclonal neoantigen. In some embodiments, the neoantigen is present in at least about any of 10%, 20%, 30%, 40%, 50%, 60%, 70%, 80%, 90%, 95% or more tumor cells in the individual. In some embodiments, the neoantigen peptide comprises an MHC-I restricted neoepitope. In some embodiments, the neoantigen peptide comprises an MHC-II restricted neoepitope. In some embodiments, the neoantigen peptide is designed to facilitate presentation of the neoepitope by both class I and class II MHC molecules, for example, by extending the neoepitope at both the N- and the C-termini. Exemplary neoantigen peptides include, but are not limited to, neoepitope derived from mutant KRAS (e.g., KRAS$^{G12A}$), PARP4 (e.g., PARP4$^{T1170I}$), MLL3 (e.g., MLL3$^{C988F}$), and MTHFR (e.g., MTHFR$^{A222V}$). In some embodiments, the neoantigen peptide comprises an epitope having a point mutation in a sequence selected from the group consisting of SEQ ID Nos: 41-45. In some embodiments, the neoantigen peptide comprises an epitope selected from the group consisting of SEQ ID NOs: 36-40.

Neoantigen peptides can be selected based on the genetic profile of one or more tumor sites of the individual being treated. In some embodiments, the genetic profile of the tumor sample comprises sequence information of the full genome. In some embodiments, the genetic profile of the tumor sample comprises sequence information of the exome. In some embodiments, the genetic profile of the tumor sample comprises sequence information of cancer-associated genes.

Neoantigen peptides suitable for use in the present invention may be derived from any mutant proteins, such as those encoded by mutant cancer-associated genes, in the tumor cells. In some embodiments, the neoantigen peptide comprises a single neoepitope derived from a cancer-associated gene. In some embodiments, the neoantigen peptide comprises more than one (such as 2, 3, or more) neoepitope derived from a cancer-associated gene. In some embodiments, the neoantigen peptide comprises more than one (such as 2, 3, or more) neoepitope derived from more than one (such as 2, 3, or more) cancer-associated genes. In some embodiments, the plurality of tumor antigens comprises a plurality of neoantigen peptides derived from a single cancer-associated gene. In some embodiments, the plurality of tumor antigens comprises a plurality of neoantigen peptides derived from more than one (such as any of 2, 3, 4, 5, or more) cancer-associated genes.

Cancer-associated genes are genes that are overexpressed or only expressed in cancer cells, but not normal cells. Exemplary cancer-associated genes include, but are not limited to, ABL1, AKT1, AKT2, AKT3, ALK, ALOX12B, APC, AR, ARAF, ARID1A, ARID1B, ARID2, ASXL1, ATM, ATRX, AURKA, AURKB, AXL, B2M, BAP1, BCL2, BCL2L1, BCL2L12, BCL6, BCOR, BCORL1, BLM, BMPR1A, BRAF, BRCA1, BRCA2, BRD4, BRIP1, BUB1B, CADM2, CARD11, CBL, CBLB, CCND1, CCND2, CCND3, CCNE1, CD274, CD58, CD79B, CDC73, CDH1, CDK1, CDK2, CDK4, CDK5, CDK6, CDK9, CDKN1A, CDKN1B, CDKN1C, CDKN2A, CDKN2B, CDKN2C, CEBPA, CHEK2, CIITA, CREBBP, CRKL, CRLF2, CRTC1, CRTC2, CSF1R, CSF3R, CTNNB1, CUX1, CYLD, DDB2, DDR2, DEPDC5, DICER1, DIS3, DMD, DNMT3A, EED, EGFR, EP300, EPHA3, EPHA5, EPHA7, ERBB2, ERBB3, ERBB4, ERCC2, ERCC3, ERCC4, ERCC5, ESR1, ETV1, ETV4, ETV5, ETV6, EWSR1, EXT1, EXT2, EZH2, FAM46C, FANCA, FANCC, FANCD2, FANCE, FANCF, FANCG, FAS, FBXW7, FGFR1, FGFR2, FGFR3, FGFR4, FH, FKBP9, FLCN, FLT1, FLT3, FLT4, FUS, GATA3, GATA4, GATA6, GLI1, GLI2, GLI3, GNA11, GNAQ, GNAS, GNB2L1, GPC3, GSTM5, H3F3A, HNF1A, HRAS, ID3, IDH1, IDH2, IGF1R, IKZF1, IKZF3, INSIG1, JAK2, JAK3, KCNIP1, KDM5C, KDM6A, KDM6B, KDR, KEAP1, KIT, KRAS, LINC00894, LMO1, LMO2, LMO3, MAP2K1, MAP2K4, MAP3K1, MAPK1, MCL1, MDM2, MDM4, MECOM, MEF2B, MEN1, MET, MITF, MLH1, MLL (KMT2A), MLL2 (KTM2D), MPL, MSH2, MSH6, MTOR, MUTYH, MYB, MYBL1, MYC, MYCL1 (MYCL), MYCN, MYD88, NBN, NEGR1, NF1, NF2, NFE2L2, NFKBIA, NFKBIZ, NKX2-1, NOTCH1, NOTCH2, NPM1, NPRL2, NPRL3, NRAS, NTRK1, NTRK2, NTRK3, PALB2, PARK2, PAX5, PBRM1, PDCD1LG2, PDGFRA, PDGFRB, PHF6, PHOX2B, PIK3C2B, PIK3CA, PIK3R1, PIM1, PMS1, PMS2, PNRC1, PRAME, PRDM1, PRF1, PRKARIA, PRKCI, PRKCZ, PRKDC, PRPF40B, PRPF8, PSMD13, PTCH1, PTEN, PTK2, PTPN11, PTPRD, QKI, RAD21, RAF1, RARA, RB1, RBL2, RECQL4, REL, RET, RFWD2, RHEB, RHPN2, ROS1, RPL26, RUNX1, SBDS, SDHA, SDHAF2, SDHB, SDHC, SDHD, SETBP1, SETD2, SF1, SF3B1, SH2B3, SLITRK6, SMAD2, SMAD4, SMARCA4, SMARCB1, SMC1A, SMC3, SMO, SOCS1, SOX2. SOX9, SQSTM1, SRC, SRSF2, STAG1, STAG2, STAT3, STAT6, STKI 1, SUFU, SUZ12, SYK, TCF3, TCF7L1, TCF7L2, TERC, TERT, TET2, TLR4, TNFAIP3, TP53, TSC1, TSC2, U2AF1, VHL, WRN, WT1, XPA, XPC, XPO1, ZNF217, ZNF708, and ZRSR2.

In some embodiments, the plurality of tumor antigen peptides comprises at least one (such as at least about any of 1, 5, 10, 15, 20, 25, 30, 35, or 40) epitope selected from the group consisting of SEQ ID NOs: 1-40. In some embodiments, the plurality of tumor antigen peptides comprises at least one (such as at least about any of 1, 5, 10, 15, 20, or 24) epitope selected from the group consisting of SEQ ID NOs: 1-24. In some embodiments, the plurality of tumor antigen peptides comprises at least one (such as about any of 1, 2, 3, 4, 5, or 6) epitope selected from the group consisting of SEQ ID NOs:25-30. In some embodiments, the plurality of tumor antigen peptides comprises at least one (such as about any of 1, 2, 3, 4, or 5) epitope selected from the group consisting of SEQ ID NOs:31-35. In some embodiments, the plurality of tumor antigen peptides comprises at least one (such as about any of 1, 2, 3, 4, or 5) epitope selected from the group consisting of SEQ ID NOs:36-40 In some embodiments, the plurality of tumor antigen peptides comprises at least one (such as at least about any of 1, 2, 3, 4, 5, 6, 7, 8, 9, or 10) of the general tumor antigen peptides in FIG. 2B, or 2C. In some embodiments, the plurality of tumor antigen peptides comprises at least one (such as at least about any of 1, 2, 3, 4, or 5) neoantigen peptide in FIG. 29A. In some embodiments, the plurality of tumor antigen peptides comprises at least one (such as at least about any of 1, 2, 3, 4, 5, 6, 7, 8, 9, 10, 11, 12, 13, 14, or more) tumor antigen peptide in FIG. 2B, 2C, or 29A. In some embodiments, the plurality of tumor antigen peptides comprises at least one (such as at least about any of 1, 2, 3, 4, 5, 6, 7, 8, 9, 10, 11, 12, 13, 14, or more) tumor antigen peptide each comprising one or more epitopes encoded by a cancer-associated gene selected from the group consisting of hTERT, p53, Survivin, NY-ESO-1, CEA, CCND1, MET, RGS5, MMP7, VEGFR, AFP, GPC3, HBVc, HBVp, CDCA, KRAS, PARP4, MLL3, and MTHFR.

In some embodiments, the plurality of tumor antigen peptides comprises at least 10 tumor antigen peptides. In some embodiments, each of the at least 10 tumor antigen peptides comprises at least one epitope selected from the group consisting of SEQ ID NOs: 1-40. In some embodiments, each of the at least 10 tumor antigen peptides comprises at least one epitope selected from the group consisting of SEQ ID NOs: 1-24. In some embodiments, the plurality of tumor antigen peptides comprises at least 10 tumor antigen peptides selected from the group consisting of the tumor antigen peptides in FIG. 2B. In some embodiments, the plurality of tumor antigen peptides comprises at least 10 tumor antigen peptides selected from the group consisting of the tumor antigen peptides in 2C. In some embodiments, the plurality of tumor antigen peptides comprises at least one neoantigen peptide in FIG. 29A.

In some embodiments, there is provided a composition comprising at least 10 tumor antigen peptides, wherein each of the at least 10 tumor antigen peptides comprises at least one epitope selected from the group consisting of SEQ ID NOs: 1-40. In some embodiments, there is provided a composition comprising at least 10 tumor antigen peptides, wherein each of the at least 10 tumor antigen peptides comprising at least one epitope selected from the group consisting of SEQ ID NOs: 1-24. In some embodiments, there is provided a composition comprising at least 10 tumor antigen peptides selected from the group consisting of the tumor antigen peptides in FIG. 2B. In some embodiments, there is provided a composition comprising at least 10 tumor antigen peptides selected from the group consisting of the tumor antigen peptides in FIG. 2C and FIG. 29A. In some embodiments, there is provided a composition comprising at least 10 tumor antigen peptides each comprising an epitope encoded by a cancer-associated gene selected from the group consisting of hTERT, p53, Survivin, NY-ESO-1, CEA, CCND1, MET, RGS5, MMP7, VEGFR, AFP, GPC3, HBVc, HBVp, CDCA, KRAS, PARP4, MLL3, and MTHFR.

In some embodiments, there is provided an isolated population of dendritic cells loaded with a plurality of tumor antigen peptides prepared by contacting a population of dendritic cells with a plurality of tumor antigen peptides, wherein the plurality of tumor antigen peptides comprises at least 10 tumor antigen peptides. In some embodiments, the plurality of tumor antigen peptides comprises at least 10 tumor antigen peptides comprising a first core group of general tumor antigen peptides and optionally a second group of cancer-type specific antigen peptides. In some embodiments, the plurality of tumor antigen peptides comprises one or more neoantigen peptides. In some embodiments, each of the at least 10 tumor antigen peptides comprises at least one epitope selected from the group consisting of SEQ ID NOs: 1-40. In some embodiments, the plurality of tumor antigen peptides comprises at least 10 tumor antigen peptides selected from the group consisting of the tumor antigen peptides in FIG. 2C and FIG. 29A. In some embodiments, the plurality of tumor antigen peptides comprises at least 10 tumor antigen peptides each comprising one or more epitopes encoded by a cancer-associated gene selected from the group consisting of hTERT, p53, Survivin, NY-ESO-1, CEA, CCND1, MET, RGS5, MMP7, VEGFR, AFP, GPC3, HBVc, HBVp, CDCA, KRAS, PARP4, MLL3, and MTHFR.

In some embodiments, there is provided a method of preparing a population of activated T cells, comprising co-culturing a population of T cells with a population of dendritic cells loaded with a plurality of tumor antigen peptides, wherein the plurality of tumor antigen peptides comprises at least 10 tumor antigen peptides. In some embodiments, there is provided an isolated population of activated T cells prepared by co-culturing a population of T cells with a population of dendritic cells loaded with a plurality of tumor antigen peptides, wherein the plurality of tumor antigen peptides comprises at least 10 tumor antigen peptides. In some embodiments, the plurality of tumor antigen peptides comprises at least 10 tumor antigen peptides comprising a first core group of general tumor antigen peptides and optionally a second group of cancer-type specific antigen peptides. In some embodiments, the plurality of tumor antigen peptides comprises one or more neoantigen peptides. In some embodiments, each of the at least 10 tumor antigen peptides comprises at least one epitope selected from the group consisting of SEQ ID NOs: 1-40. In some embodiments, the plurality of tumor antigen peptides comprises at least 10 tumor antigen peptides selected from the group consisting of the tumor antigen peptides in FIG. 2C and FIG. 29A. In some embodiments, the plurality of tumor antigen peptides comprises at least 10 tumor antigen peptides each comprising one or more epitopes encoded by a cancer-associated gene selected from the group consisting of hTERT, p53, Survivin, NY-ESO-1, CEA, CCND1, MET, RGS5, MMP7, VEGFR, AFP, GPC3, HBVc, HBVp, CDCA, KRAS, PARP4, MLL3, and MTHFR.

In some embodiments, there is provided a method of preparing a population of activated T cells, comprising: (a) inducing differentiation of a population of monocytes into a population of dendritic cells; (b) contacting the population of dendritic cells with a plurality of tumor antigen peptides to obtain a population of dendritic cells loaded with the plurality of tumor antigen peptides; (c) co-culturing the population of dendritic cells loaded with the plurality of tumor antigen peptides and a population of non-adherent PBMCs to obtain the population of activated T cells, wherein the population of monocytes and the population of non-adherent PBMCs are obtained from a population of PBMCs (such as from the individual), and wherein the plurality of tumor antigen peptides comprises at least 10 tumor antigen peptides. In some embodiments, there is provided an isolated population of activated T cells prepared by (a) inducing differentiation of a population of monocytes into a population of dendritic cells; (b) contacting the population of dendritic cells with a plurality of tumor antigen peptides to obtain a population of dendritic cells loaded with the plurality of tumor antigen peptides; (c) co-culturing the population of dendritic cells loaded with the plurality of tumor antigen peptides and a population of non-adherent PBMCs to obtain the population of activated T cells, wherein the population of monocytes and the population of non-adherent PBMCs are obtained from a population of PBMCs (such as from the individual), and wherein the plurality of tumor antigen peptides comprises at least 10 tumor antigen peptides. In some embodiments, the plurality of tumor antigen peptides comprises at least 10 tumor antigen peptides comprising a first core group of general tumor antigen peptides and optionally a second group of cancer-type specific antigen peptides. In some embodiments, the plurality of tumor antigen peptides comprises one or more neoantigen peptides. In some embodiments, each of the at least 10 tumor antigen peptides comprises at least one epitope selected from the group consisting of SEQ ID NOs: 1-40. In some embodiments, the plurality of tumor antigen peptides comprises at least 10 tumor antigen peptides selected from the group consisting of the tumor antigen peptides in FIG. 2C and FIG. 29A. In some embodiments, the plurality of tumor antigen peptides comprises at least 10 tumor antigen peptides each comprising one or more epitopes encoded by a cancer-associated gene selected from the group consisting of hTERT, p53, Survivin, NY-ESO-1, CEA, CCND1, MET, RGS5, MMP7, VEGFR, AFP, GPC3, HBVc, HBVp, CDCA, KRAS, PARP4, MLL3, and MTHFR.

In some embodiments, there is provided a method of treating a cancer in an individual, comprising contacting a population of PBMCs with a plurality of tumor antigen peptides to obtain a population of activated PBMCs, and administering to the individual an effective amount of the activated PBMCs, wherein the plurality of tumor antigen peptides comprises at least 10 tumor antigen peptides. In some embodiments, the population of PBMCs is contacted with the plurality of tumor antigen peptides in the presence of an immune checkpoint inhibitor, such as an inhibitor of PD-1, PD-L1, CTLA-4, IDO, TIM-3, BTLA, VISTA, and LAG-3. In some embodiments, the activated PBMCs are administered for at least three times. In some embodiments, the interval between each administration of the activated PBMCs is about 2 weeks to about 5 months (such as about 3 months). In some embodiments, the population of PBMCs is obtained from the individual being treated. In some embodiments, the method further comprises administering to the individual an effective amount of an immune checkpoint inhibitor, such as an inhibitor of PD-1, PD-L1, CTLA-4, IDO, TIM-3, BTLA, VISTA, or LAG-3. In some embodiments, the plurality of tumor antigen peptides comprises at least 10 tumor antigen peptides comprising a first core group of general tumor antigen peptides and optionally a second group of cancer-type specific antigen peptides. In some embodiments, the plurality of tumor antigen peptides comprises one or more neoantigen peptides. In some embodiments, each of the at least 10 tumor antigen peptides comprises at least one epitope selected from the group consisting of SEQ ID NOs: 1-40. In some embodiments, the plurality of tumor antigen peptides comprises at least 10 tumor antigen peptides selected from the group consisting of the tumor antigen peptides in FIG. 2C and FIG. 29A. In some embodiments, the plurality of tumor antigen peptides comprises at least 10 tumor antigen peptides each comprising one or more epitopes encoded by a cancer-associated gene selected from the group consisting of hTERT, p53, Survivin, NY-ESO-1, CEA, CCND1, MET, RGS5, MMP7, VEGFR, AFP, GPC3, HBVc, HBVp, CDCA, KRAS, PARP4, MLL3, and MTHFR.

In some embodiments, there is provided a method of treating a cancer in an individual, comprising optionally administering to the individual an effective amount of dendritic cells loaded with a plurality of tumor antigen peptides, and administering to the individual an effective amount of activated T cells, wherein the activated T cells are prepared by co-culturing (such as in the presence of an immune checkpoint inhibitor) a population of T cells with a population of dendritic cells loaded with the plurality of tumor antigen peptides, wherein the plurality of tumor antigen peptides comprises at least 10 tumor antigen peptides. In some embodiments, the population of T cells is contacted with an immune checkpoint inhibitor (such as an inhibitor of PD-1, PD-L1, or CTLA-4) prior to and/or during the co-culturing. In some embodiments, the population of dendritic cells loaded with the plurality of tumor antigen peptides is prepared by contacting a population of dendritic cells with the plurality of tumor antigen peptides. In some embodiments, the population of T cells and the population of dendritic cells are derived from the same individual. In some embodiments, the population of T cells, the population of dendritic cells, the population of PBMCs, or any combination thereof is derived from the individual being treated. In some embodiments, the method further comprises administering to the individual an effective amount of an immune checkpoint inhibitor, such as an inhibitor of PD-1, PD-L1, CTLA-4, IDO, TIM-3, BTLA, VISTA, or LAG-3. In some embodiments, the plurality of tumor antigen peptides comprises at least 10 tumor antigen peptides comprising a first core group of general tumor antigen peptides and optionally a second group of cancer-type specific antigen peptides. In some embodiments, the plurality of tumor antigen peptides comprises one or more neoantigen peptides. In some embodiments, each of the at least 10 tumor antigen peptides comprises at least one epitope selected from the group consisting of SEQ ID NOs: 1-40. In some embodiments, the plurality of tumor antigen peptides comprises at least 10 tumor antigen peptides selected from the group consisting of the tumor antigen peptides in FIG. 2C and FIG. 29A. In some embodiments, the plurality of tumor antigen peptides comprises at least 10 tumor antigen peptides each comprising one or more epitopes encoded by a cancer-associated gene selected from the group consisting of hTERT, p53, Survivin, NY-ESO-1, CEA, CCND1, MET, RGS5, MMP7, VEGFR, AFP, GPC3, HBVc, HBVp, CDCA, KRAS, PARP4, MLL3, and MTHFR.

In some embodiments, there is provided a method of treating a cancer in an individual, comprising: (a) inducing differentiation of a population of monocytes into a population of dendritic cells; (b) contacting the population of dendritic cells with a plurality of tumor antigen peptides to obtain a population of dendritic cells loaded with the plurality of tumor antigen peptides; (c) optionally administering to the individual an effective amount of the dendritic cells loaded with the plurality of tumor antigen peptides; (d) co-culturing the population of dendritic cells loaded with the plurality of tumor antigen peptides and a population of non-adherent PBMCs to obtain the population of activated T cells; and (e) administering to the individual an effective amount of the activated T cells, wherein the population of monocytes and the population of non-adherent PBMCs are obtained from a population of PBMCs (such as from the individual), and wherein the plurality of tumor antigen peptides comprises at least 10 tumor antigen peptides. In some embodiments, the population of non-adherent PBMCs is contacted with an immune checkpoint inhibitor (such as an inhibitor of PD-1, PD-L1, or CTLA-4) prior to and/or during the co-culturing. In some embodiments, the method further comprises administering to the individual an effective amount of an immune checkpoint inhibitor, such as an inhibitor of PD-1, PD-L1, CTLA-4, IDO, TIM-3, BTLA, VISTA, or LAG-3. In some embodiments, the plurality of tumor antigen peptides comprises at least 10 tumor antigen peptides comprising a first core group of general tumor antigen peptides and optionally a second group of cancer-type specific antigen peptides. In some embodiments, the plurality of tumor antigen peptides comprises one or more neoantigen peptides. In some embodiments, each of the at least 10 tumor antigen peptides comprises at least one epitope selected from the group consisting of SEQ ID NOs: 1-40. In some embodiments, the plurality of tumor antigen peptides comprises at least 10 tumor antigen peptides selected from the group consisting of the tumor antigen peptides in FIG. 2C and FIG. 29A. In some embodiments, the plurality of tumor antigen peptides comprises at least 10 tumor antigen peptides each comprising one or more epitopes encoded by a cancer-associated gene selected from the group consisting of hTERT, p53, Survivin, NY-ESO-1, CEA, CCND1, MET, RGS5, MMP7, VEGFR, AFP, GPC3, HBVc, HBVp, CDCA, KRAS, PARP4, MLL3, and MTHFR.

Precision MASCT

Further provided herein are precision MASCT methods that are customized to the individual being treated based on the genetics and therapeutic response of the individual. Any of the MASCT methods described above may be customized to provide a precision MASCT method.

The MASCT methods described herein in some embodiments are particularly suitable for a certain population of individuals, such as individuals with a low mutation load (such as in the MHC genes) in the cancer (such as all or a subset of cancer cells), and/or individuals with one or more neoantigens.

Mutation Load

In some embodiments, the MASCT methods are particularly suitable for an individual with a low total mutation load in the cancer of the individual. In some embodiments, the MASCT methods are particularly suitable for an individual with a low mutation load in the cancer-associated genes in the cancer of the individual. In some embodiments, the MASCT methods are particularly suitable for an individual with a low mutation load in immune genes related to T cell response in the cancer of the individual. In some embodiments, the MASCT methods are particularly suitable for an individual with a low mutation load in the MHC genes in the cancer of the individual. The mutation load may be mutation load in all cancer cells, or a subset of cancer cells, such as a primary or metastatic tumor site, for example, cells in a tumor biopsy sample.

Thus, in some embodiments, there is provided a method of treating a cancer in an individual, comprising: (a) optionally administering an effective amount of dendritic cells loaded with a plurality of tumor antigen peptides; and (b) administering to the individual an effective amount of activated T cells, wherein the activated T cells are prepared by co-culturing a population of T cells with the population of dendritic cells loaded with the plurality of tumor antigen peptides, and wherein the individual has a low mutation load in the cancer. In some embodiments, the interval between the administration of the dendritic cells and the administration of the activated T cells is about 7 days to about 21 days (such as about 7 days to about 14 days, about 14 days to about 21 days, about 10 days or about 14 days). In some embodiments, the dendritic cells loaded with the plurality of tumor antigen peptides are administered subcutaneously. In some embodiments, the dendritic cells loaded with the plurality of tumor antigen peptides are administered for at least three times. In some embodiments, the activated T cells are administered intravenously. In some embodiments, the activated T cells are administered for at least three times. In some embodiments, the co-culturing is for about 7 days to about 21 days (such as about 7 days to about 14 days, or about 14 days to about 21 days). In some embodiments, the population of T cell is contacted with an immune checkpoint inhibitor (such as an inhibitor of PD-1, PD-L1, or CTLA-4) prior to and/or during the co-culturing. In some embodiments, the population of dendritic cells and the population of T cells are derived from the same individual, such as the individual being treated. In some embodiments, the plurality of tumor antigen peptides comprises at least 10 tumor antigen peptides. In some embodiments, the plurality of tumor antigen peptides comprises a first core group of general tumor antigen peptides and optionally a second group of cancer-type specific antigen peptides. In some embodiments, the plurality of tumor antigen peptides comprises one or more neoantigen peptides. In some embodiments, the method further comprises administering to the individual an effective amount of an immune checkpoint inhibitor, such as an inhibitor of PD-1, PD-L1, CTLA-4, IDO, TIM-3, BTLA, VISTA, or LAG-3. In some embodiments, the mutation load of the cancer is determined by sequencing a tumor sample from the individual. In some embodiments, the individual has a low mutation load (such as no more than about 10 mutations, no mutations in B2M, and/or no mutation in the functional regions) in one or more MHC genes (such as MHC-I genes) in the cancer.

In some embodiments, there is provided a method of treating a cancer in an individual, comprising: (a) selecting the individual for the method based on the mutation load in the cancer; (b) optionally administering an effective amount of dendritic cells loaded with a plurality of tumor antigen peptides; and (c) administering to the individual an effective amount of activated T cells, wherein the activated T cells are prepared by co-culturing a population of T cells with the population of dendritic cells loaded with the plurality of tumor antigen peptides. In some embodiments, the interval between the administration of the dendritic cells and the administration of the activated T cells is about 7 days to about 21 days (such as about 7 days to about 14 days, about 14 days to about 21 days, about 10 days or about 14 days). In some embodiments, the dendritic cells loaded with the plurality of tumor antigen peptides are administered subcutaneously. In some embodiments, the dendritic cells loaded with the plurality of tumor antigen peptides are administered for at least three times. In some embodiments, the activated T cells are administered intravenously. In some embodiments, the activated T cells are administered for at least three times. In some embodiments, the co-culturing is for about 7 days to about 21 days (such as about 7 days to about 14 days, or about 14 days to about 21 days). In some embodiments, the population of T cell is contacted with an immune checkpoint inhibitor (such as an inhibitor of PD-1, PD-L1, or CTLA-4) prior to and/or during the co-culturing. In some embodiments, the population of dendritic cells and the population of T cells are derived from the same individual, such as the individual being treated. In some embodiments, the plurality of tumor antigen peptides comprises at least 10 tumor antigen peptides. In some embodiments, the plurality of tumor antigen peptides comprises a first core group of general tumor antigen peptides and optionally a second group of cancer-type specific antigen peptides. In some embodiments, the plurality of tumor antigen peptides comprises one or more neoantigen peptides. In some embodiments, the method further comprises administering to the individual an effective amount of an immune checkpoint inhibitor, such as an inhibitor of PD-1, PD-L1, CTLA-4, IDO, TIM-3, BTLA, VISTA, or LAG-3. In some embodiments, the mutation load of the cancer is determined by sequencing a tumor sample from the individual. In some embodiments, the individual has a low mutation load (such as no more than about 10 mutations, no mutations in B2M, and/or no mutation in the functional regions) in one or more MHC genes (such as MHC-I genes) in the cancer.

In some embodiments, there is provided a method of treating a cancer in an individual, comprising: (a) optionally administering an effective amount of dendritic cells loaded with a plurality of tumor antigen peptides; and (b) administering to the individual an effective amount of activated T cells, wherein the activated T cells are prepared by co-culturing a population of T cells with the population of dendritic cells loaded with the plurality of tumor antigen peptides, and wherein the individual is selected for treatment based on having a low mutation load in the cancer. In some embodiments, the interval between the administration of the dendritic cells and the administration of the activated T cells is about 7 days to about 21 days (such as about 7 days to about 14 days, about 14 days to about 21 days, about 10 days or about 14 days). In some embodiments, the dendritic cells loaded with the plurality of tumor antigen peptides are administered subcutaneously. In some embodiments, the dendritic cells loaded with the plurality of tumor antigen peptides are administered for at least three times. In some embodiments, the activated T cells are administered intravenously. In some embodiments, the activated T cells are administered for at least three times. In some embodiments, the co-culturing is for about 7 days to about 21 days (such as about 7 days to about 14 days, or about 14 days to about 21 days). In some embodiments, the population of T cell is contacted with an immune checkpoint inhibitor (such as an inhibitor of PD-1, PD-L1, or CTLA-4) prior to and/or during the co-culturing. In some embodiments, the population of dendritic cells and the population of T cells are derived from the same individual, such as the individual being treated. In some embodiments, the plurality of tumor antigen peptides comprises at least 10 tumor antigen peptides. In some embodiments, the plurality of tumor antigen peptides comprises a first core group of general tumor antigen peptides and optionally a second group of cancer-type specific antigen peptides. In some embodiments, the plurality of tumor antigen peptides comprises one or more neoantigen peptides. In some embodiments, the method further comprises administering to the individual an effective amount of an immune checkpoint inhibitor, such as an inhibitor of PD-1, PD-L1, CTLA-4, IDO, TIM-3, BTLA, VISTA, or LAG-3. In some embodiments, the mutation load of the cancer is determined by sequencing a tumor sample from the individual. In some embodiments, the individual has a low mutation load (such as no more than about 10 mutations, no mutations in B2M, and/or no mutation in the functional regions) in one or more MHC genes (such as MHC-I genes) in the cancer.

In some embodiments, there is provided a method of treating a cancer in an individual, comprising: (a) inducing differentiation of a population of monocytes into a population of dendritic cells (such as in the presence of GM-CSF and IL-4); (b) contacting the population of dendritic cells with a plurality of tumor antigen peptides (such as in the presence of a plurality of Toll-like Receptor (TLR) agonists)

to obtain a population of dendritic cells loaded with the plurality of tumor antigen peptides; (c) optionally administering to the individual an effective amount of the dendritic cells loaded with the plurality of tumor antigen peptides; (d) co-culturing (such as in the presence of a plurality of cytokines and optionally an anti-CD3 antibody) the population of dendritic cells loaded with the plurality of tumor antigen peptides and a population of non-adherent PBMCs to obtain the population of activated T cells; and (e) administering to the individual an effective amount of the activated T cells, wherein the population of monocytes and the population of non-adherent PBMCs are obtained from a population of PBMCs (such as from the individual), and wherein the individual has a low mutation load in the cancer. In some embodiments, the interval between the administration of the dendritic cells and the administration of the activated T cells is about 7 days to about 21 days (such as about 7 days to about 14 days, about 14 days to about 21 days, about 10 days or about 14 days). In some embodiments, the dendritic cells loaded with the plurality of tumor antigen peptides are administered subcutaneously. In some embodiments, the dendritic cells loaded with the plurality of tumor antigen peptides are administered for at least three times. In some embodiments, the activated T cells are administered intravenously. In some embodiments, the activated T cells are administered for at least three times. In some embodiments, the co-culturing is for about 7 days to about 21 days (such as about 7 days to about 14 days, or about 14 days to about 21 days). In some embodiments, the population of non-adherent PBMCs is contacted with an immune checkpoint inhibitor (such as an inhibitor of PD-1, PD-L1, or CTLA-4) prior to and/or during the co-culturing. In some embodiments, the plurality of tumor antigen peptides comprises at least 10 tumor antigen peptides. In some embodiments, the plurality of tumor antigen peptides comprises a first core group of general tumor antigen peptides and optionally a second group of cancer-type specific antigen peptides. In some embodiments, the plurality of tumor antigen peptides comprises one or more neoantigen peptides. In some embodiments, the method further comprises administering to the individual an effective amount of an immune checkpoint inhibitor, such as an inhibitor of PD-1, PD-L1, CTLA-4, IDO, TIM-3, BTLA, VISTA, or LAG-3. In some embodiments, the mutation load of the cancer is determined by sequencing a tumor sample from the individual. In some embodiments, the individual has a low mutation load (such as no more than about 10 mutations, no mutations in B2M, and/or no mutation in the functional regions) in one or more MHC genes (such as MHC-I genes) in the cancer.

In some embodiments, there is provided a method of treating a cancer in an individual, comprising: (a) selecting the individual for the method based on the mutation load in the cancer; (b) inducing differentiation of a population of monocytes into a population of dendritic cells (such as in the presence of GM-CSF and IL-4); (c) contacting the population of dendritic cells with a plurality of tumor antigen peptides (such as in the presence of a plurality of Toll-like Receptor (TLR) agonists) to obtain a population of dendritic cells loaded with the plurality of tumor antigen peptides; (d) optionally administering to the individual an effective amount of the dendritic cells loaded with the plurality of tumor antigen peptides; (e) co-culturing (such as in the presence of a plurality of cytokines and optionally an anti-CD3 antibody) the population of dendritic cells loaded with the plurality of tumor antigen peptides and a population of non-adherent PBMCs to obtain the population of activated T cells; and (f) administering to the individual an effective amount of the activated T cells, wherein the population of monocytes and the population of non-adherent PBMCs are obtained from a population of PBMCs (such as from the individual). In some embodiments, the interval between the administration of the dendritic cells and the administration of the activated T cells is about 7 days to about 21 days (such as about 7 days to about 14 days, about 14 days to about 21 days, about 10 days or about 14 days). In some embodiments, the dendritic cells loaded with the plurality of tumor antigen peptides are administered subcutaneously. In some embodiments, the dendritic cells loaded with the plurality of tumor antigen peptides are administered for at least three times. In some embodiments, the activated T cells are administered intravenously. In some embodiments, the activated T cells are administered for at least three times. In some embodiments, the co-culturing is for about 7 days to about 21 days (such as about 7 days to about 14 days, or about 14 days to about 21 days). In some embodiments, the population of non-adherent PBMCs is contacted with an immune checkpoint inhibitor (such as an inhibitor of PD-1, PD-L1, or CTLA-4) prior to and/or during the co-culturing. In some embodiments, the plurality of tumor antigen peptides comprises at least 10 tumor antigen peptides. In some embodiments, the plurality of tumor antigen peptides comprises a first core group of general tumor antigen peptides and optionally a second group of cancer-type specific antigen peptides. In some embodiments, the plurality of tumor antigen peptides comprises one or more neoantigen peptides. In some embodiments, the method further comprises administering to the individual an effective amount of an immune checkpoint inhibitor, such as an inhibitor of PD-1, PD-L1, CTLA-4, IDO, TIM-3, BTLA, VISTA, or LAG-3. In some embodiments, the mutation load of the cancer is determined by sequencing a tumor sample from the individual. In some embodiments, the individual has a low mutation load (such as no more than about 10 mutations, no mutations in B2M, and/or no mutation in the functional regions) in one or more MHC genes (such as MHC-I genes) in the cancer.

In some embodiments, there is provided a method of treating a cancer in an individual, comprising: (a) inducing differentiation of a population of monocytes into a population of dendritic cells (such as in the presence of GM-CSF and IL-4); (b) contacting the population of dendritic cells with a plurality of tumor antigen peptides (such as in the presence of a plurality of Toll-like Receptor (TLR) agonists) to obtain a population of dendritic cells loaded with the plurality of tumor antigen peptides; (c) optionally administering to the individual an effective amount of the dendritic cells loaded with the plurality of tumor antigen peptides; (d) co-culturing (such as in the presence of a plurality of cytokines and optionally an anti-CD3 antibody) the population of dendritic cells loaded with the plurality of tumor antigen peptides and a population of non-adherent PBMCs to obtain the population of activated T cells; and (e) administering to the individual an effective amount of the activated T cells, wherein the population of monocytes and the population of non-adherent PBMCs are obtained from a population of PBMCs (such as from the individual), and wherein the individual is selected for treatment based on having a low mutation load in the cancer. In some embodiments, the interval between the administration of the dendritic cells and the administration of the activated T cells is about 7 days to about 21 days (such as about 7 days to about 14 days, about 14 days to about 21 days, about 10 days or about 14 days). In some embodiments, the co-culturing is for about 7 days to about 21 days (such as about 7 days to about 14 days, or about 14 days to about 21 days). In some embodiments, the population of non-adherent PBMCs is contacted with an immune checkpoint inhibitor (such as an inhibitor of PD-1, PD-L1, or CTLA-4) prior to and/or during the co-culturing. In some embodiments, the activated T cells are administered intravenously. In some embodiments, the activated T cells are administered for at least three times. In some embodiments, the dendritic cells loaded with the plurality of tumor antigen peptides are administered subcutaneously. In some embodiments, the dendritic cells loaded with the plurality of tumor antigen peptides are administered for at least three times. In some embodiments, the plurality of tumor antigen peptides comprises at least 10 tumor antigen peptides. In some embodiments, the plurality of tumor antigen peptides comprises a first core group of general tumor antigen peptides and optionally a second group of cancer-type specific antigen peptides. In some embodiments, the plurality of tumor antigen peptides comprises one or more neoantigen peptides. In some embodiments, the method further comprises administering to the individual an effective amount of an immune checkpoint inhibitor, such as an inhibitor of PD-1, PD-L1, CTLA-4, IDO, TIM-3, BTLA, VISTA, or LAG-3. In some embodiments, the mutation load of the cancer is determined by sequencing a tumor sample from the individual. In some embodiments, the individual has a low mutation load (such as no more than about 10 mutations, no mutations in B2M, and/or no mutation in the functional regions) in one or more MHC genes (such as MHC-I genes) in the cancer.

In some embodiments, there is provided a method of treating a cancer in an individual, comprising: (a) contacting a population of PBMCs with a plurality of tumor antigen peptides to obtain a population of activated PBMCs (such as in the presence of an immune checkpoint inhibitor); and (b) administering to the individual an effective amount of the activated PBMCs, wherein the individual has a low mutation load in the cancer. In some embodiments, the activated PBMCs are administered for at least three times. In some embodiments, the interval between each administration of the activated PBMCs is about 2 weeks to about 5 months (such as about 3 months). In some embodiments, the activated PBMCs are administered intravenously. In some embodiments, the population of PBMCs is obtained from the individual being treated. In some embodiments, the plurality of tumor antigen peptides comprises at least 10 tumor antigen peptides. In some embodiments, the plurality of tumor antigen peptides comprises a first core group of general tumor antigen peptides and optionally a second group of cancer-type specific antigen peptides. In some embodiments, the plurality of tumor antigen peptides comprises one or more neoantigen peptides. In some embodiments, the method further comprises administering to the individual an effective amount of an immune checkpoint inhibitor, such as an inhibitor of PD-1, PD-L1, CTLA-4, IDO, TIM-3, BTLA, VISTA, or LAG-3. In some embodiments, the mutation load of the cancer is determined by sequencing a tumor sample from the individual. In some embodiments, the individual has a low mutation load (such as no more than about 10 mutations, no mutations in B2M, and/or no mutation in the functional regions) in one or more MHC genes (such as MHC-I genes) in the cancer.

In some embodiments, there is provided a method of treating a cancer in an individual, comprising: (a) selecting the individual for the method based on the mutation load in the cancer; (b) contacting a population of PBMCs with a plurality of tumor antigen peptides to obtain a population of activated PBMCs (such as in the presence of an immune checkpoint inhibitor); and (c) administering to the individual an effective amount of the activated PBMCs. In some embodiments, the activated PBMCs are administered for at least three times. In some embodiments, the interval between each administration of the activated PBMCs is about 2 weeks to about 5 months (such as about 3 months). In some embodiments, the activated PBMCs are administered intravenously. In some embodiments, the population of PBMCs is obtained from the individual being treated. In some embodiments, the plurality of tumor antigen peptides comprises at least 10 tumor antigen peptides. In some embodiments, the plurality of tumor antigen peptides comprises a first core group of general tumor antigen peptides and optionally a second group of cancer-type specific antigen peptides. In some embodiments, the plurality of tumor antigen peptides comprises one or more neoantigen peptides. In some embodiments, the method further comprises administering to the individual an effective amount of an immune checkpoint inhibitor, such as an inhibitor of PD-1, PD-L1, CTLA-4, IDO, TIM-3, BTLA, VISTA, or LAG-3. In some embodiments, the mutation load of the cancer is determined by sequencing a tumor sample from the individual. In some embodiments, the individual has a low mutation load (such as no more than about 10 mutations, no mutations in B2M, and/or no mutation in the functional regions) in one or more MHC genes (such as MHC-I genes) in the cancer.

In some embodiments, there is provided a method of treating a cancer in an individual, comprising: (a) contacting a population of PBMCs with a plurality of tumor antigen peptides to obtain a population of activated PBMCs (such as in the presence of an immune checkpoint inhibitor); and (b) administering to the individual an effective amount of the activated PBMCs, wherein the individual is selected for treatment based on having a low mutation load in the cancer. In some embodiments, the activated PBMCs are administered for at least three times. In some embodiments, the interval between each administration of the activated PBMCs is about 2 weeks to about 5 months (such as about 3 months). In some embodiments, the activated PBMCs are administered intravenously. In some embodiments, the population of PBMCs is obtained from the individual being treated. In some embodiments, the plurality of tumor antigen peptides comprises at least 10 tumor antigen peptides. In some embodiments, the plurality of tumor antigen peptides comprises a first core group of general tumor antigen peptides and optionally a second group of cancer-type specific antigen peptides. In some embodiments, the plurality of tumor antigen peptides comprises one or more neoantigen peptides. In some embodiments, the method further comprises administering to the individual an effective amount of an immune checkpoint inhibitor, such as an inhibitor of PD-1, PD-L1, CTLA-4, IDO, TIM-3, BTLA, VISTA, or LAG-3. In some embodiments, the mutation load of the cancer is determined by sequencing a tumor sample from the individual. In some embodiments, the individual has a low mutation load (such as no more than about 10 mutations, no mutations in B2M, and/or no mutation in the functional regions) in one or more MHC genes (such as MHC-I genes) in the cancer.

In some embodiments, a low mutation load of one or more genes is a low number of mutations accumulated on the one or more genes. In some embodiments, a total number of no more than about any of 500, 400, 300, 200, 100, 50, 40, 30, 20, 10, 5 or fewer mutations indicate a low mutation load. In some embodiments, no more than about any of 50, 40, 30, 25, 20, 15, 14, 13, 12, 11, 10, 9, 8, 7, 6, 5, 4, 3, 2 or 1 mutations in the one or more MHC genes indicate a low mutation load of the one or more MHC genes. In some embodiments, a low mutation load of one or more genes is a low ratio between the number of mutations accumulated on the one or more genes (such as MHC genes) and the total number of mutations in a selected set of genes (such as cancer-associated genes) or the full genome. In some embodiments, a ratio of less than about any of 1:10, 1:15, 1:20, 1:25, 1:30, 1:40, 1:50, 1:60, 1:70, 1:80, 1:90, 1:100, 1:200 or less between the number of mutations in the one or more MHC genes and the total number of 333 cancer-associated genes described in Example 5 indicate a low mutation load of the one or more MHC genes.

In some embodiments, the one or more MHC genes comprise MHC class I genes (or loci). In some embodiments, the one or more MHC genes comprise MHC class II genes (or loci). In some embodiments, wherein the individual is a human individual, the one or more MHC genes are selected from the group consisting of HLA-A, HLA-B, HLA-C and B2M.

Exemplary mutations include, but are not limited to, deletion, frameshift, insertion, indel, missense mutation, nonsense mutation, point mutation, copy number variation, single nucleotide variation (SNV), silent mutation, splice site mutation, splice variant, gene fusion, and translocation. In some embodiments, the copy number variation of the MHC gene is caused by structural rearrangement of the genome, including deletions, duplications, inversion, and translocation of a chromosome or a fragment thereof. In some embodiments, the mutations in the one or more MHC genes are selected from point mutations, frameshift mutations, gene fusions, and copy number variations. In some embodiments, the mutations are in the protein-coding region of the MHC genes. In some embodiments, the mutation is a nonsynonymous mutation. In some embodiments, the mutation is not a polymorphism. In some embodiments, the mutation is present in normal cells of the individual. In some embodiments, the mutation is not present in normal cells of the individual. In some embodiments, the mutation affects the physiochemical or functional properties, such as stability or binding affinity, of the MHC molecule encoded by the affected gene. In some embodiments, the mutation results in an irreversible deficiency in the MHC molecule. In some embodiments, the mutation reduces the binding affinity of the MHC molecule to T cell epitopes and/or T cell receptors. In some embodiments, the mutation is a loss-of-function mutation. In some embodiments, the mutation results in reversible deficiency in the MHC molecule. In some embodiments, the mutation does not affect the binding affinity of the MHC molecule to T cell epitopes and/or T cell receptors. In some embodiments, the mutation is a somatic mutation. In some embodiments, the mutation is a germline mutation.

The mutations counted towards the mutation load may be present in all cancer cells or in a subset of cancer cells. In some embodiments, the mutations are present in all cancer cells in the individual. In some embodiments, the mutations are present in all cancer cells of a tumor site. In some embodiments, the mutations are clonal. In some embodiments, the mutations are subclonal. In some embodiments, the mutations are present in at least about any of 10%, 20%, 30%, 40%, 50%, 60%, 70%, 80%, 90%, 95%, or more cancer cells of the individual.

The mutations in certain MHC genes and/or in certain domains or positions of the one or more MHC genes may have more profound influence on the clinical response of the individual to the MASCT methods described herein. For example, loss-of-function mutations may occur in the leader peptide sequence, a3 domain (which binds the CD8 co-receptor of T cells), a1 peptide binding domain, or a2 peptide binding domain of the HLA molecule; see, for example, Shukla S. et al. *Nature Biotechnology* 33, 1152-1158 (2015), incorporated herein by reference. Mutations in B2M (β2-macroglobulin) gene may also promote tumor escape phenotypes. See, for example, Monica B et al. *Cancer Immunol. Immu.*, (2012) 61: 1359-1371. In some embodiments, presence of any number (such as 1, 2, 3, 4, 5, or more) of mutations in the functional regions of the one or more MHC genes, such as the leader peptide sequence, a1 domain, a2 domain, or a3 domain, indicates a high mutation load. In some embodiments, presence of any number (such as 1, 2, 3, 4, 5, or more) loss-of-function mutations in the one or more MHC genes (such as HLA-A, HLA-B or HLA-C genes in human individuals) indicates a high mutation load. In some embodiments, a low mutation load in the one or more MHC genes comprises no mutation in the functional regions, including leader peptide sequence, a1 domain (for example, residues in direct contact with the CD8 co-receptor), a2 domain, and a3 domain (for example, residues in direct contact with the epitope), of the one or more MHC genes (such as HLA-A, HLA-B or HLA-C genes). In some embodiments, presence of any number of mutations (such as loss-of-function mutations) in the B2M gene indicates a high mutation load. In some embodiments, a low mutation load in the one or more MHC genes comprises no mutation in the B2M gene.

The mutation load of one or more genes (such as MHC genes) may be determined by any known methods in the art, including, but not limited to, genomic DNA sequencing, exome sequencing, or other DNA sequencing-based methods using Sanger sequencing or next generation sequencing platforms; polymerase chain reaction assays; in situ hybridization assays; and DNA microarrays.

In some embodiments, the mutation load of the one or more MHC genes is determined by sequencing a tumor sample from the individual. In some embodiments, the sequencing is next generation sequencing. In some embodiments, the sequencing is full genome sequencing. In some embodiments, the sequencing is exome sequencing. In some embodiments, the sequencing is targeted sequencing of candidate genes, such as cancer-associated genes plus HLA genes. For example, ONCOGXONE™ Plus (Admera Health), are available to sequence cancer-associated genes and HLA loci with high sequencing depth. In some embodiments, the same sequencing data can be used to determine the mutation load of the one or more MHC genes and to identify neoantigens in the individual.

In some embodiments, the tumor sample is a tissue sample. In some embodiments, the tumor sample is a tumor biopsy sample, such as fine needle aspiration of tumor cells or laparoscopy obtained tumor cells (such as including tumor stroma). In some embodiments, the tumor sample is freshly obtained. In some embodiments, the tumor sample is frozen. In some embodiments, the tumor sample is a Formaldehyde Fixed-Paraffin Embedded (FFPE) sample. In some embodiments, the tumor sample is a cell sample. In some embodiments, the tumor sample comprises a circulating metastatic cancer cell. In some embodiments, the tumor sample is obtained by sorting circulating tumor cells (CTCs) from blood. In some embodiments, nucleic acids (such as DNA and/or RNA) are extracted from the tumor sample for the sequencing analysis. In some embodiments, the sequencing data of the tumor sample is compared to the sequencing data of a reference sample, such as a sample of a healthy tissue from the same individual, or a sample of a healthy individual, to identify mutations and determine mutation load in the tumor cells. In some embodiments, the sequencing data of the tumor sample is compared to the reference sequences from a genome database to identify mutations and determine mutation load in the tumor cells.

Neoantigen Peptides

In some embodiments, the MASCT methods described herein are particularly suitable for treating an individual with one or more neoantigens. Any of the MASCT methods described herein using one or more neoantigen peptides in the plurality of tumor antigen peptides may further comprise the steps of selecting the individual for the method of treating based on having one or more (such as at least 5) neoantigens in the individual, and/or the steps of: (i) identifying a neoantigen of the individual; and (ii) incorporating a neoantigen peptide derived from the neoantigen in the plurality of tumor antigen peptides for use in the MASCT method.

Thus, in some embodiments, there is provided a method of treating a cancer in an individual, comprising: (a) identifying a neoantigen of the individual; (b) incorporating a neoantigen peptide in a plurality of tumor antigen peptides, wherein the neoantigen peptide comprises a neoepitope in the neoantigen; (c) preparing a population of dendritic cells loaded with the plurality of tumor antigen peptides; (d) optionally administering an effective amount of dendritic cells loaded with the plurality of tumor antigen peptides; (e) co-culturing a population of T cells with the population of dendritic cells loaded with the plurality of tumor antigen peptides; and (f) administering to the individual an effective amount of activated T cells, wherein the individual has one or more neoantigens. In some embodiments, the interval between the administration of the dendritic cells and the administration of the activated T cells is about 7 days to about 21 days (such as about 7 days to about 14 days, about 14 days to about 21 days, about 10 days or about 14 days). In some embodiments, the co-culturing is for about 7 days to about 21 days (such as about 7 days to about 14 days, or about 14 days to about 21 days). In some embodiments, the population of T cell is contacted with an immune checkpoint inhibitor (such as an inhibitor of PD-1, PD-L1, or CTLA-4) prior to and/or during the co-culturing. In some embodiments, the dendritic cells loaded with the plurality of tumor antigen peptides are administered subcutaneously. In some embodiments, the dendritic cells loaded with the plurality of tumor antigen peptides are administered for at least three times. In some embodiments, the activated T cells are administered intravenously. In some embodiments, the activated T cells are administered for at least three times. In some embodiments, the population of dendritic cells and the population of T cells are derived from the same individual, such as the individual being treated. In some embodiments, the plurality of tumor antigen peptides comprises at least 10 tumor antigen peptides. In some embodiments, the plurality of tumor antigen peptides comprises a first core group of general tumor antigen peptides and optionally a second group of cancer-type specific antigen peptides. In some embodiments, the plurality of tumor antigen peptides comprises a plurality of neoantigen peptides. In some embodiments, the method further comprises administering to the individual an effective amount of an immune checkpoint inhibitor, such as an inhibitor of PD-1, PD-L1, CTLA-4, IDO, TIM-3, BTLA, VISTA, or LAG-3. In some embodiments, the individual is selected for the method of treating based on having a low mutation load (such as in one or more MHC genes) in the cancer.

In some embodiments, there is provided a method of treating a cancer in an individual, comprising: (a) selecting the individual for the method of treating based having one or more (such as at least 5) neoantigens in the individual; (b) identifying a neoantigen of the individual; (c) incorporating a neoantigen peptide in a plurality of tumor antigen peptides, wherein the neoantigen peptide comprises a neoepitope in the neoantigen; (d) preparing a population of dendritic cells loaded with the plurality of tumor antigen peptides; (e) optionally administering an effective amount of dendritic cells loaded with the plurality of tumor antigen peptides; (f) co-culturing a population of T cells with the population of dendritic cells loaded with the plurality of tumor antigen peptides; and (g) administering to the individual an effective amount of activated T cells. In some embodiments, the interval between the administration of the dendritic cells and the administration of the activated T cells is about 7 days to about 21 days (such as about 7 days to about 14 days, about 14 days to about 21 days, about 10 days or about 14 days). In some embodiments, the co-culturing is for about 7 days to about 21 days (such as about 7 days to about 14 days, or about 14 days to about 21 days). In some embodiments, the population of T cell is contacted with an immune checkpoint inhibitor (such as an inhibitor of PD-1, PD-L1, or CTLA-4) prior to and/or during the co-culturing. In some embodiments, the dendritic cells loaded with the plurality of tumor antigen peptides are administered subcutaneously. In some embodiments, the dendritic cells loaded with the plurality of tumor antigen peptides are administered for at least three times. In some embodiments, the activated T cells are administered intravenously. In some embodiments, the activated T cells are administered for at least three times. In some embodiments, the population of dendritic cells and the population of T cells are derived from the same individual, such as the individual being treated. In some embodiments, the plurality of tumor antigen peptides comprises at least 10 tumor antigen peptides. In some embodiments, the plurality of tumor antigen peptides comprises a first core group of general tumor antigen peptides and optionally a second group of cancer-type specific antigen peptides. In some embodiments, the plurality of tumor antigen peptides comprises a plurality of neoantigen peptides. In some embodiments, the method further comprises administering to the individual an effective amount of an immune checkpoint inhibitor, such as an inhibitor of PD-1, PD-L1, CTLA-4, IDO, TIM-3, BTLA, VISTA, or LAG-3. In some embodiments, the individual is selected for the method of treating based on having a low mutation load (such as in one or more MHC genes) in the cancer.

In some embodiments, there is provided a method of treating a cancer in an individual, comprising: (a) identifying a neoantigen of the individual; (b) incorporating a neoantigen peptide in a plurality of tumor antigen peptides, wherein the neoantigen peptide comprises a neoepitope in the neoantigen; (c) preparing a population of dendritic cells loaded with the plurality of tumor antigen peptides; (d) optionally administering an effective amount of dendritic cells loaded with the plurality of tumor antigen peptides; (e) co-culturing a population of T cells with the population of dendritic cells loaded with the plurality of tumor antigen peptides; and (f) administering to the individual an effective amount of activated T cells, wherein the individual is selected for the method of treating based on having one or more (such as at least 5) neoantigens. In some embodiments, the interval between the administration of the dendritic cells and the administration of the activated T cells is about 7 days to about 21 days (such as about 7 days to about 14 days, about 14 days to about 21 days, about 10 days or about 14 days). In some embodiments, the co-culturing is for about 7 days to about 21 days (such as about 7 days to about 14 days, or about 14 days to about 21 days). In some embodiments, the population of T cell is contacted with an immune checkpoint inhibitor (such as an inhibitor of PD-1, PD-L1, or CTLA-4) prior to and/or during the co-culturing. In some embodiments, the dendritic cells loaded with the plurality of tumor antigen peptides are administered subcutaneously. In some embodiments, the dendritic cells loaded with the plurality of tumor antigen peptides are administered for at least three times. In some embodiments, the activated T cells are administered intravenously. In some embodiments, the activated T cells are administered for at least three times. In some embodiments, the population of dendritic cells and the population of T cells are derived from the same individual, such as the individual being treated. In some embodiments, the plurality of tumor antigen peptides comprises at least 10 tumor antigen peptides. In some embodiments, the plurality of tumor antigen peptides comprises a first core group of general tumor antigen peptides and optionally a second group of cancer-type specific antigen peptides. In some embodiments, the plurality of tumor antigen peptides comprises a plurality of neoantigen peptides. In some embodiments, the method further comprises administering to the individual an effective amount of an immune checkpoint inhibitor, such as an inhibitor of PD-1, PD-L1, CTLA-4, IDO, TIM-3, BTLA, VISTA, or LAG-3. In some embodiments, the individual is selected for the method of treating based on having a low mutation load (such as in one or more MHC genes) in the cancer.

In some embodiments, there is provided a method of treating a cancer in an individual, comprising: (a) identifying a neoantigen of the individual; (b) incorporating a neoantigen peptide in a plurality of tumor antigen peptides, wherein the neoantigen peptide comprises a neoepitope in the neoantigen; (c) inducing differentiation of a population of monocytes into a population of dendritic cells (such as in the presence of GM-CSF and IL-4); (d) contacting the population of dendritic cells with a plurality of tumor antigen peptides (such as in the presence of a plurality of Toll-like Receptor (TLR) agonists) to obtain a population of dendritic cells loaded with the plurality of tumor antigen peptides; (e) optionally administering to the individual an effective amount of the dendritic cells loaded with the plurality of tumor antigen peptides; (f) co-culturing (such as in the presence of a plurality of cytokines and optionally an anti-CD3 antibody) the population of dendritic cells loaded with the plurality of tumor antigen peptides and a population of non-adherent PBMCs to obtain the population of activated T cells; and (g) administering to the individual an effective amount of the activated T cells, wherein the population of monocytes and the population of non-adherent PBMCs are obtained from a population of PBMCs (such as from the individual), and wherein the individual has one or more neoantigens. In some embodiments, the interval between the administration of the dendritic cells and the administration of the activated T cells is about 7 days to about 21 days (such as about 7 days to about 14 days, about 14 days to about 21 days, about 10 days or about 14 days). In some embodiments, the co-culturing is for about 7 days to about 21 days (such as about 7 days to about 14 days, or about 14 days to about 21 days). In some embodiments, the population of non-adherent PBMCs is contacted with an immune checkpoint inhibitor (such as an inhibitor of PD-1, PD-L1, or CTLA-4) prior to and/or during the co-culturing. In some embodiments, the activated T cells are administered intravenously. In some embodiments, the activated T cells are administered for at least three times. In some embodiments, the dendritic cells loaded with the plurality of tumor antigen peptides are administered subcutaneously. In some embodiments, the dendritic cells loaded with the plurality of tumor antigen peptides are administered for at least three times. In some embodiments, the plurality of tumor antigen peptides comprises at least 10 tumor antigen peptides. In some embodiments, the plurality of tumor antigen peptides comprises a first core group of general tumor antigen peptides and optionally a second group of cancer-type specific antigen peptides. In some embodiments, the plurality of tumor antigen peptides comprises a plurality of neoantigen peptides of the individual. In some embodiments, the method further comprises administering to the individual an effective amount of an immune checkpoint inhibitor, such as an inhibitor of PD-1, PD-L1, CTLA-4, IDO, TIM-3, BTLA, VISTA, or LAG-3. In some embodiments, the individual is selected for the method of treating based on having a low mutation load (such as in one or more MHC genes) in the cancer.

In some embodiments, there is provided a method of treating a cancer in an individual, comprising: (a) selecting the individual for the method of treating based on having one or more (such as at least 5) neoantigens in the individual; (b) identifying a neoantigen of the individual; (c) incorporating a neoantigen peptide in a plurality of tumor antigen peptides, wherein the neoantigen peptide comprises a neoepitope in the neoantigen; (d) inducing differentiation of a population of monocytes into a population of dendritic cells (such as in the presence of GM-CSF and IL-4); (e) contacting the population of dendritic cells with a plurality of tumor antigen peptides (such as in the presence of a plurality of Toll-like Receptor (TLR) agonists) to obtain a population of dendritic cells loaded with the plurality of tumor antigen peptides; (f) optionally administering to the individual an effective amount of the dendritic cells loaded with the plurality of tumor antigen peptides; (g) co-culturing (such as in the presence of a plurality of cytokines and optionally an anti-CD3 antibody) the population of dendritic cells loaded with the plurality of tumor antigen peptides and a population of non-adherent PBMCs to obtain the population of activated T cells; and (h) administering to the individual an effective amount of the activated T cells, wherein the population of monocytes and the population of non-adherent PBMCs are obtained from a population of PBMCs (such as from the individual). In some embodiments, the interval between the administration of the dendritic cells and the administration of the activated T cells is about 7 days to about 21 days (such as about 7 days to about 14 days, about 14 days to about 21 days, about 10 days or about 14 days). In some embodiments, the co-culturing is for about 7 days to about 21 days (such as about 7 days to about 14 days, or about 14 days to about 21 days). In some embodiments, the population of non-adherent PBMCs is contacted with an immune checkpoint inhibitor (such as an inhibitor of PD-1, PD-L1, or CTLA-4) prior to and/or during the co-culturing. In some embodiments, the activated T cells are administered intravenously. In some embodiments, the activated T cells are administered for at least three times. In some embodiments, the dendritic cells loaded with the plurality of tumor antigen peptides are administered subcutaneously. In some embodiments, the dendritic cells loaded with the plurality of tumor antigen peptides are administered for at least three times. In some embodiments, the plurality of tumor antigen peptides comprises at least 10 tumor antigen peptides. In some embodiments, the plurality of tumor antigen peptides comprises a first core group of general tumor antigen peptides and optionally a second group of cancer-type specific antigen peptides. In some embodiments, the plurality of tumor antigen peptides comprises a plurality neoantigen peptides of the individual. In some embodiments, the method further comprises administering to the individual an effective amount of an immune checkpoint inhibitor, such as an inhibitor of PD-1, PD-L1, CTLA-4, IDO, TIM-3, BTLA, VISTA, or LAG-3. In some embodiments, the individual is selected for the method of treating based on having a low mutation load (such as in one or more MHC genes) in the cancer.

In some embodiments, there is provided a method of treating a cancer in an individual, comprising: (a) identifying a neoantigen of the individual; (b) incorporating a neoantigen peptide in a plurality of tumor antigen peptides, wherein the neoantigen peptide comprises a neoepitope in the neoantigen; (c) inducing differentiation of a population of monocytes into a population of dendritic cells (such as in the presence of GM-CSF and IL-4); (d) contacting the population of dendritic cells with a plurality of tumor antigen peptides (such as in the presence of a plurality of Toll-like Receptor (TLR) agonists) to obtain a population of dendritic cells loaded with the plurality of tumor antigen peptides; (e) optionally administering to the individual an effective amount of the dendritic cells loaded with the plurality of tumor antigen peptides; (f) co-culturing (such as in the presence of a plurality of cytokines and optionally an anti-CD3 antibody) the population of dendritic cells loaded with the plurality of tumor antigen peptides and a population of non-adherent PBMCs to obtain the population of activated T cells; and (g) administering to the individual an effective amount of the activated T cells, wherein the population of monocytes and the population of non-adherent PBMCs are obtained from a population of PBMCs (such as from the individual), and wherein the individual is selected for the method of treating based on having one or more (such as at least 5) neoantigens. In some embodiments, the interval between the administration of the dendritic cells and the administration of the activated T cells is about 7 days to about 21 days (such as about 7 days to about 14 days, about 14 days to about 21 days, about 10 days or about 14 days). In some embodiments, the co-culturing is for about 7 days to about 21 days (such as about 7 days to about 14 days, or about 14 days to about 21 days). In some embodiments, the population of non-adherent PBMCs is contacted with an immune checkpoint inhibitor (such as an inhibitor of PD-1, PD-L1, or CTLA-4) prior to and/or during the co-culturing. In some embodiments, the activated T cells are administered intravenously. In some embodiments, the activated T cells are administered for at least three times. In some embodiments, the dendritic cells loaded with the plurality of tumor antigen peptides are administered subcutaneously. In some embodiments, the dendritic cells loaded with the plurality of tumor antigen peptides are administered for at least three times. In some embodiments, the plurality of tumor antigen peptides comprises at least 10 tumor antigen peptides. In some embodiments, the plurality of tumor antigen peptides comprises a first core group of general tumor antigen peptides and optionally a second group of cancer-type specific antigen peptides. In some embodiments, the plurality of tumor antigen peptides comprises a plurality neoantigen peptides of the individual. In some embodiments, the method further comprises administering to the individual an effective amount of an immune checkpoint inhibitor, such as an inhibitor of PD-1, PD-L1, CTLA-4, IDO, TIM-3, BTLA, VISTA, or LAG-3. In some embodiments, the individual is selected for the method of treating based on having a low mutation load (such as in one or more MHC genes) in the cancer.

In some embodiments, there is provided a method of treating a cancer in an individual, comprising: (a) identifying a neoantigen of the individual; (b) incorporating a neoantigen peptide in a plurality of tumor antigen peptides, wherein the neoantigen peptide comprises a neoepitope in the neoantigen; (c) contacting a population of PBMCs with the plurality of tumor antigen peptides to obtain a population of activated PBMCs (such as in the presence of an immune checkpoint inhibitor); and (d) administering to the individual an effective amount of the activated PBMCs, wherein the individual has one or more neoantigens. In some embodiments, the activated PBMCs are administered for at least three times. In some embodiments, the interval between each administration of the activated PBMCs is about 2 weeks to about 5 months (such as about 3 months). In some embodiments, the activated PBMCs are administered intravenously. In some embodiments, the population of PBMCs is obtained from the individual being treated. In some embodiments, the plurality of tumor antigen peptides comprises at least 10 tumor antigen peptides. In some embodiments, the plurality of tumor antigen peptides comprises a first core group of general tumor antigen peptides and optionally a second group of cancer-type specific antigen peptides. In some embodiments, the plurality of tumor antigen peptides comprises a plurality of neoantigen peptides. In some embodiments, the method further comprises administering to the individual an effective amount of an immune checkpoint inhibitor, such as an inhibitor of PD-1, PD-L1, CTLA-4, IDO, TIM-3, BTLA, VISTA, or LAG-3. In some embodiments, the individual is selected for the method of treating based on having a low mutation load (such as in one or more MHC genes) in the cancer.

In some embodiments, there is provided a method of treating a cancer in an individual, comprising: (a) selecting the individual for the method of treating based on having one or more (such as at least 5) neoantigens in the individual; (b) identifying a neoantigen of the individual; (c) incorporating a neoantigen peptide in a plurality of tumor antigen peptides, wherein the neoantigen peptide comprises a neoepitope in the neoantigen; (d) contacting a population of PBMCs with the plurality of tumor antigen peptides to obtain a population of activated PBMCs (such as in the presence of an immune checkpoint inhibitor); and (e) administering to the individual an effective amount of the activated PBMCs. In some embodiments, the activated PBMCs are administered for at least three times. In some embodiments, the interval between each administration of the activated PBMCs is about 2 weeks to about 5 months (such as about 3 months). In some embodiments, the activated PBMCs are administered intravenously. In some embodiments, the population of PBMCs is obtained from the individual being treated. In some embodiments, the plurality of tumor antigen peptides comprises at least 10 tumor antigen peptides. In some embodiments, the plurality of tumor antigen peptides comprises a first core group of general tumor antigen peptides and optionally a second group of cancer-type specific antigen peptides. In some embodiments, the plurality of tumor antigen peptides comprises a plurality of neoantigen peptides. In some embodiments, the method further comprises administering to the individual an effective amount of an immune checkpoint inhibitor, such as an inhibitor of PD-1, PD-L1, CTLA-4, IDO, TIM-3, BTLA, VISTA, or LAG-3. In some embodiments, the individual is selected for the method of treating based on having a low mutation load (such as in one or more MHC genes) in the cancer.

In some embodiments, there is provided a method of treating a cancer in an individual, comprising: (a) identifying a neoantigen of the individual; (b) incorporating a neoantigen peptide in a plurality of tumor antigen peptides, wherein the neoantigen peptide comprises a neoepitope in the neoantigen; (c) contacting a population of PBMCs with the plurality of tumor antigen peptides to obtain a population of activated PBMCs (such as in the presence of an immune checkpoint inhibitor); and (d) administering to the individual an effective amount of the activated PBMCs, wherein the individual is selected for the method of treating based on having one or more (such as at least 5) neoantigens. In some embodiments, the activated PBMCs are administered for at least three times. In some embodiments, the interval between each administration of the activated PBMCs is about 2 weeks to about 5 months (such as about 3 months). In some embodiments, the activated PBMCs are administered intravenously. In some embodiments, the population of PBMCs is obtained from the individual being treated. In some embodiments, the plurality of tumor antigen peptides comprises at least 10 tumor antigen peptides. In some embodiments, the plurality of tumor antigen peptides comprises a first core group of general tumor antigen peptides and optionally a second group of cancer-type specific antigen peptides. In some embodiments, the plurality of tumor antigen peptides comprises a plurality of neoantigen peptides. In some embodiments, the method further comprises administering to the individual an effective amount of an immune checkpoint inhibitor, such as an inhibitor of PD-1, PD-L1, CTLA-4, IDO, TIM-3, BTLA, VISTA, or LAG-3. In some embodiments, the individual is selected for the method of treating based on having a low mutation load (such as in one or more MHC genes) in the cancer.

The individual may have any number (such as any of at least 1, 2, 4, 5, 6, 7, 8, 9, 10, 11, 12, 13, 14, 15, 20, 50, 100 or more) of neoantigens in order to benefit from the MASCT method using a plurality of tumor antigen peptides comprising a neoantigen peptide. In some embodiments, the MASCT method is particularly suitable for an individual having at least about any of 4, 5, 6, 7, 8, 10, 15, 20, 50, 100 or more neoantigens. In some embodiments, the neoantigen comprises one or more neoepitopes. In some embodiments, the MASCT method is particularly suitable for an individual having at least about any of 4, 5, 6, 7, 8, 10, 15, 20, 50, 100 or more neoepitopes. In some embodiments, the T cell epitopes are MHC-I restricted epitopes. In some embodiments, the neoepitope has a higher affinity to the MHC molecules of the individual than the corresponding wildtype T cell epitope. In some embodiments, the neoepitope has higher affinity to a model T cell receptor than the corresponding wildtype T cell epitope. In some embodiments, the neoantigen (or neoepitope) is a clonal neoantigen. In some embodiments, the neoantigen (or neoepitope) is a subclonal neoantigen. In some embodiments, the neoantigen (or neoepitope) is present in at least about any of 10%, 20%, 30%, 40%, 50%, 60%, 70%, 80%, 90%, 95% or more tumor cells in the individual.

The number of neoantigens may be combined with other biomarkers or selection criteria to select an individual for any of the MASCT methods described herein. In some embodiments, the MASCT method is particularly suitable for an individual having a low mutation load (such as in one or more MHC genes) in the cancer cells, and at least about any of 4, 5, 6, 7, 8, 10 or more neoantigens (such as neoantigens with high affinity MHC-I restricted neoepitopes).

In some embodiments, there is provided a method of providing a prognosis for the individual based on the mutation load in the cancer of the individual, and/or the number of neoantigens in the individual, wherein the prognosis predicts the clinical response of the individual to any of the MASCT methods described herein. In some embodiments, the individual is categorized based on the prognosis into one of the following three categories: (1) benefit from MHC-restricted intervention (such as MASCT treatment); (2) potential benefit from MHC-restricted intervention (such as MASCT treatment); and (3) no benefit from MHC-restricted intervention (such as MASCT treatment). In some embodiments, an individual is predicted to benefit from MHC-restricted intervention (such as MASCT treatment) if the individual has no mutation in B2M gene, no mutation in the functional regions (such as leader peptide sequence, a1 domain, a2 domain or a3 domain) of MHC genes, no more than 2 mutations in an MHC-I gene (such as HLA-I A, B, and/or C gene), and/or more than 5 mutations. In some embodiments, an individual is predicted to potentially benefit from MHC-restricted intervention (such as MASCT treatment) if the individual has no mutation in B2M gene, no mutation in the functional regions (such as leader peptide sequence, a1 domain, a2 domain or a3 domain) of MHC genes, no more than about 10 mutations in MHC-I genes (such as HLA-I A, B, and/or C gene), and/or no more than 5 mutations. In some embodiments, an individual is predicted to have no benefit from MHC-restricted intervention (such as MASCT treatment) if the individual has a mutation in B2M, or have a high mutation load (such as at least 10 mutations) in the MHC genes (such as MHC-I genes). In some embodiments, the individual is selected for the MASCT method if the individual is predicted to benefit or potentially benefit from MHC-restricted intervention (such as MASCT treatment).

Any number (such as any of 1, 2, 3, 4, 5, 6, 7, 8, 9, 10, or more) of neoantigen peptides may be designed based on the neoantigens of the individual and to be incorporated in the plurality of tumor antigen peptides for use in any of the MASCT methods described herein. In some embodiments, the plurality of tumor antigen peptides comprises a single neoantigen peptide. In some embodiments, the plurality of tumor antigen peptides comprises a plurality of neoantigen peptides. Each neoantigen peptide may comprise one or more neoepitopes from a neoantigen of the individual. In some embodiments, the neoepitope is a T cell epitope. Methods of designing a neoantigen peptide based on a neoantigen are described in the section "Plurality of tumor antigen peptides."

The neoantigens in the individual may be identified using any known methods in the art. In some embodiments, the neoantigen is identified based on the genetic profile of a tumor sample from the individual. Each neoantigen comprises one or more neoepitopes. In some embodiments, the one or more neoepitopes in the neoantigen are identified based on the genetic profile of the tumor sample. Any known genetic profiling methods, such as next generation sequencing (NGS) methods, microarrays, or proteomic methods may be used to provide the genetic profile of the tumor sample.

In some embodiments, the neoantigen is identified by sequencing a tumor sample from the individual. In some embodiments, the sequencing is next generation sequencing. In some embodiments, the sequencing is full-genome sequencing. In some embodiments, the sequencing is exome sequencing. In some embodiments, the sequencing is targeted sequencing of candidate genes, such as cancer-associated genes. Many commercial NGS cancer panels, for example, ONCOGXONE™ Plus (Admera Health), are available to sequence cancer-associated genes with high sequencing depth.

In some embodiments, the tumor sample is a tissue sample. In some embodiments, the tumor sample is a tumor biopsy sample, such as fine needle aspiration of tumor cells or laparoscopy obtained tumor cells (such as including tumor stroma). In some embodiments, the tumor sample is freshly obtained. In some embodiments, the tumor sample is frozen. In some embodiments, the tumor sample is a Formaldehyde Fixed-Paraffin Embedded (FFPE) sample. In some embodiments, the tumor sample is a cell sample. In some embodiments, the tumor sample comprises a circulating metastatic cancer cell. In some embodiments, the tumor sample is obtained by sorting circulating tumor cells (CTCs) from blood. In some embodiments, nucleic acids (such as DNA and/or RNA) are extracted from the tumor sample for the sequencing analysis. In some embodiments, proteins are extracted from the tumor sample for the sequencing analysis.

In some embodiments, the genetic profile of the tumor sample is compared to the genetic profile of a reference sample, such as a sample of a healthy tissue from the same individual, or a sample of a healthy individual, to identify candidate mutant genes in the tumor cells. In some embodiments, the genetic profile of the tumor sample is compared to the reference sequences from a genome database to identify candidate mutant genes in the tumor cells. In some embodiments, the candidate mutant genes are cancer-associated genes. In some embodiments, each candidate mutant gene comprises one or more mutations, such as non-synonymous substitutions, indel (insertion or deletion), or gene fusion, which may give rise to a neoantigen. Common Single Nucleotide Polymorphisms (SNPs) are excluded from the candidate mutations.

In some embodiments, neoepitopes in neoantigens are identified from the candidate mutant proteins. In some embodiments, the neoepitopes are predicted in silico. Exemplary bioinformatics tools for T cell epitope prediction are known in the art, for example, see Yang X. and Yu X. (2009) "An introduction to epitope prediction methods and software" Rev. Med. Virol. 19(2): 77-96. Factors considered in the T cell epitope prediction algorithms include, but are not limited to, MHC subtype of the individual, sequence-derived physiochemical properties of the T cell epitope, MHC binding motifs, proteasomal cleavage pattern, transporter associated with antigen processing (TAP) transport efficiency, MHC binding affinity, peptide-MHC stability, and T-cell receptor binding affinity. In some embodiments, the neoepitope is an MHC-I restricted epitope. In some embodiments, the neoepitope is an MHC-II restricted epitope.

In some embodiments, the neoepitope has high affinity to the MHC molecules of the individual. In some embodiments, the method further comprises determining the MHC subtype of the individual, for example, from the sequencing data, to identify one or more MHC molecules of the individual. In some embodiments, the method further comprises determining the affinity of the neoepitope to an MHC molecule, such as an MHC class I molecule. In some embodiments, the method comprises determining the affinity of the neoepitope to one or more MHC (such as MHC class I) molecules of the individual. In some embodiments, the affinity of the neoepitope to one or more MHC molecules of the individual is compared to the affinity of the corresponding wildtype epitope to the one or more MHC molecules of the individual. In some embodiments, the neoepitope is selected for having a higher (such as at least about any of 1.5, 2, 5, 10, 15, 20, 25, 50, 100, or more times) affinity to the one or more MHC molecules (such as MHC-I molecules) of the individual than the corresponding wildtype epitope. In some embodiments, the MHC binding affinity is predicted in silico using any known tools or methods in the art. In some embodiments, the MHC binding affinity is determined experimentally, such as using an in vitro binding assay.

In some embodiments, the method further comprises determining the affinity of the complex comprising the neoepitope and an MHC molecule (such as an MHC class I molecule of the individual) to a T cell receptor. In some embodiments, the affinity of the complex comprising the neoepitope and the MHC molecule to the T cell receptor is compared to that of the complex comprising the corresponding wildtype epitope and the MHC molecule. In some embodiments, the MHC molecule is from the individual. In some embodiments, the T cell receptor is on the surface of one or more T cells of the individual. In some embodiments, the neoepitope is selected for having a higher (such as at least about any of 1.5, 2, 5, 10, 15, 20, 25, 50, 100, or more times) affinity in a complex comprising the neoepitope and an MHC molecule to a T cell receptor model than the corresponding wildtype epitope. In some embodiments, the TCR binding affinity is predicted in silico using any known tools or methods in the art. In some embodiments, the TCR binding affinity is determined experimentally, for example, by determining the T cell response against the neoepitope.

In some embodiments, the neoantigen (or the neoepitope) is identified further based on the expression level of the neoantigen (or the neoepitope) in the tumor sample. Expression level of the neoantigen (or the neoepitope) may be determined using any methods for quantification of mRNA or protein levels known in the art, such as RT-PCR, antibody-based assays, mass spectrometry. In some embodiments, the expression level of the neoantigen (or the neoepitope) is determined from the sequencing data of the tumor sample. In some embodiments, the neoantigen (or the neoepitope) is expressed in the tumor cells at a level of at least about any of 10, 20, 50, 100, 200, 500, 1000, 2000, 5000, $10^4$, or more copies per cell. In some embodiments, the neoantigen (or the neoepitope) is expressed at a level of more than about any of 1.5, 2, 5, 10, 20, 50, 100, or more times than the corresponding wildtype protein (or the corresponding wildtype epitope) in the tumor cells.

In some embodiments, the neoantigen peptide is selected or identified by the steps comprising: (a) sequencing a tumor sample from the individual to identify a neoantigen; (b) identifying a neoepitope in the neoantigen; optionally (c) determining the MHC subtype of the individual (e.g., using the sequencing data) to identify an MHC molecule of the individual, optionally (d) determining the affinity of the neoepitope to the MHC molecule of the individual; optionally (e) determining the affinity of the complex comprising the neoepitope and the MHC molecule to a T cell receptor; and (f) obtaining a peptide comprising the neoepitope to provide the neoantigen peptide. In some embodiments, the neoepitope has higher affinity to the MHC molecule (such as MHC-I molecule) of the individual and/or higher affinity in the complex comprising the neoepitope and the MHC molecule to the TCR as compared to the complex comprising the corresponding wildtype T cell epitope and the MHC molecule. In some embodiments, the neoepitope is extended at the N terminus or the C terminus or both termini according to the natural sequence of the neoantigen harboring the epitope to obtain an extended sequence, wherein the extended sequence is amenable for presentation by both class I and class II MHC molecules. Any of the MASCT methods described herein using one or more neoantigen peptides may further comprise any one or more of the neoantigen selection/identification steps.

Thus, in some embodiments, there is provided a method of treating a cancer in an individual, comprising: (a) sequencing a tumor sample from the individual to identify a neoantigen; (b) identifying a neoepitope in the neoantigen; optionally (c) determining the MHC subtype of the individual (e.g., using the sequencing data) to identify an MHC molecule of the individual; optionally (d) determining the affinity of the neoepitope to the MHC molecule of the individual; optionally (e) determining the affinity of the complex comprising the neoepitope and the MHC molecule to a T cell receptor; (f) incorporating a neoantigen peptide comprising the neoepitope in a plurality of tumor antigen peptides; (g) preparing a population of dendritic cells loaded with the plurality of tumor antigen peptides; (h) optionally administering an effective amount of dendritic cells loaded with the plurality of tumor antigen peptides; (i) co-culturing a population of T cells with the population of dendritic cells loaded with the plurality of tumor antigen peptides; and (j) administering to the individual an effective amount of activated T cells. In some embodiments, the interval between the administration of the dendritic cells and the administration of the activated T cells is about 7 days to about 21 days (such as about 7 days to about 14 days, about 14 days to about 21 days, about 10 days or about 14 days). In some embodiments, the co-culturing is for about 7 days to about 21 days (such as about 7 days to about 14 days, or about 14 days to about 21 days). In some embodiments, the population of T cell is contacted with an immune checkpoint inhibitor (such as an inhibitor of PD-1, PD-L1, or CTLA-4) prior to and/or during the co-culturing. In some embodiments, the activated T cells are administered intravenously. In some embodiments, the activated T cells are administered for at least three times. In some embodiments, the dendritic cells loaded with the plurality of tumor antigen peptides are administered subcutaneously. In some embodiments, the dendritic cells loaded with the plurality of tumor antigen peptides are administered for at least three times. In some embodiments, the population of dendritic cells and the population of T cells are derived from the same individual, such as the individual being treated. In some embodiments, the plurality of tumor antigen peptides comprises at least 10 tumor antigen peptides. In some embodiments, the plurality of tumor antigen peptides comprises a first core group of general tumor antigen peptides and optionally a second group of cancer-type specific antigen peptides. In some embodiments, the plurality of tumor antigen peptides comprises a plurality of neoantigen peptides. In some embodiments, the method further comprises administering to the individual an effective amount of an immune checkpoint inhibitor, such as an inhibitor of PD-1, PD-L1, CTLA-4, IDO, TIM-3, BTLA, VISTA, or LAG-3. In some embodiments, the individual is selected for the method of treating based on having a low mutation load (such as in one or more MHC genes) in the cancer. In some embodiments, the method further comprises selecting the individual for the method of treating based on having one or more (such as at least 5) neoantigens in the individual.

In some embodiments, there is provided a method of treating a cancer in an individual, comprising: (a) sequencing a tumor sample from the individual to identify a neoantigen; (b) identifying a neoepitope in the neoantigen; optionally (c) determining the MHC subtype of the individual (e.g., using the sequencing data) to identify an MHC molecule of the individual; optionally (d) determining the affinity of the neoepitope to the MHC molecule of the individual; optionally (e) determining the affinity of the complex comprising the neoepitope and the MHC molecule to a T cell receptor; (f) incorporating a neoantigen peptide comprising the neoepitope in a plurality of tumor antigen peptides; (g) inducing differentiation of a population of monocytes into a population of dendritic cells (such as in the presence of GM-CSF and IL-4); (h) contacting the population of dendritic cells with a plurality of tumor antigen peptides (such as in the presence of a plurality of Toll-like Receptor (TLR) agonists) to obtain a population of dendritic cells loaded with the plurality of tumor antigen peptides; (i) optionally administering to the individual an effective amount of the dendritic cells loaded with the plurality of tumor antigen peptides; (j) co-culturing (such as in the presence of a plurality of cytokines and optionally an anti-CD3 antibody) the population of dendritic cells loaded with the plurality of tumor antigen peptides and a population of non-adherent PBMCs to obtain the population of activated T cells; and (k) administering to the individual an effective amount of the activated T cells, wherein the population of monocytes and the population of non-adherent PBMCs are obtained from a population of PBMCs (such as from the individual), and wherein the individual has one or more neoantigens. In some embodiments, the interval between the administration of the dendritic cells and the administration of the activated T cells is about 7 days to about 21 days (such as about 7 days to about 14 days, about 14 days to about 21 days, about 10 days or about 14 days). In some embodiments, the co-culturing is for about 7 days to about 21 days (such as about 7 days to about 14 days, or about 14 days to about 21 days). In some embodiments, the population of non-adherent PBMCs is contacted with an immune checkpoint inhibitor (such as an inhibitor of PD-1, PD-L1, or CTLA-4) prior to and/or during the co-culturing. In some embodiments, the activated T cells are administered intravenously. In some embodiments, the activated T cells are administered for at least three times. In some embodiments, the dendritic cells loaded with the plurality of tumor antigen peptides are administered subcutaneously. In some embodiments, the dendritic cells loaded with the plurality of tumor antigen peptides are administered for at least three times. In some embodiments, the plurality of tumor antigen peptides comprises at least 10 tumor antigen peptides. In some embodiments, the plurality of tumor antigen peptides comprises a first core group of general tumor antigen peptides and optionally a second group of cancer-type specific antigen peptides. In some embodiments, the plurality of tumor antigen peptides comprises a plurality neoantigen peptides of the individual. In some embodiments, the method further comprises administering to the individual an effective amount of an immune checkpoint inhibitor, such as an inhibitor of PD-1, PD-L1, CTLA-4, IDO, TIM-3, BTLA, VISTA, or LAG-3. In some embodiments, the individual is selected for the method of treating based on having a low mutation load (such as in one or more MHC genes) in the cancer. In some embodiments, the method further comprises selecting the individual for the method of treating based on having one or more (such as at least 5) neoantigens in the individual.

In some embodiments, there is provided a method of treating a cancer in an individual, comprising: (a) sequencing a tumor sample from the individual to identify a neoantigen; (b) identifying a neoepitope in the neoantigen; optionally (c) determining the MHC subtype of the individual (e.g., using the sequencing data) to identify an MHC molecule of the individual; optionally (d) determining the affinity of the neoepitope to the MHC molecule of the individual; optionally (e) determining the affinity of the complex comprising the neoepitope and the MHC molecule to a T cell receptor; (f) incorporating a neoantigen peptide comprising the neoepitope in a plurality of tumor antigen peptides; (g) contacting a population of PBMCs with the plurality of tumor antigen peptides to obtain a population of activated PBMCs (such as in the presence of an immune checkpoint inhibitor); and (h) administering to the individual an effective amount of the activated PBMCs. In some embodiments, the activated PBMCs are administered for at least three times. In some embodiments, the interval between each administration of the activated PBMCs is about 2 weeks to about 5 months (such as about 3 months). In some embodiments, the activated PBMCs are administered intravenously. In some embodiments, the population of PBMCs is obtained from the individual being treated. In some embodiments, the plurality of tumor antigen peptides comprises at least 10 tumor antigen peptides. In some embodiments, the plurality of tumor antigen peptides comprises a first core group of general tumor antigen peptides and optionally a second group of cancer-type specific antigen peptides. In some embodiments, the plurality of tumor antigen peptides comprises a plurality of neoantigen peptides. In some embodiments, the method further comprises administering to the individual an effective amount of an immune checkpoint inhibitor, such as an inhibitor of PD-1, PD-L1, CTLA-4, IDO, TIM-3, BTLA, VISTA, or LAG-3. In some embodiments, the individual is selected for the method of treating based on having a low mutation load (such as in one or more MHC genes) in the cancer.

Monitoring after MASCT

Any of the MASCT methods described herein may further comprise a monitoring step after the individual receives the MASCT. Post-treatment monitoring may be beneficial for adjusting the treatment regimen of the individual to optimize treatment outcome.

For example, the plurality of tumor antigen peptides described herein may be adjusted or customized based on the specific immune response of the individual against each of the plurality of tumor antigen peptides and/or the clinical response of the individual to the activated T cells or activated PBMCs in order to provide a plurality of customized tumor antigen peptides, which may be used for repeated MASCT treatment(s). In some embodiments, tumor antigen peptides that do not elicit a strong specific immune response can be removed from the antigen peptide pool for future preparations of the pulsed DCs, activated T cells, or activated PBMCs. In some embodiments, if the individual does not respond (such as having signs of disease progression, metastasis, etc.) to the MASCT treatment using one antigen peptide pool, the antigen peptide pool may be adjusted, or neoantigens may be incorporated in the antigen peptide pool for use in a second cycle of MASCT treatment.

Thus, in some embodiments, there is provided a method of treating a cancer in an individual, comprising: (a) optionally administering to the individual an effective amount of dendritic cells loaded with a plurality of tumor antigen peptides; (b) administering to the individual an effective amount of activated T cells, wherein the activated T cells are prepared by co-culturing a population of T cells with a population of dendritic cells loaded with the plurality of tumor antigen peptides; and (c) monitoring the individual after the administration of the activated T cells. In some embodiments, the interval between the administration of the dendritic cells and the administration of the activated T cells is about 7 days to about 21 days (such as about 7 days to about 14 days, about 14 days to about 21 days, about 10 days or about 14 days). In some embodiments, the co-culturing is for about 7 days to about 21 days (such as about 7 days to about 14 days, or about 14 days to about 21 days). In some embodiments, the population of T cell is contacted with an immune checkpoint inhibitor (such as an inhibitor of PD-1, PD-L1, or CTLA-4) prior to and/or during the co-culturing. In some embodiments, the activated T cells are administered intravenously. In some embodiments, the activated T cells are administered for at least three times. In some embodiments, the dendritic cells loaded with the plurality of tumor antigen peptides are administered subcutaneously. In some embodiments, the dendritic cells loaded with the plurality of tumor antigen peptides are administered for at least three times. In some embodiments, the population of dendritic cells and the population of T cells are derived from the same individual, such as the individual being treated. In some embodiments, the plurality of tumor antigen peptides comprises at least 10 tumor antigen peptides. In some embodiments, the plurality of tumor antigen peptides comprises a first core group of general tumor antigen peptides and optionally a second group of cancer-type specific antigen peptides. In some embodiments, the plurality of tumor antigen peptides comprises one or more neoantigen peptides. In some embodiments, the method further comprises administering to the individual an effective amount of an immune checkpoint inhibitor, such as an inhibitor of PD-1, PD-L1, CTLA-4, IDO, TIM-3, BTLA, VISTA, or LAG-3. In some embodiments, the individual is selected for the method of treating based on having a low mutation load (such as in one or more MHC genes) in the cancer. In some embodiments, the individual is selected for the method of treating based on having one or more (such as at least 5) neoantigens in the individual. In some embodiments, the method further comprises identifying a neoantigen of the individual (such as by sequencing a tumor sample from the individual), and incorporating a neoantigen peptide in the plurality of tumor antigen peptides, wherein the neoantigen peptide comprises a neoepitope in the neoantigen. In some embodiments, the method further comprises monitoring the individual after the administration of the activated T cells. In some embodiments, the monitoring comprises determining the number of circulating tumor cells (CTC) in the individual. In some embodiments, the monitoring comprises detecting a specific immune response against the plurality of tumor antigen peptides in the individual. In some embodiments, the plurality of tumor antigen peptides is adjusted based on the specific immune response to provide a plurality of customized tumor antigen peptides. In some embodiments, the method is repeated using the plurality of customized tumor antigen peptides.

In some embodiments, there is provided a method of monitoring a treatment in an individual having a cancer with activated T cells, comprising determining the number of circulating tumor cells (CTC) in the individual, and/or detecting a specific immune response against each of a plurality of tumor antigen peptides in the individual, wherein the activated T cells are obtained by co-culturing a population of T cells with a population of dendritic cells loaded with the plurality of tumor antigen peptides, and wherein the treatment comprises optionally administering to the individual an effective amount of the dendritic cells loaded with the plurality of tumor antigen peptides, and administering to the individual an effective amount of the activated T cells. In some embodiments, the interval between the administration of the dendritic cells and the administration of the activated T cells is about 7 days to about 21 days (such as about 7 days to about 14 days, about 14 days to about 21 days, about 10 days or about 14 days). In some embodiments, the co-culturing is for about 7 days to about 21 days (such as about 7 days to about 14 days, or about 14 days to about 21 days). In some embodiments, the population of T cell is contacted with an immune checkpoint inhibitor (such as an inhibitor of PD-1, PD-L1, or CTLA-4) prior to and/or during the co-culturing. In some embodiments, the activated T cells are administered intravenously. In some embodiments, the activated T cells are administered for at least three times. In some embodiments, the dendritic cells loaded with the plurality of tumor antigen peptides are administered subcutaneously. In some embodiments, the dendritic cells loaded with the plurality of tumor antigen peptides are administered for at least three times. In some embodiments, the population of dendritic cells and the population of T cells are derived from the same individual, such as the individual being treated. In some embodiments, the plurality of tumor antigen peptides comprises at least 10 tumor antigen peptides. In some embodiments, the plurality of tumor antigen peptides comprises a first core group of general tumor antigen peptides and optionally a second group of cancer-type specific antigen peptides. In some embodiments, the plurality of tumor antigen peptides comprises one or more neoantigen peptides. In some embodiments, the method further comprises administering to the individual an effective amount of an immune checkpoint inhibitor, such as an inhibitor of PD-1, PD-L1, CTLA-4, IDO, TIM-3, BTLA, VISTA, or LAG-3. In some embodiments, the individual is selected for the method of treating based on having a low mutation load (such as in one or more MHC genes) in the cancer. In some embodiments, the method further comprises selecting the individual for the method of treating based on having one or more (such as at least 5) neoantigens in the individual. In some embodiments, the method further comprises identifying a neoantigen of the individual (such as by sequencing a tumor sample from the individual), providing a neoantigen peptide based on the neoantigen, and incorporating the neoantigen peptide in the plurality of tumor antigen peptides. In some embodiments, the plurality of tumor antigen peptides is adjusted based on the specific immune response to provide a plurality of customized tumor antigen peptides. In some embodiments, the treatment is repeated using the plurality of customized tumor antigen peptides.

In some embodiments, there is provided a method of treating a cancer in an individual, comprising: (a) inducing differentiation of a population of monocytes into a population of dendritic cells (such as in the presence of GM-CSF and IL-4); (b) contacting the population of dendritic cells with a plurality of tumor antigen peptides (such as in the presence of a plurality of Toll-like Receptor (TLR) agonists) to obtain a population of dendritic cells loaded with the plurality of tumor antigen peptides; (c) optionally administering to the individual an effective amount of the dendritic cells loaded with the plurality of tumor antigen peptides; (d) co-culturing (such as in the presence of a plurality of cytokines and optionally an anti-CD3 antibody) the population of dendritic cells loaded with the plurality of tumor antigen peptides and a population of non-adherent PBMCs to obtain the population of activated T cells; (e) administering to the individual an effective amount of the activated T cells; and (f) monitoring the individual after the administration of the activated T cells, wherein the population of monocytes and the population of non-adherent PBMCs are obtained from a population of PBMCs (such as from the individual). In some embodiments, the interval between the administration of the dendritic cells and the administration of the activated T cells is about 7 days to about 21 days (such as about 7 days to about 14 days, about 14 days to about 21 days, about 10 days or about 14 days). In some embodiments, the co-culturing is for about 7 days to about 21 days (such as about 7 days to about 14 days, or about 14 days to about 21 days). In some embodiments, the population of non-adherent PBMCs is contacted with an immune checkpoint inhibitor (such as an inhibitor of PD-1, PD-L1, or CTLA-4) prior to and/or during the co-culturing. In some embodiments, the activated T cells are administered intravenously. In some embodiments, the activated T cells are administered for at least three times. In some embodiments, the dendritic cells loaded with the plurality of tumor antigen peptides are administered subcutaneously. In some embodiments, the dendritic cells loaded with the plurality of tumor antigen peptides are administered for at least three times. In some embodiments, the population of PBMCs is obtained from the individual being treated. In some embodiments, the plurality of tumor antigen peptides comprises at least 10 tumor antigen peptides. In some embodiments, the plurality of tumor antigen peptides comprises a first core group of general tumor antigen peptides and optionally a second group of cancer-type specific antigen peptides. In some embodiments, the plurality of tumor antigen peptides comprises one or more neoantigen peptides. In some embodiments, the method further comprises administering to the individual an effective amount of an immune checkpoint inhibitor, such as an inhibitor of PD-1, PD-L1, CTLA-4, IDO, TIM-3, BTLA, VISTA, or LAG-3. In some embodiments, the individual is selected for the method of treating based on having a low mutation load (such as in one or more MHC genes) in the cancer. In some embodiments, the individual is selected for the method of treating based on having one or more (such as at least 5) neoantigens in the individual. In some embodiments, the method further comprises identifying a neoantigen of the individual (such as by sequencing a tumor sample from the individual), and incorporating a neoantigen peptide in the plurality of tumor antigen peptides, wherein the neoantigen peptide comprises a neoepitope in the neoantigen. In some embodiments, the method further comprises monitoring the individual after the administration of the activated T cells. In some embodiments, the monitoring comprises determining the number of circulating tumor cells (CTC) in the individual. In some embodiments, the monitoring comprises detecting a specific immune response against the plurality of tumor antigen peptides in the individual. In some embodiments, the plurality of tumor antigen peptides is adjusted based on the specific immune response to provide a plurality of customized tumor antigen peptides. In some embodiments, the method is repeated using the plurality of customized tumor antigen peptides.

In some embodiments, there is provided a method of monitoring a treatment in an individual having a cancer with activated T cells, comprising determining the number of circulating tumor cells (CTC) in the individual, and/or detecting a specific immune response against each of a plurality of tumor antigen peptides in the individual, wherein the activated T cells are obtained by steps comprising: (a) inducing differentiation of a population of monocytes into a population of dendritic cells (such as in the presence of GM-CSF and IL-4); (b) contacting the population of dendritic cells with a plurality of tumor antigen peptides (such as in the presence of a plurality of Toll-like Receptor (TLR) agonists) to obtain a population of dendritic cells loaded with the plurality of tumor antigen peptides; and (c) co-culturing (such as in the presence of a plurality of cytokines and optionally an anti-CD3 antibody) the population of dendritic cells loaded with the plurality of tumor antigen peptides and a population of non-adherent PBMCs to obtain the population of activated T cells, wherein the population of monocytes and the population of non-adherent PBMCs are obtained from a population of PBMCs (such as from the individual); and wherein the treatment comprises optionally administering to the individual an effective amount of the dendritic cells loaded with the plurality of tumor antigen peptides, and administering to the individual an effective amount of the activated T cells. In some embodiments, the interval between the administration of the dendritic cells and the administration of the activated T cells is about 7 days to about 21 days (such as about 7 days to about 14 days, about 14 days to about 21 days, about 10 days or about 14 days). In some embodiments, the co-culturing is for about 7 days to about 21 days (such as about 7 days to about 14 days, or about 14 days to about 21 days). In some embodiments, the population of non-adherent PBMCs is contacted with an immune checkpoint inhibitor (such as an inhibitor of PD-1, PD-L1, or CTLA-4) prior to and/or during the co-culturing. In some embodiments, the activated T cells are administered intravenously. In some embodiments, the activated T cells are administered for at least three times. In some embodiments, the dendritic cells loaded with the plurality of tumor antigen peptides are administered subcutaneously. In some embodiments, the dendritic cells loaded with the plurality of tumor antigen peptides are administered for at least three times. In some embodiments, the population of PBMCs is obtained from the individual being treated. In some embodiments, the plurality of tumor antigen peptides comprises at least 10 tumor antigen peptides. In some embodiments, the plurality of tumor antigen peptides comprises a first core group of general tumor antigen peptides and optionally a second group of cancer-type specific antigen peptides. In some embodiments, the plurality of tumor antigen peptides comprises one or more neoantigen peptides. In some embodiments, the method further comprises administering to the individual an effective amount of an immune checkpoint inhibitor, such as an inhibitor of PD-1, PD-L1, CTLA-4, IDO, TIM-3, BTLA, VISTA, or LAG-3. In some embodiments, the individual is selected for the method of treating based on having a low mutation load (such as in one or more MHC genes) in the cancer. In some embodiments, the method further comprises selecting the individual for the method of treating based on having one or more (such as at least 5) neoantigens in the individual. In some embodiments, the method further comprises identifying a neoantigen of the individual (such as by sequencing a tumor sample from the individual), providing a neoantigen peptide based on the neoantigen, and incorporating the neoantigen peptide in the plurality of tumor antigen peptides. In some embodiments, the plurality of tumor antigen peptides is adjusted based on the specific immune response to provide a plurality of customized tumor antigen peptides. In some embodiments, the treatment is repeated using the plurality of customized tumor antigen peptides.

In some embodiments, there is provided a method of treating a cancer in an individual, comprising: (a) contacting a population of PBMCs with a plurality of tumor antigen peptides (such as in the presence of an immune checkpoint inhibitor) to obtain a population of activated PBMCs; (b) administering to the individual an effective amount of the activated PBMCs; and (c) monitoring the individual after the administration of the activated PBMCs. In some embodiments, the activated PBMCs are administered for at least three times. In some embodiments, the interval between each administration of the activated PBMCs is about 2 weeks to about 5 months (such as about 3 months). In some embodiments, the activated PBMCs are administered intravenously. In some embodiments, the population of PBMCs is obtained from the individual being treated. In some embodiments, the plurality of tumor antigen peptides comprises at least 10 tumor antigen peptides. In some embodiments, the plurality of tumor antigen peptides comprises a first core group of general tumor antigen peptides and optionally a second group of cancer-type specific antigen peptides. In some embodiments, the plurality of tumor antigen peptides comprises one or more neoantigen peptides. In some embodiments, the method further comprises administering to the individual an effective amount of an immune checkpoint inhibitor, such as an inhibitor of PD-1, PD-L1, CTLA-4, IDO, TIM-3, BTLA, VISTA, or LAG-3. In some embodiments, the individual is selected for the method of treating based on having a low mutation load (such as in one or more MHC genes) in the cancer. In some embodiments, the individual is selected for the method of treating based on having one or more (such as at least 5) neoantigens in the individual. In some embodiments, the method further comprises identifying a neoantigen of the individual (such as by sequencing a tumor sample from the individual), and incorporating a neoantigen peptide in the plurality of tumor antigen peptides, wherein the neoantigen peptide comprises a neoepitope in the neoantigen. In some embodiments, the method further comprises monitoring the individual after the administration of the activated PBMCs. In some embodiments, the monitoring comprises determining the number of circulating tumor cells (CTC) in the individual. In some embodiments, the monitoring comprises detecting a specific immune response against the plurality of tumor antigen peptides in the individual. In some embodiments, the plurality of tumor antigen peptides is adjusted based on the specific immune response to provide a plurality of customized tumor antigen peptides. In some embodiments, the method is repeated using the plurality of customized tumor antigen peptides.

In some embodiments, there is provided a method of monitoring a treatment in an individual having a cancer with activated PBMCs, comprising determining the number of circulating tumor cells (CTC) in the individual, and/or detecting a specific immune response against each of a plurality of tumor antigen peptides in the individual, wherein the activated PBMCs are obtained by contacting a population of PBMCs with a plurality of tumor antigen peptides (such as in the presence of an immune checkpoint inhibitor), and wherein the treatment comprises administering to the individual an effective amount of the activated PBMCs. In some embodiments, the activated PBMCs are administered for at least three times. In some embodiments, the interval between each administration of the activated PBMCs is about 2 weeks to about 5 months (such as about 3 months). In some embodiments, the activated PBMCs are administered intravenously. In some embodiments, the population of PBMCs is obtained from the individual being treated. In some embodiments, the plurality of tumor antigen peptides comprises at least 10 tumor antigen peptides. In some embodiments, the plurality of tumor antigen peptides comprises a first core group of general tumor antigen peptides and optionally a second group of cancer-type specific antigen peptides. In some embodiments, the plurality of tumor antigen peptides comprises one or more neoantigen peptides. In some embodiments, the method further comprises administering to the individual an effective amount of an immune checkpoint inhibitor, such as an inhibitor of PD-1, PD-L1, CTLA-4, IDO, TIM-3, BTLA, VISTA, or LAG-3. In some embodiments, the individual is selected for the method of treating based on having a low mutation load (such as in one or more MHC genes) in the cancer. In some embodiments, the method further comprises selecting the individual for the method of treating based on having one or more (such as at least 5) neoantigens in the individual. In some embodiments, the method further comprises identifying a neoantigen of the individual (such as by sequencing a tumor sample from the individual), providing a neoantigen peptide based on the neoantigen, and incorporating the neoantigen peptide in the plurality of tumor antigen peptides. In some embodiments, the plurality of tumor antigen peptides is adjusted based on the specific immune response to provide a plurality of customized tumor antigen peptides. In some embodiments, the treatment is repeated using the plurality of customized tumor antigen peptides.

Specific immune response against an individual tumor antigen peptide may be determined using any known methods in the art, for example, by measuring levels of cytotoxic factor (such as perforin or granzyme B), or cytokine release (such as IFNγ or TNFα) from T cells (or PBMCs) after stimulation by the individual tumor antigen peptide. An antibody-based assay, such as ELISPOT, may be used to quantify the cytotoxic factor, or cytokine (such as IFNγ) levels. Exemplary embodiments of the ELISPOT assay are described in the Examples. In some embodiments, the cytokine (such as IFNγ) release level from T cells (or PBMCs) in response to a tumor antigen peptide is normalized to a reference, such as a baseline cytokine release level, or a nonspecific cytokine release level of from T cells (or PBMCs) in response to an irrelevant peptide, to provide a cytokine (such as IFNγ) fold change value. In some embodiments, a cytokine (such as IFNγ) fold change value of more than about any of 1.2, 1.5, 2, 2.5, 3, 4, 5, 6, 8, 10, or more in an ELISPOT assay indicate strong specific immune response against the tumor antigen peptide. In some embodiments, a tumor antigen peptide with a cytokine (such as IFNγ) fold change value of less than about any of 10, 8, 6, 5, 4, 3, 2.5, 2, 1.5, 1.2 or less in an ELISPOT assay is removed from the plurality of tumor antigen peptides to provide a plurality of customized tumor antigen peptides for future MASCT.

Clinical response of the individual to MASCT methods may be assessed by known methods in the art by a physician, such as by imaging methods, blood tests, biomarker assessment, and biopsy. In some embodiments, the clinical response is monitored by determining the number of circulating tumor cells (CTC) in the individual before and after receiving MASCT. In some embodiments, the CTCs have detached from a primary tumor and circulate in a bodily fluid. In some embodiments, the CTCs have detached from a primary tumor and circulate in the bloodstream. In some embodiments, the CTCs are an indication of metastasis. CTC numbers can be determined by a variety of methods known in the art, including, but not limited to, CellSearch method, Epic Science method, isoflux, and maintrac. In some embodiments, the number of single CTCs, including specific subtypes of CTCs, in a blood sample of the individual is determined. In some embodiments, a number of more than about any of 10, 20, 50, 100, 150, 200, 300 or more of single CTCs per mL of the blood sample in the individual after receiving MASCT indicates an increased risk of metastasis, and/or poor clinical response to MASCT. In some embodiments, an increased number (such as at least about any of 1.5, 2, 3, 4, 5, 10, or more fold increase) of single CTCs of the individual after receiving MASCT compared to before receiving MASCT indicates poor clinical response to MASCT. In some embodiments, the number of CTC clusters in a blood sample of the individual is determined. In some embodiments, detection of at least about any of 1, 5, 10, 50, 100, or more CTC clusters in a blood sample of the individual after receiving MASCT indicates an increased risk of metastasis, and/or poor clinical response to MASCT. In some embodiments, an increased number (such as at least about any of 1.5, 2, 3, 4, 5, 10, or more fold increase) of CTC clusters of the individual after receiving MASCT compared to before receiving MASCT indicates poor clinical response to MASCT.

Dosing and Method of Administration

Generally, dosages, schedules, and routes of administration of the activated T cells, the population of dendritic cells loaded with the plurality of tumor antigen peptides, and the activated PBMCs may be determined according to the size and condition of the individual, and according to standard pharmaceutical practice. Exemplary routes of administration include intravenous, intra-arterial, intraperitoneal, intrapulmonary, intravesicular, intramuscular, intra-tracheal, subcutaneous, intraocular, intrathecal, or transdermal. In some embodiments of the MASCT method, the dendritic cells loaded with the plurality of tumor antigen peptides are administered subcutaneously. In some embodiments of the MASCT method, the activated T cells are administered intravenously. In some embodiments of the PBMC-based MASCT method, the activated PBMCs are administered intravenously.

The dose of the cells administered to an individual may vary according to, for example, the particular type of cells being administered, the route of administration, and the particular type and stage of cancer being treated. The amount should be sufficient to produce a desirable response, such as a therapeutic response against cancer, but without severe toxicity or adverse events. In some embodiments, the amount of the activated T cells or the dendritic cells to be administered is a therapeutically effective amount. In some embodiments, the amount of the cells (such as multiple-antigen loaded dendritic cells, the activated T cells, or the activated PBMCs) is an amount sufficient to decrease the size of a tumor, decrease the number of cancer cells, or decrease the growth rate of a tumor by at least about any of 10%, 20%, 30%, 40%, 50%, 60%, 70%, 80%, 90%, 95% or 100% compared to the corresponding tumor size, number of cancer cells, or tumor growth rate in the same individual prior to treatment or compared to the corresponding activity in other individuals not receiving the treatment. Standard methods can be used to measure the magnitude of this effect, such as in vitro assays with purified enzyme, cell-based assays, animal models, or human testing.

In some embodiments, the population of dendritic cells loaded with the plurality of tumor antigen peptides are administered at a dose at least about any of $1\times10^5$, $5\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$ or $5\times10^7$ cells/individual. In some embodiments, the population of dendritic cells loaded with the plurality of tumor antigen peptides are administered at a dose about any of $1\times10^5$-$5\times10^5$, $5\times10^5$-$1\times10^6$, $1\times10^6$-$2\times10^6$, $2\times10^6$-$3\times10^6$, $3\times10^6$-$4\times10^6$, $4\times10^6$-$5\times10^6$, $5\times10^6$-$6\times10^6$, $6\times10^6$-$7\times10^6$, $7\times10^6$-$8\times10^6$, $8\times10^6$-$1\times10^8$, $1\times10^6$-$3\times10^6$, $3\times10^6$-$5\times10^6$, $5\times10^6$-$7\times10^6$, $2\times10^6$-$4\times10^6$, $1\times10^6$-$5\times10^6$, or $5 \times 10^6$-$1 \times 10^7$ cells/individual. In some embodiments, the dendritic cells loaded with the plurality of tumor antigen peptides are administered at a dose of at least about $1 \times 10^6$ cells/individual. In some embodiments, the dendritic cells loaded with the plurality of tumor antigen peptides are administered at a dose of about $1 \times 10^6$ to about $5 \times 10^6$ cells/individual.

In some embodiments, the population of dendritic cells loaded with the plurality of tumor antigen peptides are administered at a dose at least about any of $1 \times 10^4$, $5 \times 10^4$, $1 \times 10^5$, $2 \times 10^5$, $4 \times 10^5$, $6 \times 10^5$, $8 \times 10^5$, $1 \times 10^6$, $2 \times 10^6$ or $1 \times 10^7$ cells/kg. In some embodiments, the population of dendritic cells loaded with the plurality of tumor antigen peptides are administered at a dose about any of $1 \times 10^4$-$5 \times 10^4$, $5 \times 10^4$-$1 \times 10^5$, $1 \times 10^5$-$2 \times 10^5$, $2 \times 10^5$-$4 \times 10^5$, $4 \times 10^5$-$6 \times 10^5$, $6 \times 10^5$-$8 \times 10^5$, $8 \times 10^5$-$1 \times 10^6$, $1 \times 10^6$-$2 \times 10^6$, $2 \times 10^6$-$1 \times 10^7$, $1 \times 10^4$-$1 \times 10^5$, $1 \times 10^5$-$1 \times 10^6$, $1 \times 10^6$-$1 \times 10^7$, $1 \times 10^4$-$1 \times 10^6$, or $1 \times 10^5$-$1 \times 10^7$ cells/kg. In some embodiments, the dendritic cells loaded with the plurality of tumor antigen peptides are administered at a dose of at least about $2 \times 10^5$ cells/kg. In some embodiments, the dendritic cells loaded with the plurality of tumor antigen peptides are administered at a dose of about $2 \times 10^5$ to about $1 \times 10^6$ cells/kg.

In some embodiments, the activated T cells are administered at a dose of at least about any of $1 \times 10^8$, $5 \times 10^8$, $1 \times 10^9$, $2 \times 10^9$, $3 \times 10^9$, $4 \times 10^9$, $5 \times 10^9$, $6 \times 10^9$, $7 \times 10^9$, $8 \times 10^9$, $9 \times 10^9$, $1 \times 10^{10}$, $1.5 \times 10^{10}$, $2 \times 10^{10}$, or $5 \times 10^{10}$ cells/individual. In some embodiments, the activated T cells are administered at a dose of any of about $1 \times 10^8$ to about $5 \times 10^8$, about $5 \times 10^8$ to about $9 \times 10^8$, about $9 \times 10^8$ to about $1 \times 10^9$, about $1 \times 10^9$ to about $2 \times 10^9$, about $2 \times 10^9$ to about $3 \times 10^9$, about $3 \times 10^9$ to about $4 \times 10^9$, about $4 \times 10^9$ to about $5 \times 10^9$, about $5 \times 10^9$ to about $6 \times 10^9$, about $6 \times 10^9$ to about $1 \times 10^{10}$, about $1 \times 10^9$ to about $3 \times 10^9$, about $3 \times 10^9$ to about $5 \times 10^9$, about $5 \times 10^9$ to about $7 \times 10^9$, about $7 \times 10^9$ to about $1 \times 10^{10}$, about $1 \times 10^9$ to about $5 \times 10^9$, about $5 \times 10^9$ to about $1 \times 10^{10}$, about $3 \times 10^9$ to about $7 \times 10^9$, about $1 \times 10^{10}$ to about $1.5 \times 10^{10}$, about $1 \times 10^{10}$ to about $2 \times 10^{10}$, or about $1 \times 10^9$ to about $1 \times 10^{10}$ cells/individual. In some embodiments, the activated T cells are administered at a dose of at least about $3 \times 10^9$ cells/individual. In some embodiments, the activated T cells are administered at a dose of about $1 \times 10^9$ to about $1 \times 10^{10}$ cells/individual.

In some embodiments, the activated T cells are administered at a dose of at least about any of $1 \times 10^7$, $1 \times 10^8$, $2 \times 10^8$, $4 \times 10^8$, $6 \times 10^8$, $8 \times 10^8$, $1 \times 10^9$, $2 \times 10^9$, $4 \times 10^9$, $6 \times 10^9$, $8 \times 10^9$, $1 \times 10^{10}$ cells/kg. In some embodiments, the activated T cells are administered at a dose of any of about $1 \times 10^7$ to about $1 \times 10^8$, about $1 \times 10^8$ to about $2 \times 10^8$, about $2 \times 10^8$ to about $4 \times 10^8$, about $4 \times 10^8$ to about $6 \times 10^8$, about $6 \times 10^8$ to about $8 \times 10^8$, about $8 \times 10^8$ to about $1 \times 10^9$, about $1 \times 10^9$ to about $2 \times 10^9$, about $2 \times 10^9$ to about $4 \times 10^9$, about $4 \times 10^9$ to about $1 \times 10^{10}$, about $2 \times 10^8$ to about $6 \times 10^8$, about $6 \times 10^8$ to about $1 \times 10^9$, about $1 \times 10^8$ to about $2 \times 10^8$, about $2 \times 10^8$ to about $2 \times 10^9$, about $1 \times 10^7$ to about $1 \times 10^8$, about $1 \times 10^8$ to about $1 \times 10^9$, about $1 \times 10^9$ to about $1 \times 10^{10}$, or about $1 \times 10^7$ to about $1 \times 10^9$ cells/kg. In some embodiments, the activated T cells are administered at a dose of at least about $6 \times 10^8$ cells/kg. In some embodiments, the activated T cells are administered at a dose of about $2 \times 10^8$ to about $2 \times 10^9$ cells/kg.

In some embodiments, the activated PBMCs are administered at a dose of at least about any of $1 \times 10^8$, $5 \times 10^8$, $1 \times 10^9$, $2 \times 10^9$, $3 \times 10^9$, $4 \times 10^9$, $5 \times 10^9$, $6 \times 10^9$, $7 \times 10^9$, $8 \times 10^9$, $9 \times 10^9$, $1 \times 10^{10}$, $1.5 \times 10^{10}$, $2 \times 10^{10}$, or $5 \times 10^{10}$ cells/individual. In some embodiments, the activated PBMCs are administered at a dose of any of about $1 \times 10^8$ to about $5 \times 10^8$, about $5 \times 10^8$ to about $9 \times 10^8$, about $9 \times 10^8$ to about $1 \times 10^9$, about $1 \times 10^9$ to about $2 \times 10^9$, about $2 \times 10^9$ to about $3 \times 10^9$, about $3 \times 10^9$ to about $4 \times 10^9$, about $4 \times 10^9$ to about $5 \times 10^9$, about $5 \times 10^9$ to about $6 \times 10^9$, about $6 \times 10^9$ to about $1 \times 10^{10}$, about $1 \times 10^9$ to about $3 \times 10^9$, about $3 \times 10^9$ to about $5 \times 10^9$, about $5 \times 10^9$ to about $7 \times 10^9$, about $7 \times 10^9$ to about $1 \times 10^{10}$, about $1 \times 10^9$ to about $5 \times 10^9$, about $5 \times 10^9$ to about $1 \times 10^{10}$, about $3 \times 10^9$ to about $7 \times 10^9$, about $1 \times 10^{10}$ to about $1.5 \times 10^{10}$, about $1 \times 10^{10}$ to about $2 \times 10^{10}$, or about $1 \times 10^9$ to about $1 \times 10^{10}$ cells/individual. In some embodiments, the activated PBMCs are administered at a dose of at least about $1 \times 10^9$ cells/individual. In some embodiments, the activated PBMCs are administered at a dose of about $1 \times 10^9$ to about $1 \times 10^{10}$ cells/individual.

In some embodiments, the activated PBMCs are administered at a dose of at least about any of $1 \times 10^7$, $1 \times 10^8$, $2 \times 10^8$, $4 \times 10^8$, $6 \times 10^8$, $8 \times 10^8$, $1 \times 10^9$, $2 \times 10^9$, $4 \times 10^9$, $6 \times 10^9$, $8 \times 10^9$, $1 \times 10^{10}$ cells/kg. In some embodiments, the activated PBMCs are administered at a dose of any of about $1 \times 10^7$ to about $1 \times 10^8$, about $1 \times 10^8$ to about $2 \times 10^8$, about $2 \times 10^8$ to about $4 \times 10^8$, about $4 \times 10^8$ to about $6 \times 10^8$, about $6 \times 10^8$ to about $8 \times 10^8$, about $8 \times 10^8$ to about $1 \times 10^9$, about $1 \times 10^9$ to about $2 \times 10^9$, about $2 \times 10^9$ to about $4 \times 10^9$, about $4 \times 10^9$ to about $1 \times 10^{10}$, about $2 \times 10^8$ to about $6 \times 10^8$, about $6 \times 10^8$ to about $1 \times 10^9$, about $1 \times 10^8$ to about $2 \times 10^8$, about $2 \times 10^8$ to about $2 \times 10^9$, about $1 \times 10^7$ to about $1 \times 10^8$, about $1 \times 10^8$ to about $1 \times 10^9$, about $1 \times 10^9$ to about $1 \times 10^{10}$, or about $1 \times 10^7$ to about $1 \times 10^9$ cells/kg. In some embodiments, the activated PBMCs are administered at a dose of about $2 \times 10^8$ to about $2 \times 10^9$ cells/kg.

In some embodiments, a stabilizing agent or an excipient, such as human albumin, is used together with the activated T cells, the population of dendritic cells loaded with the plurality of tumor antigen peptides, and/or the activated PBMC cells when administered.

Figures 2A, 2B:
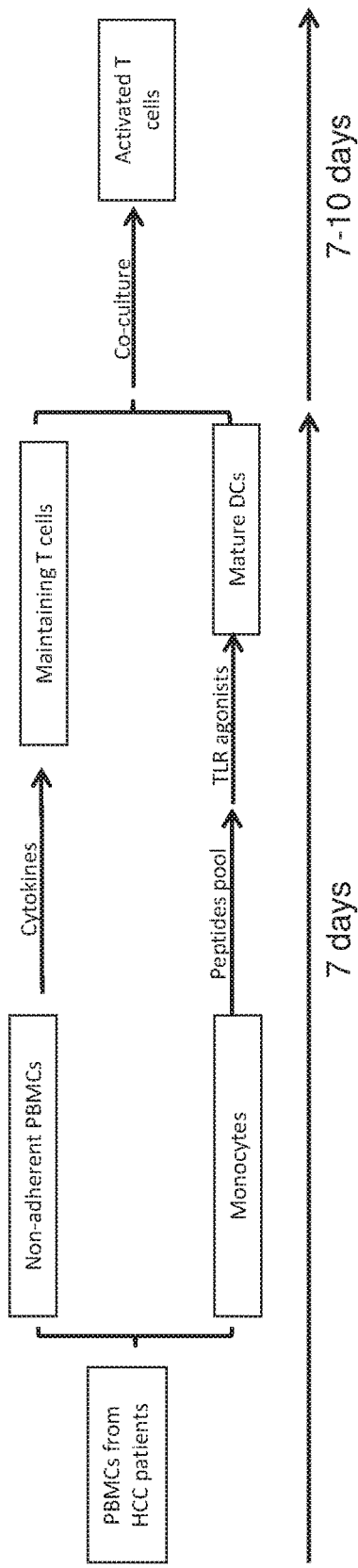

The dosage and dosing schedule of the cells in the MASCT method (including the PBMC-based MASCT method) may be adjusted over the course of the treatment, based on the judgment of the administering physician. In some embodiments, the activated T cells are administered about any one of 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, or 1 month, after the dendritic cells loaded with the plurality of tumor antigen peptides are administered. In some embodiments, the activated T cells are administered concurrently with the dendritic cells. In some embodiments, the activated T cells are administered about 14-21 days after the dendritic cells are administered. In some exemplary embodiments, the activated T cells are administered about 14 days after the dendritic cells are administered. Exemplary embodiments of the MASCT methods with exemplary schedule of administration are shown in FIG. 1 and FIG. 2A.

The MASCT method (including the PBMC-based MASCT method, and precision MASCT method) may involve a single treatment, or repeated treatments. In some embodiments, the activated T cells are administered for any one of 1, 2, 3, 4, 5, 6, 7, 8, 9, 10, or more than 10 times. In some embodiments, the activated T cells are administered at least 3 times. In some embodiments, the dendritic cells are administered for any one of 1, 2, 3, 4, 5, 6, 7, 8, 9, 10, or more than 10 times. In some embodiments, the dendritic cells are administered at least 3 times. In some embodiments of the PBMC-based MASCT method, the activated PBMCs are administered for any one of 1, 2, 3, 4, 5, 6, 7, 8, 9, 10, or more than 10 times. In some embodiments of the PBMC-based MASCT method, the activated PBMCs are administered at least 3 times. In some embodiments, one or more cell (such as antigen-loaded dendritic cell or activated T cells) preparation steps are repeated prior to the repeated administration of the dendritic cells, the activated T cells, or both. In some embodiments, the MASCT method (including the PBMC-based MASCT method, and precision MASCT method) is repeated once per week, once 2 weeks, once 3 weeks, once 4 weeks, once per month, once per 2 months, once per 3 months, once per 4 months, once per 5 months, once per 6 months, once per 7 months, once per 8 months, once per 9 months, or once per year. In some embodiments, the interval between each administration of the dendritic cells, the activated T cells, or the PBMCs is about any one of 1 week to 2 weeks, 2 weeks to 1 month, 2 weeks to 2 months, 1 month to 2 months, 1 month to 3 months, 3 months to 6 months, or 6 months to a year. In some embodiments, the interval between each administration of the dendritic cells, the activated T cells, or the PBMCs is about 0.5 to about 5 months, such as about 2 weeks to about 2 months, or about 2 months to about 5 months. In some exemplary embodiments, all step(s) of the MASCT method (including the PBMC-based MASCT method, and precision MASCT method) are repeated once per month during the first 6 months of treatment, every two months for the second 6 months of treatment, and every half a year after first 12 months of treatment if the individual has stable disease. Any embodiment of the MASCT method described herein (including the PBMC-based MASCT method, and precision MASCT method) can be combined with any other embodiment of the MASCT method (including the PBMC-based MASCT method, and precision MASCT method) during the full course of a repeated treatment.

The MASCT method (including the PBMC-based MASCT method, and precision MASCT method) provided herein may be used as a first therapy, second therapy, third therapy, or combination therapy with other types of cancer therapies known in the art, such as chemotherapy, surgery, radiation, gene therapy, immunotherapy, bone marrow transplantation, stem cell transplantation, targeted therapy, cryotherapy, ultrasound therapy, photodynamic therapy, radiofrequency ablation or the like, in an adjuvant setting or a neoadjuvant setting. In some embodiments, the present invention provides a method of treating a cancer in an individual comprising a first therapy comprising administering to the individual an effective amount of activated T cells, wherein the T cells are activated by co-culturing with a population of dendritic cells loaded with a plurality of tumor antigen peptides. In some embodiments of the method used as a first therapy, there exists no other approved anti-cancer therapy for the individual. In some embodiments, the MASCT method (including the PBMC-based MASCT method, and precision MASCT method) is used as a second therapy, wherein the individual has previously received resection, radio-frequency ablation, chemotherapy, radiation therapy, or other types of cancer therapy. In some embodiments, the individual has progressed or has not been able to tolerate standard anti-cancer therapy. In some embodiments, the individual receives other types of cancer therapy prior to, concurrently with, or after the MASCT treatment(s). For example, the MASCT method (including the PBMC-based MASCT method, and precision MASCT method) may precede or follow the other cancer therapy (such as chemotherapy, radiation, surgery or combination thereof) by intervals ranging from minutes, days, weeks to months. In some embodiments, the interval between the first and the second therapy is such that the activated T cells of the MASCT method (including the PBMC-based MASCT method, and precision MASCT method) and the other cancer therapy (such as chemotherapy, radiation, surgery, or combination thereof) would be able to exert an advantageously combined effect on the individual. In some embodiments, the MASCT method (including the PBMC-based MASCT method, and precision MASCT method) is used in conjunction with other cancer therapy (such as chemotherapy, radiation, surgery, or combination thereof) treat cancer in an individual. The combination therapy methods described herein may be performed alone or in conjunction with another therapy, such as surgery, radiation, gene therapy, immunotherapy, bone marrow transplantation, stem cell transplantation, hormone therapy, targeted therapy, cryotherapy, ultrasound therapy, photodynamic therapy, chemotherapy or the like. Additionally, a person having a greater risk of developing a proliferative disease may receive treatments to inhibit and/or delay the development of the disease.

In some embodiments, the method comprises a method of inhibiting cancer cell proliferation (such as tumor growth) in an individual, comprising administering to the individual an effective amount of activated T cells, wherein the activated T cells are prepared by co-culturing a population of T cells with a population of dendritic cells loaded with a plurality of tumor antigen peptides. In some embodiments, the method comprises a method of inhibiting cancer cell proliferation (such as tumor growth) in an individual, comprising administering to the individual an effective amount of dendritic cells loaded with a plurality of tumor antigen peptide, and administering to the individual an effective amount of activated T cells, wherein the activated T cells are prepared by co-culturing a population of T cells with a population of dendritic cells loaded with a plurality of tumor antigen peptides. In some embodiments, the method comprises a method of inhibiting cancer cell proliferation (such as tumor growth) in an individual, comprising contacting a population of PBMCs with a plurality of tumor antigen peptides to obtain a population of activated PBMCs, and administering to the individual an effective amount of the activated PBMCs. In some embodiments, the method further comprises administering to the individual an effective amount of an immune checkpoint inhibitor, such as an inhibitor of PD-1, PD-L1, CTLA-4, IDO, TIM-3, BTLA, VISTA, or LAG-3. In some embodiments, the activated T cells or PBMCs are administered for at least three times. In some embodiments, at least about 10% (including for example at least about any of 20%, 30%, 40%, 60%, 70%, 80%, 90%, or 100%) cell proliferation is inhibited.

In some embodiments, the method comprises a method of inhibiting tumor metastasis in an individual, comprising administering to the individual an effective amount of activated T cells, wherein the activated T cells are prepared by co-culturing a population of T cells with a population of dendritic cells loaded with a plurality of tumor antigen peptides. In some embodiments, the method comprises a method of inhibiting tumor metastasis in an individual, comprising administering to the individual an effective amount of dendritic cells loaded with a plurality of tumor antigen peptide, and administering to the individual an effective amount of activated T cells, wherein the activated T cells are prepared by co-culturing a population of T cells with a population of dendritic cells loaded with a plurality of tumor antigen peptides. In some embodiments, the method comprises a method of inhibiting tumor metastasis in an individual, comprising contacting a population of PBMCs with a plurality of tumor antigen peptides to obtain a population of activated PBMCs, and administering to the individual an effective amount of the activated PBMCs. In some embodiments, the activated T cells or PBMCs are administered for at least three times. In some embodiments, the method further comprises administering to the individual an effective amount of an immune checkpoint inhibitor, such as an inhibitor of PD-1, PD-L1, CTLA-4, IDO, TIM-3, BTLA, VISTA, or LAG-3. In some embodiments, at least about 10% (including for example at least about any of 20%, 30%, 40%, 60%, 70%, 80%, 90%, or 100%) metastasis is inhibited. In some embodiments, method of inhibiting metastasis to lymph node is provided.

In some embodiments, the method comprises a method of reducing tumor size in an individual, comprising administering to the individual an effective amount of activated T cells, wherein the activated T cells are prepared by co-culturing a population of T cells with a population of dendritic cells loaded with a plurality of tumor antigen peptides. In some embodiments, the method comprises a method of reducing tumor size in an individual, comprising administering to the individual an effective amount of dendritic cells loaded with a plurality of tumor antigen peptide, and administering to the individual an effective amount of activated T cells, wherein the activated T cells are prepared by co-culturing a population of T cells with a population of dendritic cells loaded with a plurality of tumor antigen peptides. In some embodiments, the method comprises a method of reducing tumor size in an individual, comprising contacting a population of PBMCs with a plurality of tumor antigen peptides to obtain a population of activated PBMCs, and administering to the individual an effective amount of the activated PBMCs. In some embodiments, the activated T cells or PBMCs are administered for at least three times. In some embodiments, the method further comprises administering to the individual an effective amount of an immune checkpoint inhibitor, such as an inhibitor of PD-1, PD-L1, CTLA-4, IDO, TIM-3, BTLA, VISTA, or LAG-3. In some embodiments, the tumor size is reduced at least about 10% (including for example at least about any of 20%, 30%, 40%, 60%, 70%, 80%, 90%, or 100%).

In some embodiments, the method comprises a method of prolonging progression-free survival of cancer in an individual, comprising administering to the individual an effective amount of activated T cells, wherein the activated T cells are prepared by co-culturing a population of T cells with a population of dendritic cells loaded with a plurality of tumor antigen peptides. In some embodiments, the method comprises a method of prolonging progression-free survival of cancer in an individual, comprising administering to the individual an effective amount of dendritic cells loaded with a plurality of tumor antigen peptide, and administering to the individual an effective amount of activated T cells, wherein the activated T cells are prepared by co-culturing a population of T cells with a population of dendritic cells loaded with a plurality of tumor antigen peptides. In some embodiments, the method comprises a method of prolonging progression-free survival of cancer in an individual, comprising contacting a population of PBMCs with a plurality of tumor antigen peptides to obtain a population of activated PBMCs, and administering to the individual an effective amount of the activated PBMCs. In some embodiments, the activated T cells or PBMCs are administered for at least three times. In some embodiments, the method further comprises administering to the individual an effective amount of an immune checkpoint inhibitor, such as an inhibitor of PD-1, PD-L1, CTLA-4, IDO, TIM-3, BTLA, VISTA, or LAG-3. In some embodiments, the method prolongs the time to disease progression by at least any of 1, 2, 3, 4, 5, 6, 7, 8, 9, 10, 11, or 12 weeks.

In some embodiments, the method comprises a method of prolonging survival of an individual having cancer, comprising administering to the individual an effective amount of activated T cells, wherein the activated T cells are prepared by co-culturing a population of T cells with a population of dendritic cells loaded with a plurality of tumor antigen peptides. In some embodiments, the method comprises a method of prolonging survival of an individual having cancer, comprising administering to the individual an effective amount of dendritic cells loaded with a plurality of tumor antigen peptide, and administering to the individual an effective amount of activated T cells, wherein the activated T cells are prepared by co-culturing a population of T cells with a population of dendritic cells loaded with a plurality of tumor antigen peptides. In some embodiments, the method comprises a method of prolonging survival of an individual having cancer, comprising contacting a population of PBMCs with a plurality of tumor antigen peptides to obtain a population of activated PBMCs, and administering to the individual an effective amount of the activated PBMCs. In some embodiments, the activated T cells or PBMCs are administered for at least three times. In some embodiments, the method further comprises administering to the individual an effective amount of an immune checkpoint inhibitor, such as an inhibitor of PD-1, PD-L1, CTLA-4, IDO, TIM-3, BTLA, VISTA, or LAG-3. In some embodiments, the method prolongs the time to disease progression by at least any of 1, 2, 3, 4, 5, 6, 7, 8, 9, 10, 11, or 12 weeks. In some embodiments, the method prolongs the survival of the individual by at least any of 1, 2, 3, 4, 5, 6, 7, 8, 9, 10, 11, 12, 18, or 24 months.

In some embodiments of any of the methods, the method comprises a method of reducing AEs and SAEs in an individual having cancer, comprising administering to the individual an effective amount of activated T cells, wherein the activated T cells are prepared by co-culturing a population of T cells with a population of dendritic cells loaded with a plurality of tumor antigen peptides. In some embodiments of any of the methods, the method comprises a method of reducing AEs and SAEs in an individual having cancer, comprising administering to the individual an effective amount of dendritic cells loaded with a plurality of tumor antigen peptide, and administering to the individual an effective amount of activated T cells, wherein the activated T cells are prepared by co-culturing a population of T cells with a population of dendritic cells loaded with a plurality of tumor antigen peptides. In some embodiments of any of the methods, the method comprises a method of reducing AEs and SAEs in an individual having cancer, comprising contacting a population of PBMCs with a plurality of tumor antigen peptides to obtain a population of activated PBMCs, and administering to the individual an effective amount of the activated PBMCs. In some embodiments, the activated T cells or PBMCs are administered for at least three times. In some embodiments, the method further comprises administering to the individual an effective amount of an immune checkpoint inhibitor, such as an inhibitor of PD-1, PD-L1, CTLA-4, IDO, TIM-3, BTLA, VISTA, or LAG-3.

In some embodiments, the method is predictive of and/or results in an objective response (such as a partial response or complete response). In some embodiments, the method is predictive of and/or results in improved quality of life.

Some cancer immunotherapies are associated with immune-related adverse events (irAEs) in additional to common adverse events generally associated with other cancer therapies. IrAEs are usually mechanistically related to either on-target T-cell toxicity against target antigens that are expressed in normal, non-tumor tissue, so called on-target off-tumor effect, or off-target effects such as breaking of self-tolerance or epitope cross-reaction. IrAEs can lead to severe symptoms and conditions on the dermatologic, gastrointestinal, endocrine, hepatic, ocular, neurologic, and other tissues or organs. Typical irAEs reported for cancer immunotherapy methods known in the art include fatal immune-mediated dermatitis, pneumonia, colitis, lymphocytic hypophysitis, pancreatitis, lymphadenopathy, endocrine disorders, CNS toxicity, and the like. In some embodiments, the MASCT methods (including the PBMC-based MASCT methods) described herein are associated with low incidence of adverse events, such as irAEs. In some embodiments, less than about any one of 50%, 40%, 30%, 20%, 10%, 5%, 4%, 3%, 2%, or 1% of individuals experience irAEs, such as irAEs of Grade 2-5.

Immune Checkpoint Inhibitors

The MASCT methods in some embodiments use immune checkpoint inhibitors, for example, in the preparation of the activated T cells or PBMCs (such as prior to and/or during the co-culturing step), and/or in combination therapy. Any known immune checkpoint inhibitors may be used, including, but not limited to the immune checkpoint inhibitors described in this section.

In some embodiments, the immune checkpoint inhibitor is a natural or engineered ligand of an inhibitory immune checkpoint molecule, including, for example, ligands of CTLA-4 (e.g., B7.1, B7.2), ligands of TIM-3 (e.g., Galectin-9), ligands of A2a Receptor (e.g., adenosine, Regadenoson), ligands of LAG-3 (e.g., MHC class I or MHC class II molecules), ligands of BTLA (e.g., HVEM, B7-H4), ligands of KIR (e.g., MHC class I or MHC class II molecules), ligands of PD-1 (e.g., PD-L1, PD-L2), ligands of IDO (e.g., NKTR-218, Indoximod, NLG919), and ligands of CD47 (e.g., SIRP-alpha receptor).

The immune checkpoint inhibitors may be of any suitable molecular modality, including, but not limited to, small molecules, nucleic acids (such as DNA, RNAi, or aptamer), peptides, or proteins (such as antibodies).

In some embodiments, the immune checkpoint inhibitor is an antibody (such as antagonist antibody) that targets an inhibitory immune checkpoint protein selected from the group consisting of anti-CTLA-4 (e.g., Ipilimumab, Tremelimumab, KAHR-102), anti-TIM-3 (e.g., F38-2E2, ENUM005), anti-LAG-3 (e.g., BMS-986016, IMP701, IMP321, C9B7W), anti-KIR (e.g., Lirilumab and IPH2101), anti-PD-1 (e.g., Nivolumab, Pidilizumab, Pembrolizumab, BMS-936559, atezolizumab, Pembrolizumab, MK-3475, AMP-224, AMP-514, STI-A1110, TSR-042), anti-PD-L1 (e.g., KY-1003 (EP20120194977), MCLA-145, RG7446, BMS-936559, MEDI-4736, MSB0010718C, AUR-012, STI-A1010, PCT/US2001/020964, MPDL3280A, AMP-224, Dapirolizumab pegol (CDP-7657), MEDI-4920), anti-CD73 (e.g., AR-42 (OSU-HDAC42,HDAC-42,AR42,AR 42,OSU-HDAC 42,OSU-HDAC-42,NSC D736012,HDAC-42,HDAC 42,HDAC42,NSCD736012,NSC-D736012), MEDI-9447), anti-B7-H3 (e.g., MGA271, DS-5573a, 8H9), anti-CD47 (e.g., CC-90002, TTI-621, VLST-007), anti-BTLA, anti-VISTA, anti-A2aR, anti-B7-1, anti-B7-H4, anti-CD52 (such as alemtuzumab), anti-IL-10, anti-IL-35, and anti-TGF-β (such as Fresolumimab). In some embodiments, the antibody is a monoclonal antibody. In some embodiments, the antibody is a full-length antibody. In some embodiments, the antibody is an antigen-binding fragment selected from the group consisting of Fab, Fab', F(ab')$_2$, Fv, scFv, BiTE, nanobody, and other antigen-binding subsequences of the full length antibody or engineered combinations thereof. In some embodiments, the antibody is a human antibody, a humanized antibody, or a chimeric antibody. In some embodiments, the antibody is a bispecific or multi-specific antibody.

In some embodiments, the immune checkpoint inhibitor is an inhibitor of PD-1. In some embodiments, the immune checkpoint inhibitor is an anti-PD-1 antibody. Exemplary anti-PD-1 antibodies include, but are not limited to, Nivolumab, pembrolizumab, pidilizumab, BMS-936559, and atezolizumab, Pembrolizumab, MK-3475, AMP-224, AMP-514, STI-A1110, and TSR-042. In some embodiments, the immune checkpoint inhibitor is nivolumab (for example, OPDIVO®). In some embodiments, the immune checkpoint inhibitor is Pembrolizumab (for example, KEYTRUDA®). In some embodiments, the immune checkpoint inhibitor is SHR-1210.

In some embodiments, the immune checkpoint inhibitor is an inhibitor of PD-L1. In some embodiments, the immune checkpoint inhibitor is an anti-PD-L1 antibody. Exemplary anti-PD-L1 antibodies include, but are not limited to, KY-1003, MCLA-145, RG7446, BMS935559, MPDL3280A, MED14736, Avelumab, or STI-A1010.

In some embodiments, the immune checkpoint inhibitor is an inhibitor of CTLA-4. In some embodiments, the immune checkpoint inhibitor is an anti-CTLA-4 antibody. Exemplary anti-CTLA-4 antibodies include, but are not limited to, Ipilimumab, Tremelimumab, and KAHR-102. In some embodiments, the immune checkpoint inhibitor is Ipilimumab (for example, YERVOY®).

A suitable concentration of the immune checkpoint inhibitor in the culturing media include, but are not limited to, at least about any of 1 µg/mL, 10 µg/mL, 15 µg/mL, 25 µg/mL, 50 µg/mL, 100 µg/mL, 200 µg/mL, 500 µg/mL, or 1 mg/mL. In some embodiments, the concentration of the immune checkpoint inhibitor in the culturing media is any one of about 1 µg/mL to about 10 µg/mL, about 10 µg/mL to about 25 µg/mL, about 25 µg/mL to about 50 µg/mL, about 50 µg/mL to about 100 µg/mL, about 100 µg/mL to about 200 µg/mL, about 200 µg/mL to about 500 µg/mL, about 100 µg/mL to about 1 mg/mL, about 10 µg/mL to about 100 µg/mL, or about 1 µg/mL to about 100 µg/mL.

Any of the above MASCT methods (including PMBC-based MASCT methods and precision MASCT methods) can be applied in combination with administration of one or more immune checkpoint inhibitors. Exemplary routes of administration of the immune checkpoint inhibitor include, but are not limited to, intratumoral, intravesical, intramuscular, intraperitoneal, intravenous, intra-arterial, intracranial, intrapleural, subcutaneous, and epidermal routes, or be delivered into lymph glands, body spaces, organs or tissues known to contain such live cancer cells. In some embodiments, the immune checkpoint inhibitor is administered intravenously. In some embodiments, the immune checkpoint inhibitor is administered by infusion. In some embodiments, the immune checkpoint inhibitor is infused over at least about any of 10 minutes, 30 minutes, 1 hour, 2 hours, 4 hours, 6 hours, or more. In some embodiments, the immune checkpoint inhibitor is administered via the same administration route as the activated T cells or the activated PBMCs. In some embodiments, the immune checkpoint inhibitor is administered via a different administration route as the activated T cells or the activated PBMCs.

Suitable dose of the immune checkpoint inhibitor include, but are not limited to, about any one of 1 mg/m$^2$, 5 mg/m$^2$, 10 mg/m$^2$, 20 mg/m$^2$, 50 mg/m$^2$, 100 mg/m$^2$, 200 mg/m$^2$, 300 mg/m$^2$, 400 mg/m$^2$, 500 mg/m$^2$, 750 mg/m$^2$, 1000 mg/m$^2$, or more. In some embodiments, the dose of immune checkpoint inhibitor is any one of about 1 to about 5 mg/m$^2$, about 5 to about 10 mg/m$^2$, about 10 to about 20 mg/m$^2$, about 20 to about 50 mg/m$^2$, about 50 to about 100 mg/m$^2$, about 100 mg/m$^2$ to about 200 mg/m$^2$, about 200 to about 300 mg/m$^2$, about 300 to about 400 mg/m$^2$, about 400 to about 500 mg/m$^2$, about 500 to about 750 mg/m$^2$, or about 750 to about 1000 mg/m$^2$. In some embodiments, the dose of immune checkpoint inhibitor is about any one of 1 µg/kg, 2 µg/kg, 5 µg/kg, 10 µg/kg, 20 µg/kg, 50 µg/kg, 0.1 mg/kg, 0.2 mg/kg, 0.3 mg/kg, 0.4 mg/kg, 0.5 mg/kg, 1 mg/kg, 2 mg/kg, 5 mg/kg, 10 mg/kg, 20 mg/kg, 50 mg/kg, 100 mg/kg, or more. In some embodiments, the dose of the immune checkpoint inhibitor is any one of about 1 µg/kg to about 5 µg/kg, about 5 µg/kg to about 10 µg/kg, about 10 µg/kg to about 50 µg/kg, about 50 µg/kg to about 0.1 mg/kg, about 0.1 mg/kg to about 0.2 mg/kg, about 0.2 mg/kg to about 0.3 mg/kg, about 0.3 mg/kg to about 0.4 mg/kg, about 0.4 mg/kg to about 0.5 mg/kg, about 0.5 mg/kg to about 1 mg/kg, about 1 mg/kg to about 5 mg/kg, about 5 mg/kg to about 10 mg/kg, about 10 mg/kg to about 20 mg/kg, about 20 mg/kg to about 50 mg/kg, about 50 mg/kg to about 100 mg/kg, or about 1 mg/kg to about 100 mg/kg.

In some embodiments, the immune checkpoint inhibitor is administered daily. In some embodiments, the immune checkpoint inhibitor is administered is administered at least about any one of 1×, 2×, 3×, 4×, 5×, 6×, or 7× (i.e., daily) a week. In some embodiments, the immune checkpoint inhibitor is administered weekly. In some embodiments, the immune checkpoint inhibitor is administered weekly without break; weekly, two out of three weeks; weekly three out of four weeks; once every two weeks; once every 3 weeks; once every 4 weeks; once every 6 weeks, once every 8 weeks, monthly, or every two to 12 months. In some embodiments, the intervals between each administration are less than about any one of 6 months, 3 months, 1 month, 20 days, 15, days, 12 days, 10 days, 9 days, 8 days, 7 days, 6 days, 5 days, 4 days, 3 days, 2 days, or 1 day. In some embodiments, the intervals between each administration are more than about any one of 1 month, 2 months, 3 months, 4 months, 5 months, 6 months, 8 months, or 12 months. In some embodiments, the immune checkpoint inhibitor is administered once every 3 months. In some embodiments, there is no break in the dosing schedule. In some embodiments, the interval between each administration is no more than about a week. In some embodiments, the immune checkpoint inhibitor is administered with the same dosing schedule as the activated T cells or the activated PBMCs. In some embodiments, the immune checkpoint inhibitor is administered with a different dosing schedule as the activated T cells or the activated PBMCs.

In some embodiments, the immune checkpoint inhibitor is administered in every MASCT treatment cycle. For example, the immune checkpoint inhibitor may be administered about any of 1, 2, 3, 4, 5, 6, or more times every MASCT treatment cycle. In some embodiments, the immune checkpoint inhibitor is not administered in every MASCT treatment cycle. For example, the immune checkpoint inhibitor may be administered about once every 1, 2, 3, 4, 5, or more MASCT treatment cycles.

The administration of the immune checkpoint inhibitor can be over an extended period of time, such as from about a month up to about seven years. In some embodiments, the immune checkpoint inhibitor is administered over a period of at least about any one of 1, 2, 3, 4, 5, 6, 7, 8, 9, 10, 11, 12, 18, 24, 30, 36, 48, 60, 72, or 84 months. In some embodiments, the immune checkpoint inhibitor is administered for a single time. In some embodiments, the immune checkpoint inhibitor is administered repeatedly. In some embodiments, the immune checkpoint inhibitor is administered repeatedly until disease progression.

T Cell Receptors (TCR)

The present invention in one aspect further provides a method of cloning a tumor-specific T cell receptor from an individual treated with any of the MASCT methods (including PBMC-based MASCT and precision MASCT) described herein.

Thus, in some embodiments, there is provided a method of cloning a tumor-specific T cell receptor, comprising: (a) optionally administering to an individual having a cancer an effective amount of dendritic cells loaded with a plurality of tumor antigen peptides, (b) administering to the individual an effective amount of activated T cells, wherein the activated T cells are prepared by co-culturing a population of T cells with a population of dendritic cells loaded with the plurality of tumor antigen peptides, (c) isolating a T cell from the individual, wherein the T cell specifically recognizes a tumor antigen peptide in the plurality of tumor antigen peptides; and (d) cloning a T cell receptor from the T cell to provide the tumor-specific T cell receptor. In some embodiments, the interval between the administration of the dendritic cells and the administration of the activated T cells is about 7 days to about 21 days (such as about 7 days to about 14 days, about 14 days to about 21 days, about 10 days or about 14 days). In some embodiments, the co-culturing is for about 7 days to about 21 days (such as about 7 days to about 14 days, or about 14 days to about 21 days). In some embodiments, the population of T cell is contacted with an immune checkpoint inhibitor (such as an inhibitor of PD-1, PD-L1, or CTLA-4) prior to and/or during the co-culturing. In some embodiments, the activated T cells are administered intravenously. In some embodiments, the activated T cells are administered for at least three times. In some embodiments, the dendritic cells loaded with the plurality of tumor antigen peptides are administered subcutaneously. In some embodiments, the dendritic cells loaded with the plurality of tumor antigen peptides are administered for at least three times. In some embodiments, the population of dendritic cells and the population of T cells are derived from the same individual, such as the individual being treated. In some embodiments, the plurality of tumor antigen peptides comprises at least 10 tumor antigen peptides. In some embodiments, the plurality of tumor antigen peptides comprises a first core group of general tumor antigen peptides and optionally a second group of cancer-type specific antigen peptides. In some embodiments, the plurality of tumor antigen peptides comprises one or more neoantigen peptides. In some embodiments, the method further comprises administering to the individual an effective amount of an immune checkpoint inhibitor, such as an inhibitor of PD-1, PD-L1, CTLA-4, IDO, TIM-3, BTLA, VISTA, or LAG-3. In some embodiments, the individual is selected for the method of treating based on having a low mutation load (such as in one or more MHC genes) in the cancer. In some embodiments, the individual is selected for the method of treating based on having one or more (such as at least 5) neoantigens in the individual. In some embodiments, the method further comprises identifying a neoantigen of the individual (such as by sequencing a tumor sample from the individual), and incorporating a neoantigen peptide in the plurality of tumor antigen peptides, wherein the neoantigen peptide comprises a neoepitope in the neoantigen. In some embodiments, the method further comprises monitoring the individual after the administration of the activated T cells. In some embodiments, the monitoring comprises determining the number of circulating tumor cells (CTC) in the individual. In some embodiments, the monitoring comprises detecting a specific immune response against the plurality of tumor antigen peptides in the individual. In some embodiments, the plurality of tumor antigen peptides is adjusted based on the specific immune response to provide a plurality of customized tumor antigen peptides. In some embodiments, the method is repeated using the plurality of customized tumor antigen peptides.

In some embodiments, there is provided a method of cloning a tumor-specific T cell receptor, comprising: (a) inducing differentiation of a population of monocytes into a population of dendritic cells (such as in the presence of GM-CSF and IL-4); (b) contacting the population of dendritic cells with a plurality of tumor antigen peptides (such as in the presence of a plurality of Toll-like Receptor (TLR) agonists) to obtain a population of dendritic cells loaded with the plurality of tumor antigen peptides; (c) optionally administering to the individual an effective amount of the dendritic cells loaded with the plurality of tumor antigen peptides; (d) co-culturing (such as in the presence of a plurality of cytokines and optionally an anti-CD3 antibody) the population of dendritic cells loaded with the plurality of tumor antigen peptides and a population of non-adherent PBMCs to obtain the population of activated T cells; wherein the population of monocytes and the population of non-adherent PBMCs are obtained from a population of PBMCs (such as from the individual); (e) administering to the individual an effective amount of the activated T cells; (f) isolating a T cell from the individual, wherein the T cell specifically recognizes a tumor antigen peptide in the plurality of tumor antigen peptides; and (g) cloning a T cell receptor from the T cell to provide the tumor-specific T cell receptor. In some embodiments, the interval between the administration of the dendritic cells and the administration of the activated T cells is about 7 days to about 21 days (such as about 7 days to about 14 days, about 14 days to about 21 days, about 10 days or about 14 days). In some embodiments, the co-culturing is for about 7 days to about 21 days (such as about 7 days to about 14 days, or about 14 days to about 21 days). In some embodiments, the population of non-adherent PBMCs is contacted with an immune checkpoint inhibitor (such as an inhibitor of PD-1, PD-L1, or CTLA-4) prior to and/or during the co-culturing. In some embodiments, the activated T cells are administered intravenously. In some embodiments, the activated T cells are administered for at least three times. In some embodiments, the dendritic cells loaded with the plurality of tumor antigen peptides are administered subcutaneously. In some embodiments, the dendritic cells loaded with the plurality of tumor antigen peptides are administered for at least three times. In some embodiments, the population of PBMCs is obtained from the individual being treated. In some embodiments, the plurality of tumor antigen peptides comprises at least 10 tumor antigen peptides. In some embodiments, the plurality of tumor antigen peptides comprises a first core group of general tumor antigen peptides and optionally a second group of cancer-type specific antigen peptides. In some embodiments, the plurality of tumor antigen peptides comprises one or more neoantigen peptides. In some embodiments, the method further comprises administering to the individual an effective amount of an immune checkpoint inhibitor, such as an inhibitor of PD-1, PD-L1, CTLA-4, IDO, TIM-3, BTLA, VISTA, or LAG-3. In some embodiments, the individual is selected for the method of treating based on having a low mutation load (such as in one or more MHC genes) in the cancer. In some embodiments, the individual is selected for the method of treating based on having one or more (such as at least 5) neoantigens in the individual. In some embodiments, the method further comprises identifying a neoantigen of the individual (such as by sequencing a tumor sample from the individual), and incorporating a neoantigen peptide in the plurality of tumor antigen peptides, wherein the neoantigen peptide comprises a neoepitope in the neoantigen. In some embodiments, the method further comprises monitoring the individual after the administration of the activated T cells. In some embodiments, the monitoring comprises determining the number of circulating tumor cells (CTC) in the individual. In some embodiments, the monitoring comprises detecting a specific immune response against the plurality of tumor antigen peptides in the individual. In some embodiments, the plurality of tumor antigen peptides is adjusted based on the specific immune response to provide a plurality of customized tumor antigen peptides. In some embodiments, the method is repeated using the plurality of customized tumor antigen peptides.

In some embodiments, there is provided a method of cloning a tumor-specific T cell receptor, comprising: (a) contacting a population of PBMCs with a plurality of tumor antigen peptides (such as in the presence of an immune checkpoint inhibitor) to obtain a population of activated PBMCs, (b) administering to an individual having a cancer an effective amount of PBMCs; (c) isolating a T cell from the individual, wherein the T cell specifically recognizes a tumor antigen peptide in the plurality of tumor antigen peptides; and (d) cloning a T cell receptor from the T cell to provide the tumor-specific T cell receptor. In some embodiments, the activated PBMCs are administered for at least three times. In some embodiments, the interval between each administration of the activated PBMCs is about 2 weeks to about 5 months (such as about 3 months). In some embodiments, the activated PBMCs are administered intravenously. In some embodiments, the population of PBMCs is obtained from the individual being treated. In some embodiments, the plurality of tumor antigen peptides comprises at least 10 tumor antigen peptides. In some embodiments, the plurality of tumor antigen peptides comprises a first core group of general tumor antigen peptides and optionally a second group of cancer-type specific antigen peptides. In some embodiments, the plurality of tumor antigen peptides comprises one or more neoantigen peptides. In some embodiments, the method further comprises administering to the individual an effective amount of an immune checkpoint inhibitor, such as an inhibitor of PD-1, PD-L1, CTLA-4, IDO, TIM-3, BTLA, VISTA, or LAG-3. In some embodiments, the individual is selected for the method of treating based on having a low mutation load (such as in one or more MHC genes) in the cancer. In some embodiments, the individual is selected for the method of treating based on having one or more (such as at least 5) neoantigens in the individual. In some embodiments, the method further comprises identifying a neoantigen of the individual (such as by sequencing a tumor sample from the individual), and incorporating a neoantigen peptide in the plurality of tumor antigen peptides, wherein the neoantigen peptide comprises a neoepitope in the neoantigen. In some embodiments, the method further comprises monitoring the individual after the administration of the activated PBMCs. In some embodiments, the monitoring comprises determining the number of circulating tumor cells (CTC) in the individual. In some embodiments, the monitoring comprises detecting a specific immune response against the plurality of tumor antigen peptides in the individual. In some embodiments, the plurality of tumor antigen peptides is adjusted based on the specific immune response to provide a plurality of customized tumor antigen peptides. In some embodiments, the method is repeated using the plurality of customized tumor antigen peptides.

In some embodiments, the TCR is cloned from an individual that responds to the MASCT method, for example, an individual having reduced CTC number or a low CTC number after the MASCT, an individual having a clinical evaluation of Stable Disease (SD), Complete Response (CR), or Partial Response (PR). In some embodiments, the TCR is cloned from an individual that does not respond to the MASCT method. In some embodiments, the individual has a strong specific immune response against the tumor antigen peptide. Specific immune response against an individual tumor antigen peptide may be determined using any known methods in the art, for example, by measuring levels of cytotoxic factor (such as perforin or granzyme B), or cytokine release (such as IFNγ or TNFα) from T cells (or PBMCs) after stimulation by the individual tumor antigen peptide. An antibody-based assay, such as ELISPOT, may be used to quantify the cytotoxic factor, or cytokine (such as IFNγ) levels. In some embodiments, the cytokine (such as IFNγ) release level from T cells (or PBMCs) in response to a tumor antigen peptide is normalized to a reference, such as a baseline cytokine release level, or a nonspecific cytokine release level of from T cells (or PBMCs) in response to an irrelevant peptide, to provide a cytokine (such as IFNγ) fold change value. In some embodiments, a cytokine (such as IFNγ) fold change value of more than about any of 1.2, 1.5, 2, 2.5, 3, 4, 5, 6, 8, 10, or more in an ELISPOT assay indicate strong specific immune response against the tumor antigen peptide. In some embodiments, the method of cloning a TCR further comprises determining the specific immune response of each of the plurality of tumor antigen peptides in the individual, such as in a PBMC sample of the individual.

The T cell may be isolated from a biological sample from the individual after receiving the MASCT. In some embodiments, the biological sample is obtained from the individual after one cycle of MASCT. In some embodiments, the biological sample is obtained from the individual after at least any of 2, 3, 4, 5, or more cycles of MASCT. In some embodiments, the biological sample is obtained from the individual after at least about any of 1 week, 2 weeks, 3 weeks, 4 weeks 5 weeks, 6 weeks, 2 months, or 3 months after receiving the MASCT. In some embodiments, the biological sample is obtained from the individual after no more than about any of 6 months, 3 months, 2 months, 1 month, or less after receiving the MASCT. In some embodiments, the biological sample is a blood sample. In some embodiments, the biological sample is a PBMC sample. In some embodiments, the biological sample is a T cell sample. In some embodiments, the biological sample is a tumor sample containing CTLs. T cells may be isolated from the biological sample using any known methods in the art, for example, by flow cytometry or centrifugation methods. In some embodiments, a plurality of T cells obtained from the biological sample are screened for their specific immune response against the plurality of tumor antigen peptides, for example, by staining with multimers (such as pentamers or dextramers), or by determining the level of cytotoxic factor (such as perforin or granzyme B), or cytokine release (such as IFNγ or TNFα) by the cell.

The tumor antigen peptide that the T cell specifically recognizes can be any one from the tumor antigen peptide pool. In some embodiments, the tumor antigen peptide comprises an MHC-I restricted epitope. In some embodiments, the tumor antigen peptide comprises an MHC-II restricted epitope. In some embodiments, the tumor antigen peptide is a general cancer tumor antigen peptide. In some embodiments, the tumor antigen peptide is a cancer-type specific tumor antigen peptide. In some embodiments, the tumor antigen peptide is a neoantigen peptide. In some embodiments, the tumor antigen peptide comprises an epitope derived from CEA or hTERT.

TCRs can be cloned from T cells using any methods known in the art, including, but not limited to, PCR methods using primers that specifically annealing to known TCR variable domains. In some embodiments, amplicon rescued multiplex PCR (or arm-PCR) is used to clone the tumor-specific TCR. See, for example, U.S. Pat. No. 7,999,092. Methods for cloning tumor antigen-specific TCRs from single T cells may also be used to clone the TCR. See, for example, E. Kobayashi et al. Nature Medicine 19.11 (2013): 1542-1546. In some embodiments, the T cell is sequenced to determine the sequence of TCR genes, thereby allowing cloning of the TCR.

In some embodiments, the cloned TCRs are further incorporated in an expression vector. In some embodiments, the cloned TCRs are further transduced (such as by a viral vector, or by physical or chemical methods) into a host cell (such as T cell) to express the TCR. In some embodiments, the host cell is a T cell. In some embodiments, the host cell expressing the TCR is assayed for specific immune response to the tumor antigen peptide for validation. In some embodiments, the host cell is derived from a cell line. In some embodiments, the host cell is a primary cell. In some embodiments, the host cell is a T cell. In some embodiments, the host cell is derived from a cancer patient.

Further provided herein are tumors-specific TCRs cloned using any of the methods described herein. In some embodiments, the tumor-specific TCR is further engineered to improve the physical/chemical properties and/or functions of the TCR. For example, the engineered tumor-specific TCR may have enhanced expression level, improved stability, enhanced binding affinity to the MHC-tumor-specific antigen peptide complexes, and/or enhanced signaling. In some embodiments, the tumor-specific TCRs are engineered based on the MHC subtype of the individual receiving immunotherapy treatment using the tumor-specific TCRs. In some embodiments, the engineering comprises mutating one or more positions in the variable regions of the cloned tumor-specific TCR. In some embodiments, the engineering comprises providing a fusion protein comprising one or more domains or fragments of the cloned tumor-specific TCR.

In some embodiments, there is provided an isolated nucleic acid encoding the tumor-specific TCR or components or derivatives thereof (such as the TCRα chain, the TCRβ chain, or the engineered tumor-specific TCR). In some embodiments, there is provided an expression vector encoding the tumor-specific TCR or components or derivatives thereof (such as the TCRα chain, the TCRβ chain, or the engineered tumor-specific TCR). In some embodiments, there is provided an isolated host cell expressing the tumor-specific TCR or components or derivatives thereof (such as the TCRα chain, the TCRβ chain, or the engineered tumor-specific TCR).

In some embodiments, there is provided an isolated T cell comprising the tumor-specific TCR or components or derivatives thereof (such as the TCRα chain, the TCRβ chain, or the engineered tumor-specific TCR). In some embodiments, the endogenous TCR of the isolated T cell is knocked out. In some embodiments, the isolated T cell is a TCR-T cell. In some embodiments, there is provided a pharmaceutical composition comprising the isolated T cell and a pharmaceutically acceptable excipient. In some embodiments, the isolated T cell is derived from the individual having the cancer. In some embodiments, the isolated T cell is derived from the individual to be treated with the isolated T cell or pharmaceutical composition thereof.

The isolated T cells or pharmaceutical compositions thereof may be useful for treating the individual from whom the tumor-specific TCR is cloned, or for treating another individual, such as an allogenic individual, or an individual having the same MHC genotype and/or expressing the same epitope on the cancer cells. In some embodiments, there is provided a method of treating a cancer in an individual comprising administering to the individual an effective amount of any of the isolated T cells described herein or pharmaceutical compositions thereof. The immunotherapy using the isolated T cell comprising the cloned tumor-specific TCR may be used singly or in combination with other treatments, such as immune checkpoint inhibitor, MASCT (including PBMC-based MASCT and precision MASCT), chemotherapy, radiation, surgery, targeted therapy, etc., to achieve the desired clinical outcome.

Activated T Cells

The present invention further provides an isolated population of cells comprising activated T cells, wherein less than about 1% of the activated T cells are regulatory T ($T_{REG}$) cells. The isolated population of cells described herein may be prepared by any of the method of preparing a population of activated T cells described in the previous section. The isolated population of cells described herein is useful for treating cancer, preventing tumor progression, or reducing immune escape in an individual.

The isolated population of cells described herein comprise mainly of activated T cells. In some embodiments, at least about 90% of the cells in the isolated population are activated T cells. In some embodiments, at least about any of 50%, 60%, 70%, 80%, 90%, 95%, 98%, or 99% of the cells in the population are activated T cells. In some embodiments, about any of 50-60%, 60-70%, 70-80%, 80-90%, 90-95%, 95-98%, 50-70%, 60-80%, 90-99%, 50-80%, 80-99%, 50-90%, 60-90%, 70-99%, or 50-99% of the cells in the isolated population are activated T cells.

In some embodiments, the isolated population of cells comprises $CD4^+CD25^+Foxp3^+$ cells. In some embodiments, the isolated population of cells comprise less than about any of 10%, 5%, 3%, 1%, 0.9%, 0.8%, 0.7%, 0.6%, 0.5%, 0.4%, 0.3%, 0.2%, 0.1%, or 0.01% $CD4^+CD25^+Foxp3^+$ cells. In some embodiments, the isolated population of cells comprise less than about any of 5-10%, 3-5%, 1-3%, 0.9-1%, 0.8-0.9%, 0.7-0.8%, 0.6-0.7%, 0.5-0.6%, 0.4-0.5%, 0.3-0.4%, 0.2-0.3%, 0.1-0.2%, 0.1-0.5%, 0.5-1%, 0.2-0.6%, 0.4-0.8%, 0.3-0.7%, or 0.3-0.5% $CD4^+CD25^+Foxp3^+$ cells. In some embodiments, the isolated population of cells comprises about 0.3% to about 0.5% $CD4^+CD25^+Foxp3^+$ cells.

In some embodiments, the isolated population of cells comprises regulatory T cells ($T_{REG}$). In some embodiments, the isolated population of cells comprise less than about any of 10%, 5%, 3%, 1%, 0.9%, 0.8%, 0.7%, 0.6%, 0.5%, 0.4%, 0.3%, 0.2%, 0.1%, or 0.01% $T_{REG}$ cells. In some embodiments, the isolated population of cells comprise less than about any of 5-10%, 3-5%, 1-3%, 0.9-1%, 0.8-0.9%, 0.7-0.8%, 0.6-0.7%, 0.5-0.6%, 0.4-0.5%, 0.3-0.4%, 0.2-0.3%, 0.1-0.2%, 0.1-0.5%, 0.5-1%, 0.2-0.6%, 0.4-0.8%, 0.3-0.7%, or 0.3-0.5% $T_{REG}$ cells. In some embodiments, the isolated population of cells comprises about 0.3% to about 0.5% $T_{REG}$ cells.

In some embodiments, the isolated population of cells comprises $CD3^+CD8^+$ cells. In some embodiments, the isolated population of cells comprises about any of 50%, 55%, 60%, 65%, 70%, 75%, or 80% $CD3^+CD8^+$ cells. In some embodiments, the isolated population of cells comprise less than about any of 50-60%, 60-65%, 65-70%, 70-75%, 75-80%, 50-65%, 65-80%, 65-70%, or 65-75% $CD3^+CD8^+$ cells. In some embodiments, the isolated population of cells comprises about 65% to about 75% $CD3^+CD8^+$ cells.

In some embodiments, the isolated population of cells comprises cytotoxic T cells. In some embodiments, the isolated population of cells comprises about any of 50%, 55%, 60%, 65%, 70%, 75%, or 80% cytotoxic T cells. In some embodiments, the isolated population of cells comprise less than about any of 50-60%, 60-65%, 65-70%, 70-75%, 75-80%, 50-65%, 65-80%, 65-70%, or 65-75% cytotoxic T cells. In some embodiments, the isolated population of cells comprises about 65% to about 75% cytotoxic T cells.

In some embodiments, the isolated population of cells comprises $CD3^+CD4^+$ cells. In some embodiments, the isolated population of cells comprise about any of 10%, 13%, 16%, 18%, 20/c %, 22%, 25% or 30% $CD3^+CD4^+$ cells. In some embodiments, the isolated population of cells comprise less than about any of 10-13%, 13-16%, 16-18%, 18-20%, 20-22%, 22-25%, 25-30%, 16-20%, 18-22%, or 16-22% $CD3^+CD4^+$ cells. In some embodiments, the isolated population of cells comprises about 16% to about 22% $CD3^+CD4^+$ cells.

In some embodiments, the isolated population of cells comprises helper T cells. In some embodiments, the isolated population of cells comprise about any of 100%, 13%, 16%, 18%, 20%, 22%, 25% or 30%0/helper T cells. In some embodiments, the isolated population of cells comprise less than about any of 10-13%, 13-16%, 16-18%, 18-20%, 20-22%, 22-25%, 25-30%, 16-20%, 18-22%, or 16-22% helper T cells. In some embodiments, the isolated population of cells comprises about 16% to about 22% helper T cells.

In some embodiments, the isolated population of cells comprises $CD3^+CD56^+$ cells. In some embodiments, the isolated population of cells comprise about any of 10%, 12%, 13%, 13.50%, 14%, 14.5%, 15%, or 20% $CD3^+CD56^+$ cells. In some embodiments, the isolated population of cells comprise less than about any of 10-12%, 12-13%, 13-13.5%, 13.5-14%, 14-14.5%, 14.5-15%, 15-20%, 13-14%, 14-15%, 13.5-14.5%, or 13-15% $CD3^+CD56^+$ cells. In some embodiments, the isolated population of cells comprises about 13% to about 15% $CD3^+CD56^+$ cells.

In some embodiments, the isolated population of cells comprises Natural Killer (NK) T cells. In some embodiments, the isolated population of cells comprise about any of 10%, 12%, 13%, 13.5%, 14%, 14.5%, 15%, or 20% NK T cells. In some embodiments, the isolated population of cells comprise less than about any of 10-12%, 12-13%, 13-13.5%, 13.5-14%, 14-14.5%, 14.5-15%, 15-20%, 13-14%, 14-15%, 13.5-14.5%, or 13-15% NK T cells. In some embodiments, the isolated population of cells comprises about 13% to about 15% NK T cells.

In some embodiments, the isolated population of cells comprises about 0.3% to about 0.5% CD4⁺CD25⁺Foxp3⁺ cells, about 65% to about 75% CD3⁺CD8⁺ cells, and about 16% to about 22% CD3⁺CD4⁺ cells. In some embodiments, the isolated population of cells comprises about 0.3% to about $T_{REG}$ cells, about 65% to about 75% cytotoxic T cells, and about 16% to about 22% helper T cells. In some embodiments, the isolated population of cells further comprises memory T cells.

In some embodiments, the activated T cells in any embodiment of the isolated population of cells are capable of eliciting specific immune response to a plurality of tumor antigen peptides in vivo or ex vivo. In some embodiments, the activated T cells are capable of increasing cytotoxic T cell activity in a human individual against more than one tumor antigen peptides. In some embodiments, the activated T cells are characterized by high expression or secretion level of pro-inflammatory signal molecules, and low expression or secretion level of immunosuppressive cytokines. In some embodiments, the expression or secretion level is determined by comparing the expression or secretion level of a molecule (such as a pro-inflammatory signal molecule, or an immunosuppressive cytokine) of the activated T cells to the control expression or secretion level. In some embodiments, the control expression or secretion level of a molecule is the expression or secretion level of the molecule in a control population of T cells measured under the same assay conditions. In some embodiments, the control population of T cells is a population of T cells induced by a plurality of irrelevant peptides (such as peptides not corresponding to T cell receptor antigens, or random peptides). In some embodiments, the control expression or secretion level of a molecule is an average or median expression or secretion level of the molecule in a plurality of control populations of T cells. In some embodiments, a high level of expression or secretion of a molecule in the activated T cells is at least about any of 1.5, 2, 2.5, 3, 4, 5, 10, 20, 50, 100, 1000, or more times of the control expression or secretion level. In some embodiments, a low level of expression or secretion of a molecule in the activated T cells is less than any of 0.001, 0.01, 0.05, 0.1, 0.2, 0.3, 0.4, 0.5, 0.6, 0.75, or 0.8 times of the control expression or secretion level.

In some embodiments, the activated T cells express a plurality of pro-inflammatory molecules, such as IFNγ, TNFα, granzyme B, perforin, or any combination thereof. In some embodiments, the activated T cells have no or low expression of immunosuppressive cytokines, such as IL-10 and/or IL-4. In some embodiments, the frequency of the activated T cells (such as CD3⁺CD4⁺ cells or CD3⁺CD8⁺ cells) expressing immune-inhibitory molecules, such as PD-1, is low. In some embodiments, the frequency of the activated T cells expressing PD-1 is less than about any of 10%, 5%, 3%, 2%, or 1%. In some embodiment, less than about 5% of the activated T cells express immune-inhibitory molecule PD-1.

The isolated population of cells described herein can be used to generate specific immune memory in an individual when administered to the individual. In some embodiments, the individual has memory T cells that can elicit specific T cell response against a plurality of tumor antigen peptides after about any of 2 weeks, 1 month, 2 months, 3 months, 4 months, 6 months, 12 months, or more after administration of the isolated population of cells.

The isolated population of cells described herein can also be used to alter immune-inhibitory signals in vivo. In some embodiments, the isolated population of cells reduces immune-inhibitory molecule (such as PD-1) expression frequency on T cells (such as cytotoxic T cells or helper T cells) in an individual when administered to the individual. In some embodiments, the isolated population of cells reduces immune tolerance or immune escape of cancer cells in an individual. Accordingly, there is provided a method of reducing expression frequency of an immune-inhibitory molecule, such as PD-1, in T cells of an individual, comprising administering to the individual an effective amount of any embodiment of the isolated population of cells described herein. Also provided herein is an immunotherapeutic composition comprising any embodiment of the isolated population of cells comprising activated T cells, and use of any embodiment of the isolated population of cells in the manufacture of a medicament for treating a cancer in an individual.

Compositions, Kits and Articles of Manufacture

The present invention further provides kits, compositions (such as pharmaceutical compositions), and commercial batches of the tumor antigen peptides for use in any embodiment of the MASCT method (including the PBMC-based MASCT method and precision MASCT) or the cell (such as antigen-loaded DCs, activated T cells, or activated PBMCs) preparation methods described herein.

In some embodiments, there is provided a kit useful for cancer immunotherapy, comprising at least 10 tumor antigen peptides. In some embodiments, the kit comprises more than about any of 10, 15, 20, 25, 30, 35, 40, 45, or 50 tumor antigen peptides. In some embodiments, the plurality of tumor antigen peptides comprises a first core group of general tumor antigen peptides. In some embodiments, the plurality of tumor antigen peptides comprises a first core group of general tumor antigen peptides and a second group of cancer-type specific antigen peptides. In some embodiments, the first core group comprises about 10 to about 20 general tumor antigen peptides. In some embodiments, the first core group comprises more than 1 general tumor antigen peptides. In some embodiments, the first core group comprises more than about any of 1, 2, 3, 4, 5, 6, 7, 8, 9, 10, 11, 12, 13, 14, 15, 16, 17, 18, 19, 20, 22, 25, 30, 40, or 50 general tumor antigen peptides. In some embodiments, the second group comprises about 1 to about 10 cancer-type specific antigen peptides. In some embodiments, the second group comprises more than about any of 0, 1, 2, 3, 4, 5, 6, 7, 8, 9, 10, 11, 12, 13, 14, 15, 16, 17, 18, 19, 20, 22, 25, 30, 40, or 50 cancer-type specific antigen peptides. In some embodiments, the second group comprises more than about any of 0, 1, 2, 3, 4, 5, 6, 7, 8, 9, 10, 11, 12, 13, 14, 15, 16, 17, 18, 19, 20, 22, 25, 30, 40, or 50 virus-specific antigen peptides. In some embodiments, the kit further comprises about any of 1, 2, 3, 4, 5, 6, 7, 8, 9, 10, 11, 12, 13, 14, 15, 16, 17, 18, 19, 20, 22, 25, 30, 40, or 50 neoantigen peptides.

In some embodiments, there is provided a kit useful for cancer immunotherapy, comprising at least 10 tumor antigen peptides, wherein each of the at least 10 tumor antigen peptides comprises at least one epitope selected from the group consisting of SEQ ID NOs: 1-40. In some embodiments, there is provided a kit useful for cancer immunotherapy, comprising at least 10 tumor antigen peptides, wherein each of the at least 10 tumor antigen peptides comprises at least one epitope selected from the group consisting of SEQ ID NOs: 1-24. In some embodiments, there is provided a kit useful for cancer immunotherapy, comprising at least 10 tumor antigen peptides selected from the group consisting of the tumor antigen peptides in FIG. 2B. In some embodiments, there is provided a kit useful for cancer immunotherapy, comprising at least 10 tumor antigen peptides comprising at least 10 tumor antigen peptides selected from the group consisting of the tumor antigen peptides in FIG. 2C and FIG. 29A. In some embodiments, there is provided a kit useful for cancer immunotherapy, comprising at least 10 tumor antigen peptides derived from proteins selected from the group consisting of hTERT, p53, Survivin, NY-ESO-1, CEA, CCND1, MET, RGS5, MMP7, VEGFR, AFP, GPC3, HBVc, HBVp, CDCA1, KRAS, PARP4, MLL3, and MTHFR.

A person skilled in the art may use any combinations of tumor antigen peptides from the first core group and optionally any combinations of cancer-type specific antigen peptides from the second group, and/or neoantigen peptides to load a population of dendritic cells, which can further be used to prepare activated T cells useful for treating cancer in an individual. The kit may also be useful for PBMC-based MASCT methods, precision MASCT methods, or for cloning a tumor-specific TCR from an individual receiving the MASCT.

The kit may contain additional components, such as containers, reagents, culturing media, cytokines, buffers, antibodies, and the like to facilitate execution of any embodiment of the MASCT method (including the PBMC-based MASCT method, and precision MASCT method), or methods for cloning a tumor-specific TCR from an individual receiving the MASCT. For example, in some embodiments, the kit further comprises a peripheral blood collection and storage apparatus, which can be used to collect an individual's peripheral blood. In some embodiments, the kit further comprises containers and reagents for density gradient centrifugation of peripheral blood, which can be used to isolate PBMCs from a sample of human peripheral blood. In some embodiments, the kit further comprises culturing media, cytokines, or buffers for obtaining dendritic cells from peripheral blood. In some embodiments, the kit further comprises culturing media, TLR agonists, reagents and buffers for loading the first core group and optionally the second group into dendritic cells to obtain dendritic cells loaded with a plurality of tumor antigen peptides. In some embodiments, the kit further comprises cytokine, anti-CD3 antibody, buffers, immune checkpoint inhibitor, or culturing media for co-culturing T cells obtained from the peripheral blood with the dendritic cells loaded with the plurality of tumor antigen peptides. In some embodiments, the kit further comprises reagents for determining the mutation load (such as in one or more MHC genes) in cancer cells. In some embodiments, the kit further comprises an immune checkpoint inhibitor for combination therapy with the MASCT. In some embodiments, the kit further comprises reagents for identifying a neoantigen (such as by sequencing) in a tumor sample. In some embodiments, the kit further comprises an ELISPOT assay for assessing specific immune response against the plurality of tumor antigen peptides. In some embodiments, the kit further comprises reagents for cloning a tumor-specific TCR The kits of the invention are in suitable packaging. Suitable packaging include, but is not limited to, vials, bottles, jars, flexible packaging (e.g., Mylar or plastic bags), and the like. Kits may optionally provide additional components such as buffers and interpretative information. The present application thus also provides articles of manufacture, which include vials (such as sealed vials), bottles, jars, flexible packaging, and the like.

The instructions may also comprise instructions relating to the use of the tumor antigen peptides (and optionally additional components described above). In some embodiments, the kit further comprises an instructional manual, such as a manual describing a protocol of an embodiment of the MASCT methods (including the PBMC-based MASCT methods and precision MASCT methods), an embodiment of the cell preparation methods as described herein, or an embodiment of the methods of cloning a tumor-specific TCR. The instructions may also include information on dosage, dosing schedule, and route of administration of the antigen presenting cells (such as dendritic cells), the activated T cells, and/or the activated PBMCs prepared using the kit for the intended treatment. In some embodiments, the kit further comprises instructions for selecting an individual for the MASCT method. In some embodiments, the kit further comprises instructions for determining the mutation load of cancer cells, and/or determining the number of neoantigens in an individual. In some embodiments, the kit further comprises instructions for administering an immune checkpoint inhibitor in combination with the MASCT, including, for example, information on dosage, dosing schedule, and route of administration of the immune checkpoint inhibitor. In some embodiments, the kit further comprises instructions for identifying a neoantigen (such as by sequencing) in a tumor sample. In some embodiments, the kit further comprises instructions for monitoring an individual after receiving the MASCT. In some embodiments, the kit further comprises instructions for cloning a tumor-specific TCR The containers may be unit doses, bulk packages (e.g., multi-dose packages) or sub-unit doses. For example, kits may be provided that contain sufficient tumor antigen peptides as disclosed herein to prepare sufficient activated T cells and/or antigen-loaded dendritic cells (such as dendritic cells) to provide effective treatment of an individual for an extended period, such as any of 3 weeks, 6 weeks, 9 weeks, 3 months, 4 months, 5 months, 6 months, 8 months, 9 months, 1 year or more.

Kits may also include multiple unit doses of tumor antigen peptides and instructions for use and packaged in quantities sufficient for storage and use in pharmacies, for example, hospital pharmacies and compounding pharmacies.

In some embodiments, there is provided a commercial batch of the population of tumor antigen peptides or the kit as described herein. "Commercial batch" used herein refers to a batch size that is at least about 10 mg. In some embodiments, the batch size is at least about any of 10, 50, 100, 200, 300, 400, 500, 600, 700, 800, 900, 1000, 2000, 5000, or 10000 mg. In some embodiments, the commercial batch comprises a plurality of vials comprising any of the compositions (such as the population of tumor antigen peptides or the kits) as described herein. In some embodiments, the commercial batch comprises at least about any of 5, 10, 15, 20, 25, 50, 75, 100, 200, 300, 400, 500, 1000, 2000, 5000, or 10000 vials. For example, each vial contains at least about 0.1 mg of tumor antigen peptides. In some embodiments, the tumor antigen peptides are in a liquid suspension. In some embodiments, the tumor antigen peptides are in a powder form, such as a lyophilized powder.

Further provided are kits, compositions (such as pharmaceutical compositions), and commercial batches of any of the isolated population of cells (such as dendritic cells, activated T cells, activated PBMCs, or isolated T cells comprising the tumor specific TCR) described herein.

The isolated population of cells described herein may be used in pharmaceutical compositions or formulations, by combining the isolated population of cells described with a pharmaceutically acceptable carrier, excipients, stabilizing agents and/or other agents, which are known in the art, for use in the methods of treatment, methods of administration, and dosage regimens described herein. In some embodiments, human albumin is used as a pharmaceutically acceptable carrier.

Suitable pharmaceutical carriers include sterile water; saline, dextrose; dextrose in water or saline; condensation products of castor oil and ethylene oxide combining about 30 to about 35 moles of ethylene oxide per mole of castor oil; liquid acid; lower alkanols; oils such as corn oil; peanut oil, sesame oil and the like, with emulsifiers such as mono- or di-glyceride of a fatty acid, or a phosphatide, e.g., lecithin, and the like; glycols; polyalkylene glycols; aqueous media in the presence of a suspending agent, for example, sodium carboxymethylcellulose; sodium alginate; poly(vinylpyrolidone); and the like, alone, or with suitable dispensing agents such as lecithin; polyoxyethylene stearate; and the like. The carrier may also contain adjuvants such as preserving stabilizing, wetting, emulsifying agents and the like together with the penetration enhancer. The final form may be sterile and may also be able to pass readily through an injection device such as a hollow needle. The proper viscosity may be achieved and maintained by the proper choice of solvents or excipients.

The pharmaceutical compositions described herein may include other agents, excipients, or stabilizers to improve properties of the composition. Examples of suitable excipients and diluents include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline solution, syrup, methylcellulose, methyl- and propylhydroxybenzoates, talc, magnesium stearate and mineral oil. In some embodiments, the pharmaceutical composition is formulated to have a pH in the range of about 4.5 to about 9.0, including for example pH ranges of about any one of 5.0 to about 8.0, about 6.5 to about 7.5, or about 6.5 to about 7.0. In some embodiments, the pharmaceutical composition can also be made to be isotonic with blood by the addition of a suitable tonicity modifier, such as glycerol.

In some embodiments, the isolated cell compositions (such as pharmaceutical compositions) is suitable for administration to a human. In some embodiments, the compositions (such as pharmaceutical compositions) is suitable for administration to a human by parenteral administration. Formulations suitable for parenteral administration include aqueous and non-aqueous, isotonic sterile injection solutions, which can contain anti-oxidants, buffers, bacteriostats, and solutes that render the formulation compatible with the blood of the intended recipient, and aqueous and non-aqueous sterile suspensions that can include suspending agents, solubilizers, thickening agents, stabilizing agents, and preservatives. The formulations can be presented in unit-dose or multi-dose sealed containers, such as ampules and vials, and can be stored in a condition requiring only the addition of the sterile liquid excipient methods of treatment, methods of administration, and dosage regimens described herein (i.e., water) for injection, immediately prior to use. In some embodiments, the compositions (such as pharmaceutical compositions) is contained in a single-use vial, such as a single-use sealed vial. In some embodiments, each single-use vial contains about $10^9$ activated T cells. In some embodiments, each single-use vial contains enough activated T cells to be expanded to about $10^9$ activated T cells. In some embodiments, the compositions (such as pharmaceutical compositions) is contained in a multi-use vial. In some embodiments, the compositions (such as pharmaceutical compositions) is contained in bulk in a container.

Also provided are unit dosage forms comprising the isolated cell compositions (such as pharmaceutical compositions) and formulations described herein. These unit dosage forms can be stored in a suitable packaging in single or multiple unit dosages and may also be further sterilized and sealed. In some embodiments, the composition (such as pharmaceutical composition) also includes one or more other compounds (or pharmaceutically acceptable salts thereof) that are useful for treating cancer. In various variations, the number of activated T cells in the pharmaceutical composition is included in any one of the following ranges: about $1 \times 10^8$ to about $5 \times 10^8$, about $5 \times 10^8$ to about $9 \times 10^8$, about $9 \times 10$ to about $1 \times 10^9$, about $1 \times 10^9$ to about $2 \times 10^9$, about $2 \times 10^9$ to about $3 \times 10^9$, about $3 \times 10^9$ to about $4 \times 10^9$, about $4 \times 10^9$ to about $5 \times 10^9$, about $5 \times 10^9$ to about $6 \times 10^9$, about $6 \times 10^9$ to about $1 \times 10^{10}$, about $1 \times 10^9$ to about $3 \times 10^9$, about $3 \times 10^9$ to about $5 \times 10^9$, about $5 \times 10^9$ to about $7 \times 10^9$, about $7 \times 10^9$ to about $1 \times 10^{10}$, about $1 \times 10^9$ to about $5 \times 10^9$, about $5 \times 10^9$ to about $1 \times 10^{10}$, about $3 \times 10^9$ to about $7 \times 10^9$, about $1 \times 10^{10}$ to about $1.5 \times 10^{10}$, about $1 \times 10^{10}$ to about $2 \times 10^{10}$, or about $1 \times 10^9$ to about $1 \times 10^{10}$ cells. In some embodiments, the activated T cells are the only pharmaceutically active agent for the treatment of cancer that is contained in the composition.

In some embodiments, there is provided a dosage form (e.g., a unit dosage form) for the treatment of cancer comprising any one of the isolated cell compositions (such as pharmaceutical compositions) described herein. In some embodiments, there are provided articles of manufacture comprising the compositions (such as pharmaceutical compositions), formulations, and unit dosages described herein in suitable packaging for use in the methods of treatment, methods of administration, and dosage regimens described herein. Suitable packaging for compositions (such as pharmaceutical compositions) described herein are known in the art, and include, for example, vials (such as sealed vials), vessels (such as sealed vessels), ampules, bottles, jars, flexible packaging (e.g., sealed Mylar or plastic bags), and the like. These articles of manufacture may further be sterilized and/or sealed.

The present application further provides kits comprising any of the isolated population of cells, compositions (such as pharmaceutical compositions), formulations, unit dosages, and articles of manufacture described herein for use in the methods of treatment, methods of administration, and dosage regimens described herein. Kits described herein include one or more containers comprising the activated T cells.

In some embodiments, there is provided a commercial batch of activated T cells described herein. "Commercial batch" used herein refers to a batch size that is at least about $1 \times 10^9$ activated T cells. In some embodiments, the batch size is at least about any of $1 \times 10^9$, $2 \times 10^9$, $3 \times 10^9$, $4 \times 10^9$, $5 \times 10^9$, $6 \times 10^9$, $7 \times 10^9$, $8 \times 10^9$, $9 \times 10^9$, $1 \times 10^{10}$, $2 \times 10^{10}$, $5 \times 10^{10}$, or $1 \times 10^{11}$ cells. In some embodiments, the commercial batch comprises a plurality of vials comprising any of the compositions (such as pharmaceutical compositions) described herein. In some embodiments, the commercial batch comprises at least about any of 5, 10, 15, 20, 25, 50, 75, or 100 vials. For example, each vial contains at least about $1 \times 10^9$ activated T cells.

The examples and exemplary embodiments below are intended to be purely exemplary of the invention and should therefore not be considered to limit the invention in any way. The following examples and detailed description are offered by way of illustration and not by way of limitation.

EXEMPLARY EMBODIMENTS

Embodiment 1

In some embodiments, there is provided a method of treating a cancer in an individual, comprising administering to the individual an effective amount of activated T cells, wherein the activated T cells are prepared by co-culturing a population of T cells with a population of dendritic cells loaded with a plurality of tumor antigen peptides.

Embodiment 2

In some further embodiments of embodiment 1, the individual has previously been administered with an effective amount of dendritic cells loaded with the plurality of tumor antigen peptides.

Embodiment 3

In some further embodiments of embodiment 1, the method further comprises administering to the individual an effective amount of the dendritic cells loaded with the plurality of tumor antigen peptides.

Embodiment 4

In some further embodiments of embodiment 3, the dendritic cells are administered prior to the administration of the activated T cells.

Embodiment 5

In some further embodiments of embodiment 4, the dendritic cells are administered about 7 days to about 21 days (such as about 7 days to about 14 days, or about 14 days to about 21 days) prior to the administration of the activated T cells.

Embodiment 6

In some further embodiments of any one of embodiments 1-5, the method further comprises preparing the activated T cells by co-culturing the population of T cells with the population of dendritic cells loaded with the plurality of tumor antigen peptides.

Embodiment 7

In some further embodiments of embodiment 6, the population of T cells is co-cultured with the population of dendritic cells for about 7 days to about 21 days (such as about 7 days to about 14 days, or about 14 days to about 21 days).

Embodiment 8

In some further embodiments of any one of embodiments 1-7, the population of T cells is contacted with an immune checkpoint inhibitor prior to the co-culturing.

Embodiment 9

In some further embodiments of any one of embodiments 1-8, the population of T cells is co-cultured with the population of dendritic cells loaded with the plurality of tumor antigen peptides in the presence of an immune checkpoint inhibitor.

Embodiment 10

In some further embodiments of embodiment 8 or embodiment 9, the immune checkpoint inhibitor is an inhibitor of an immune checkpoint molecule selected from the group consisting of PD-1, PD-L1, and CTLA-4.

Embodiment 11

In some further embodiments of any one of embodiments 1-10, the method further comprises preparing the population of dendritic cells loaded with the plurality of tumor antigen peptides.

Embodiment 12

In some further embodiments of embodiment 11, the population of dendritic cells loaded with the plurality of tumor antigen peptides is prepared by contacting a population of dendritic cells with the plurality of tumor antigen peptides.

Embodiment 13

In some further embodiments of embodiment 12, the population of dendritic cells loaded with the plurality of tumor antigen peptides is prepared by contacting the population of dendritic cells with the plurality of tumor antigen peptides in the presence of a composition that facilitates the uptake of the plurality of tumor antigen peptides by the dendritic cells.

Embodiment 14

In some further embodiments of any one of embodiments 1-13, the population of T cells and the population of dendritic cells are derived from the same individual.

Embodiment 15

In some further embodiments of embodiment 14, the population of T cells and the population of dendritic cells are derived from the individual being treated.

Embodiment 16

In some embodiments, there is provided a method of preparing a population of activated T cells, wherein the method comprises: a) inducing differentiation of the population of monocytes into a population of dendritic cells; b) contacting the population of dendritic cells with a plurality of tumor antigen peptides to obtain a population of dendritic cells loaded with the plurality of tumor antigen peptides; and c) co-culturing the population of dendritic cells loaded with the plurality of tumor antigen peptides and the population of non-adherent PBMCs to obtain the population of activated T cells, wherein the population of monocytes and the population of non-adherent PBMCs are obtained from a population of PBMCs from an individual.

Embodiment 17

In some further embodiments of embodiment 16, step b) comprises contacting the population of dendritic cells with the plurality of tumor antigen peptides in the presence of a composition that facilitates the uptake of the plurality of tumor antigen peptides by the dendritic cells.

Embodiment 18

In some further embodiments of embodiment 16 or embodiment 17, step d) further comprises contacting the population of dendritic cells loaded with the plurality of tumor antigen peptides with a plurality of Toll-like Receptor (TLR) agonists to induce maturation of the population of dendritic cells loaded with the plurality of tumor antigen peptides.

Embodiment 19

In some further embodiments of any one of embodiments 16-18, step f) further comprises contacting the population of activated T cells with a plurality of cytokines to induce proliferation and differentiation of the population of activated T cells.

Embodiment 20

In some further embodiments of embodiment 19, the plurality of cytokines comprises IL-2, IL-7, IL-15 or IL-21.

Embodiment 21

In some further embodiments of any one of embodiments 16-20, the population of non-adherent PBMCs is contacted with an immune checkpoint inhibitor prior to the co-culturing.

Embodiment 22

In some further embodiments of any one of embodiments 16-21, step c) comprises co-culturing the population of dendritic cells loaded with the plurality of tumor antigen peptides and the population of non-adherent PBMCs in the presence of an immune checkpoint inhibitor.

Embodiment 23

In some further embodiments of embodiment 21 or embodiment 22, the immune checkpoint inhibitor is an inhibitor of an immune checkpoint molecule selected from the group consisting of PD-1, PD-L1, and CTLA-4.

Embodiment 24

In some embodiments, there is provided a method of treating a cancer in an individual, comprising administering to the individual an effective amount of a population of activated T cells prepared by the method of any one of the methods described in embodiments 16-23.

Embodiment 25

In some further embodiments of embodiments 24, the population of PBMCs is obtained from the individual being treated.

Embodiment 26

In some further embodiments of any one of embodiments 1-15 and 24-25, the activated T cells are administered to the individual for at least three times.

Embodiment 27

In some further embodiments of embodiment 26, interval between each administration of the activated T cells is about 0.5 month to about 5 months.

Embodiment 28

In some further embodiments of any one of embodiments 1-15 and 24-27, the activated T cells are administered intravenously.

Embodiment 29

In some further embodiments of any one of embodiments 1-15 and 24-28, the activated T cells are administered at a dose of at least about $3 \times 10^9$ cells/individual.

Embodiment 30

In some further embodiments of embodiment 29, the activated T cells are administered at about $1 \times 10^9$ to about $1 \times 10^{10}$ cells/individual.

Embodiment 31

In some further embodiments of any one of embodiments 2-15 and 24-30, the dendritic cells loaded with the plurality of tumor antigen peptides are administered for at least three times.

Embodiment 32

In some further embodiments of embodiment 31, the interval between each administration of the dendritic cells is about 0.5 month to about 5 months.

Embodiments 33

In some further embodiments of any one of embodiments 2-15 and 24-32, the dendritic cells loaded with the plurality of tumor antigen peptides are administered subcutaneously.

Embodiment 34

In some further embodiments of any one of embodiments 2-15 and 24-33, the dendritic cells are administered at a dose of about $1 \times 10^6$ to about $5 \times 10^6$ cells/individual.

Embodiment 35

In some embodiments, there is provided a method of treating a cancer in an individual, comprising: a) contacting a population of PBMCs with a plurality of tumor antigen peptides to obtain a population of activated PBMCs, and b) administering to the individual an effective amount of the activated PBMCs.

Embodiment 36

In some further embodiments of embodiment 35, step (a) comprises contacting the population of PBMCs with a plurality of tumor antigen peptides in the presence of an immune checkpoint inhibitor.

Embodiment 37

In some further embodiments of embodiment 36, the immune checkpoint inhibitor is an inhibitor of an immune checkpoint molecule selected from the group consisting of PD-1, PD-L1, and CTLA-4.

Embodiment 38

In some further embodiments of any one of embodiments 35-37, the activated PBMCs are administered for at least three times.

Embodiment 39

In some further embodiments of embodiment 38, the interval between each administration of the activated PBMCs is about 0.5 month to about 5 months.

Embodiment 40

In some further embodiments of any one of embodiments 35-39, the activated PBMCs are administered intravenously.

Embodiment 41

In some further embodiments of any one of embodiments 35-40, the activated PBMCs are administered at a dose of about $1\times10^9$ to about $1\times10^{10}$ cells/individual.

Embodiment 42

In some further embodiments of any one of embodiments 1-41, the plurality of tumor antigen peptides is each about 20 to about 40 amino acids long.

Embodiment 43

In some further embodiments of any one of embodiments 1-42, the plurality of tumor antigen peptides comprises at least one peptide comprising an MHC-I epitope.

Embodiment 44

In some further embodiments of any one of embodiments 1-43, the plurality of tumor antigen peptides comprises at least one peptide comprising an MHC-II epitope.

Embodiment 45

In some further embodiments of embodiment 43 or embodiment 44, the at least one peptide comprising an MHC-I epitope or MHC-II epitope further comprise additional amino acids flanking the epitope at the N-terminus, the C-terminus, or both.

Embodiment 46

In some further embodiments of any one of embodiments 1-45, the plurality of tumor antigen peptides comprises a first core group of general tumor antigen peptides.

Embodiment 47

In some further embodiments of embodiment 46, the plurality of tumor antigen peptides further comprises a second group of cancer-type specific antigen peptides.

Embodiment 48

In some further embodiments of any one of embodiment 46 or embodiment 47, the first core group comprises about 10 to about 20 general tumor antigen peptides.

Embodiment 49

In some further embodiments of embodiment 47 or embodiment 48, the second group comprises about 1 to about 10 cancer-type specific antigen peptides.

Embodiment 50

In some further embodiments of any one of embodiments 1-49, the plurality of tumor antigen peptides comprises a neoantigen peptide.

Embodiment 51

In some further embodiments of embodiment 50, the neoantigen peptide is selected based on the genetic profile of a tumor sample from the individual.

Embodiment 52

In some further embodiments of any one of embodiments 1-15 and 24-51, the cancer is selected from the group consisting of hepatic cellular carcinoma, cervical cancer, lung cancer, colorectal cancer, lymphoma, renal cancer, breast cancer, pancreatic cancer, gastric cancer, esophageal cancer, ovarian cancer, prostate cancer, nasopharyngeal cancer, melanoma and brain cancer.

Embodiment 53

In some further embodiments of any one of embodiments 1-15 and 24-52, the method further comprises administering to the individual an effective amount of an immune checkpoint inhibitor.

Embodiment 54

In some further embodiments of embodiment 53, the immune checkpoint inhibitor is an inhibitor of an immune checkpoint molecule selected from the group consisting of PD-1, PD-L1, and CTLA-4.

Embodiment 55

In some further embodiments of any one of embodiments 1-15 and 24-54, the individual is selected for the method of treating based on the mutation load in the cancer.

Embodiment 56

In some further embodiments of any one of embodiments 1-15 and 24-55, the individual has a low mutation load in the cancer.

Embodiment 57

In some further embodiments of embodiment 56, the individual has a low mutation load in one or more MHC genes.

Embodiment 58

In some further embodiments of embodiment 57, the individual has no more than about 10 mutations in the one or more MHC genes.

Embodiment 59

In some further embodiments of embodiment 57 or embodiment 58, the individual has no mutation in B2M.

Embodiment 60

In some further embodiments of any one of embodiments 57-59, wherein the individual has no mutation in the functional regions of the one or more MHC genes.

Embodiment 61

In some further embodiments of any one of embodiments 55-60, the mutation load of the cancer is determined by sequencing a tumor sample from the individual.

Embodiment 62

In some further embodiments of any one of embodiments 1-15 and 24-61, the individual is selected for the method of treating based on having one or more neoantigens in the cancer.

Embodiment 63

In some further embodiments of any one of embodiments 1-15 and 24-62, the individual has at least 5 neoantigens.

Embodiment 64

In some further embodiments of embodiment 62 or embodiment 63, the method further comprises identifying a neoantigen of the cancer, and incorporating a neoantigen peptide in the plurality of tumor antigen peptides, wherein the neoantigen peptide comprises a neoepitope in the neoantigen.

Embodiment 65

In some further embodiments of any one of embodiments 62-64, the neoantigen is identified by sequencing a tumor sample from the individual.

Embodiment 66

In some further embodiments of embodiment 65, said sequencing is targeted sequencing of cancer-associated genes.

Embodiment 67

In some further embodiments of any one of embodiments 64-66, the method further comprises determining the affinity of the neoepitope to an MHC molecule.

Embodiment 68

In some further embodiments of any one of embodiments 64-67, the method further comprises determining the affinity of the complex comprising the neoepitope and an MHC molecule to a T cell receptor.

Embodiment 69

In some further embodiments of embodiment 67 or embodiment 68, the MHC molecule is an MHC class I molecule.

Embodiment 70

In some further embodiments of any one of embodiments 67-69, the MHC molecule is from the individual.

Embodiment 71

In some further embodiments of any one of embodiments 1-15 and 24-70, the method further comprises monitoring the individual after the administration of the activated T cells or the activated PBMCs.

Embodiment 72

In some further embodiments of embodiment 71, the monitoring comprises determining the number of circulating tumor cells (CTC) in the individual.

Embodiment 73

In some further embodiments of embodiment 71 or embodiment 72, the monitoring comprises detecting a specific immune response against the plurality of tumor antigen peptides in the individual.

Embodiment 74

In some further embodiments of embodiment 73, the plurality of tumor antigen peptides is adjusted based on the specific immune response to provide a plurality of customized tumor antigen peptides.

Embodiment 75

In some further embodiments of embodiment 74, the method of treating is repeated using the plurality of customized tumor antigen peptides.

Embodiment 76

In some further embodiments of any one of embodiments 1-15 and 24-75, the individual is a human individual.

Embodiment 77

In some embodiments, there is provided a method of cloning a tumor-specific T cell receptor, comprising: (a) treating an individual with the method of any one of embodiments 1-15 and 24-76; (b) isolating a T cell from the individual, wherein the T cell specifically recognizes a tumor antigen peptide in the plurality of tumor antigen peptides; and (c) cloning a T cell receptor from the T cell to provide the tumor-specific T cell receptor.

Embodiment 78

In some further embodiments of embodiment 77, the individual has a strong specific immune response against the tumor antigen peptide.

Embodiment 79

In some further embodiments of embodiment 77 or embodiment 78, the T cell is isolated from a PBMC sample of the individual.

Embodiment 80

In some further embodiments of any one of embodiments 77-79, the tumor antigen peptide is a neoantigen peptide.

Embodiment 81

In some embodiments, there is provided a tumor-specific T cell receptor cloned using the method of any one of embodiments 77-80.

Embodiment 82

In some embodiments, there is provided an isolated T cell comprising the tumor-specific T cell receptor of embodiment 81.

Embodiment 83

In some embodiments, there is provided a method of treating a cancer in an individual comprising administering to the individual an effective amount of the isolated T cell of embodiment 82.

Embodiment 84

In some embodiments, there is provided an isolated population of cells prepared by the method of any one of embodiments 16-23 and 42-51.

Embodiment 85

In some embodiments, there is provided an isolated population of cells comprising activated T cells, wherein less than about 1% of the activated T cells are regulatory T ($T_{REG}$) cells.

Embodiment 86

In some further embodiments of embodiment 84 or embodiment 85, the isolated population of cells comprises about 0.3% to about 0.5% $CD4^+CD25^+Foxp3^+$ cells.

Embodiment 87

In some further embodiments of any one of embodiments 84-86, the isolated population of cells comprises about 65%0/to about 75% $CD3^+CD8^+$ cells.

Embodiment 88

In some further embodiments of any one of embodiments 84-87, the isolated population of cells comprises about 16% to about 22% of $CD3^+CD4^+$ cells.

Embodiment 89

In some further embodiments of any one of embodiments 84-88, the isolated population of cells comprises about 13% to about 15% $CD3^+CD56^+$ cells.

Embodiment 90

In some further embodiments of any one of embodiments 84-89, the activated T cells are capable of eliciting specific response to a plurality of tumor antigen peptides in vivo or ex vivo.

Embodiment 91

In some further embodiments of embodiment 90, the activated T cells express a plurality of pro-inflammatory molecules.

Embodiment 92

In some further embodiments of embodiment 91, the plurality of pro-inflammatory molecules comprises IFNγ, TNFα, granzyme B, or perforin.

Embodiment 93

In some further embodiments of any one of embodiments 84-92, the activated T cells have no or low expression of a plurality of immunosuppressive cytokines.

Embodiment 94

In some further embodiments of embodiment 93, the plurality of immunosuppressive cytokines comprises IL-10 or IL-4.

Embodiment 95

In some further embodiments of any one of embodiments 84-94, less than about 5% of the activated T cells express immune-inhibitory molecule PD-1.

Embodiment 96

In some further embodiments of any one of embodiments 84-95, at least about 90% of the cells in the isolated population of cells are activated T cells.

Embodiment 97

In some embodiments, there is provided a composition comprising at least 10 tumor antigen peptides, wherein each of the at least 10 tumor antigen peptides comprises at least one epitope selected from the group consisting of SEQ ID NOs: 1-40.

Embodiment 98

In some further embodiments of embodiment 56, the at least 10 tumor antigen peptides each comprises one or more epitopes encoded by a cancer-associated gene selected from the group consisting of hTERT, p53, Survivin, NY-ESO-1, CEA, CCND1, MET, RGS5, MMP7, VEGFR, AFP, GPC3, HBVc, HBVp, CDCA, KRAS, PARP4, MLL3, and MTHFR

EXAMPLES

The examples described herein are not intended to represent that the experiments below are all or the only experiments performed. Efforts have been made to ensure accuracy with respect to numbers used (for example, amounts, temperature, etc.), but some experimental errors and deviations should be accounted for. Unless indicated otherwise, parts are parts by weight, molecular weight is weight average molecular weight, temperature is in degrees Centigrade, and pressure is at or near atmospheric.

Example 1—A Clinical and Mechanistic Study of MASCT in Treating HCC

Introduction

Hepatocellular carcinoma (HCC) is one of cancers with high mortality, and frequently occurs in the Chinese patients with chronic hepatitis B virus (HBV) infection. Although current standard of cares (SOC), such as resection, liver transplantation, transcatheter arterial chemoembolization (TACE), may improve the survival of patients, HCC is rarely cured and has a high risk of recurrence and metastasis. Here, we applied the MASCT method to a group of Chinese patients suffering from HCC and co-infected with HBV.

Autologous T celled activated by multiple tumor antigens were prepared ex vivo from patients' PBMC according to an embodiment of the MASCT method, and administered to the patients by infusion. With the MASCT strategy, we selectively activated and amplified tumor antigen-specific T cells from the autologous T cell repertoires of the patients with relevant tumor antigen peptides. This ensures that the resulting cells would specifically recognize tumor cells without cross-reactivity against healthy tissue, since these T cells have survived from central selection in the thymus, where all the strong self-reacting T cells that are harmful to the hosts have been removed. We found that the activated T cells led to the expansion of HCC-specific T cells including both effecter and memory T cells in vivo and improved the progression free outcome in patients with HCC.

Results

The Manufacturing Process and Characteristics of MASCT

The cell manufacturing process of MASCT cell therapy is shown in FIG. 2A. Briefly, the immature dendritic cells (iDCs), differentiated from monocytes isolated from patients' PBMC, were pulsed with tumor antigen peptides pool to become mature DCs (mDCs) under the help of TLR agonists. The autologous T cells from the same source of PBMCs were maintained in cytokines and followed co-culturing with mDCs prepared as described above for another 7-10 days. The antigen peptide pool consisted of multiple tumor associate antigens which were overexpressed in cancerous hepatocytes of the patients with HCC. Some of them were already used in clinical trials (FIG. 2B)(1-15). The HCC antigen peptides pool included ten tumor-associated antigens (TAAs), such as survivin, NY-ESO-1, carcinoembryonic antigen (CEA), and so on, which were overexpressed in numerous kinds of tumor cells including HCC; and two HCC specific antigens, named alpha fetoprotein (AFP) and glypican-3 (GPC3), which were commonly expressed in cancerous hepatocytes of the patients with HCC. Two of the HBV associated antigens named HBV core antigen and HBV DNA polymerase, were also included in the peptides pool, since HCC patients in China were mostly correlated with chronic hepatitis B virus (HBV) infection. Moreover, each of the peptides was synthesized with a length of 20-40 amino acids and containing several previously identified T cell recognition epitopes (FIG. 2C) for both class I and class II HLA molecules. The peptides were chemically synthesized under GMP condition.

Figure 3:
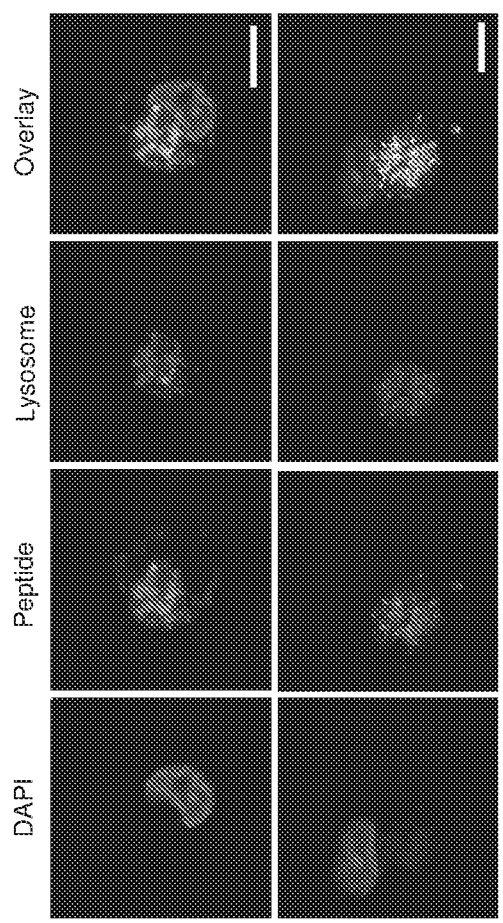
FIG. 3 shows cellular uptake of tumor antigen peptides by iDCs. Human monocytes derived iDCs were pulsed with fluorescent labeled peptides of survivin (second column on the left, 2.5 µg/ml) for 2 hours, followed by labeling with DAPI (first column on the left) and LYSOTRACKER® (second column on the right) to identify nuclei and lysosomes, respectively. Fluorescent images were recorded with confocal microscopy (Leica TCSST5), the scale bar is 7.5 µm, and the images are representative of four independent experiments.
Figure 4A:
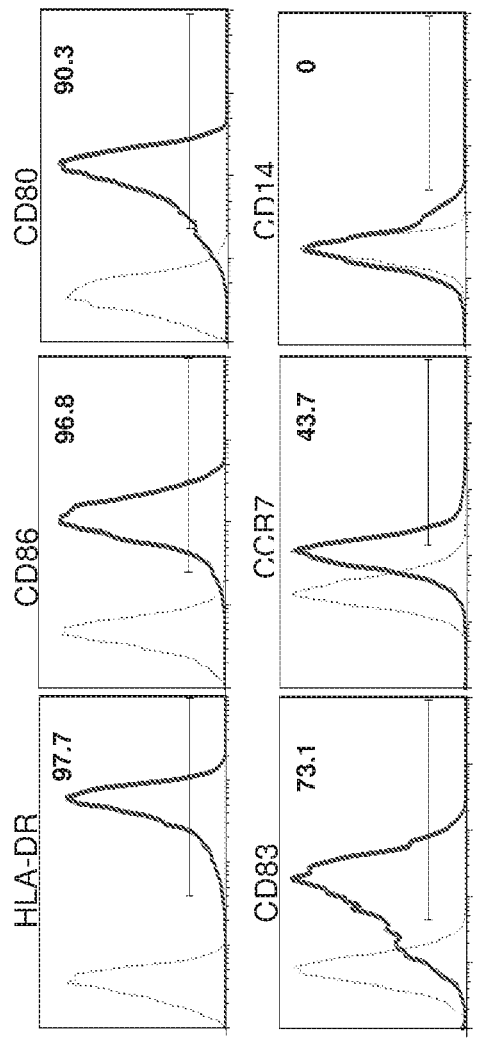
FIGS. 4A-4B show characterization of mature DCs prepared in Example 1.
Figure 4B:
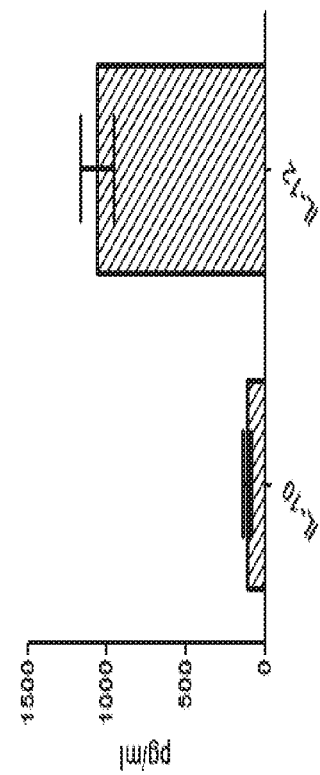

Experiments showed that peptides were effectively internalized by iDCs and primarily localized in the cytosol (FIG. 3), which would consequently promote the cross-presentation by MHC I molecules. After stimulation with toll-like receptor (TLR) ligands, mDCs demonstrated full immune functional properties, especially for the high level secretion of IL12 (FIG. 4 A-B).

After co-culturing, the resulting T cells had proliferated for at least 45-times greater, from median, $8.9 \times 10^7$ cells (range, $5 \times 10^7 \sim 1.6 \times 10^8$ cells) to median, $6.2 \times 10^9$ cells (range, $4.1 \times 10^9 \sim 9 \times 10^9$ cells; FIG. 5A). The resulting cells were almost exclusively $CD3^+T$ cells (95%±1%) with a major phenotype of $CD3^+CD8^+$ (70%±5%) and small part of $CD3^+CD4^+$ (19%±3%) and $CD3^+CD56^+$ (14%±1%), but nearly no $CD4^+CD25^+Foxp3^+$ regulatory T cells ($T_{REG}$, 0.4%±0.1%) (FIG. 5B).

The Immunological Function of the Resulting T Cells

Figure 6D:
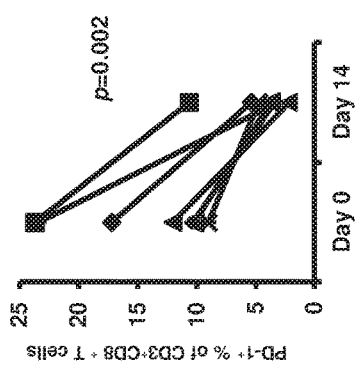
FIGS. 6A-6F depict molecular and functional characterizations of the activated T cells prepared in Example 1.
Figure 6E:
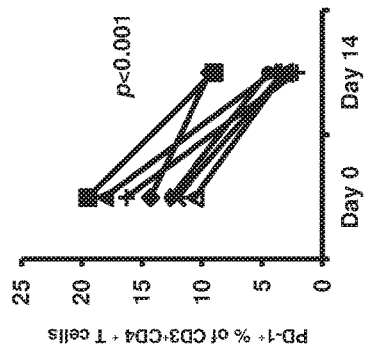
Figure 6F:
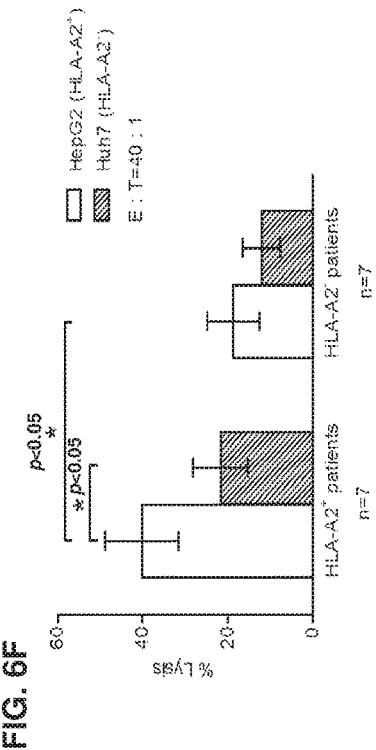
Figure 6A:
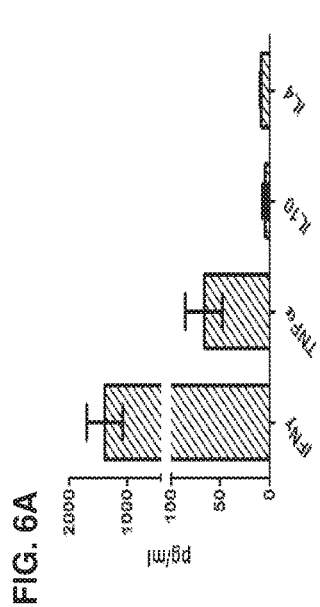
Figure 6B:
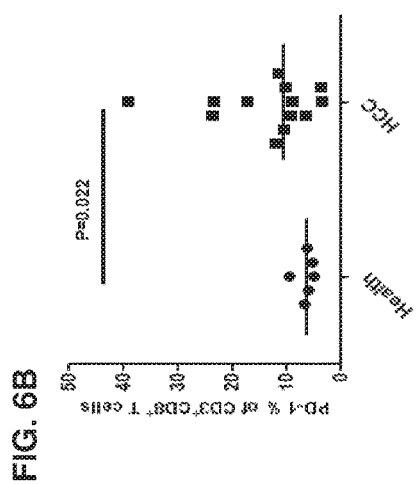
Figure 6C:
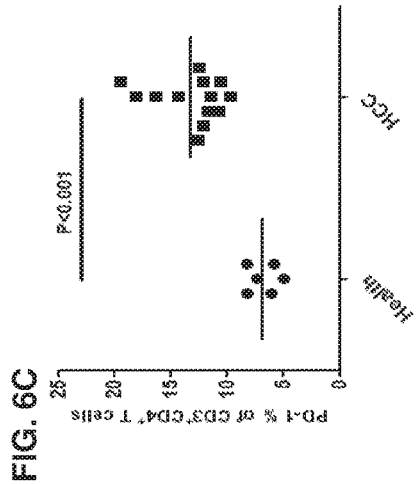

The subsets analysis of the resulting T cells revealed a poly-functional property in the major subset of $CD3^+CD8^+$ cytotoxic T cells, as well as in the minor subsets of $CD3^+CD4^+$ helper T cells and $CD3^+CD56^+$ NKT cells (16), characterized by the co-expression of IFNγ, TNFα and granzyme B (FIG. 5C, D), as compared to the non-activated T cells isolated from patients (FIG. 5E). The pro-inflammatory cytokines such as IFNγ and TNFα were also found in supernatants of the resulting cells, but barely immunosuppressive cytokines such as IL10 and IL4 were detected (FIG. 6A). Others (17, 18) and we have detected a higher frequency of both $CD3^+CD8^+$ and $CD3^+CD4^+$ subsets of T cells expressing immune inhibitory molecule PD-1 on their surface from HCC patients compared to healthy donors, suggesting a T cells exhaustion in HCC patients (FIG. 6B-C). However, this immune tolerance status of T cells could be significantly reversed in both $CD3^+CD8^+$ T cell subset (n=7, p=0.02) and $CD3^+CD4^+$ T cell subset (n=7, p<0.01) by the stimulation of DCs pulsed with multiple tumor antigens (FIG. 6D-E). Moreover, the activated T cells generated from HLA-A2$^+$ patients exhibited superior cytotoxic activity against the HLA-A2$^+$ HCC cell line HepG2 than the HLA-A2$^-$Huh-7 cells suggesting a HLA-restricted killing. While the resulting T cells generated from HLA-A2$^-$ patients (n=7) exhibited similar cytotoxic activity against both the HLA-A2$^+$ and the HLA-A2$^-$HCC cell lines, which may contribute to the non-specific killing performed by $CD3^+CD56^+$ NKT cells (FIG. 6F).

MASCT-Induced Antigen Specific Immune Responses in HCC Patients

Figure 11A:
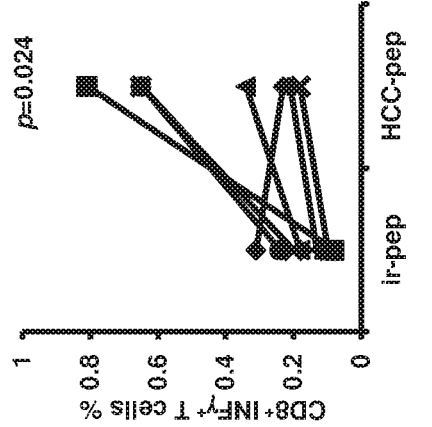
FIGS. 11A-11F depict immune responses raised in patients with HCC after MASCT treatment(s) as described in Example 1.
Figure 11B:
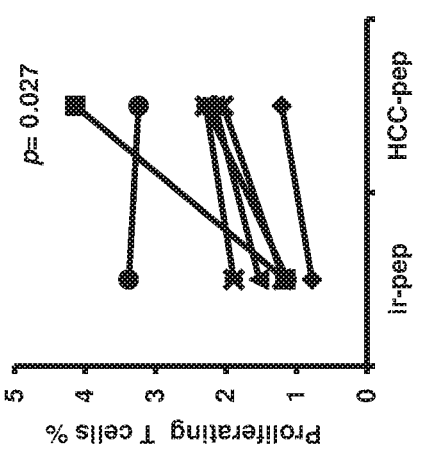
Figure 11C:
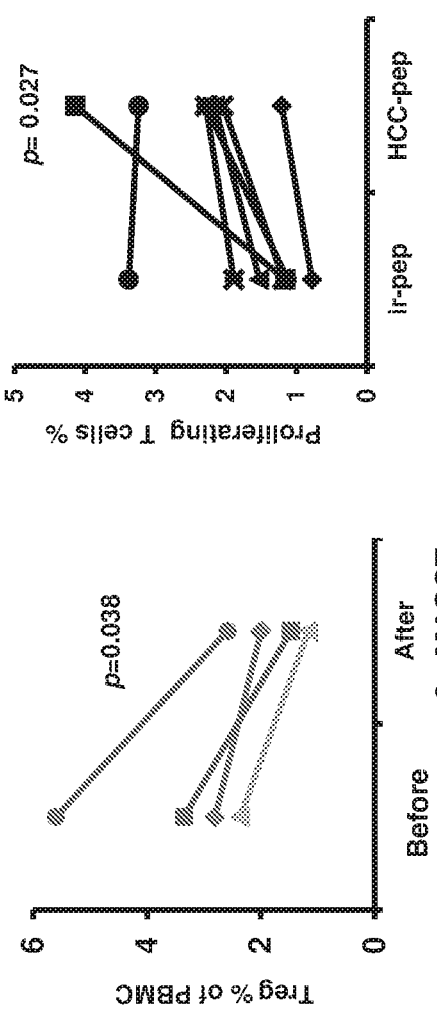
Figure 11D:
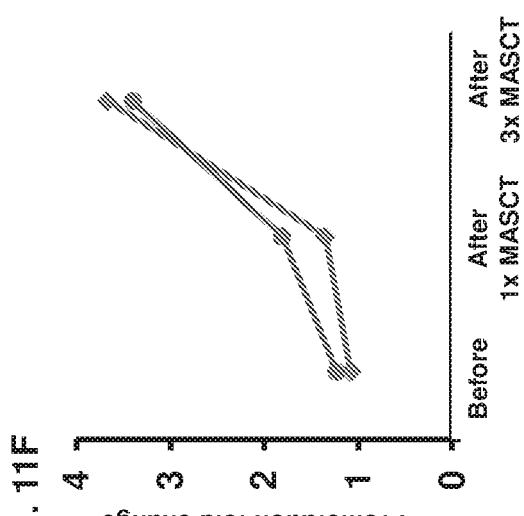
Figure 11E:
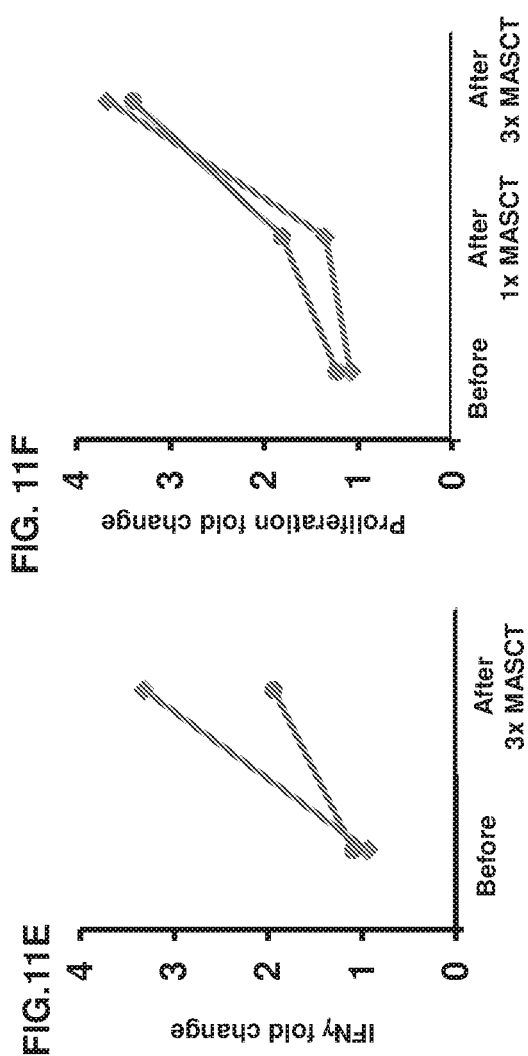
Figure 11F:
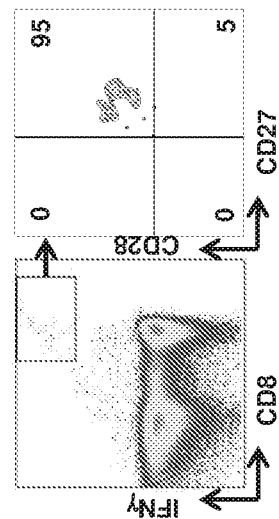

To investigate whether MASCT treatment could bring an improvement of the immune environment in HCC patients, we measured the frequency of $T_{REG}$ in patents' PBMCs and found a significant down-regulation of these cells after three applications of MASCT (FIG. 11A). We also detected the proliferation (FIG. 11B) and IFNγ production (FIG. 11C) of specific T cells against tumor antigens in the patients' PBMCs after stimulation with peptides pool compared to stimulation with irrelevant peptides. And we have observed a significantly increased response in HCC patients' PBMCs (n=6) after stimulation with HCC-antigen peptides pool, as compared to PBMCs stimulated with irrelevant peptides (Antigen specific proliferation: p=0.027; antigen specific IFNγ production: p=0.024, FIGS. 11B and 11C). The IFNγ producing HCC specific CD8+ T cells also co-expressed CD27 and CD28 on their surfaces (FIG. 11D), suggesting a high potential to acquire immune memory phenotype (19, 20). Moreover, to investigate whether the HCC antigen-specific T cell proliferation and IFNγ production were induced or enhanced during the MASCT treatment, we compared these immune responses of patients' PBMCs before and after 3 times treatment of MASCT. The results show that these HCC specific T cell proliferation and IFNγ production were robust, and gradually accumulative immune responses were detected in patients after multiple treatment of MASCT (FIGS. 11E, and 11F). Thus, in MASCT treated patients, both down-regulation of $T_{REG}$ and up-regulation of tumor-specific T cells were detected, demonstrating the improvement of immune environment in HCC patients after MASCT treatment.

The MASCT-Induced Immune Responses Against Each Antigen Peptide in the Pool

To further examine the specific response against each kind of tumor antigen peptide out of the pool, PBMCs from 6 HCC patients (all of them were HBV$^+$) after multiple treatments of MASCT cell therapy were isolated and stimulated with individual antigen peptides. The production of IFNγ was measured by ELISPOT assay. The specific responses against tumor antigen peptides were clearly raised in all of the 6 patients (HBV$^+$), whereas the specific immune responding pattern against each antigen peptides was distinct. Most patients responded to CEA (5/6), HBV core antigen (5/6) survivin (4/6), VEGFR (4/6), AFP (4/6), GPC3 (4/6) and HBV DNA polymerase (4/6). But fewer patients responded to p53 (2/6), CCDN1 (2/6) and MET (1/6) (FIG. 12A), which may due to the diversity of antigen expression in tumors and variability of immune environments in different patients. However, very few immune responses against these tumor antigens were observed in patients (n=5) without MASCT cell therapy (FIG. 12B). Moreover, we have longitudinally studied the dynamic changes of immune responses in 2 patients with HCC (B stage) during their treatments of MASCT cell therapy and discovered that the specific immune responses against tumor antigen peptides were gradually increased, and the immune responses patterns for the 2 patients were different (FIGS. 12C, 12D). We were able to detect tumor antigen specific responses of T cells in patients more than 4 months after the last MASCT treatment (data now shown), suggesting establishment of long-term immune response by memory T cells. Both the raised level of tumor antigens specific T cells and the decreased level of $T_{REG}$ may lead to a better clinical outcome for patients.

Interim Analysis of Clinical Benefits of MASCT

Figure 7A:
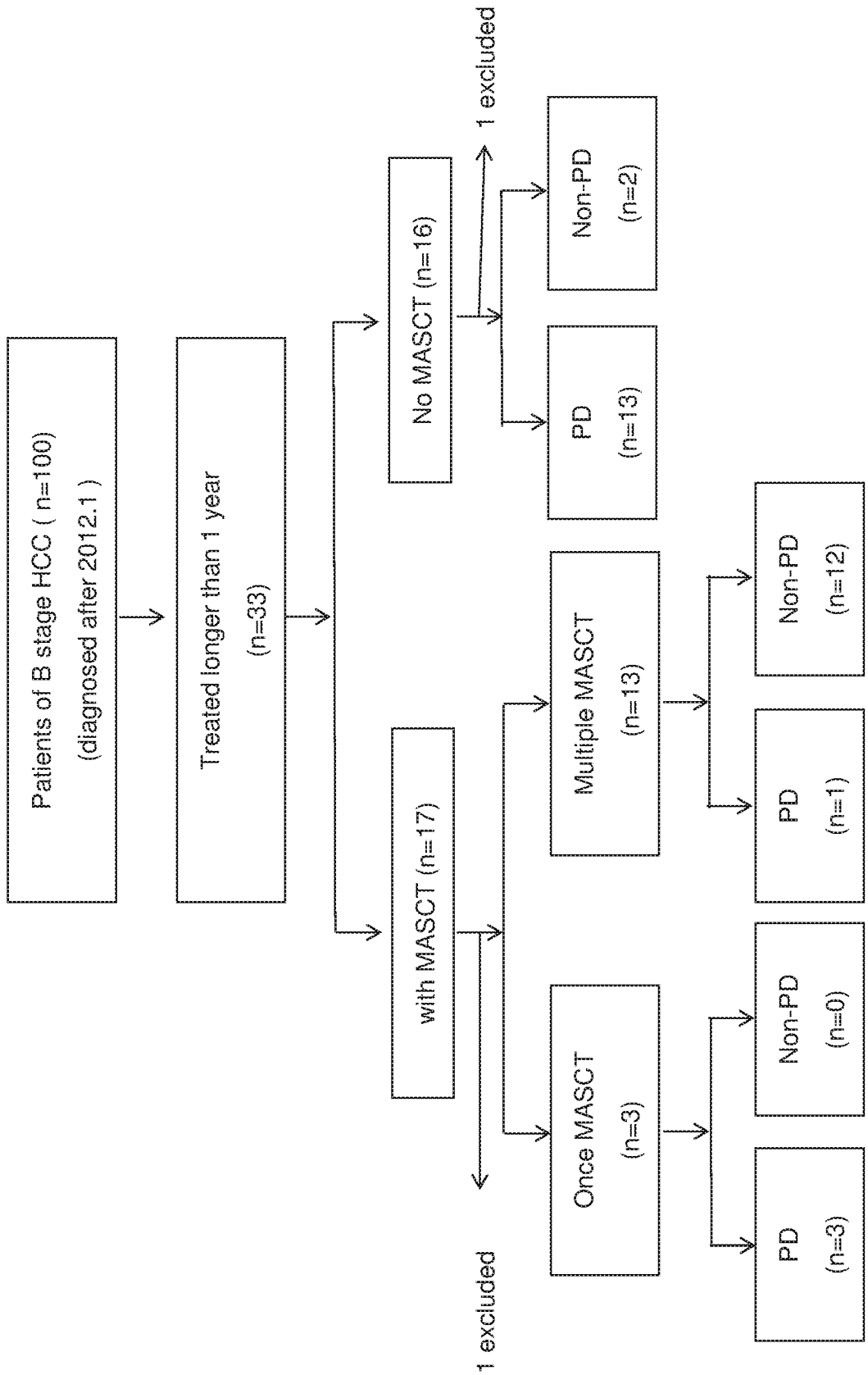
FIG. 7A depicts a flow chart illustrating inclusion and exclusion of patients in the retrospective analysis of clinical data of a MASCT treatment as described in Example 1.

To investigate the clinical benefits of MASCT cell therapy, we have retrospectively studied the cancer progressive circumstances of HCC patients. From 2012 up to present, 100 patients were diagnosed as B stage of HCC (FIG. 7A). Out of all patients, 33 were further analyzed, since they were continuously treated for at least 1 year. 15 of them have only received conventional treatments for HCC such as resection, TACE and RFA (FIG. 8A). The other 16 patients have received MASCT cell therapies in addition to the standard of care. Among them, 13 patients have received repeat MASCT cell therapies (≥3) every 1-3 months combined with conventional treatments (FIG. 9A); 3 patients who only had a single MASCT cell therapy were not further analyzed, since they did not follow the protocol of repeating treatments. During each treatment, 2-5×10$^7$ cells/kg body weight (or at least 1×10$^9$ per person) were infused. No clear toxicity was observed. If the tumors were detected as recurrence, growth or metastasis by Computed Tomography (CT) scan, the patients were evaluated as PD (progressive disease). The time and received treatments from diagnosis to disease progression were indicated. If the tumors were not progressive, the evaluation of the patients on the time point of 1 year after diagnosis were shown, as well as the treatments received during the whole 1 year. Two patients were excluded from the analysis because one patient lacked the evaluation of 1 year, and the other patient did not receive any treatment until her disease was progressed. The disease progressive incidence of the patients who have received multiple treatments of MASCT cell therapy is significantly reduced (p<0.0001), since only 1 patient (n=13, PD: 7.69%) had progressive disease (Table 1). We also found that the average time to disease progression was shorter (median: 6 months) of the patients received only conventional therapies, although average numbers of treatments received by each patient was relatively higher (11 months, Table 1 and FIG. 10A). Moreover, single MASCT cell therapy was not able to improve any progressive free outcome (data not shown) in this patient cohort, suggesting a causative effect for better clinical outcome attributed to multiple treatments of MASCT cell therapies in patients with HCC, which may relate to the total amount of activated T cells infused.

TABLE 1

The comparison of RECIST evaluation between patients with hepatocellular carcinoma (B stage) with or without multiple treatments of MASCT cell therapy during 1 year after diagnosis

|  | Multiple MASCT n = 13 | No MASCT n = 15 | p-values |
|---|---|---|---|
| Overall response, No. (%) | 2 (15.4) | 1 (6.7) | 0.583$^a$ |
| Complete response (CR) | 1 (7.7) | 1 (6.7) | 1$^a$ |
| Partial response (PR) | 1 (7.7) | 0 (NA) | 0.464$^a$ |
| Stable disease (SD), No. (%) | 10 (76.9) | 1 (6.7) | <0.0005$^b$ |
| Progressive disease (PD), No. (%) | 1 (7.69) | 13 (86.7) | <0.0001$^b$ |
| Time to PD, median month | 11 | 6 | NT |

NA: not available;
NT: not tested;
$^a$Analyzed by Fisher's Exact Test(2-sided);
$^b$Analyzed by Pearson Chi-Square (2-sided)

Our study, for the first time, demonstrated that specific responses of T cells against tumor antigens can be robustly raised in vivo, and suggest MASCT cell therapy as a safe and practical immunotherapy improving the immunologic function and clinical outcome of patients with HCC.

Second Analysis of Clinical Benefits of MASCT

Figure 7B:
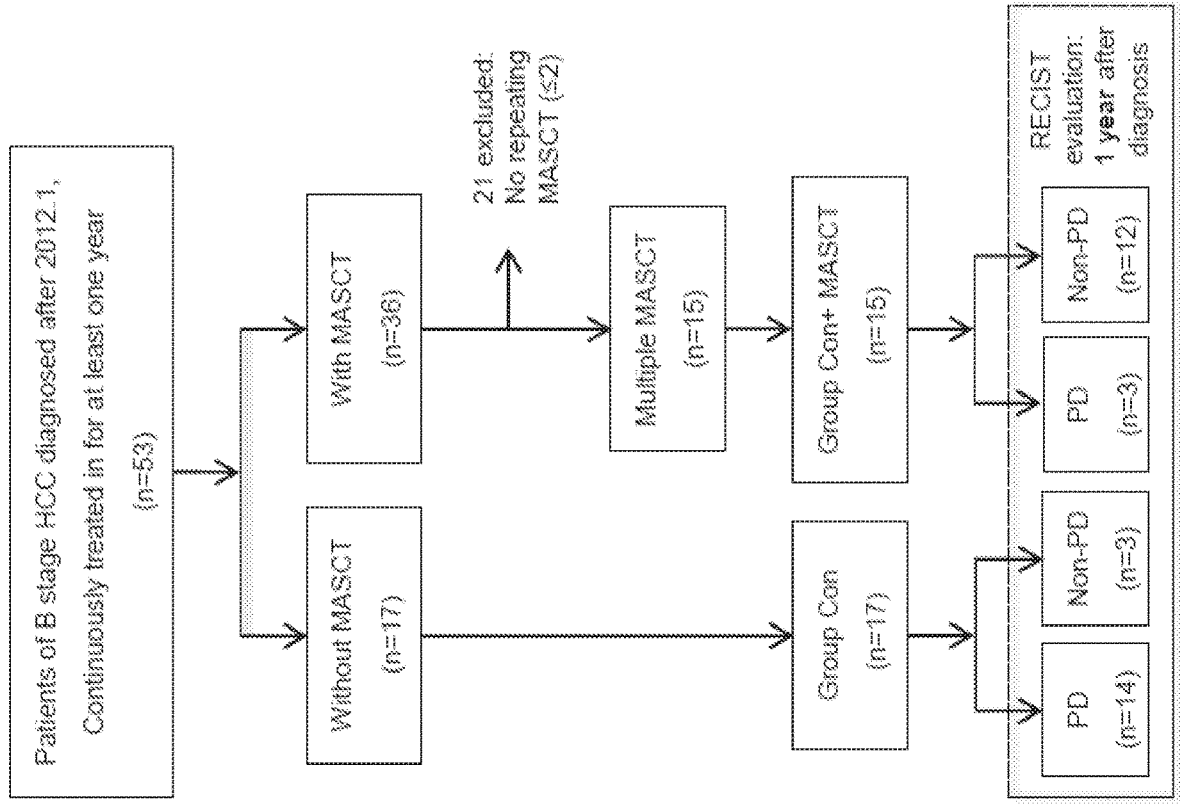
FIG. 7B depicts a schematic diagram of the retrospective analysis of stage B (according to Barcelona Clinic Liver Cancer staging classification) HCC patients continuously treated and regularly followed-up.

We have retrospectively studied the disease control rate (DCR) of patients with stage B HCC, who were diagnosed after 2012 and were continuously treated (with or without MASCT) and regularly followed-up for longer than one year (FIG. 7B and Table 2). Through reviewing of medical records, we found seventeen patients had received conventional treatments (Group Con), such as resection, TACE, and RFA (radiofrequency ablation) (FIG. 8B). Meanwhile, fifteen patients had repeatedly received MASCT treatments (≥3) every 2-3 months, in addition to the conventional treatments (Group Con+MASCT, FIG. 9B). For these 15 patients, we performed routine blood tests and blood biochemistry tests before and after treatment. And no skin rashes, fatigue, fever, diarrhea, anemia, thrombocytopenia, or any other severe side effects were reported, which indicates that MASCT is well tolerant. One year after diagnosis, the DCR was 80% (12 out of 15) of Group Con+MASCT including 4 patient with overall responses (1 patient with CR and 3 patients with PR), and 8 patients with stable disease (SD). This DCR was significantly better (p<0.0001) than the DCR of Group Con (17.65%), in which only 3 out of 17 patients shown as controlled disease (Table 2 and FIG. 9B). Moreover, we have compared the median time to disease progression in the patients who had been evaluated as PD in both group, and found that the time was longer for the patients of Group Con+MASCT (11 months) than that of Group Con (6 months). The average number of conventional treatments received by each patient of Group Con+MASCT was 2.6 (FIG. 10B), as compared to the average number for Group Con which was 3.71. These data clearly showed that MASCT treatment brings up clinical benefits to stage B HCC patients.

TABLE 2

The comparison of disease control rate (DCR) between Stage B HCC patients who had received conventional therapies combined with (Group Con + MASCT) or without (Group Con) multiple treatment of MASCT cell therapy during 1 year after diagnosis.

| | Con + MASCT (n = 15): | Con (n = 17): | p-values |
|---|---|---|---|
| Disease control rate (DCR), No. (%) | 12 (80%) | 3 (17.65%) | <0.0001[b] |
| Overall response rate (ORR) | 4 (26.67%) | 1 (5.88%) | 0.161[a] |
| Complete response (CR) | 1 (6.67%) | 1 (5.88%) | 0.726[a] |
| Partial response (PR) | 3 (20%) | 0 | 0.092[a] |
| Stable disease (SD), No. | 8 (53.33%) | 2 (11.76%) | 0.021[a] |
| Progressive disease (PD), No. (%) | 3 (20%) | 14 (82.35%) | <0.0001[b] |
| Time to PD, median month | 11 | 6.5 | |

[a]Analyzed by Fisher's Exact Test (2-sided);
[b]Analyzed by Pearson Chi-Square (2-sided)

Materials and Methods
Patients

The HCC patients from the department of liver diseases, Nanfang Hospital of Southern Medical University who have received MASCT cell therapy must sign the patients' informed consent before the treatment. All of these patients received infusions of the resulting T cells every 1-3 months with $5-10 \times 10^7$ cells/kg body weight. The eligible criterion included: age between 25 and 80, an Eastern Cooperative Oncology Group (ECOG) performance status score of no more than 2, a life expectancy of more than 3 months, and without severe cardiovascular disease, autoimmune disease, or pregnancy.

Interim Analysis Study Design

The medical records of patients with HCC from a computerized database in the Department of Liver Diseases, Nanfang Hospital of Southern Medical University were reviewed. This database recorded the clinical pathologic information of these patients included details about age, gender, tumor characteristics, BCLC stage, treatment, and outcome. 100 patients with B stage of HCC were diagnosed in the department after 2012. Among them, 33 patients were enrolled in this study since they were continuously treated in the Department for at least 1 year. Out of them, 3 patients who received only once MASCT cell therapy were not further analyzed, since they did not follow the protocol of repeating treatments. The rest patients (n=30) were assigned into one of two treatment groups according to the patients' preference: patients in group 1 received standard therapies only, while patients in group 2 received standard treatments combined with multiple MASCT cell therapy treatments. One patient in group 1 (n=13) was excluded since the patient lacked the evaluation of 1 year. Another patient in group 2 (n=15) was excluded since she did not receive any treatment until her disease was progressed. The characteristics of the patients in these two groups are shown in FIG. 8A and FIG. 9A. The primary endpoint was to investigate the rate of patients with progressive disease (PD) in one year and the time to PD. This study was approved by the Ethics Committee of Nanfang Hospital of Southern Medical University.

Safety Endpoint in Interim Analysis

For the 15 patients who received multiple MASCT cell therapy treatments, we have done the routine blood tests and the blood biochemistry test before and after MASCT cell therapy treatments respectively. No significant difference was detected for the inflammation associated indicators, such as leucocyte count, neutrophil count and lymphocyte count. No clear variety of liver function associated indicators was detected either, such as AST, ALT and total bilirubin. Moreover, no skin rash, fatigue, fever, diarrhea, anemia and thrombocytopenia were observed.

Second Retrospective Analysis

During the second retrospective analysis, the medical records of patients were used from a computerized database in the Centre of Liver Diseases, Nanfang Hospital of Southern Medical University. This database recorded the clinical pathologic information of all patients, including age, gender, tumor characteristics, stages, treatment, and RECIST evaluation. We have analyzed the DCR of patients who were diagnosed as stage B HCC after 2012, and were continuously treated and regularly followed-up in this center for at least one year (FIG. 7B). There were in total 53 patients matching the criteria. Out of them 17 patients had taken SOC but no MASCT, and were distributed into Group Con. The other 36 patients with stage B HCC had received MASCT in addition to conventional treatments. However, 21 out of them were excluded since they had not finished the requirements of repeating treatments (≥3) of MASCT in one year. The remaining 15 patients were distributed into Group Con+MASCT. The characteristics of the patients in these two groups are shown in FIGS. 8B and 9B. According to Response Evaluation Criteria In Solid Tumors (RECIST v1.1), patients were determined as having a complete response (CR), partial response (PR), stable disease (SD), or progressive disease (PD) according to a computed tomography (CT) scan. The primary objective was to investigate the disease control rate of stage B HCC patients one year after diagnosis. This study was approved by the Ethics Committee of the Nanfang Hospital, Southern Medical University.

Cells Preparation

Peripheral blood mononuclear cells (PBMCs) from HCC patients were obtained by density gradient centrifugation on Lymphoprep (Nycomed Pharma, Oslo, Norway). The adherent monocytes were continued to be cultured in AIM-V medium with 1000 U/mL GM-CSF and 500 U/mL IL-4 to differentiate into immature dendritic cells (DCs). The resulting immature DCs were pulsed by multiple tumor antigens peptide pool (1 μg/mL/peptide), followed up with TLR agonists, to differentiate into mature DCs. Meanwhile, the non-adherent PBMCs were maintained in AIM-V medium with anti-CD3 (eBioscience, San Diego, Calif.) and interleukin-2 (rIL-2; R&D Systems, Minneapolis, Minn.), and were then co-cultured with mature DCs for 7-14 days (such as 7-10 days, or 9-13 days) in the presence of cytokines.

Patients received infusions of the resulting T cells every 1-3 months with 5-10×10⁷ cells/kg body weight.

Immunofluorescence

Dendritic cells (DCs) were cultured in a Chamber slides (Thermo Scientific, USA) and pulsed with FITC labeled peptides with or without liposome encapsulation. After 2 h, DCs were labeled with DAPI (Molecular Probes) and LYSOTRACKER™ (Molecular Probes) to identify nuclei and lysosomes, respectively. The fluorescent images were recorded using a confocal laser scanning microscopy (TCS SP5II, Leica, Ernst-Leitz-Strasse, Germany).

Flow Cytometry

Antibodies for cell surface staining were obtained from BD Biosciences (anti-human CD3-PE, CD3-FITC, CD8-PerCP, CD8-APC, CD56-PE, NKG2D-APC, CD4-FITC, CD4-PerCP, CD107a-FITC, CD25-APC, CD45RO-FITC, CD27-PerCPCY5.5, CD57-APC, CCR7-PE, PD-1-PE). Antibodies for monocyte and dendritic cell surface staining were also obtained from BD Biosciences (anti-human CD14-APC, CD80-PE, CD83-APC, CD86-FITC, HLA-DR-FITC). Antibodies for intracellular cytokine staining were obtained from BD Biosciences (anti-human IFN-γ-APC, TNF-α-PECY7, GranzymeB-FITC, FoxP3-PE). Intracellular cytokine staining was performed by fixing and permeabilizing cells with cytofix/cytoperm (BD Biosciences). Flow cytometry was performed using FACS Cantol (BD Biosciences) flow cytometers and data was analyzed with the Flowjo program.

ELISA for Cytokine Detection

The supernatants of mature DCs or cultured T cells were centrifuged to remove particulate debris and stored at −80° C. until use. IL-12p70 and IL-10 were measured by specific ELISA kits (eBioscience) according to the manufacturer's protocols. IFN-γ, TNF-α and IL-4 were detected by Procarta Plex Multiplex Immunoassays (Affymetrix).

Functional and Cytotoxicity Studies

HepG2 or Huh7 were cultured in DMEM supplemented with 10% inactivated fetal bovine serum, 100 U/mL penicillin, 100 μg/mL streptomycin, Glutamax, MEM NEAA, (Gibico, Carlsbad, Calif.). The cytotoxicity assay was performed as in the manufacturer's manual. HepG2 or Huh7 cells were washed with D-PBS (Invitrogen) and co-cultured with the patient's effector T cells at an effector:target (E:T) ratio of 40:1 in 96-well round-bottom plates in triplicates in AIM-V for 4 hours. Cytotoxicity was shown as the percentage of maximal LDH released after lysis and measured by the Cytotox 96 Assay kit (Promega G1780, Canada).

Proliferation Assay and IFNγ Production of Antigen Specific T Cells

PBMCs from patients were plated (1×10⁶ cells/well) in AIM-V medium containing 50 U/mL IL-2 and stimulated with 10 μg/mL peptide pool for 3 days. To determine the proliferative percentage of specific T cells, FACS analysis was performed as described in the Click-iT EdU Alexa Fluor 488 Flow Cytometry Assay Kit (Invitrogen). The IFNγ production of specific T cells was also detected by intracellular cytokine staining and FACS analysis. PBMCs incubated with 10 μg/mL irrelevant peptide were used as negative controls. The results were shown as a fold index compute by specific peptide group: irrelevant peptide group.

ELISPOT Assay

PBMCs from patients were plated (1×10⁶ cells/well) in AIM-V medium without any cytokines on cell culture plate, and were further stimulated with irrelevant peptides, MASCT antigen peptide pool, and individual antigen peptides respectively for 48 h. The PBMCs were then transferred onto a 96-well ELISPOT assay plate (U-CyTech Biosciences) for IFNγ detection. The PBMCs were further stimulated with peptides for another 16 h. The ELISPOT assay was performed and analyzed according to the manufacturer's instructions. The number of spot-forming units was determined with computer-assisted image analysis software (ChampSpot; Saizhi). The responses were shown as spot-forming units per 10⁵ PBMC/well. Results were demonstrated as an IFNγ-producing fold index computed by the ratio of specific peptide stimulation to irrelevant peptide stimulation.

Discussion

Adoptive cell therapy (ACT) are recently well accepted as an effectively alternative therapy to treat cancer patients, especially for those who had failed to be treated with conventional cancer therapies, such as surgery, radiation therapies, and chemotherapies. Though the tumor specific TILs had successfully treated metastatic melanoma patients with more than 50% overall responses [21], and the anti-CD19 CAR-modified T cells had shown extraordinary clinical benefits both in chronic lymphatic leukemia (CLL) and acute lymphatic leukemia (ALL) [22, 23], the ACT using tumor specific T cells still faced to great challenge. In the tumor environment, tumor cells, which express and present a particular tumor antigen on their surface, could be targeted by the tumor infiltrating T cells which specifically recognized the epitopes of the particular tumor antigen. After recognition, the T cells will release cytotoxic factors such as perforin and granzyme B, as well as the functional cytokines such as IFNγ and TNFα to lysate the tumor cells. However, this mechanism of immune surveillance is high likely to be shut down in cancer patients. The large number of inhibitor cells such as $T_{REG}$, the lack of tumor specific TILs, and the loss of tumor antigen expression in tumor cells could all contribute to the failure.

Here, we have presented a novel and practical strategy, MASCT, by preparing multiple tumor antigens activated T lymphocytes ex vivo from patients' PBMCs. In MASCT strategy, we used long antigen peptides instead of tumor antigen protein or tumor lysate. We demonstrated the stimulation of T cells with multiple tumor antigen epitopes at the same time, which may more effectively prevent the immune escape of tumor cells caused by the loss of a particular tumor antigen expression. In our study, distinct patterns of specific T cell responses against each kind of tumor antigens were observed in different HCC patients after multiple treatments of MASCT. This may be due to the diversity of antigen expression and presentation, as well as the variability of the tumor microenvironment. This phenomenon also suggests the need to use multiple antigens to target tumor cells instead of a single tumor antigen. Moreover, each tumor antigen peptide was designed to contain 20-40 amino acids which enables the presentation of both class I and class II HLA molecules on the DCs in patients with different kinds of HLA subtypes. Indeed, we have observed specific immune responses against tumor antigens in different HCC patients by both the T cell proliferation assay and the IFNγ stimulation assay, as well as the decrease of T G in patients' PBMCs after multiple treatment of MASCT. And these immune responses were gradually enhanced during multiple treatment of MASCT, indicating that repeating treatment may correlate with a better clinical outcome.

It has been reported that 240 million people worldwide (including one-tenth population in China) are chronically infected with HBV, who have high risk to develop HCC later in their life. With few effective conventional therapies, HCC in China is a kind of cancer with high morbidity and mortality. Trying to solve this problem, we have applied MASCT in HCC patients to stimulate specific T cell responses against tumor antigens and HBV associated antigens, intending to improve the clinical outcome of patients by the combination treatment of MASCT and conventional therapy. Through retrospective analysis, we have investigated the clinical effects of patients with stage B HCC after receiving multiple treatments of MASCT. The one-year DCR was significantly increased in the group of patients treated with MASCT every 2-3 months combined with conventional therapies (Group Con+MASCT), compared to the control group (80% vs. 17.65%). We have further analyzed the DCR two years after diagnosis of the 12 patients from Group Con+MASCT who demonstrated disease control in the first year. Excluding two patients whose disease courses were less than two years, 9 out of 10 patients still demonstrated as disease control (data not shown).

For the first time, our study has demonstrated that specific responses of T cells against tumor antigens can be strongly induced and increased in vivo by MASCT, and that MASCT treatment is a well tolerant immunotherapy to improve both the immunologic function and disease control of patients with HCC. The same principle and methodology is undergoing a perspective and randomized clinical trial for HCC patients (NCT02026362), and is being explored for other tumors as well. Furthermore, we speculate that MASCT treatment can be combined with immune checkpoint blockade therapy, such as anti-PD1 antibody, given the fact that anti-PD1 antibody therapy brings only clinical benefits to average 20% patients in different kinds of cancer. The 80% non-responding patients are thought to have not enough pre-existing tumor specific T cells, which may be able to be rescued by MASCT treatment.

REFERENCES

1. A. J. Gehring et al., Gastroenterology 137, 682 (2009).
2. E. Mizukoshi et al., Hepatology 43, 1284 (2006).
3. V. R. Cicinnati et al., Int J Cancer 119, 2851 (2006).
4. S. Idenoue et al., Clin Cancer Res 11, 1474 (2005).
5. T. Ito et al., Hepatology 31, 1080 (2000).
6. J. L. Chen et al., J Immunol 165, 948 (2000).
7. J. L. Marshall et al., J Clin Oncol 23, 720 (2005).
8. S. Walter et al., Nat Med 18, 1254 (2012).
9. N. Nishida et al., Cancer Res 54, 3107 (1994).
10. K. Schag et al., Clin Cancer Res 10, 3658 (2004).
11. C. N. Boss et al., Clin Cancer Res 13, 3347 (2007).
12. H. Suzuki et al., J Transl Med 11, 97 (2013).
13. L. H. Butterfield et al., Clin Cancer Res 12, 2817 (2006).
14. H. Komori et al., Clin Cancer Res 12, 2689 (2006).
15. A. J. Gehring et al., J Hepatol 55, 103 (2011).
16. J. Yuan et al., Proc Natl Acad Sci USA 105, 20410 (2008).
17. B. Martin et al., J Hepatol (2014).
18. A. Schurich et al., Hepatology 53, 1494 (2011).
19. A. G. Chapuis et al., Proc Natl Acad Sci USA 109, 4592 (Mar. 20, 2012).
20. D. J. Powell, Jr., M. E. Dudley, P. F. Robbins, S. A. Rosenberg, Blood 105, 241 (2005).
21. Restifo N P, Dudley M E, Rosenberg S A. Adoptive immunotherapy for cancer: harnessing the T cell response. Nature reviews Immunology 2012; 12:269-281.
22. Porter D L, Levine B L, Kalos M, Bagg A, June C H. Chimeric antigen receptor-modified T cells in chronic lymphoid leukemia. N Engl J Med 2011; 365:725-733.
23. Grupp S A, Kalos M, Barrett D, Aplenc R, Porter D L, Rheingold S R, et al. Chimeric antigen receptor-modified T cells for acute lymphoid leukemia. N Engl J Med 2013; 368:1509-1518.

Example 2—A Case Study of a Patient with Metastatic Cervical Cancer Treated with MASCT and Cloning of Tumor Specific T Cell Receptors Cervical cancer is the second most common gynecologic malignant tumor, and frequently occurs in patients with human papilloma virus (HPV) infection. Effective treatment for cervical cancer (including surgery and concurrent chemoradiation) can yield cures in 80% of women with early stage disease (stage I-II). However, vascular invasion, incomplete lymphadenectomy are most common factors predicting poor prognosis in early stage cervical cancer. Patients with vascular invasion confirmed by pathological specimens are more likely to develop metastatic disease in the near future post-surgery. Here we present an immunotherapy named MASCT (Multiple Antigen Stimulating Cellular Therapy), to treat a HPV+ metastatic cervical cancer patient with multiple tumor antigen pulsed dendritic cells (DCs) and T lymphocytes stimulated by these DCs.

Patient WJ, female, was diagnosed with cervical cancer with vascular invasion at age 41, and was tested positive with Human Papilloma Virus (HPV) DNA. She underwent curative resection, and a five-month chemo-radio therapy. The patient took a second HPV DNA test, and was confirmed to be negative in serum HPV DNA.

Figure 13C:
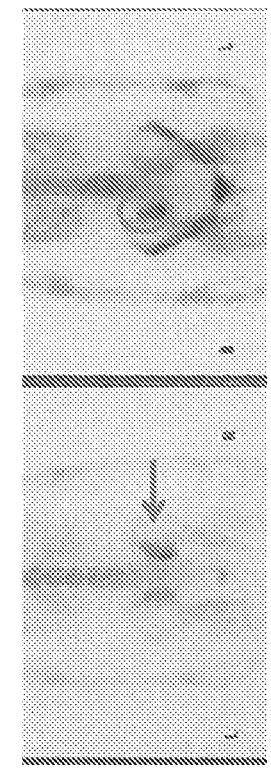
FIGS. 13A-13F show clinical data of Patient WJ with metastatic cervical cancer treated with 7 MASCT treatments.
Figure 13D:
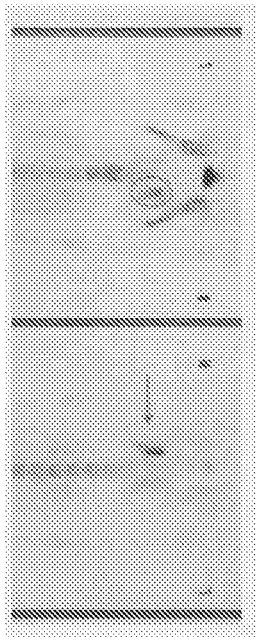
Figure 13A:
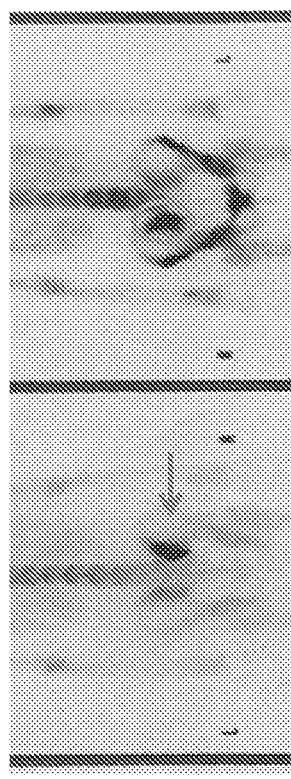

About two years after the curative resection and chemo-radio therapy, the patient was diagnosed to have metastasis tumor on the right sacroiliac joint bone according to Magnetic Resonance Imaging (MRI) and Emission Computed Tomography (ECT) (FIG. 13A). The patient then received ten local radiotherapy treatments, followed by three MASCT treatment, administered one per month. The MASCT treatment used PBMCs from the patient's own peripheral blood to prepare dendritic cells pulsed with a pool of 18 antigen peptides, including a core group of 12 tumor-associated antigen peptides, as well as a cervical cancer-specific group of 6 antigen peptides derived from viral proteins of HPV. Briefly, monocytes from the patient's PBMCs were differentiated into immature DCs and then pulsed with multiple synthetic peptide antigens including tumor-associated antigens and HPV antigens. The semi-mature DCs were further stimulated by TLR ligands to differentiate into mature DCs (mDCs). Half of mDCs were subcutaneous injected to the patient. Maintaining T cells were prepared by culturing non-adherent PBMCs with anti-CD3 antibody (e.g., OKT3), and IL2. The other half of mDCs was co-cultured with the maintaining T cells for another 7-9 days before infusion. The patient was confirmed to have HLA-A2 serotype (HLA-A0201$^+$).

Figure 13B:
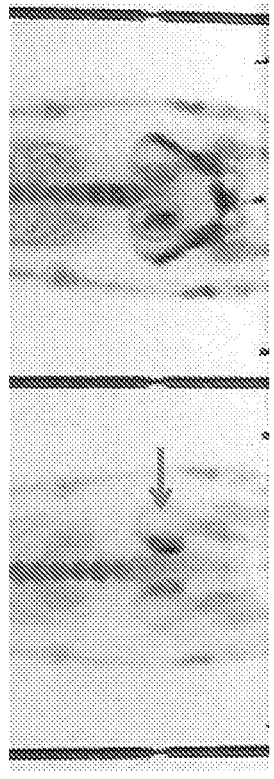
Figure 13E:
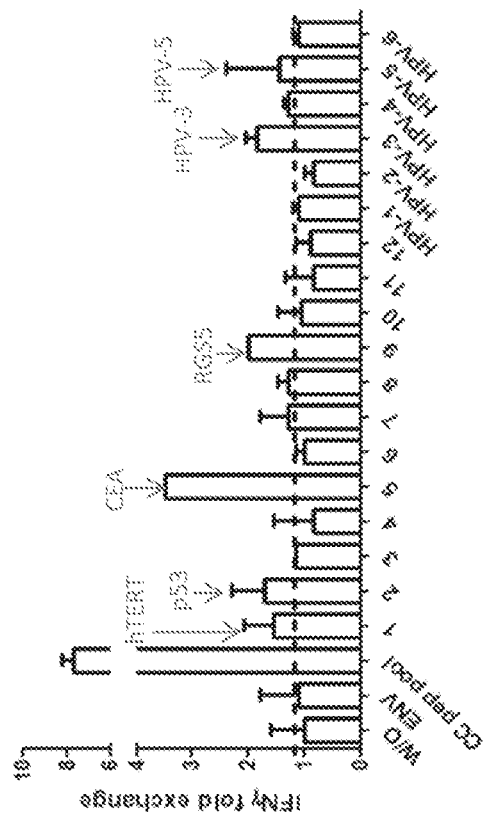

After the three MASCT treatments, the patient's ECT results showed that the right sacroiliac joint bone metastasis was reduced, and no new metastasis was detected (FIG. 13B), indicating positive treatment outcome of MASCT. The patient received four additional MASCT treatments administered with an interval of about 1 month or 2 months. After a total of 6 MASCT treatments, a sample of the patient's PBMC was obtained and tested with an ELISPOT assay to determine whether the patient had a therapeutically effective MHC-restricted T cell response to the antigen peptide pool and each of the antigen peptides within the pool. The ELISPOT results (FIG. 13E) demonstrated enhanced T-cell response to the cervical carcinoma antigen peptide pool, and individual antigen peptides within both the core group of tumor-specific antigen peptides (such as hTERT, p53, CEA, and RGS5), and the cervical cancer-specific group of tumor antigen peptides (such as HPV-3 and HPV-5). The patient's ECT after a total of 7 MASCT showed further reduction of the right sacroiliac joint bone metastasis, and no new metastasis sites (FIG. 13C), indicating that the MASCT treatment regimen was successful in reducing tumor burden in the patient and in preventing tumor progression and further metastasis.

Figure 13F:
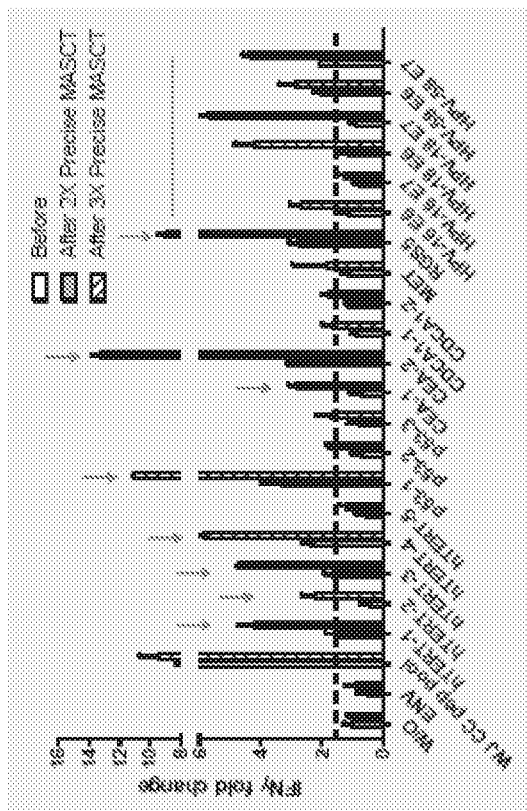

Based on the patient's specific immune response, the antigen peptide pool was customized to provide a patient-specific antigen peptide pool by saving the responsive peptides that had induced specific responses and removing the non-responsive peptides that did not induce specific responses. The patient was further treated with 3 cycles of MASCT prepared using the patient-specific antigen peptide pool (referred herein as "precise MASCT"). After the three precise MASCT, The patient's ECT showed no development of the right sacroiliac joint bone metastasis, and no new metastasis sites (FIG. 13D). The patient was evaluated as having stable disease (SD). The patient-specific antigen peptide pool further boosted the specific responses as demonstrated by the ELISPOT assay (FIG. 13F). In particular, several hTERT peptides, p53-1 peptide, CEA peptides, and RGS5 peptide yielded the strongest specific response. We are in the process of cloning the CEA and telomerase specific TCRs from this patient.

The antigen peptide pool was further adjusted based on the specific immune response of the patient, and the patient was treated with a $2^{nd}$ precise MASCT using the further adjusted peptide antigen pool.

A summary of the patient's treatment history is shown in FIG. 14.

Our study provides MASCT as a safe treatment, which has reduced the metastasis of the cervical cancer patient. Tumor antigens specific T cell responses could be robustly raised in cervical cancer patients after MASCT treatment, and were even further boosted after patient-specific antigens selection. Additionally, our study provides a promising method to clone tumor specific TCRs from cancer patients, who have shown enhanced immunological responses, as well as clinical benefits after immunotherapy with patient-specific antigens.

Example 3—Brief Description of a Phase 1/2 MASCT Clinical Trial Study Protocol

A Phase 1/2 MASCT clinical trial study, entitled "Multiple Antigen Specific Cell Therapy (MASCT) for Hepatocellular Carcinoma (HCC) Patients After Radical Resection or Radio Frequency Ablation (RFA)", commenced in July 2013, and is registered at the online database ClinicalTrials.gov with identifier NCT02026362. Description of some aspects of the study can be found at https://clinicaltrials.gov/ct2/show/NCT02026362, which is incorporated herein by reference. This clinical study is ongoing.

The Phase1/2 MASCT study is a 1:1 randomized, open-label, multi-center study that aims to investigate the safety and efficacy of an embodiment of the MASCT method in treating hepatocellular carcinoma (HCC) patients that have previously received curative resection, such as resection or RFA, as anti-HCC therapy. The study is carried out in multiple sites in China, including Nanfang Hospital of Southern Medical University (Guangzhou, PRC), Third Affiliated Hospital of Sun Yat-Sen University (Guangzhou, PRC), Cancer Center of Sun Yat-Sen University (Guangzhou, PRC), PLA 302 Hospital of China (Beijing, PRC), and Fujian Cancer Hospital (Fuzhou, PRC). The patients are randomly stratified into a control group and a test group (1:1 in number of patients of the two groups) based on standard prognostic factors, such as age, sex, previous treatment regimen, and clinical performance status. Patients in the control group receive a standard of care (SOC) according to current medical practice, including liver-protection treatment and anti-viral treatment against Hepatitis B virus (HBV) using nucleoside analogue drugs. In China, HCC is highly associated with HBV infection. Patients in the test group receive the same SOC treatment, plus MASCT treatment, which involves administration of dendritic cells loaded with a total of 14 antigens, including hTERT, surviving, p53, and CEA, and activated T cells induced by the dendritic cells. The MASCT treatment is repeated every three weeks for a total of three times. Each patient in the two study groups will receive treatment for about 9 weeks unless the patient experiences disease progression or unacceptable toxicity. If patients have not progressed after 9 weeks, treatment may be continued at the investigator's discretion. Patients will be followed for about 2.5 years or until death or disease progression of all patients, whichever occurs earlier.

Approximately 100 patients are planned to be enrolled, treated and evaluated in the study. Patients must fulfill all of the following criteria to be eligible for admission to the study.

1. The patient is diagnosed as hepatocellular carcinoma (HCC);
2. The patient underwent radical operation of HCC within 8 weeks before enrollment;
3. The number of tumors is no more than 2;
4. No cancer embolus in the main portal vein, first branch of hepatic duct, first branch of hepatic vein, or inferior vena cava;
5. No portal lymph node metastasis;
6. No extra-hepatic metastasis;
7. Complete tumor resection without residual tumor at the surgical margins as confirmed by enhanced CT or MRI imaging within 4 week (including 4 weeks) after radical operation;
8. If an increased serum AFP level was detected of the patient before the radical operation, the AFP level should be returned to normal within 8 weeks;
9. Child-Pugh Score≤9;
10. ECOG Performance status (ECOG-PS)≤2;
11. The expected survival time is more than 2 years;
12. Tests of blood, liver and kidney meeting the following criteria:
    a. WBC>3*$10^9$/L
    b. Neutrophil counts>1.5×$10^9$/L
    c. Hemoglobin≥285 g/L
    d. Platelet counts≥50×$10^9$/L
    e. PT is normal or The extend time<3 s
    f. BUN≤1.5 times the upper-limit,
    g. Serum creatinine≤1.5 times of the upper-limit
13. Patient consent obtained and signed according to local Institutional and/or University Human Experimentation Committee requirements and/or a central Institutional Review Board (IRB) or other as appropriate.

Patients who fulfill any of the following criteria are not eligible for admission to the study:

1. Women who are pregnant or during breast feeding or plan to be pregnant within 2 years;
2. Extra-hepatic metastasis or liver residual tumor;

3. Cancer embolus in the main portal vein, first branch of hepatic duct, first branch of hepatic vein, or inferior vena cava;
4. 6 months before enrollment: the duration of systemic and continuous use of immunomodulatory agents (such as interferon, thymosin, traditional Chinese medicine) was longer than 3 months;
5. 6 months before enrollment: the duration of systemic and continuous use of the immunosuppressive drugs (such as corticosteroids drug) was longer than 1 month;
6. Received any cell therapy (including NK, CIK, DC, CTL, stem cells therapy) within 6 months prior to enrollment;
7. Positive for HIV antibody or HCV antibody;
8. Have a history of immunodeficiency disease or autoimmune diseases (such as rheumatoid arthritis, Buerger's disease, multiple sclerosis or diabetes type 1);
9. Patients who suffered from other malignant tumor within 5 years before enrollment (except skin cancer, localized prostate cancer or cervix carcinoma);
10. Patients with organ failure;
11. Patients with serious mental disease;
12. Drug addiction within 1 year before enrollment, including alcoholism;
13. Participated in other clinical trials within 3 months before screening;
14. Other reasons the researchers deem unsuitable for the study.

The primary objective of the study is to demonstrate that MASCT plus SOC treatment is superior to foundation treatment alone with respect to (1) number of patients having tumor recurrence or metastasis within 2 years as a measure of efficacy; (2) time from operation to tumor recurrence or metastasis within 2 years as a measure of efficacy; (3) number of patients having adverse events within 2 years as a measure of safety and tolerability. The secondary objective of the study is to compare MASCT plus foundation treatment to foundation treatment alone with respect to their effects on (1) HBV markers, including HBeAg; (2) serum HBV DNA load; and (3) patients' quality of life. Additional clinical endpoints, such as overall response rate (RR), complete response (CR), partial response (PR) and stable disease rate (SDR) of the two patient groups will be compared. Tumor response and progression will be assessed using RECIST criteria (v1.1). Safety will be assessed on the basis of vital signs, clinical laboratory findings, and adverse events graded according to the NCI CTCAE version 4.02, 15 Oct. 2009.

Other clinical trials investigating the clinical efficacy and toxicity of embodiments of the MASCT method, similar to the Phase 1/2 MASCT clinical trial in HCC, will be conducted to treat patients suffering from liver cancer, lung cancer, colon cancer, cervical cancer, lymphoma, renal carcinoma, breast cancer, pancreatic cancer, gastric cancer, esophageal cancer, ovarian cancer, and brain cancer.

Example 4—T Cell Activation Protocols

This example compares the in vitro specificity and function of cytotoxic T cells prepared using various exemplary T cell activation protocols, including different duration and cycles of T cell co-culture, and the presence or absence of an immune checkpoint inhibitor, such as anti-PD-1 monoclonal antibodies, during the co-culture.

Use of Anti-PD-1 Antibody

Figure 15:
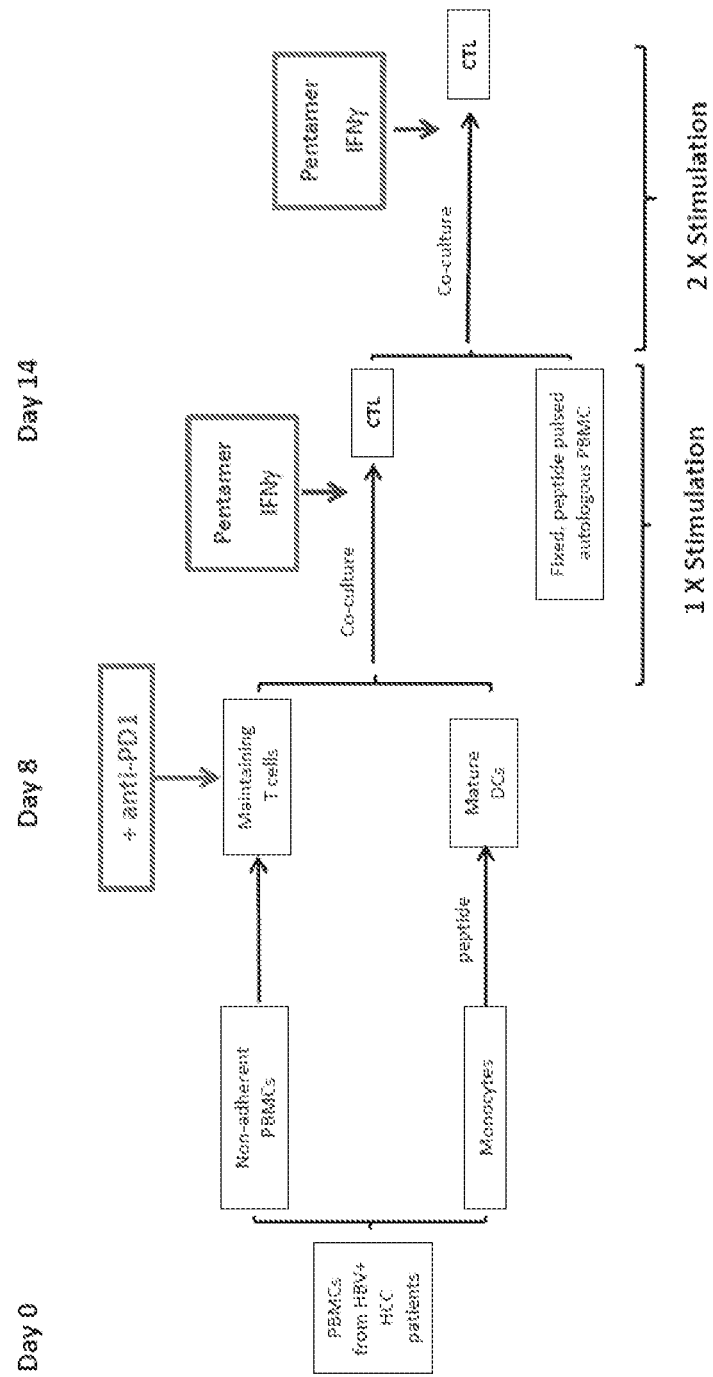
FIG. 15 shows a schematic of exemplary experimental setups for preparing activated T cells.

FIG. 15 shows a schematic of the experimental setup for preparing activated T cells. Peripheral blood mononuclear cells (PBMCs) from HCC patients that were positive in HBV were obtained by density gradient centrifugation on Lymphoprep (Nycomed Pharma, Oslo, Norway) on Day 0. The adherent monocytes were continued to be cultured in AIM-V medium with 1000 U/mL GM-CSF and 500 U/mL IL-4 to differentiate into immature dendritic cells (DCs). The immature DCs were pulsed by HBV core antigen peptide (5 tgi/mL) as well as TLR agonists to differentiate into mature DCs. A fraction of PBMCs were also pulsed with the same antigen peptide, and fixed. Meanwhile, the non-adherent PBMCs were maintained in AIM-V medium with anti-CD3 (eBioscience, San Diego, Calif.) and interleukin-2 (rIL-2; R&D Systems, Minneapolis, Minn.) until Day 8 to obtain maintaining T cells. The maintaining T cells were then co-cultured with mature DCs alone, or in combination with an anti-PD-1 antibody (nivolumab, or SHR-1210) or a negative control IgG4 from Day 9 to Day 13 in the presence of cytokines to provide activated T cells, (i.e., cytotoxic T lymphocytes or CTL). On Day 14, the fixed, peptide-pulsed PBMCs were added to the CTLs and co-cultured for 5 days for a second cycle of T cell stimulation. Alternatively, a second batch of peptide-pulsed mature DCs can be used instead of the fixed, peptide-pulsed PBMCs for the second cycle of T cell stimulation.

Peptide-pulsed mature DCs and T cells from Day 8 were analyzed using FACS to quantify subpopulations that expressed PD-L1 or PD-1 respectively. Activated T cell samples from the co-cultures were obtained on Day 13 and Day 18, and assayed by staining with pentamers followed by FACS analysis. Staining with pentamers and other multimers (such as dextramers) indicates presence of TCRs on the activated T cells specifically recognizing MHC-peptide complexes, thereby providing a measure of specificity of the activated T cells. The activated T cells from Day 13 and Day 18 were also stimulated with the tumor antigen peptides pool, and IFNγ production by the activated T cells was determined by intracellular cytokine staining followed by FACS analysis. As IFNγ was produced by T cells specifically activated by the tumor antigen peptides, the IFNγ production assay provides a measure of the cytotoxic function of the peptide-specific T cells.

Figure 16A:
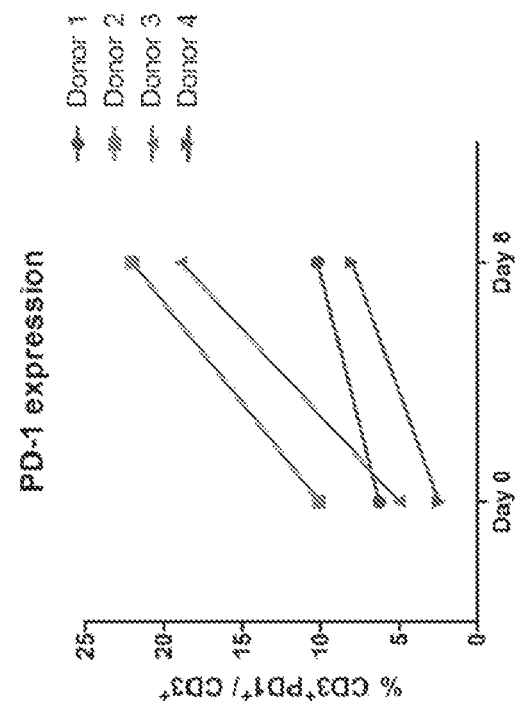
FIG. 16A shows FACS results of mature dendritic cells using anti-PD-L1 antibody and anti-CD11c antibody.
Figure 16B:
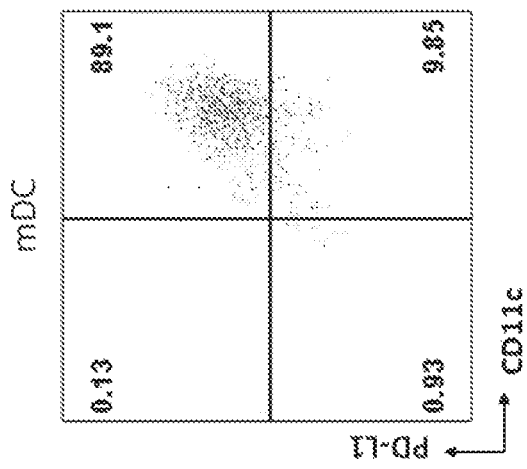
FIG. 16B shows PD-1 expression levels of T cells in the PBMC samples from four different donors before and after 8 days of activation.

As shown in FIG. 16A, about 89.1% of peptide-pulsed mature DCs expressed PD-L1. FIG. 16B shows a significant increase in the percentage of PD1$^+$ T cells among all CD3$^+$ T cells in the PBMCs from four independent donors by Day 8.

When anti-PD1 antibodies were introduced to the co-culture of T cells and DCs, both specificity and function of the activated T cells in vitro increased significantly (FIGS. 17A-17D) as compared to activated T cells prepared without anti-PD-1 antibodies or with a negative control IgG4. In particular, SHR-1210 (Hengrui Medicine) enhanced the in vitro IFNγ production by the activated T cells as compared to nivolumab (FIG. 17D).

Duration and Number of Stimulation

Figure 18:
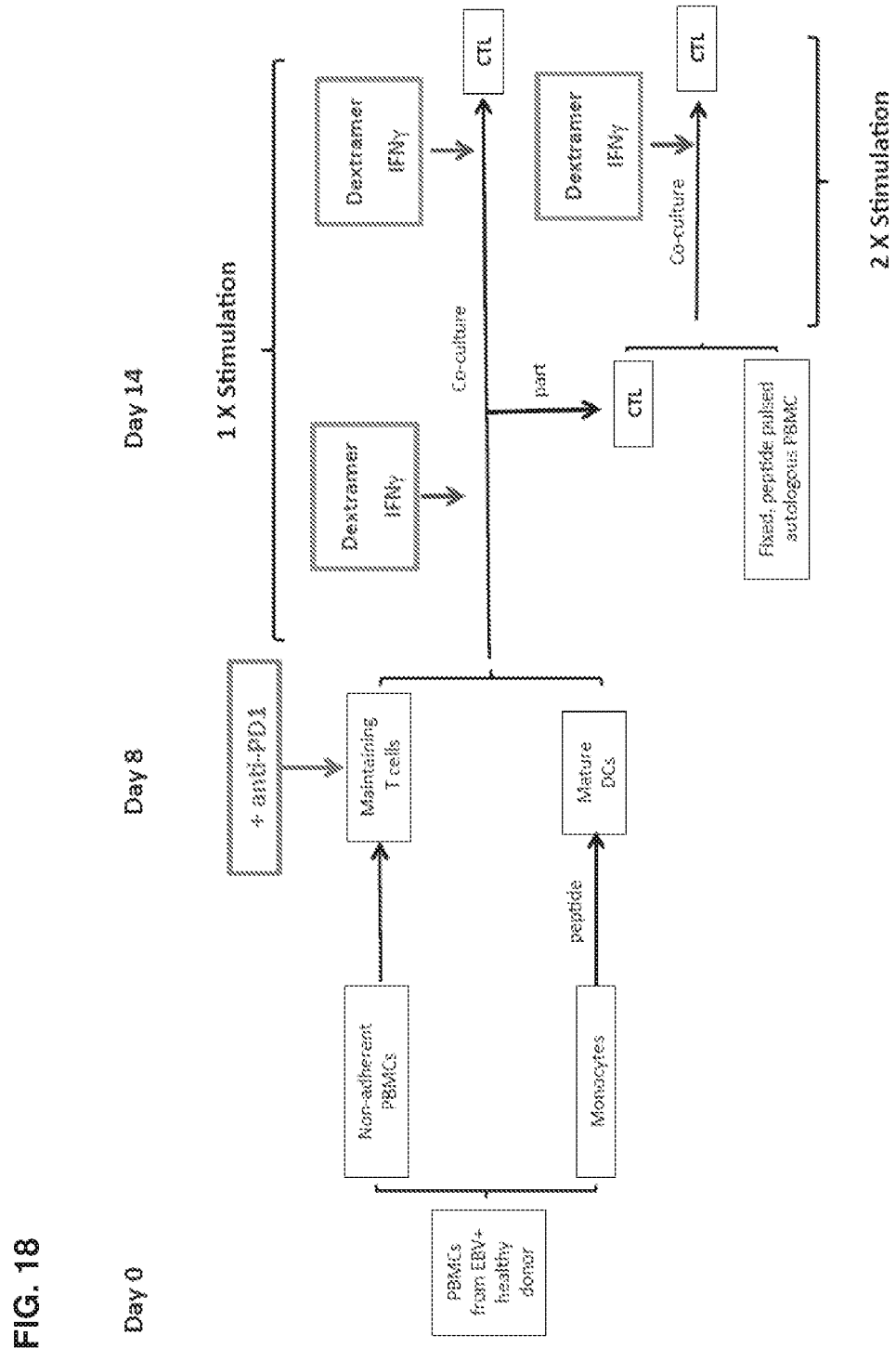
FIG. 18 shows a schematic of exemplary experimental setups for preparing activated T cells.

FIG. 18 shows a schematic of the experimental setup for preparing activated T cells. Peripheral blood mononuclear cells (PBMCs) from healthy donors that were positive in EBV were obtained by density gradient centrifugation on Lymphoprep (Nycomed Pharma, Oslo, Norway) on Day 0. The adherent monocytes were continued to be cultured in AIM-V medium with 1000 U/mL GM-CSF and 500 U/mL IL-4 to differentiate into immature dendritic cells (DCs). The immature DCs were pulsed by multiple tumor antigens peptide pool (1 g/mL/peptide) as well as TLR agonists to differentiate into mature DCs. A fraction of PBMCs were also pulsed with the same tumor antigens peptide pool, and fixed. Meanwhile, the non-adherent PBMCs were maintained in AIM-V medium with IL2, IL7, IL15 and IL21 to obtain maintaining T cells until Day 8. The maintaining T cells were then co-cultured with mature DCs alone, or in combination with an anti-PD-1 antibody (nivolumab, or SHR-1210), or a negative control IgG4 from Day 9 to Day 18 in the presence of cytokines to provide activated T cells, (i.e., cytotoxic T lymphocytes or CTL). On Day 14, a fraction of the activated T cells were mixed with the fixed, peptide-pulsed PBMCs, and cultured for 5 days for a second cycle of T cell simulation. Alternatively, a second batch of peptide-pulsed mature DCs can be used instead of the fixed, peptide-pulsed PBMCs for the second cycle of T cell stimulation.

Activated T cell samples from the co-cultures were obtained on Day 13 and Day 18, and assayed by staining with pentamers or dextramers followed by FACS analysis. The activated T cells from Day 13 and Day 18 were also stimulated with the tumor antigen peptides pool, and IFNγ production by the activated T cells was determined by intracellular cytokine staining followed by FACS analysis.

As shown in FIG. 19A, a higher percentage of peptide-specific T cells were present in the co-culture after 10 days of stimulation as compared to 5 days of stimulation. Among all culturing conditions tested, 10 days of co-culture with one time stimulation in the presence of anti-PD1 antibodies resulted in the highest specificity and cytotoxic function of the CD8$^+$ T cells, as measured by multimer staining (FIG. 19B), and IFNγ production (FIG. 19C).

Figures 20A, 20B:
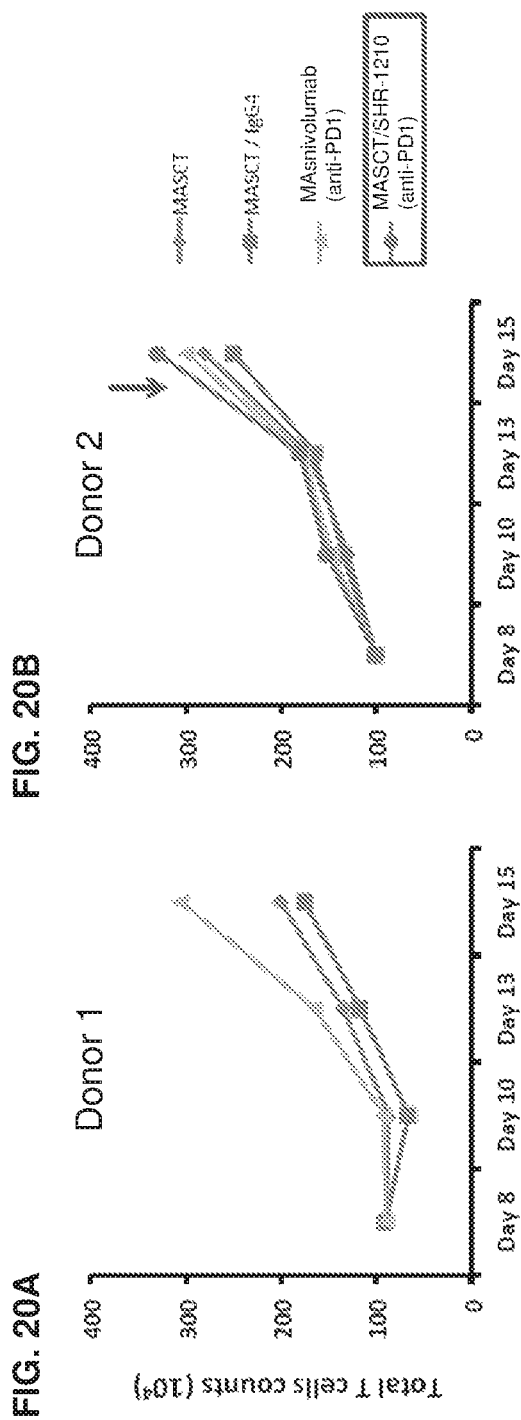
FIGS. 20A-20B show the total T cell counts in the co-cultures from PBMCs of two different donors over time with or without the presence of anti-PD-1 antibody (SHR-1210 or nivolumab).

Total number of T cells in samples taken from Day 8, Day 10, Day 13, and Day 15 of the 1-time stimulated co-culture were quantified for two preparations using PBMCs from two different donors. As shown in FIGS. 20A-20B, among all samples tested, the highest number of total T cells was found in the co-culture taken on Day 15 in the presence of SHR-1210 anti-PD1 antibody.

Additionally, PD-1 surface expression was quantified in non-adherent PBMC cells treated with an anti-PD1 antibody (nivolumab or SHR-1210) or negative control IgG4, and PMA on Day 0. PBMCs treated anti-PD1 antibodies showed reduced PD-1 expression level on the cell surface, which would be expected if the anti-PD1 antibodies could internalize the surface PD1 (FIGS. 21A-21B).

In summary of the above in vitro characterizations of T cells activated using the various preparation protocols, use of anti-PD1 monoclonal antibodies in the PBMC culture improved the specificity and function of the activated cytotoxic T cells. Anti-PD1 monoclonal antibodies seemed to both enhance the general proliferation of T cells in vitro, and promote internalization of PD1 molecules that normally express on the surface of T cells. Compared to nivolumab, SHR-1210 anti-PD1 antibody yielded activated T cells with higher specificity and function. Other immune checkpoint inhibitors, such as anti-PD-L1 antibodies or anti-CTLA-4 antibodies, can be used in place of the anti-PD1 antibodies for preparing activated T cells with enhanced specificity and cytotoxic function.

Example 5—Cancer Precision Immunotherapy Clinical Practice Case Analysis

This example describes a study aimed at predicting the response rate and effectiveness of Major Histocompatibility Complex (MHC) Class I restricted immunotherapy such as PD-1 inhibitor or multiple antigen specific cancer therapy (MASCT) by evaluating the cancer cell driver mutation and human leukocyte antigen (HLA) class I gene mutation load using the next generation sequencing (NGS).

By the next generation sequencing (NGS) of 333 cancer associated genes and using Dirichlet Multinomial Mixture package in RStudio software for classification, 35 cancer samples were clustered into two subgroups. Mutation load of HLA-I genes was evaluated from each sample, and neoantigens were predicted from non-synonymous point mutations. The combined mutational information was used to predict the response of 35 cancer patients to MHC-I restricted immunotherapy. Among the 35 patients whose samples have been sequenced and analyzed, five patients received PD-1 inhibitor monotherapy, MASCT monotherapy or combination therapy. Two patients, who had high HLA-I gene mutation load (predicted as non-responders), received PD-1 inhibitor (KEYTRUDA®) and MASCT combination therapy or MASCT monotherapy for more than three times. These two patients were clinical evaluated as having progressive disease (PD). Three patients, who had low HLA-I gene mutation load and more neoantigens (predicted as responders), received PD-1 inhibitor (KEYTRUDA®) and MASCT combination therapy or MASCT monotherapy for more than four times. Two of the three patients were clinical evaluated as having partial response (PR), and one patient was evaluated as having stable disease (SD).

The NGS analysis of mutation in cancer associated genes described in this example successfully predicted the clinical response to MHC-I restricted immunotherapy among patients who received MASCT monotherapy or MASCT combination therapy with PD-1 inhibitor. The prediction method can enable improved efficiency and precision immunotherapy for individual cancer patients.

Introduction

Next Generation Sequencing (NGS) can sequence a tumor tissue in a rapid and high-throughput manner to provide a large amount of mutation data of the tumor tissue. Bioinformatics methods can be applied to the mutation data to obtain clinically significant mutations, thereby providing useful information for the cancer patient in the following areas: 1. clinical and molecular stratification; 2. selection of suitable drug targets; and 3. prediction of effectiveness of an MHC-I restricted immunotherapy. Such information can provide precision intervention for each patient, and bring cancer immunotherapy to an era of precision medicine. Cancer precision immunotherapy, such as precision immune cell therapy, precision immunological drug therapy, promise to become an important breakthrough in cancer precision therapy, greatly improving patients' quality of life, and increasing patient's survival time (see, for example, Qian Qijun, Mengchao Wu. Precision cancer immunotherapy: From theory to practice [J]. Chin J Cancer Biother, 2015, 22(2):151-158).

Materials and Methods

Sample Source

Tumor samples from 35 patients were sequenced. Among the patients, there were 18 males, 17 females, age 27-88, with an average age of 56. Tumor samples were obtained from the patients and used for sequencing analysis focusing on 333 OncoGxOne™ cancer-associated genes and the HLA-I genes. Next-generation sequencing (NGS) was performed to obtain genetic mutation information in tumor tissue, such as point mutation, indel, fusion, copy number variation, etc., with a focus on 333 cancer-associated genes. Five of the 35 patients were further treated with PD-1 inhibitor (Keytruda) monotherapy, MASCT monotherapy, or the combined therapy (FIG. 22). Informed consent was obtained from patients for all clinical trials.

HLA-I Subtyping

Low quality reads and adaptor sequences were removed from the raw sequencing data, then Polysolver analysis tool (see, for example, Shukla S A, Rooney M S, Rajasagi M, et al. Comprehensive analysis of cancer-associated somatic mutations in class I HLA genes. Nature Biotechnology, 2015, 33:1152-1158) was used for HLA-I subtyping prediction.

Neoantigen Prediction

Based on HLA-I subtyping results of each patient, multiple algorithms including NetMHC 3.4 were employed to analyze amino acid sequences of the point mutation loci of the 333 cancer-associated genes from the tumor tissue. The affinity of the mutated amino acids to the corresponding HLA-I molecules of the patient was predicted, the affinity difference between wild-type and mutant antigen peptides was compared, and mutant antigen peptides with higher affinity than that of wild-type were selected. The T-cell receptor (TCR) binding affinity was then predicted using the mutant antigen peptides selected above with high affinity to HLA-I molecules, and the TCR binding affinity difference between wild-type and mutant antigen peptides was compared. The mutant antigen peptides with higher binding affinity to TCR than that of wild-type antigens were selected as predicted neoantigens that can induce immune response. The sequences of these predicted neoantigens were mapped to the entire human genome of healthy individuals, and neoantigens with potential cross-reacting sequences were removed from the pool, in order to avoid adverse effects in clinical trials.

Statistics 1.1 The open source software RStudio version 0.99.473 was used to perform analysis on the number of point mutation loci, number of genes with point mutation, number of indel loci, number of genes with indel, number of fusion genes, number of genes with copy number variation, and the total numbers of mutated loci and genes. These mutagenetic characteristics were employed for stratified analysis of 35 tumor samples with the Dirichlet Multinomial Mixture (DMM) model (see, for example, Holmes I K, Quince C. Harris. Dirichlet Multinomial Mixtures: Generative Models for Microbial Metagenomics [J]. PLoS ONE, 2012, 7(2): e30126).

1.2 The "pheatmap" package was used to generate clustering plot for the 35 tumor tissue samples based on mutation load of each of the 333 cancer-associated genes. The characteristic information of each tumor sample was added to the cluster plot, such as clinical trial grouping information, grouping information of whether there was DNA mismatch-repair (MMR) deficiency or not, and DMM grouping information.

1.3 The statistical difference of the number of HLA-I gene mutations in each DMM group based on the RStudio software was tested using Mann-Whitney rank-sum test, with p<0.05 as statistically significant.

Results

Stratified Cluster Analysis of 333 Cancer-Associated Genes

Figure 23B:
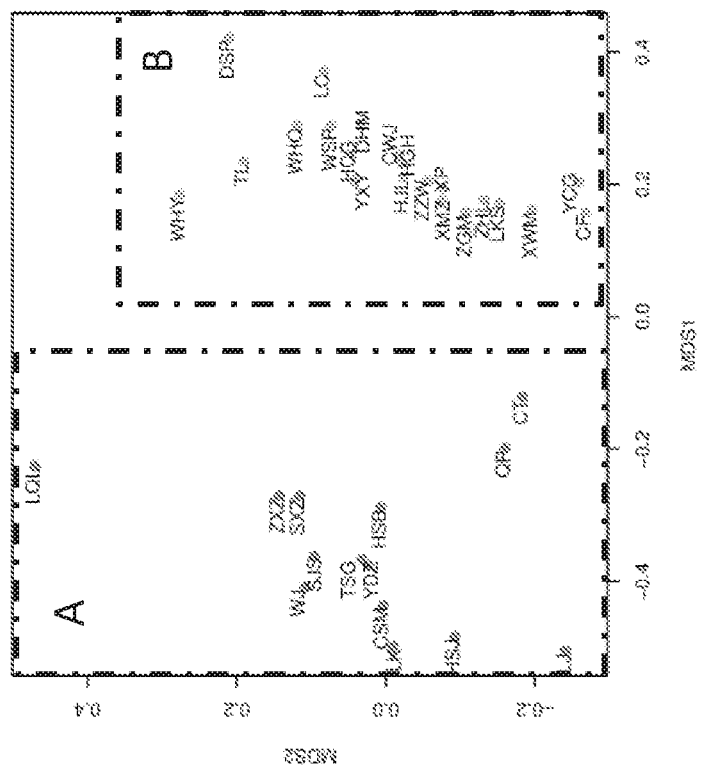
FIGS. 23A-23B depict the DMM classification analysis of 35 tumor samples.
Figure 23A:
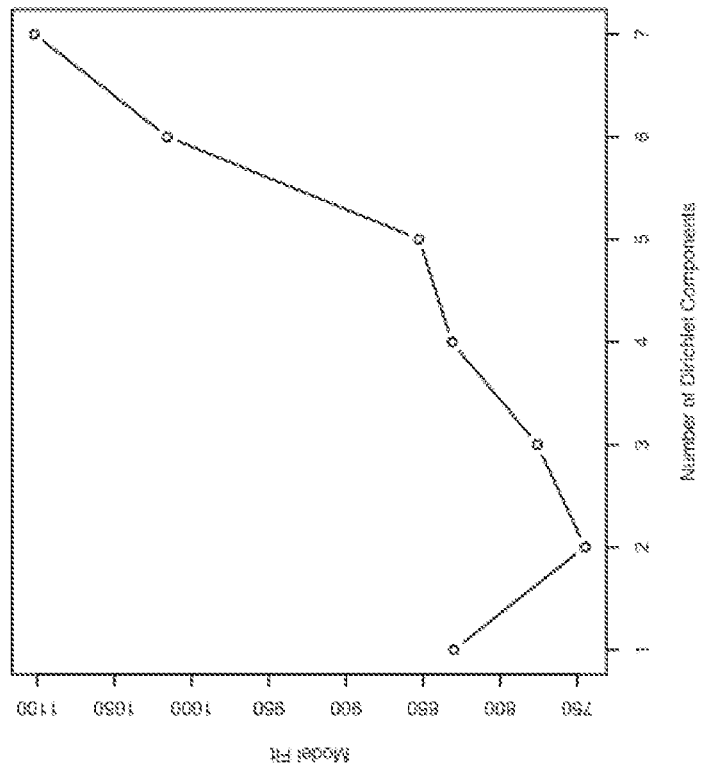

Mutagenetic characteristics data were statistically analyzed for 333 cancer-associated genes in each tumor sample, including number of point mutation loci, number of genes with point mutation, number of indel loci, number of genes with indel, number of fusion genes, number of genes with copy number variation, and the total numbers of mutated loci and genes, and these data were used for DMM stratified analysis on 35 tumor tissue samples. As depicted in FIG. 23A, the best cluster of the 35 samples is two groups. The labeled clustering of each sample is shown in FIG. 23B, which depicts the effective separation of members of the two groups based on Minimum Distance Separation (MDS1) distance: 14 tumor samples were clustered into group DMM 1, and 21 tumor samples were clustered into group DMM 0.

Figure 24A:
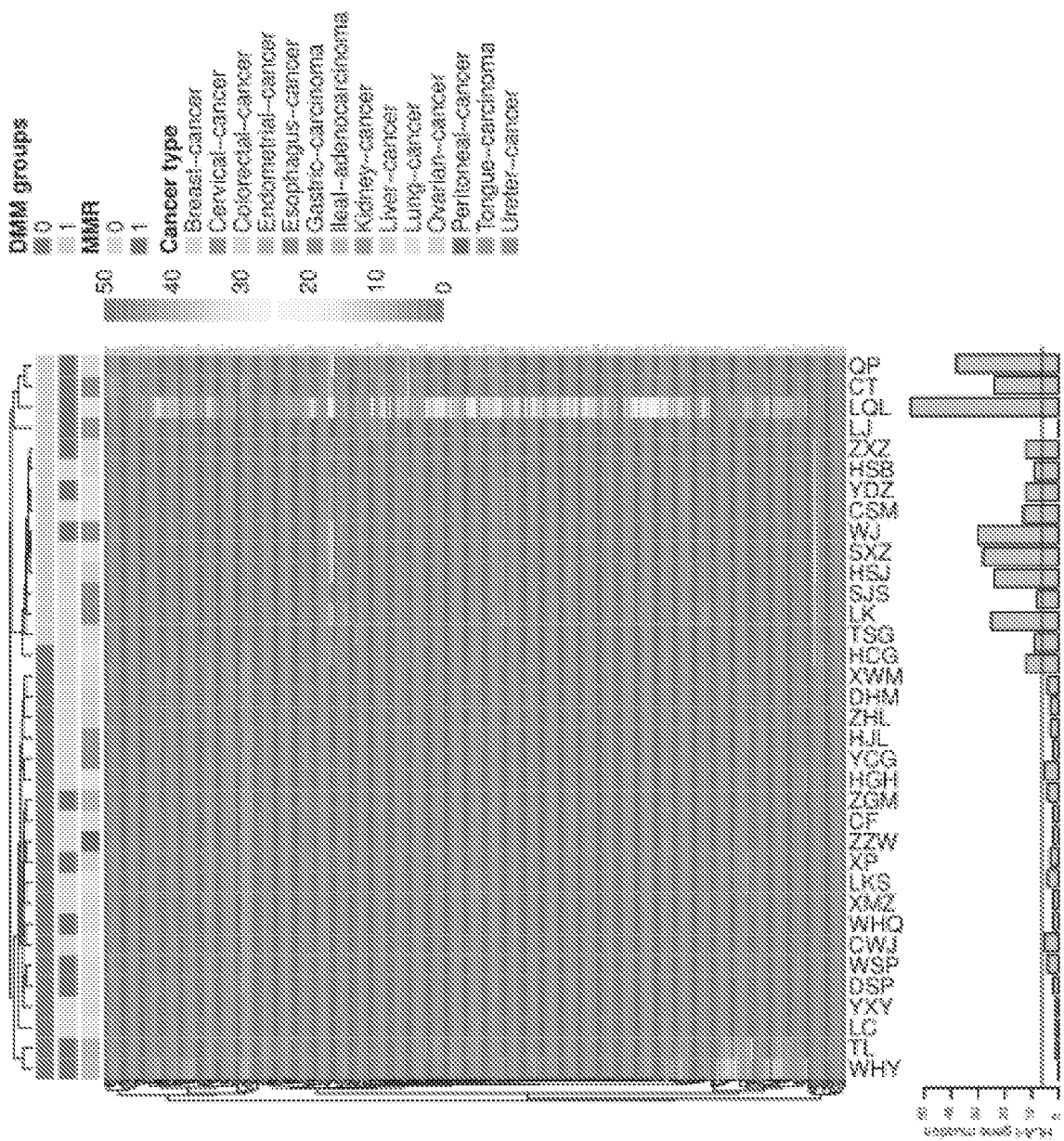
FIGS. 24A-24B depict clustering analysis of 35 tumor tissue samples based on mutation load of the 333 oncogenes in each sample.

Heatmap was generated for 35 tumor samples based on number of point mutations, number of indel loci, and number of loci with copy number variations detected for each of the 333 cancer-associated genes in each tumor sample, and cluster analysis was done for the samples and genes. As shown in FIG. 24A, two major clustering branches were observed for the 35 tumor samples. After adding clinical or molecular label for each sample, the cluster result was found to be inconsistent with that of cancer clinical types: tumor samples of the same cancer clinical type have different mutagenetic spectra, while some tumor samples of different cancer clinical types share similar mutations. The difference between cancer molecular classification and clinical types observed in this study is consistent with other reports (see, for example, Golub T R, Slonim D K, Tamayo P, et al. Molecular classification of cancer: class discovery and class prediction by gene expression monitoring [J]. Science, 1999, 286(5439):531-537). The clustering based on MMR deficiency type is also inconsistent with the clustering result shown in the heatmap. However, it was noted that the DMM groups had similar classification with the clustering results, only one sample showed inconsistency between DMM classification and clustering (FIG. 24A).

Figure 24B:

By measuring the total mutation number at HLA-A, HLA-B and HLA-C loci detected in each tumor sample, and comparing to the tumor tissue clustering result in the heatmap, a significant difference of HLA-I gene mutation load between the two DMM groups was observed (FIG. 24B).

Percentage of HLA-I Gene Mutation in the Total Mutation Number

Figure 25A:
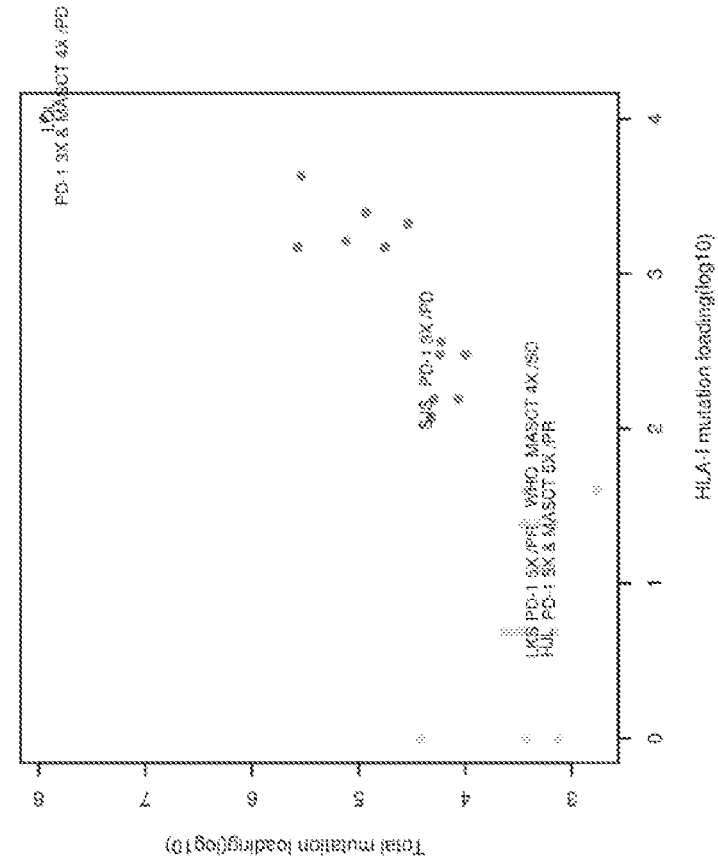
FIGS. 25A-25B depict statistical analysis of HLA-I gene mutation load of each tumor tissue sample within the two DMM groups.

Further analysis of HLA-I gene mutation number indicated statistically significant difference between the two DMM groups. The HLA-I gene mutation load of the 14 tumor samples in DMM group 1 (red) is significantly higher than that of the 21 tumor samples in DMM group 0 (green), with a p-value of 1.076e-5 (FIG. 25A). Moreover, the ratio of HLA-I gene mutation load to the total mutation load of DMM group 1 is significantly higher than that of DMM group 0 (FIG. 25A), suggesting that HLA-I gene mutation may be a critical internal mutation of cancer cells of DMM group 1. High mutation load of the HLA-I gene may facilitate escape of cancer cells from immune surveillance, leading to possible ineffectiveness of MHC-I restricted immunotherapy.

Figure 25B:
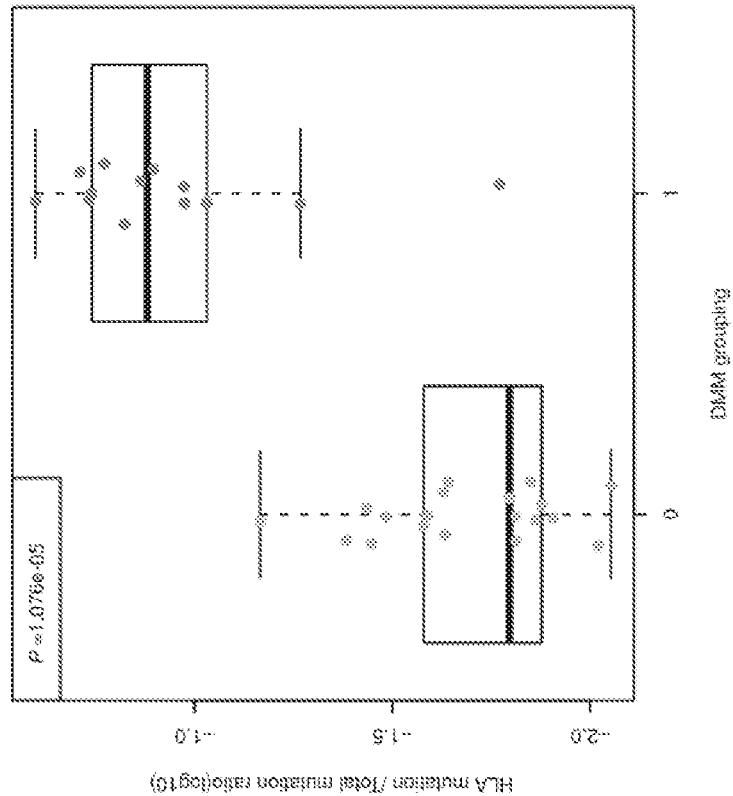

Five of the 35 cancer patients received PD-1 inhibitor (KEYTRUDA®) monotherapy, MASCT monotherapy, or their combined therapy (FIGS. 22, 25B). Two patients with high mutation load on the HLA-I genes (DMM group 1) were predicted to be unresponsive to MHC-I restricted immunotherapy. After treated with the combination therapy of PD-1 inhibitor (KEYTRUDA®) and MASCT or MASCT monotherapy for at least 3 cycles, these two patients were clinically evaluated as having progressive disease (PD) or ineffective clinical benefit response (CBR), as predicted. Three patients with low mutation load on the HLA-1 genes (DMM group 0) were predicted to be responsive to MHC-I restricted immunotherapy. Two of these three patients were treated with PD-1 inhibitor (Keytruda) monotherapy or (Keytruda) and MASCT combination therapy for 5 cycles, and were clinically evaluated as having partial response (PR) or obvious CBR; one of the three patients was treated with MASCT for 4 cycles, and was clinically evaluated as having stable disease, as predicted.

Typical Patient Case Analysis

Patient ID 1-LQL

Patient ID 1-LQL had lung adenocarcinoma, and was predicted to be of DMM group 1 based on clustering analysis. 55 mutations were detected at HLA-I gene loci, and was classified as HLA-I high mutation load (FIG. 22). MHC-I restricted immunotherapy was predicted to be clinically ineffective.

After receiving 3 cycles of PD-1 inhibitor (KEYTRUDA®) treatment and 4 cycles of MASCT treatment, the patient experienced respiratory failure and died due to ineffective disease control and pleural effusion. This patient was clinically evaluated as having progressive disease (PD), as predicted by clustering analysis.

Patient ID 2-SJS

Patient ID 2-SJS had esophageal cancer, and was predicted to be of DMM group 1 based on clustering analysis. 8 mutations were detected at HLA-I gene loci, and was classified as HLA-I high mutation load (FIG. 22), suggesting ineffectiveness with MHC-I restricted immunotherapy.

After receiving 3 cycles of MASCT monotherapy, this patient was clinically evaluated as having progressive disease (PD), as predicted by clustering analysis.

Patient ID 3-HJL

Patient ID 3-HJL, female, age 73, had transitional cell carcinoma of left renal pelvis, with multiple metastases towards left adrenal gland, left supraclavicular and mediastinal lymph nodes and two lungs. This patient was clustered into DMM group 0 based on Next Generation Sequencing (NGS) results, with 2 mutations detected at HLA-1 gene loci, and was classified as HLA-I low mutation load. 6 neoantigens were predicted based on HLA-1 subtyping of the patient. Therefore, MHC-I restricted immunotherapy was predicted to render effective CBR for this patient.

This patient was diagnosed to have transitional cell carcinoma of left renal pelvis and received radical surgery. Metastasis at left adrenal gland was discovered 2 years later, therefore, radiofrequency ablation (RFA) was applied. PET-CT scan after the RFA indicated multiple metastases at left supraclavicular and mediastinal lymph nodes and two lungs, with the biggest tumor size of ~2 cm in diameter, so the patient started to receive chemotherapy. After the fourth chemotherapy, CT re-examination indicated ineffective cancer control by chemotherapy (FIGS. 26A-C). The patient was then treated with PD-1 inhibitor (KEYTRUDA®) and MASCT combination therapy. After 3 cycles of combination therapy, the tumor size was found to have shrunk for ~50% by CT scan (FIG. 26D). After 5 cycles of PD-1 inhibitor (KEYTRUDA®) and MASCT combination therapy, CT scan suggested disappearance of tumor in lungs, stable disease at mediastinal lymph nodes, and disappearance of swollen left supraclavicular lymph nodes. The disease condition was clinically evaluated as partial response (PR, FIG. 26E). The clinical result was as predicted.

Patient ID 4-LKS

Patient ID 4-LKS, male, age 61, experienced stage IV moderately differentiated left lung adenocarcinoma after radical surgery, together with metastases at brain and mediastinal lymph nodes. This patient was clustered into DMM group 0 based on NGS results, with 2 mutations detected at HLA-I loci, and was classified as HLA-I low mutation load. 6 neoantigens were predicted based on HLA-I subtyping of the patient. Therefore, MHC-I restricted immunotherapy was predicted to render effective CBR for this patient.

This patient received radical surgery of the left lung tumor 13 years ago, followed by 4 cycles of adjuvant chemotherapy and mediastinal CT scans. Intracranial metastases were detected during the re-examination, with the tumor size of ~3 cm (FIG. 27A), accompanied with right hemiplegia. After 20 cycles of targeted radiation (dose information unavailable), the tumor shrank in size (FIG. 27B). The patient then received PD-1 inhibitor (KEYTRUDA®) monotherapy. After 2 cycles of treatment, the CT re-examination indicated further shrinkage of the intracranial tumor (FIG. 27C), and clinical symptom showed gradual recovery of muscle strength in the hemiparesis side. After receiving 6 cycles of PD-1 inhibitor (KEYTRUDA®) monotherapy, CT re-examination suggested further improved intracranial tumor and edema status (FIG. 27D), and clinical symptom indicated gradual recovery of muscle strength in the hemiparesis side and the ability of performing fine movement. After finishing radiation therapy and 6 months of PD-1 inhibitor (KEYTRUDA®) monotherapy, the patient was clinically evaluated as having partial response (PR). This clinical result was as predicated by our sequencing analysis.

Discussion

In patients with "reversible HLA-I deficiencies," after adoptive T cell immunotherapy, T cells can locally secrete IFN-γ and upregulate the expression of HLA-I molecules. Therefore, it will be of greater clinical significance to assess whether patients have "irreversible HLA-I deficiencies" prior to receiving adoptive T cell immunotherapy.

The sequencing results based on the five tumor tissue samples discussed above suggested weaker correlation between CBR after receiving PD-1 inhibitor (KEYTRUDA®) and/or MASCT and DNA MMR deficiency status (mutations detected at MLH1, MSH2, MSH6 and PMS2 loci), compared to that between CBR and HLA-I gene mutation load. MMR deficiency may lead to elevated mutation rate in cancer cells, which in turn may result in more neoantigens, theoretically. However, if these cancer cells have low or no expression of HLA-I molecules, the neoantigens would not be effectively presented for recognition and to trigger cytotoxic effect by immune cells. Therefore, the availability of HLA-I molecules for effective neoantigen presentation in cancer cells is one of the requirements for MHC-I restricted immunotherapy to be effective. The patient case 1.LQL supported this hypothesis: although many mutations were detected in the tumor tissue (a total of 3243 mutations detected), since HLA-I gene mutation load was also quite high, PD-1 inhibitor (KEYTRUDA®) therapy or MASCT did not have significant clinical effect.

Since HLA-I genes have high polymorphism, after obtaining the HLA-I gene mutation information in tumor tissue, further testing is necessary to determine whether and to what extent the amino acid mutation at certain locus would affect antigen presentation by HLA-I molecules. In this study, statistical analysis was carried out to perform stratified analysis on cancer patients, and cluster them into one responsive group and one non-responsive group to MHC-I restricted immunotherapy, based on HLA-I gene mutation load in the tumor tissue of each patient, so that a correlation between clinical response and HLA-I gene mutation load can be measured. According to the 5 case studies, 3 patients with low HLA-I mutation load showed effective CBR to MHC-I restricted immunotherapy, while 2 patients with high HLA-I mutation load did not show effective CBR to such therapy. This example reports the first clinical discovery that bioinformatics analysis on NGS data of patient samples can be performed to provide prognosis of cancer immunotherapy (such as using PD-1 inhibitor KEYTRUDA®) and adoptive T cell therapy (such as MASCT) based on number of neoantigens and HLA-I gene mutation load, thereby providing patients with precision immunotherapy. Clinical studies with a larger sample size are underway to corroborate this discovery.

Figure 28:
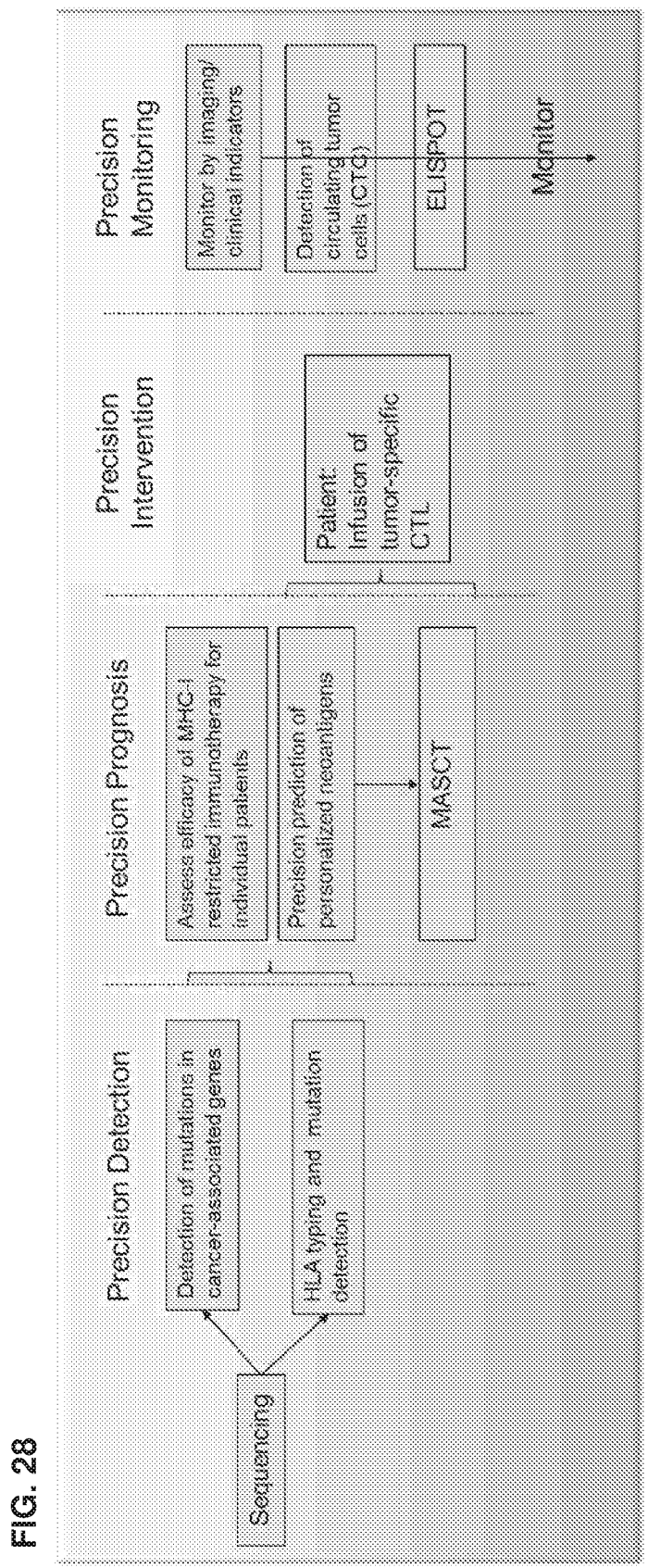
FIG. 28 shows an overview flow chart of an exemplary precision MASCT using neoantigen peptides predicted based on sequencing results of a patient's tumor sample, and prognosis based on HLA mutation status.

Example 6—A Case Study of a Patient with Colorectal Cancer Treated with Neoantigens—MASCT Patient XMZ, male, age 58, was diagnosed with colon cancer and received colectomy. Pathological analysis indicated Stage II colon cancer. Three years after the colectomy, the patient received CTC monitoring, which showed a CTC amount of 194 cells/10 mL. The patient received three treatment cycles of precision MASCT as outlined in FIG. 28.

Briefly, as the first step, a tumor biopsy sample from the patient was sequenced and analyzed using the ONCOGXONE™ cancer-associated genes plus HLA panel (Admera Health). The ONCOGXONE™ plus HLA panel used Illumina MiSeq or HiSeq sequencing platform to sequence about 150-400 genes that are specific to the cancer type, including HLA loci. Agilent SURESELECT™ target enrichment kit was used to enrich the target sequences in the sample. Target sequence regions spanned about 2-5.4 Mb of each gene locus, covering all exons, UTRs and relevant intron regions. Average coverage depth was about 100 times. Genomic variations, including point mutations, indels, rearrangements, and copy number variations (CNV) based on the sequencing data were determined.

ONCOGXONE™ plus HLA analysis of the patient's sample revealed that the patient had a G12A point mutation in the KRAS gene, which may reduce sensitivity of the patient to treatment with monoclonal antibodies against EGFR, such as cetuximab, or panitumumab. The patient had a point mutation at residue Q399 of the XRCC1 gene, suggesting a potential enhanced response to platinum-based chemotherapeutic drugs. The patient had mutations in MTHFR and TYMS, suggesting a potential enhanced response to 5-FU. The patient had mutations in CYP2D6, suggesting a potential reduced response to tamoxifen or opioid analgesics. Potentially beneficial drugs predicted based on the sequencing results include anti-PD-1 antibodies (such as OPDIVO® or KEYTRUDA®), PD-0332991 (Palbociclib), and trametinib (such as MEKINIST®).

Additionally, HLA subtyping and mutation analysis based on the sequencing results revealed that the patient had two deletion mutation in the HLA-I genes, including one in the HLA-A locus, and one in the HLA-C locus. HLA-I subtyping and mutation load results of the patient's tumor sample are shown in Tables 3 and 4 below. Functional analysis of the patient's HLA loci suggested that MHC-I restricted therapy, such as T cell-based therapy, might be effective for the patient.

TABLE 3

HLA-I subtyping results

| Locus | A1 | A2 |
|---|---|---|
| A | 0206 | 2402 |
| B | 1502 | 5101 |
| C | 0302 | 0801 |

TABLE 4

Mutations in HLA-I class genes

| Gene | Chromosome | Location | WT | Mutation | Frequency | Type | Seq. depth |
|---|---|---|---|---|---|---|---|
| HLA-A | chr6 | 29912028 | AG | A | 0.1783 | deletion | 129 |
| HLA-C | chr6 | 31236715 | CG | C | 0.9429 | deletion | 245 |

Based on the sequencing analysis, four candidate neoantigens were discovered (FIG. 29A). Two new antigen peptides were designed based on neoantigens MTHR-A222V and MLL3-C988F respectively. Also, a neoantigen peptide KRAS_G2V from our antigen peptide library was chosen. Together, 16 antigen peptides (including hTERT, p53, Survivin, NY-ESO-1, MET, MUC1, Kras-3, neoantigen 1+2) were included in the antigen peptide pool for the MASCT treatments that were specific to the patient's sigmoid colon tumor.

After three cycles of precision MASCT treatments using the antigen peptide pool comprising the neoantigen peptides, the number of circulating tumor cells (CTC) in the patient was reduced (FIG. 29B). PBMC samples from the patient were assayed by ELISPOT to assess antigen-specific T cell response. The ELISPOT results (FIG. 29C) revealed that the patient's PBMC had T lymphocytes exhibiting strong specific response against MUC1 and the neoantigens (neoantigen 1+1, Kras-3), while specific response against hTERT, p53, surviving, NY-ESO-1, and MET was also significant. Specific T cells against tumor neoantigens and tumor associated antigens were present in the patient's PBMC, and proliferated over the course of the MASCT treatments. Patient reported improved vigor and physical strength, as well as changes in physical appearance (such as hair and beard turning black) after receiving the three cycles of MASCT treatment.

Example 7—Prognosis and Stratification of Patients for MASCT Treatment

This example presents an exemplary model for providing prognosis and stratification of patients receiving MHC-restricted therapy, such as MASCT treatments (including Precision MASCT), based on the number of neoantigens (i.e. neoantigen load) and mutation load of HLA molecules in the patients.

The mutation load of HLA molecules and neoantigens in tumor samples from 40 cancer patients were determined and analyzed using the methods described in Example 5. Patients were predicted to benefit from the MHC-restricted therapy if the patients had: (1) no mutation in B2M; (2) no mutation in functional regions (such as leader peptide sequence, a1 domain, a2 domain, or a3 domain) of HLA genes; (3) less than 2 mutations in HLA-I A, B, or C genes;

and (4) more than 5 neoantigens. Patients were predicted to potentially benefit from the MHC-restricted therapy if the patients had: (1) no mutation in B2M; (2) no mutation in functional regions (such as leader peptide sequence, a1 domain, a2 domain, or a3 domain) of HLA genes; (3) at least 2 mutations and less than 10 mutations in HLA-I A, B, or C genes; and (4) less than 5 neoantigens. Patients were predicted to have no benefit from the MHC-restricted therapy if the patients have: (1) one or more mutations in B2M; or (2) at least 10 mutations in HLA-I A, B, or C genes. 9 patients received MHC-restricted therapy, including MASCT and/or immune checkpoint blockade treatment. Table 5 below shows the clinical response of the patients in the three prognosis groups.

TABLE 5

Prognosis of patients for MHC-restricted therapy

| Prognosis groups | Benefit | Potential benefit | No benefit |
|---|---|---|---|
| Number (total = 40) | 17 (42.5%) | 21 (52.5%) | 2 (5%) |
| Receive MHC-restricted therapy | 5 | 3 | 1 |
| Respond to MHC-restricted therapy | 4 | 2 | 0 |
| No response to MHC-restricted therapy | 1 | 1 | 1 |
| Response rate | 80% | 66% | 0% |
| Success rate of prognosis | 80% | NA | 100% |

Example 8—Safety of MASCT in Patients with Hepatocellular Carcinoma 45 patients with hepatocellular carcinoma were treated with MASCT, and their clinical data, including clinical response, liver and renal function, routine blood examination results, and adverse reactions, were collected and retrospectively analyzed. The patients did not receive any other immunotherapy, and their latest treatments (surgery, radiotherapy, chemotherapy) before receiving MASCT were completed at least one month or more prior to the MASCT. FIG. 30A shows the clinical characteristics of the 45 patients.

Cells were prepared for the MASCT according to the method described in Example 1. Briefly, PBMCs were isolated from each patient on Day 1, and the adherent cells were induced into DCs. DCs were loaded with 14 kinds of multiple antigen peptides to prepared the mature DCs (mDCs). A small portion of mDCs were injected to the patients subcutaneously on Day 8. The non-adherent cells from the PBMC sample were co-cultured with the rest of mDCs from Day 7, and induced into cytotoxic T cells (CTLs), which were infused intravenously on Day 26. The mDCs and CTLs were characterized to ensure quality control. In the mDCs, the percentage of CD80 cells was 98.5±5%, the percentage of CD83$^+$ cells was 88±10%, the percentage of CD86 cells was 98.4±3%, and the percentage of HLA-DR$^+$ cells was 98.8±2%. The mDCs secreted high level of IL-12 (985±312 pg/mL) and low level of IL-10 (53±10 pg/mL). In the CTLs, the percentage of CD3$^+$CD8$^+$ cells was 83±10%, and the percentage of CD3$^+$CD5$^+$ cells was 24±5%. The CTLs secreted high level of IFN-γ (1222±650 pg/mL), and low level of IL-10 (6.8±5.0 pg/mL).

All 45 patients had improved clinical conditions with varying degrees after receiving the MASCT treatment. Most patients reported improved vigor, appetite, sleep, and physical strength. The main adverse events after infusion of the active immunocytes were moderate fever (2 cases, 4.44%). The fever occurred after about 1 hour of the CTL infusion, and in both cases, the fever was no more than 38.5° C. The patients resumed normal body temperature after rest, drinking water and physical cooling. No other severe adverse events were observed.

FIG. 30B shows the results of routine blood examination of the 45 patients before MASCT treatments and after the last MASCT treatments. There was no abnormality observed in the routine blood examination results of any patient. The White Blood Cell (WBC) number (P 0.0411), and neutrophil (Neu) numbers (P=0.0015) showed significant changes before and after the MASCT treatments, but are within normal ranges, and thus do not lead to significant clinical effects. Hemoglobin (HB) and platelet (PLT) numbers showed no statistically significant change. Statistical analysis was performed using t test using SPSS 19.0 software.

FIG. 30C shows the ALT, AST, TBIL, CR and BUN levels in the 45 patients before MASCT treatments and after the last MASCT treatments. There was no abnormality observed in the liver or renal function of any patient. Data from 2 patients before MASCT treatments was unavailable. AST (p=0.0198) and TBIL (p=0.0177) levels showed statistically significant change after the MASCT treatment, and ALT also had a tendency to increase, which have clinical significance. CR and BUN levels had no statistical significant change after the MASCT treatments.

After 4-6 MASCT treatments, liver function data were available for 6 visits (baseline level to after 5 MASCT treatments). FIG. 30D shows the change in the ALT and AST levels in 10 patients over the course of 5 MASCT treatments. 2 patients with large fluctuations in the levels were excluded, including one patient that received liver transplantation at the 6$^{th}$ visit, which resulted in an increased level of ALT to 288 IU/L; and a second patient that received TACE therapy, which resulted in an increased level of 572 IU/L at the 6$^{th}$ visit. Comparing the ALT and AST levels in the patients over time, there was no statistically significant change.

The results demonstrate that MASCT treatment is safe for HCC patients.

What is claimed is:

1. A method of treating a cancer in an individual, comprising administering to the individual an effective amount of activated T cells, wherein the activated T cells are prepared by co-culturing a population of T cells with a population of dendritic cells loaded with a plurality of tumor antigen peptides having pre-determined amino acid sequences, wherein the plurality of tumor antigen peptides comprises at least one epitope having an amino acid sequence selected from the group consisting of SEQ ID NOs: 36-38 and 41-44, and wherein the population of dendritic cells loaded with the plurality of tumor antigen peptides is prepared by contacting the population of dendritic cells with the plurality of tumor antigen peptides.

2. The method of claim 1, further comprising administering to the individual an effective amount of the dendritic cells loaded with the plurality of tumor antigen peptides, wherein the dendritic cells are administered prior to the administration of the activated T cells.

3. The method of claim 1, wherein the population of T cells is co-cultured with the population of dendritic cells loaded with the plurality of tumor antigen peptides for about 7 days to about 21 days.

4. The method of claim 1, wherein the population of T cells is co-cultured with the population of dendritic cells loaded with the plurality of tumor antigen peptides in the presence of an immune checkpoint inhibitor.

5. The method of claim 1, wherein the population of T cells and the population of dendritic cells are derived from the same individual.

6. The method of claim 5, wherein the population of T cells and the population of dendritic cells are derived from the individual being treated.

7. The method of claim 1, wherein the activated T cells are administered to the individual for at least three times.

8. The method of claim 1, wherein the plurality of tumor antigen peptides comprises a first core group of general tumor antigen peptides.

9. The method of claim 8, wherein the plurality of tumor antigen peptides further comprises a second group of cancer-type specific antigen peptides.

10. The method of claim 8, wherein the first core group comprises about 10 to about 20 general tumor antigen peptides.

11. The method of claim 1, wherein the plurality of tumor antigen peptides comprises a neoantigen peptide.

12. The method of claim 11, wherein the neoantigen peptide is selected based on the genetic profile of a tumor sample from the individual.

13. The method of claim 1, further comprising administering to the individual an effective amount of an immune checkpoint inhibitor.

14. The method of claim 1, wherein the individual is selected for the method of treating based on the mutation load in the cancer.

15. The method of claim 1, wherein the population of dendritic cells loaded with the plurality of tumor antigen peptides is prepared by pulsing the plurality of tumor antigen peptides into the population of dendritic cells.

16. The method of claim 1, wherein the plurality of tumor antigen peptides are synthetic.

17. The method of claim 1, wherein the concentration of each tumor antigen peptide in the plurality of tumor antigen peptides is about 0.1-200 µg/mL.

* * * * *